US011985893B2

(12) United States Patent
Hoshi

(10) Patent No.: US 11,985,893 B2
(45) Date of Patent: May 14, 2024

(54) ORGANIC ELECTROLUMINESCENCE DEVICE AND AROMATIC COMPOUND FOR ORGANIC ELECTROLUMINESCENCE DEVICE

(71) Applicant: Samsung Display Co., Ltd., Yongin-si (KR)

(72) Inventor: Keigo Hoshi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 594 days.

(21) Appl. No.: 16/933,819

(22) Filed: Jul. 20, 2020

(65) Prior Publication Data

US 2021/0143342 A1 May 13, 2021

(30) Foreign Application Priority Data

Nov. 8, 2019 (KR) .................. 10-2019-0142840

(51) Int. Cl.
| | | |
|---|---|---|
| H01L 51/00 | (2006.01) | |
| C07D 401/14 | (2006.01) | |
| C09K 11/06 | (2006.01) | |
| H10K 85/60 | (2023.01) | |
| H10K 50/11 | (2023.01) | |

(52) U.S. Cl.
CPC ....... *H10K 85/6572* (2023.02); *C07D 401/14* (2013.01); *C09K 11/06* (2013.01); *H10K 85/654* (2023.02); *C09K 2211/1018* (2013.01); *H10K 50/11* (2023.02)

(58) Field of Classification Search
CPC .................. H10K 85/654; H10K 85/6572
See application file for complete search history.

(56) References Cited

U.S. PATENT DOCUMENTS

| | | | |
|---|---|---|---|
| 6,562,982 B1 | 5/2003 | Hu et al. | |
| 6,670,054 B1 | 12/2003 | Hu et al. | |
| 8,609,257 B2 | 12/2013 | Ise et al. | |
| 9,029,487 B2 | 5/2015 | Klosin et al. | |
| 9,246,111 B1 | 1/2016 | Kim et al. | |
| 9,273,000 B2 | 3/2016 | Hayashi et al. | |
| 9,401,484 B2 | 7/2016 | Kim et al. | |
| 10,193,079 B2 | 1/2019 | Stoessel et al. | |
| 11,121,184 B2 | 9/2021 | Song et al. | |
| 11,136,294 B2 | 10/2021 | Bergmann et al. | |
| 11,424,417 B2* | 8/2022 | Fujita | H01L 51/0072 |
| 2002/0125818 A1 | 9/2002 | Sato et al. | |
| 2003/0218418 A9 | 11/2003 | Sato et al. | |
| 2012/0126691 A1 | 5/2012 | Ise et al. | |
| 2012/0126692 A1 | 5/2012 | Ise et al. | |
| 2013/0292654 A1 | 11/2013 | Matsunaga et al. | |
| 2014/0264292 A1 | 9/2014 | Xia et al. | |
| 2015/0105564 A1 | 4/2015 | Adachi et al. | |
| 2016/0087222 A1 | 3/2016 | Huang et al. | |
| 2016/0111652 A1 | 4/2016 | Huang et al. | |
| 2016/0126478 A1 | 5/2016 | Zheng et al. | |
| 2016/0301015 A1 | 10/2016 | Zheng et al. | |
| 2016/0315269 A1 | 10/2016 | Xia et al. | |
| 2017/0098780 A1 | 4/2017 | Kim et al. | |
| 2017/0125691 A1* | 5/2017 | Kim | H10K 85/636 |
| 2017/0125699 A1 | 5/2017 | Ahn et al. | |
| 2017/0186973 A1 | 6/2017 | Ren et al. | |
| 2017/0352816 A1 | 12/2017 | Jeon et al. | |
| 2018/0026202 A1 | 1/2018 | Danz et al. | |
| 2018/0108857 A1 | 4/2018 | Adachi et al. | |
| 2018/0170914 A1 | 6/2018 | Miyata et al. | |
| 2018/0175294 A1 | 6/2018 | Duan et al. | |
| 2018/0198075 A1 | 7/2018 | Danz et al. | |
| 2018/0212158 A1 | 7/2018 | Aspuru-Guzik et al. | |
| 2018/0248127 A1 | 8/2018 | Lee et al. | |
| 2019/0013481 A1 | 1/2019 | Nasu et al. | |
| 2019/0016704 A1 | 1/2019 | Nasu et al. | |
| 2019/0103564 A1 | 4/2019 | Ogawa et al. | |
| 2019/0157570 A1 | 5/2019 | Sim et al. | |
| 2019/0198778 A1 | 6/2019 | Bergmann et al. | |

(Continued)

FOREIGN PATENT DOCUMENTS

| | | |
|---|---|---|
| CN | 103180347 A | 6/2013 |
| CN | 104119274 A | 10/2014 |

(Continued)

OTHER PUBLICATIONS

Umamahesh Balijapalli et al. ACS Appl. Mater. Interfaces 2020, 12, 9498-9506.*

U. Balijapalli, 12 ACS Applied Material & Interfaces, 9498-9506 (with supplementary pp. 1-59) (Feb. 20, 2020) (Year: 2020).*

H. Noda et al., "Excited state engineering for efficient reverse intersystem crossing", Science Advances, 2018, 4, pp. 1-7.

Yuan, Wenbo et al., "The electron inductive effect of CF3 on penta-carbazole containing blue emitters: Trade-off between color purity and luminescent efficiency in TADF OLEDs," Dyes and Pigments, vol. 159, 2018, 7 pages.

(Continued)

*Primary Examiner* — Alexander R Pagano
(74) *Attorney, Agent, or Firm* — Lewis Roca Rothgerber Christie LLP

(57) ABSTRACT

An organic electroluminescence device of an embodiment includes a first electrode, a second electrode, and an emission layer between the first electrode and the second electrode and containing an aromatic compound, wherein the aromatic compound includes a benzene ring, two unsubstituted carbazole groups directly bonded to the benzene ring, two substituted carbazole groups directly bonded to the benzene ring and each substituted with a nitrogen-containing ring group, and a substituent directly bonded to the benzene ring and selected from a cyano group, a fluorine, or a C1-C10 alkyl group substituted with a fluorine. The organic electroluminescence device may obtain good luminous efficiency and long life (long lifespan) characteristics while emitting blue light.

17 Claims, 2 Drawing Sheets

(56) References Cited

U.S. PATENT DOCUMENTS

| | | | |
|---|---|---|---|
| 2019/0198779 A1 | 6/2019 | Bergmann et al. | |
| 2019/0241549 A1* | 8/2019 | Yang | C07D 491/048 |
| 2019/0252625 A1 | 8/2019 | Adachi et al. | |
| 2019/0393428 A1 | 12/2019 | Seifermann | |
| 2020/0119287 A1 | 4/2020 | Aguilera-Iparraguirre et al. | |
| 2020/0185626 A1 | 6/2020 | Yuuki | |
| 2020/0235313 A1* | 7/2020 | Nakanotani | C07D 209/88 |
| 2021/0119146 A1 | 4/2021 | Hong et al. | |
| 2021/0155849 A1 | 5/2021 | Stubbs et al. | |
| 2021/0202864 A1* | 7/2021 | Nakanotani | C07D 209/88 |
| 2021/0343947 A1* | 11/2021 | Sugawara | C09D 11/328 |

FOREIGN PATENT DOCUMENTS

| | | |
|---|---|---|
| CN | 104119861 A | 10/2014 |
| CN | 102792777 B | 12/2015 |
| CN | 105294905 A | 2/2016 |
| CN | 106164046 A | 11/2016 |
| CN | 106316924 A | 1/2017 |
| CN | 106488965 A | 3/2017 |
| CN | 107074765 A | 8/2017 |
| CN | 107302844 A | 10/2017 |
| CN | 107925004 A | 4/2018 |
| CN | 107954922 A | 4/2018 |
| CN | 107987009 A | 5/2018 |
| CN | 109134347 A | 1/2019 |
| DE | 102016108334 B3 | 12/2016 |
| DE | 102016108335 B3 | 12/2016 |
| DE | 102016108332 B3 | 2/2017 |
| DE | 102016108327 B3 | 3/2017 |
| DE | 102016110004 B3 | 4/2017 |
| DE | 102016112082 A1 | 1/2018 |
| DE | 102017103542 B3 | 3/2018 |
| EP | 2609123 | 7/2013 |
| EP | 2711359 A1 | 3/2014 |
| EP | 2711949 A1 | 3/2014 |
| EP | 2712859 A2 | 4/2014 |
| EP | 2712860 A1 | 4/2014 |
| EP | 3113239 A1 | 1/2017 |
| EP | 3131879 | 2/2017 |
| EP | 3138137 | 3/2017 |
| EP | 2549837 B1 | 2/2018 |
| EP | 3317904 | 5/2018 |
| ES | 2659733 T3 | 3/2018 |
| JP | 5-32625 A | 2/1993 |
| JP | 8-60144 A | 3/1996 |
| JP | 8-88083 A | 4/1996 |
| JP | 2001-313179 A | 11/2001 |
| JP | 2003-31371 A | 1/2003 |
| JP | 2003-77674 A | 3/2003 |
| JP | 4474493 B1 | 6/2010 |
| JP | 4523992 B1 | 8/2010 |
| JP | 2011-044365 A | 3/2011 |
| JP | 4729642 B1 | 7/2011 |
| JP | 2011-176250 A | 9/2011 |
| JP | 2011-176258 A | 9/2011 |
| JP | 2011-192524 A | 9/2011 |
| JP | 2011-216455 A | 10/2011 |
| JP | 2014-43541 A | 3/2014 |
| JP | 2014-506262 A | 3/2014 |
| JP | 2014-94935 A | 5/2014 |
| JP | 2014-135466 A | 7/2014 |
| JP | 2015-043435 A | 3/2015 |
| JP | 2015-107982 A | 6/2015 |
| JP | 2015-107983 A | 6/2015 |
| JP | 2015-110591 A | 6/2015 |
| JP | 5914514 B2 | 5/2016 |
| JP | 2016-516085 A | 6/2016 |
| JP | 2016-520253 A | 7/2016 |
| JP | 2016-523990 A | 8/2016 |
| JP | 2016-526025 A | 9/2016 |
| JP | 5989078 B2 | 9/2016 |
| JP | 2016-539182 A | 12/2016 |
| JP | 6133494 B2 | 5/2017 |
| JP | 2017-103440 A | 6/2017 |
| JP | 2017-514302 A | 6/2017 |
| JP | 2017-119663 A | 7/2017 |
| JP | 2017-119664 A | 7/2017 |
| JP | 2018-505126 A | 2/2018 |
| KR | 10-2011-088427 A | 8/2011 |
| KR | 10-2011-0088457 A | 8/2011 |
| KR | 10-2012-0018231 A | 2/2012 |
| KR | 10-2012-0025008 A | 3/2012 |
| KR | 10-2012-0137321 A | 12/2012 |
| KR | 10-2013-0016267 A | 2/2013 |
| KR | 10-2013-0100140 A | 9/2013 |
| KR | 10-2014-0113483 A | 9/2014 |
| KR | 10-1502316 B1 | 3/2015 |
| KR | 10-2015-0132872 A | 11/2015 |
| KR | 10-2016-0007965 A | 1/2016 |
| KR | 10-2016-0007966 A | 1/2016 |
| KR | 10-2016-0028406 A | 3/2016 |
| KR | 10-2016-0030094 A | 3/2016 |
| KR | 10-2016-0030877 A | 3/2016 |
| KR | 10-2017-0015414 A | 2/2017 |
| KR | 10-2017-0040697 A | 4/2017 |
| KR | 10-1738607 B1 | 5/2017 |
| KR | 10-2017-0087845 A | 7/2017 |
| KR | 10-2017-0088822 A | 8/2017 |
| KR | 10-2017-0092138 A | 8/2017 |
| KR | 10-1772548 B1 | 8/2017 |
| KR | 10-1781114 B1 | 9/2017 |
| KR | 10-2017-0136256 A | 12/2017 |
| KR | 10-2018-0008154 A | 1/2018 |
| KR | 10-2018-0015242 A | 2/2018 |
| KR | 10-2018-0023969 A | 3/2018 |
| KR | 10-1831270 B1 | 4/2018 |
| KR | 10-2018-0066258 A | 6/2018 |
| KR | 10-2018-0098809 A | 9/2018 |
| KR | 10-2020-0071192 A | 6/2020 |
| TW | I480359 B | 4/2015 |
| TW | I498411 B | 9/2015 |
| TW | I541239 B | 7/2016 |
| TW | I541323 B | 7/2016 |
| WO | WO 2011/013843 A1 | 2/2011 |
| WO | WO 2011/013859 A1 | 2/2011 |
| WO | WO 2011/021433 A1 | 2/2011 |
| WO | WO 2011/114833 A1 | 9/2011 |
| WO | WO 2011/114886 A1 | 9/2011 |
| WO | WO 2012/005172 A1 | 1/2012 |
| WO | WO 2012/027448 A1 | 3/2012 |
| WO | WO 2012/078005 A2 | 6/2012 |
| WO | WO 2014/173323 A1 | 10/2014 |
| WO | WO 2014/173324 A1 | 10/2014 |
| WO | WO 2014/183080 A1 | 11/2014 |
| WO | WO 2015/066354 A1 | 5/2015 |
| WO | WO 2015/160224 A1 | 10/2015 |
| WO | WO 2016/138077 A1 | 9/2016 |
| WO | WO 2016/152605 A1 | 9/2016 |
| WO | WO 2016/181846 A1 | 11/2016 |
| WO | WO 2017/005698 A1 | 1/2017 |
| WO | WO 2017/005699 A1 | 1/2017 |
| WO | WO 2017/011531 A2 | 1/2017 |
| WO | WO 2017/115835 A1 | 7/2017 |
| WO | WO 2017/169497 A1 | 10/2017 |
| WO | WO 2017/190885 A1 | 11/2017 |
| WO | WO 2018/001820 A1 | 1/2018 |
| WO | WO 2018/001821 A1 | 1/2018 |
| WO | WO 2018/001822 A1 | 1/2018 |
| WO | WO 2018/037069 A1 | 3/2018 |
| WO | WO 2018/155642 A1 | 8/2018 |
| WO | WO 2019/087936 A1 | 5/2019 |

OTHER PUBLICATIONS

EPO Extended Search Report dated Dec. 18, 2019, for corresponding European Patent Application No. 19206317.0 (8 pages).

CAS reg. No. 2418657-54-0, Jun. 3, 2020. (Year: 2020); Cited in U.S. Notice of Allowance dated Apr. 19, 2022 which issued in U.S. Appl. No. 16/567,389.

U.S. Restriction Requirement dated Jan. 6, 2022, issued in U.S. Appl. No. 16/567,389 (5 pages).

(56) References Cited

OTHER PUBLICATIONS

U.S. Notice of Allowance dated Apr. 19, 2022, issued in U.S. Appl. No. 16/567,389 (8 pages).

* cited by examiner

ORGANIC ELECTROLUMINESCENCE DEVICE AND AROMATIC COMPOUND FOR ORGANIC ELECTROLUMINESCENCE DEVICE

CROSS-REFERENCE TO RELATED APPLICATION

This application claims priority to and the benefit of Korean Patent Application No. 10-2019-0142840, filed on Nov. 8, 2019, the entire content of which is hereby incorporated by reference.

BACKGROUND

1. Field

One or more aspects of embodiments of the present disclosure herein relate to an organic electroluminescence device and an aromatic compound for an organic electroluminescence device.

2. Description of the Related Art

Recently, the development of organic electroluminescence displays as an image display device is being actively conducted. Unlike liquid crystal display devices and the like, organic electroluminescence displays are self-luminescent display devices, in which holes and electrons injected from a first electrode and a second electrode recombine in an emission layer, and thus a luminescent material including an organic compound in the emission layer emits light to implement display of images.

In the application of an organic electroluminescence device to a display device, there is a demand (or desire) for an organic electroluminescence device having a high luminous efficiency and a long life, and development of materials for an organic electroluminescence device capable of stably attaining such characteristics is being continuously required.

In recent years, particularly in order to implement a highly efficient organic electroluminescence device, technologies pertaining to phosphorescence emission using triplet state energy, or delayed fluorescence using triplet-triplet annihilation (TTA) in which singlet excitons are generated by collision of triplet excitons, are being developed, and thermally activated delayed fluorescence (TADF) materials using a delayed fluorescence phenomenon are being developed.

SUMMARY

One or more aspects of embodiments of the present disclosure are directed toward a highly efficient, long-life organic electroluminescence device.

The present disclosure also provides an aromatic compound for an organic electroluminescence device having a good efficiency.

An embodiment of the present disclosure provides an organic electroluminescence device including a first electrode, a second electrode on the first electrode, and an emission layer between the first electrode and the second electrode and containing an aromatic compound, wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides thereof, wherein the aromatic compound includes a benzene ring, two unsubstituted carbazole groups directly bonded to the benzene ring, two substituted carbazole groups directly bonded to the benzene ring and substituted with a nitrogen-containing ring group, and a substituent directly bonded to the benzene ring and being a cyano group, a fluorine, or a C1-C10 alkyl group substituted with a fluorine.

The emission layer may emit delayed fluorescence.

The nitrogen-containing ring group may be a pyridine group or a pyrimidine group.

The two unsubstituted carbazole groups may be bonded to the benzene ring to be symmetric with each other with respect to the substituent, and the two substituted carbazole groups may be bonded to the benzene ring to be symmetric with each other with respect to the substituent.

The substituent and each of the two unsubstituted carbazole groups may be bonded to the benzene ring at ortho-positions respectively, and the substituent and each of the two substituted carbazole groups may be bonded to the benzene ring at meta-positions respectively.

The aromatic compound may be represented by Formula 1:

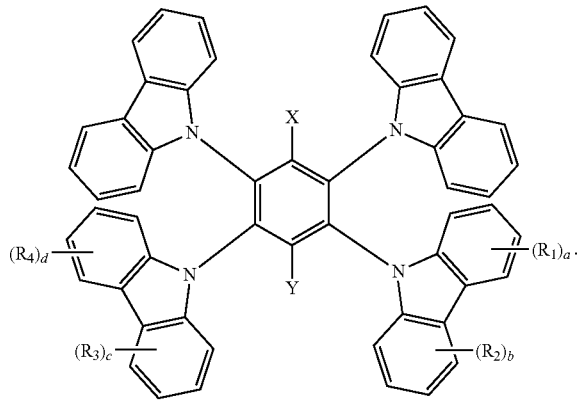

Formula 1

In Formula 1, X may be a cyano group, a fluorine, or a C1-C10 alkyl group substituted with a fluorine; Y may be a hydrogen atom, a deuterium atom, a halogen atom, a cyano group, an unsubstituted heteroaryl group having 3 to 20 ring-forming carbon atoms and at least one ring-forming nitrogen atom, a substituted or unsubstituted aryl group having 6 to 30 ring-forming carbon atoms, or a substituted or unsubstituted alkyl group having 1 to 20 carbon atoms; a to d may each independently be an integer of 1 to 4; at least one of $R_1$ to $R_4$ may be represented by Formula 2, and the remaining ones of $R_1$ to $R_4$ may each independently be a hydrogen atom, a deuterium atom, or a substituted or unsubstituted alkyl group having 1 to 4 carbon atoms:

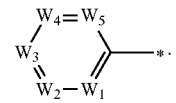

Formula 2

In Formula 2, at least one of $W_1$ to $W_5$ may be a nitrogen atom, the remaining ones of $W_1$ to $W_5$ may each independently be $CR_5$; and $R_5$ may be a hydrogen atom, a deuterium atom, or a substituted or unsubstituted alkyl group having 1 to 4 carbon atoms.

Formula 2 may be represented by Formula 2-1 or Formula 2-2.

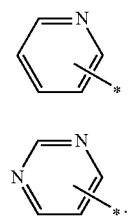

Formula 2-1

Formula 2-2

In an embodiment of the present disclosure, an organic electroluminescence device includes a first electrode, a second electrode on the first electrode, and an emission layer between the first electrode and the second electrode, wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides thereof, wherein the emission layer includes an aromatic compound represented by Formula 1.

The aromatic compound represented by Formula 1 above may be laterally symmetric with respect to X and Y.

Y may be an unsubstituted phenyl group, an unsubstituted pyridine group, an unsubstituted carbazole group, or an unsubstituted alkyl group having 1 to 4 carbon atoms.

Formula 1 may be represented by Formula 3:

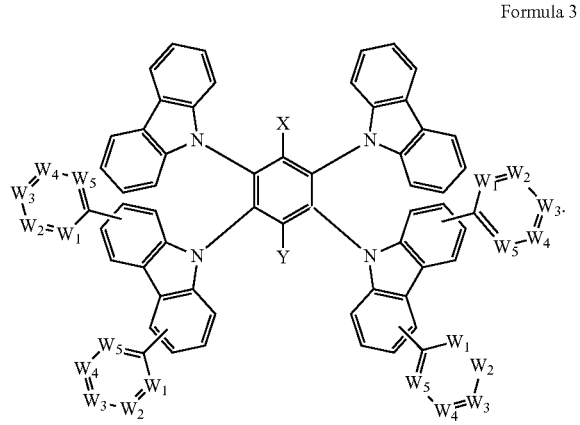

Formula 3

In Formula 3, X, Y, and $W_1$ to $W_5$ are the same as defined in Formulae 1 and 2.

The aromatic compound represented by Formula 1 above may be a thermally activated delayed fluorescence emission material.

BRIEF DESCRIPTION OF THE DRAWINGS

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
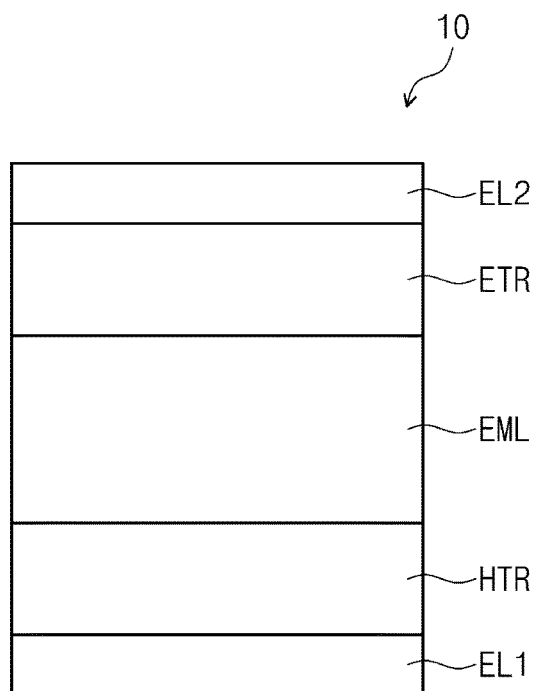
FIG. 1 is a schematic cross-sectional view of an organic electroluminescence device according to an embodiment of the present disclosure.

The present disclosure may have various modifications and may be embodied in different forms, and example embodiments will be explained in more detail with reference to the accompany drawings. The present disclosure may, however, be embodied in different forms and should not be construed as limited to the embodiments set forth herein. Rather, all modifications, equivalents, and substituents which are included in the spirit and technical scope of the present disclosure should be included in the present disclosure.

It will be understood that when an element or layer is referred to as being "on", "connected to" or "coupled to" another element or layer, it can be directly on, connected or coupled to the other element or layer (with no intervening elements and/or layers therebetween), or intervening elements and/or layers may be present.

Like numbers refer to like elements throughout. Also, in the drawings, the thickness, the ratio, and the dimensions of elements are exaggerated for an effective description of technical contents.

The term "and/or," includes all combinations of one or more of which associated configurations may define. Expressions such as "at least one of," "one of," and "selected from," when preceding a list of elements, modify the entire list of elements and do not modify the individual elements of the list. Further, the use of "may" when describing embodiments of the present disclosure refers to "one or more embodiments of the present disclosure."

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present disclosure. The terms of a singular form may include plural forms unless the context clearly indicates otherwise.

In addition, terms such as "below," "lower," "above," "upper," and the like are used to describe the relationship of the configurations shown in the drawings. The terms are used as a relative concept and are described with reference to the direction indicated in the drawings.

Unless otherwise defined, all terms (including technical and scientific terms) used herein have the same meaning as commonly understood by one of ordinary skill in the art to which the present disclosure pertains. It is also to be understood that terms defined in commonly used dictionaries should be interpreted as having meanings consistent with the meanings in the context of the related art, and are expressly defined herein unless they are interpreted in an ideal or overly formal sense.

It should be understood that the terms "comprise", or "have" are intended to specify the presence of stated features, integers, steps, operations, elements, components, or combinations thereof in the disclosure, but do not preclude the presence or addition of one or more other features, integers, steps, operations, elements, components, or combinations thereof.

Hereinafter, an organic electroluminescence device according to an embodiment of the present disclosure and an aromatic compound of an embodiment included therein will be described with reference to the accompanying drawings.

FIGS. 1 to 4 are cross-sectional views schematically illustrating an organic electroluminescence device according to an embodiment of the present disclosure.

Referring to FIGS. 1 to 4, in an organic electroluminescence device 10 according to an embodiment, a first electrode EL1 and a second electrode EL2 are provided to face each other, and an emission layer EML may be between the first electrode EL1 and the second electrode EL2.

In some embodiments, the organic electroluminescence device 10 of an embodiment may further include a plurality of functional layers between the first electrode EL1 and the second electrode EL2, in addition to the emission layer EML. The plurality of functional layers may include a hole transport region HTR and an electron transport region ETR. For example, the organic electroluminescence device 10 according to an embodiment may include the first electrode EL1, the hole transport region HTR, the emission layer EML, the electron transport region ETR, and the second electrode EL2 that are sequentially stacked. In some embodiments, the organic electroluminescence device 10 of an embodiment may include a capping layer CPL on the second electrode EL2.

The organic electroluminescence device 10 of an embodiment may include an aromatic compound of an embodiment, which will be described in more detail later, in the emission layer EML between the first electrode EL1 and the second electrode EL2.

Figure 2:
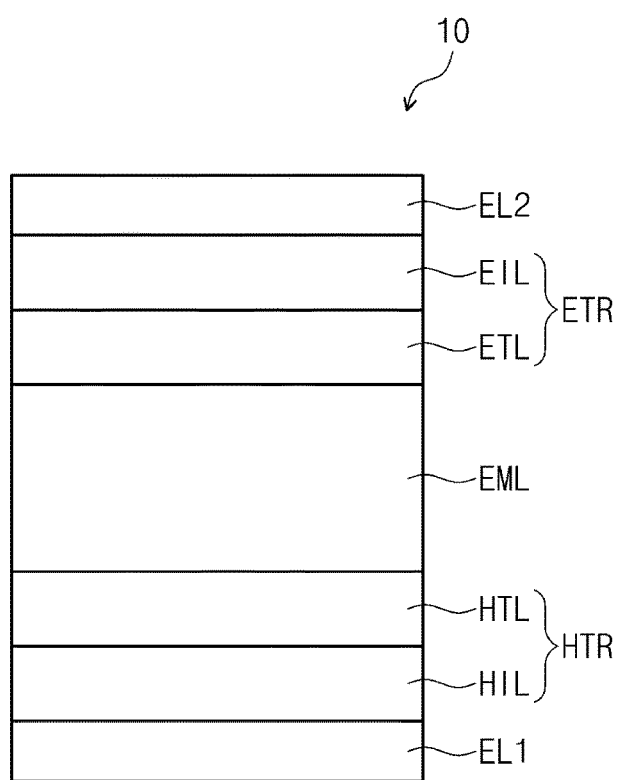
FIG. 2 is a schematic cross-sectional view of an organic electroluminescence device according to an embodiment of the present disclosure.
Figure 3:
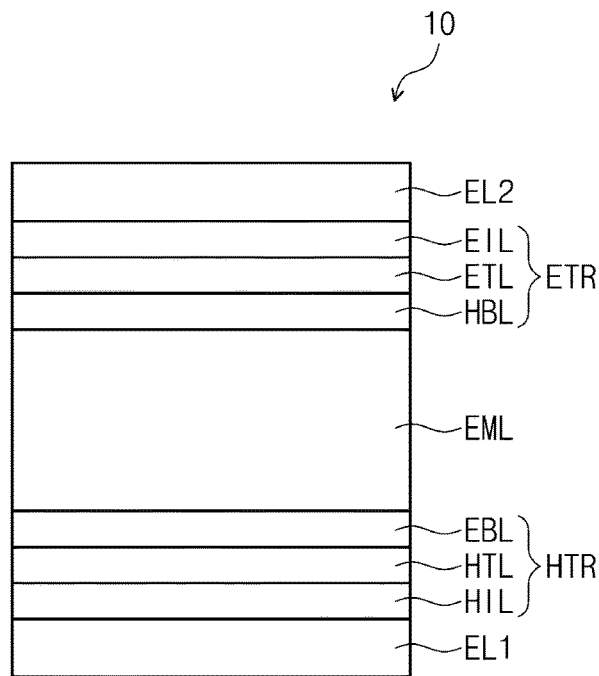
FIG. 3 is a schematic cross-sectional view of an organic electroluminescence device according to an embodiment of the present disclosure.
Figure 4:
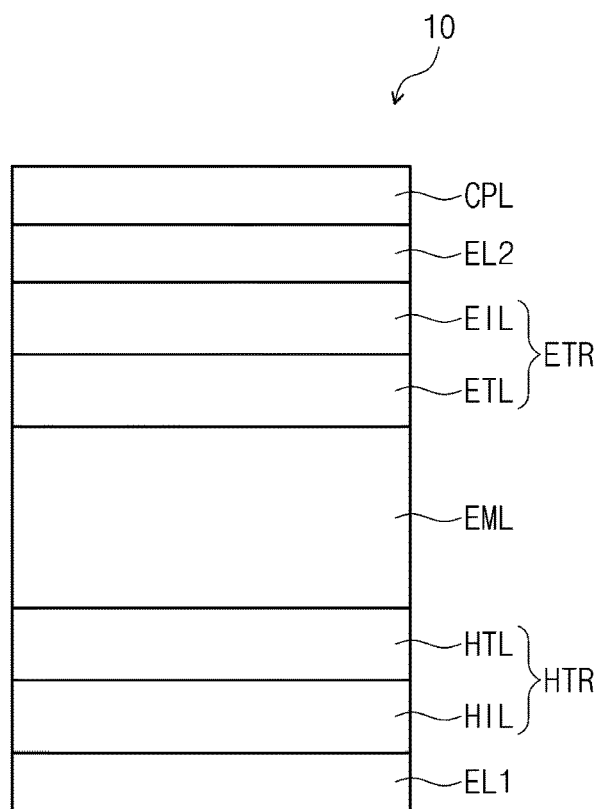
FIG. 4 is a schematic cross-sectional view of an organic electroluminescence device according to an embodiment of the present disclosure.

Compared to FIG. 1, FIG. 2 illustrates a cross-sectional view of an organic electroluminescence device 10 of an embodiment, in which a hole transport region HTR includes a hole injection layer HIL and a hole transport layer HTL, and an electron transport region ETR includes an electron injection layer EIL and an electron transport layer ETL. Compared to FIG. 1, FIG. 3 illustrates a cross-sectional view of an organic electroluminescence device 10 of an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Compared to FIG. 2, FIG. 4 illustrates a cross-sectional view of an organic electroluminescence device 10 of an embodiment including a capping layer CPL on the second electrode EL2.

The first electrode EL1 has a conductivity. The first electrode EL1 may be formed of a metal alloy or any suitable conductive compound. The first electrode EL1 may be an anode. In some embodiments, the first electrode EL1 may be a pixel electrode. The first electrode EL1 may be a transmissive electrode, a transflective electrode, or a reflective electrode. When the first electrode EL1 is the transmissive electrode, the first electrode EL1 may include a transparent metal oxide such as indium tin oxide (ITO), indium zinc oxide (IZO), zinc oxide (ZnO), and/or indium tin zinc oxide (ITZO). When the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some embodiments, the first electrode EL1 may have a multilayer structure including a reflective film or a transflective film, and a transparent conductive film formed of ITO, IZO, ZnO, ITZO, etc. For example, the first electrode EL1 may have a three-layer structure of ITO/Ag/ITO, but is not limited thereto. The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer EBL. The thickness of the hole transport region HTR may be from about 50 Å to about 1,500 Å.

The hole transport region HTR may have a single layer formed of a single material, a single layer formed of a plurality of different materials, or a multilayer structure including a plurality of layers formed of a plurality of different materials.

For example, the hole transport region HTR may have a single layer structure of a hole injection layer HIL or a hole transport layer HTL, and may have a single layer structure formed of a hole injection material and a hole transport material. In some embodiments, the hole transport region HTR may have a single layer structure formed of a plurality of different materials, or a structure in which a hole injection layer HIL/hole transport layer HTL, a hole injection layer HIL/hole transport layer HTL/hole buffer layer, a hole injection layer HIL/hole buffer layer, a hole transport layer HTL/hole buffer layer, or a hole injection layer HIL/hole transport layer HTL/electron blocking layer EBL are stacked in order from the first electrode EL1, but an embodiment is not limited thereto.

The hole transport region HTR may be formed using one or more suitable methods such as a vacuum deposition method, a spin coating method, a cast method, a Langmuir-Blodgett (LB) method, an inkjet printing method, a laser printing method, and/or a laser induced thermal imaging (LITI) method.

The hole injection layer HIL may include, for example, a phthalocyanine compound (such as copper phthalocyanine); N,N'-diphenyl-N,N'-bis-[4-(phenyl-m-tolyl-amino)-phenyl]-biphenyl-4,4'-diamine (DNTPD), 4,4',4'-[tris(3-methylphenyl)phenylamino]triphenylamine] (m-MTDATA), 4,4', 4'-tris(N,N-diphenylamino)triphenylamine (TDATA), 4,4', 4'-tris{N-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPD), triphenylamine-containing polyetherketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL, for example, may further include carbazole derivatives (such as N-phenyl carbazole and/or polyvinyl carbazole), fluorene derivatives, N,N'-bis (3-methylphenyl)-N,N'-diphenyl-[1,1-biphenyl]-4,4'-diamine (TPD), triphenylamine derivatives (such as 4,4',4'-tris(N-carbazolyl)triphenylamine (TCTA)), N,N'-di (naphtalen-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 50 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL each independently satisfy the above-described ranges, satisfactory (or suitable) hole transport properties may be achieved without a substantial increase in driving voltage.

The hole transport region HTR may further include, in addition to the above-described materials, a charge generating material to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, but is not limited thereto. Non-limiting examples of the p-dopant may include quinone derivatives (such as tetracyanoquinodimethane (TCNQ) and/or 2,3,5,6-tetrafluoro-7,7,8,8-tetracyanoquinodimethane (F4-TCNQ)), metal oxides (such as tungsten oxide and/or molybdenum oxide), etc.

As described above, the hole transport region HTR may further include at least one of a hole buffer layer or an electron blocking layer EBL in addition to the hole injection layer HIL and the hole transport layer HTL. The hole buffer layer may compensate a resonance distance according to the wavelength of light emitted from an emission layer EML and may increase light emission efficiency. Materials which may be included in the hole transport region HTR may be used as materials included in the hole buffer layer. The electron blocking layer EBL is a layer that serves to prevent or reduce electrons from being injected from the electron transport region ETR to the hole transport region HTR.

The emission layer EML is provided on the hole transport region HTR. The thickness of the emission layer EML may be, for example, from about 100 Å to about 1000 Å or from about 100 Å to about 400 Å. The emission layer EML may have a single layer formed of a single material, a single layer formed of a plurality of different materials, or a multilayer structure having a plurality of layers formed of a plurality of different materials.

The emission layer EML of the organic electroluminescence device 10 of an embodiment may include an aromatic compound of an embodiment.

The aromatic compound of an embodiment may include a benzene ring, two unsubstituted carbazole groups directly bonded to a benzene ring, two substituted carbazole groups directly bonded to a benzene ring and substituted with a nitrogen-containing ring (cyclic) group, and a substituent which is directly bonded to the benzene ring and is a cyano group, a fluorine, or a C1-C10 alkyl group substituted with a fluorine.

According to an embodiment, the nitrogen-containing ring group may be an electron withdrawing group including at least one nitrogen atom in the benzene ring. For example, the nitrogen-containing ring group may be a pyridine group or a pyrimidine group. However, the embodiment is not limited thereto.

According to an embodiment, the two substituted carbazole groups may be arranged symmetrically with respect to the directly bonded substituent. In some embodiments, the two unsubstituted carbazole groups may be arranged symmetrically with respect to the directly bonded substituent.

Two unsubstituted carbazole groups included in the aromatic compound of an embodiment may be respectively bonded to the benzene ring at ortho-positions relative to the directly bonded substituent. The two substituted carbazole groups may be respectively bonded to the benzene ring at meta-positions relative to the directly bonded substituent.

In the description, the term "substituted or unsubstituted" may indicate a group that is unsubstituted or that is substituted with at least one substituent selected from the group consisting of a deuterium atom, a halogen atom, a cyano group, a nitro group, an amino group, a silyl group, oxy group, thio group, sulfinyl group, sulfonyl group, carbonyl group, a boron group, a phosphine oxide group, a phosphine sulfide group, an alkyl group, an alkenyl group, an alkoxy group, a hydrocarbon ring group, an aryl group, and a heterocyclic group. In some embodiments, each of the substituents exemplified above may itself be substituted or unsubstituted. For example, a biphenyl group may be interpreted as an aryl group or a phenyl group substituted with a phenyl group.

In the description, examples of the halogen atom may include a fluorine atom, a chlorine atom, a bromine atom, and an iodine atom.

In the description, the alkyl group may be a linear, branched or cyclic alkyl group. The number of carbon atoms in the alkyl group is 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., but are not limited thereto.

In the description, an aryl group may refer to a functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., but are not limited thereto.

In the description, the heteroaryl group may include at least one nitrogen atom as a ring-forming hetero atom. The number of ring-forming carbon atoms in the heteroaryl group may be 2 to 30, 2 to 20, or 2 to 10.

Meanwhile, in the description, "—·" refers to a position to be connected (e.g., a binding site).

The aromatic compound of an embodiment included in the organic electroluminescence device 10 of an embodiment may be represented by Formula 1 below.

Formula 1

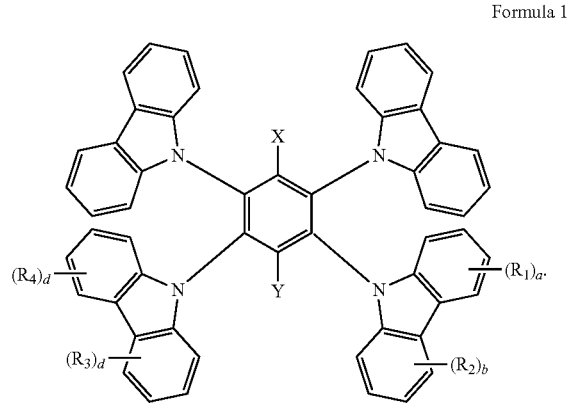

In Formula 1, X may be a cyano group, a fluorine, or a C1-C10 alkyl group substituted with a fluorine.

In Formula 1, Y may be a hydrogen atom, a deuterium atom, a halogen atom, a cyano group, an unsubstituted heteroaryl group having 3 to 20 ring-forming carbon atoms and including a nitrogen atom, a substituted or unsubstituted aryl group having 6 to 30 ring-forming carbon atoms, or a substituted or unsubstituted alkyl group having 1 to 20 carbon atoms.

For example, Y may be an unsubstituted phenyl group, an unsubstituted pyridine group, an unsubstituted carbazole group, or an unsubstituted alkyl group having 1 to 4 carbon atoms. However, the embodiment is not limited thereto.

a to d may be each independently an integer of 1 to 4. When a to d are each independently an integer of 2 or more, a plurality of $R_1$ to $R_4$ may be the same or different from each other. For example, when a is an integer of 2 or more, the plurality of $R_1$ may be all the same or different from each other.

In Formula 1, left and right portions of the compound may be laterally symmetric with respect to X and Y. For example, when a to d are all 1, and $R_1$ to $R_4$ are all the same, left and right moieties may be laterally symmetric with respect to X and Y. However, the embodiment is not limited thereto.

In Formula 1, at least one of $R_1$ to $R_4$ may be represented by Formula 2 below and the others may be a hydrogen atom, a deuterium atom, or a substituted or unsubstituted alkyl group having 1 to 4 carbon atoms.

Formula 2

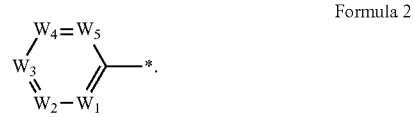

In Formula 2, at least one of $W_1$ to $W_5$ may be a nitrogen atom and the others may be $CR_5$. $R_5$ may be a hydrogen atom, a deuterium atom, or a substituted or unsubstituted alkyl group having 1 to 4 carbon atoms.

The aromatic compound of an embodiment represented by Formula 1 may include two unsubstituted carbazole groups and two substituted carbazole groups (substituted with a nitrogen-containing ring group). Carbazole groups substituted with $R_1$ to $R_4$ in Formula 1 may be the two substituted carbazole groups and the other carbazole groups may be the two unsubstituted carbazole groups. In some embodiments, the nitrogen-containing ring group substituted at (on) the carbazole group may be represented by Formula 2.

In the aromatic compound of an embodiment, a substituent (which is a cyano group, a fluorine, or a C1-C10 alkyl group substituted with a fluorine) may be represented by X in Formula 1.

Meanwhile, Formula 2 may be represented by Formula 2-1 or Formula 2-2.

Formula 2-1

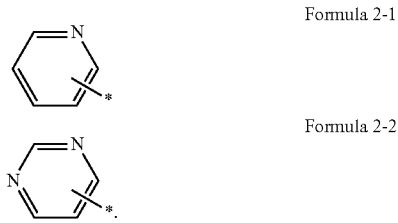

Formula 2-2

Formula 2-1 shows a case of an unsubstituted pyridine group and Formula 2-2 shows a case of an unsubstituted pyrimidine group.

Formula 1 may be represented by Formula 3 below.

Formula 3

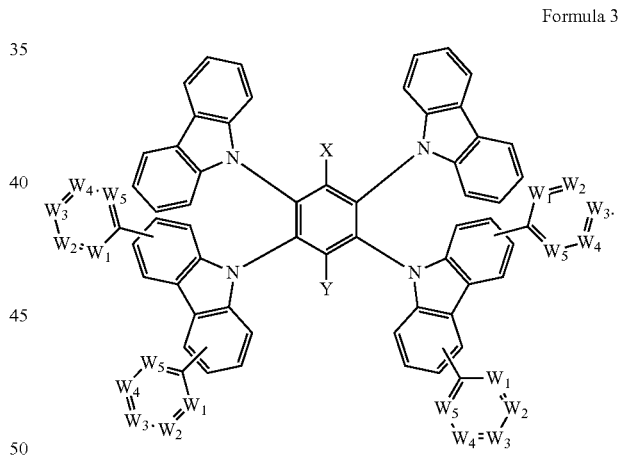

Formula 3 shows a case where a to d are all 1.

X, Y, and $W_1$ to $W_5$ in Formula 3 may be the same as those described in Formulae 1 and 2 above.

The aromatic compound of an embodiment may include at least four carbazole groups, which are directly bonded to the benzene ring and in which two of the four carbazole groups are unsubstituted carbazole groups, and the other two are substituted carbazole groups. The two substituted carbazole groups may be substituted with a nitrogen-containing ring group. The aromatic compound of an embodiment may be used as an emission material that emits deep blue light having an emission center wavelength (λmax) in a wavelength region of about 470 nm or less. For example, the aromatic compound of an embodiment may be an emission material having an emission center wavelength in a wavelength region of about 430 nm to about 490 nm.

The aromatic compound of an embodiment may be any one of the compounds represented by Compound Group 1 below. The organic electroluminescence device 10 of an embodiment may include at least one aromatic compound of the compounds represented by Compound Group 1 in the emission layer EML.
Compound Group 1
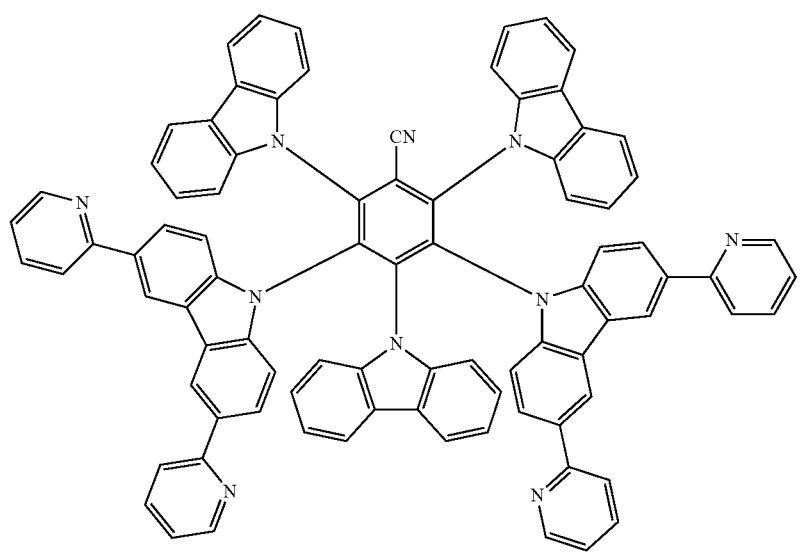
1
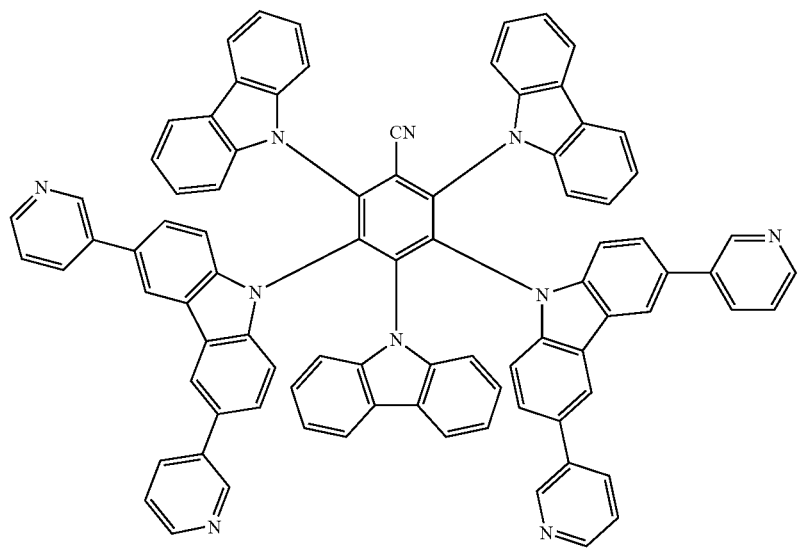
2

-continued
3
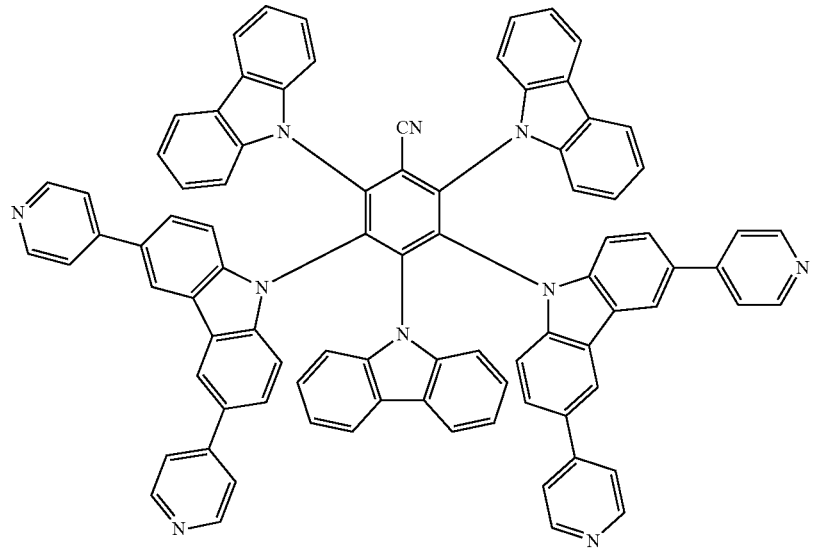
4
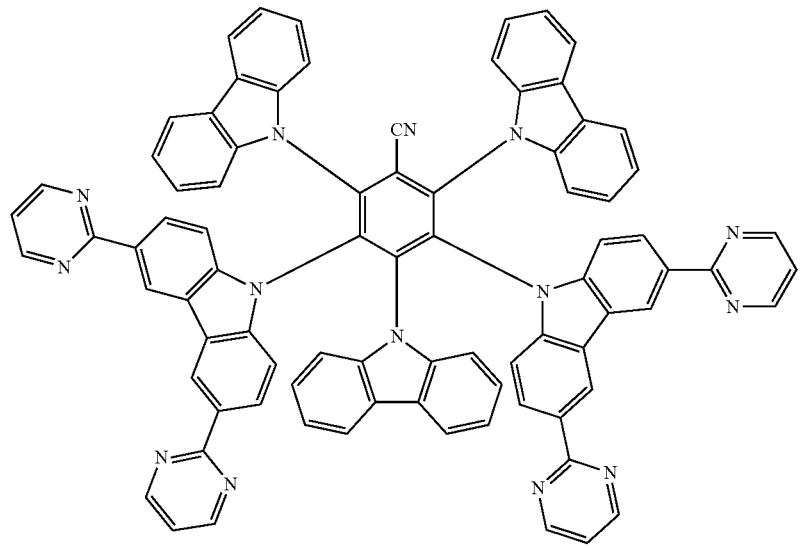
5
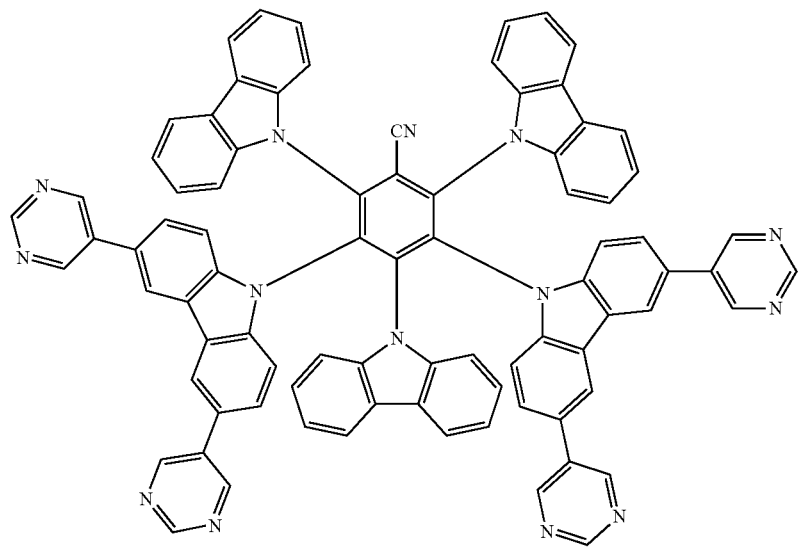

-continued
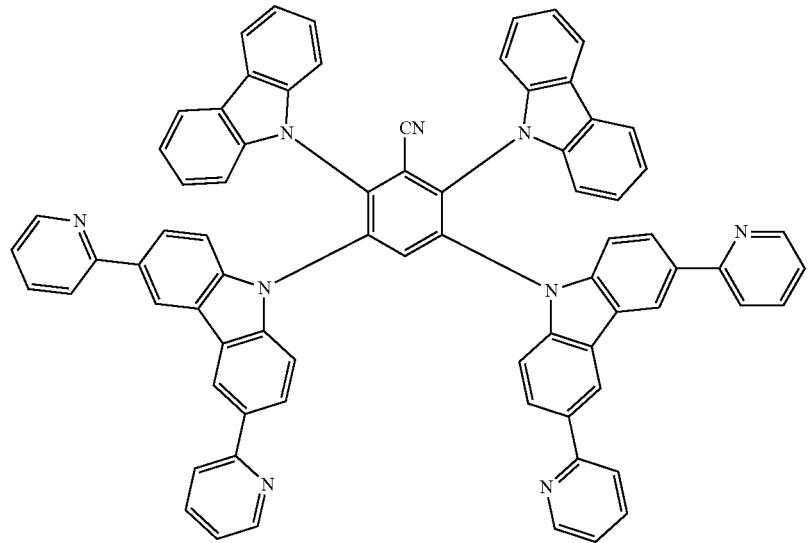
6
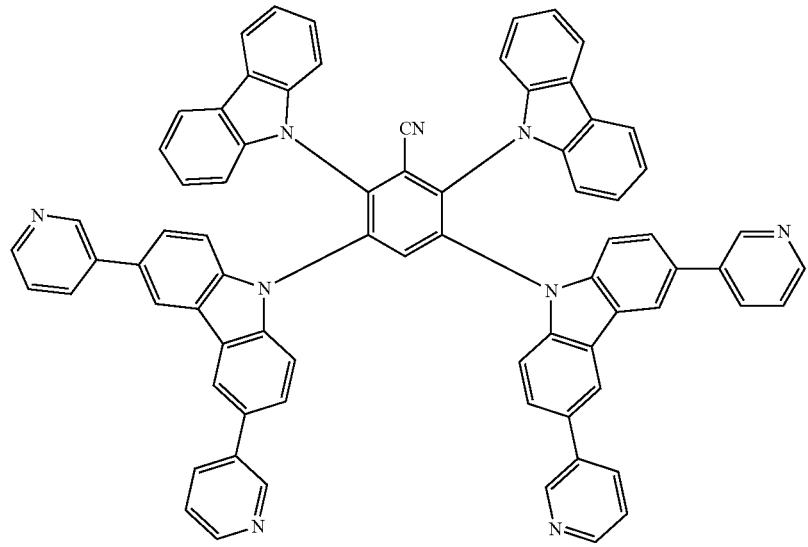
7
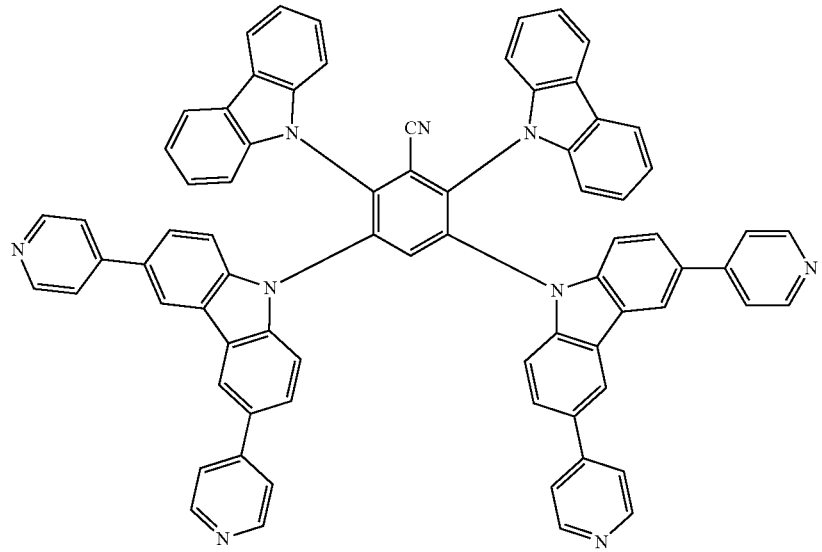
8

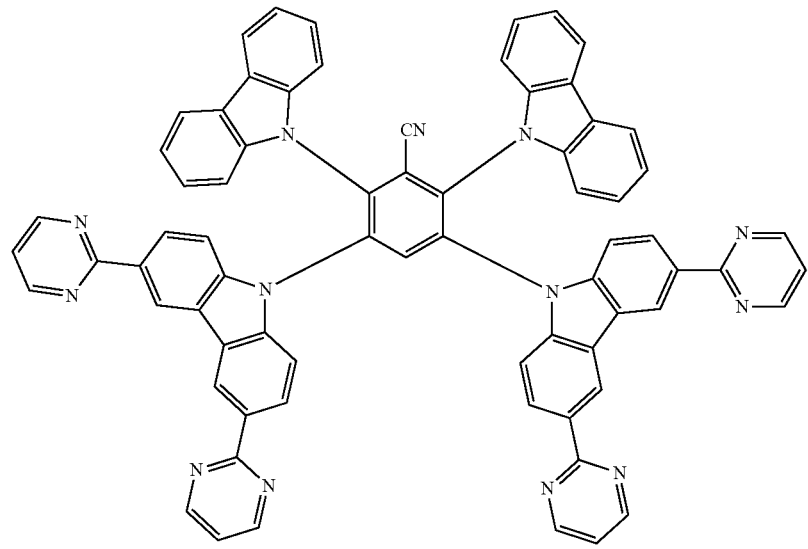
9
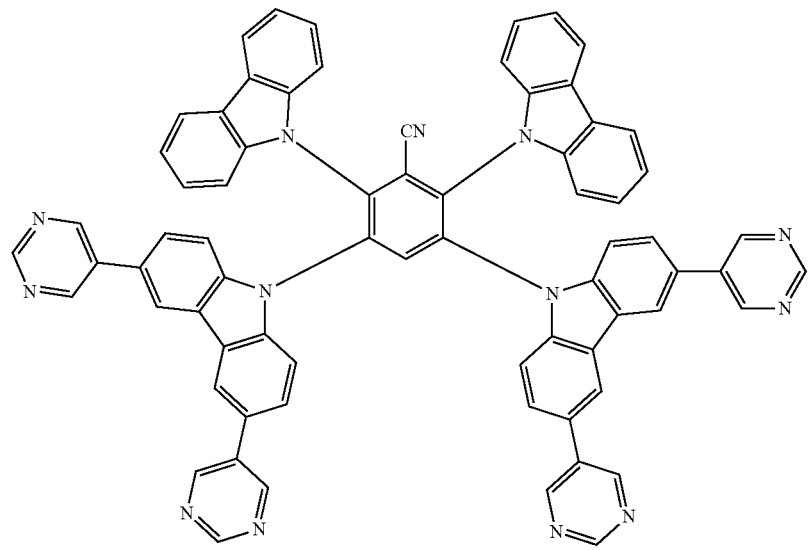
10
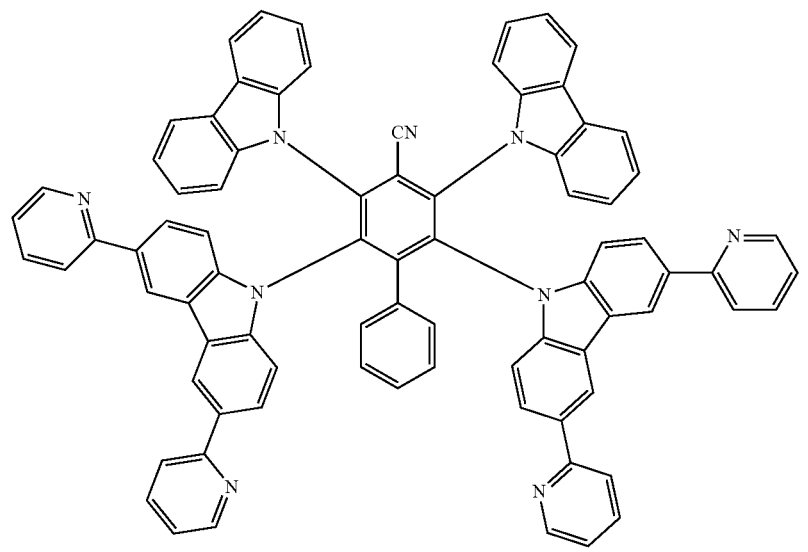
11

-continued
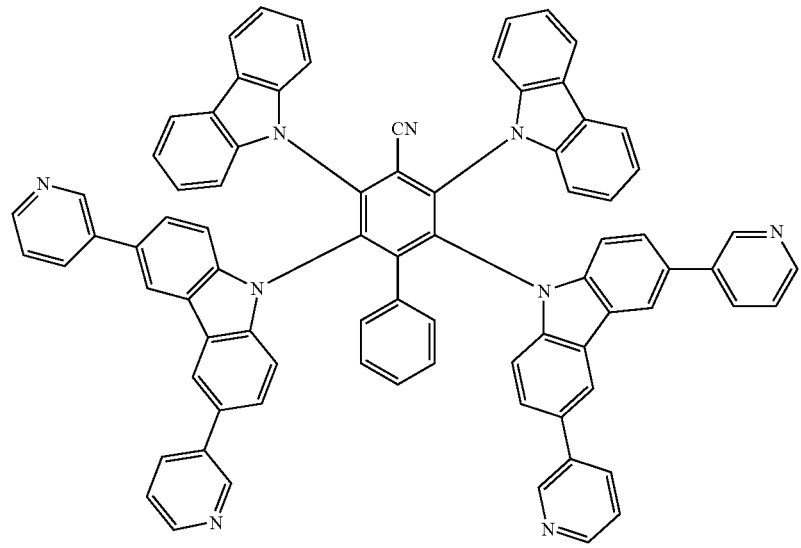
12
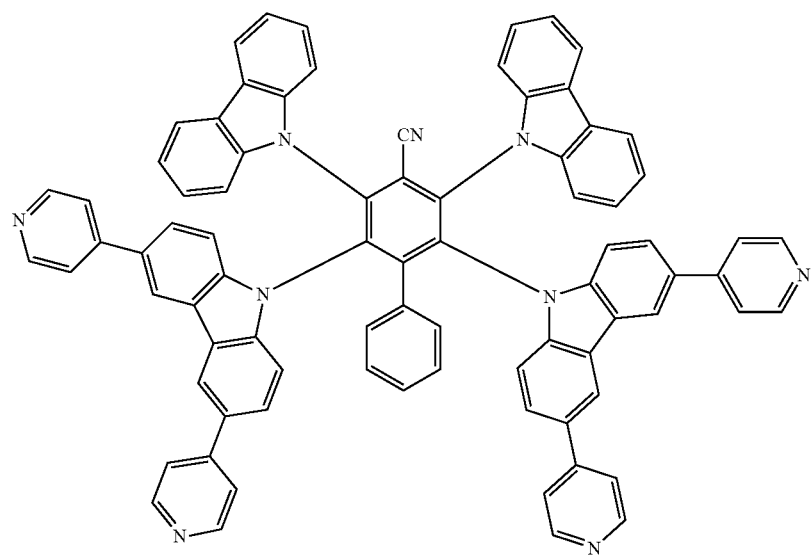
13
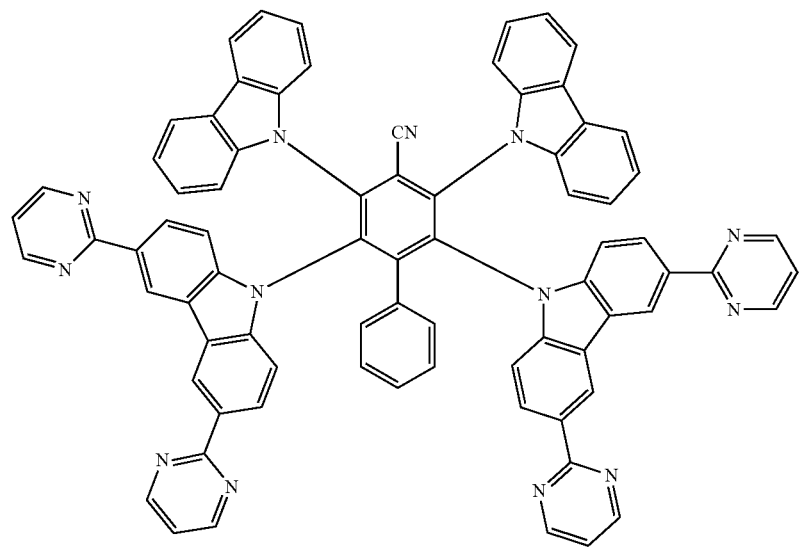
14

15
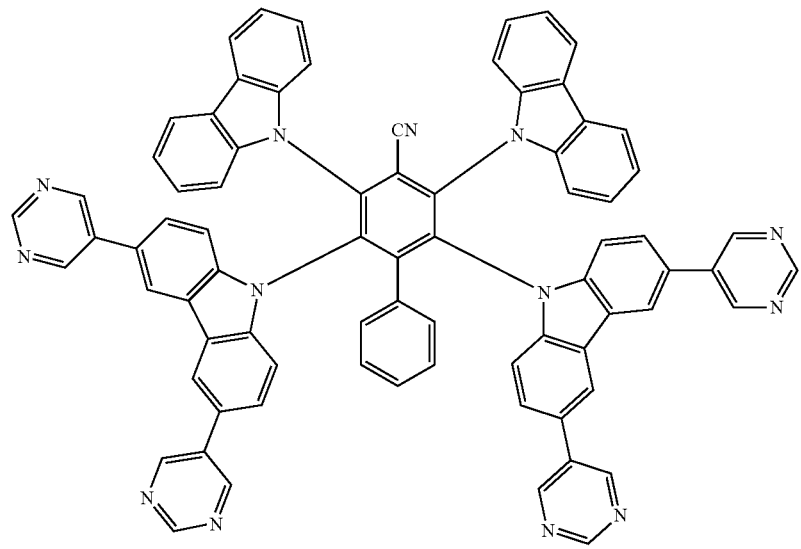
16
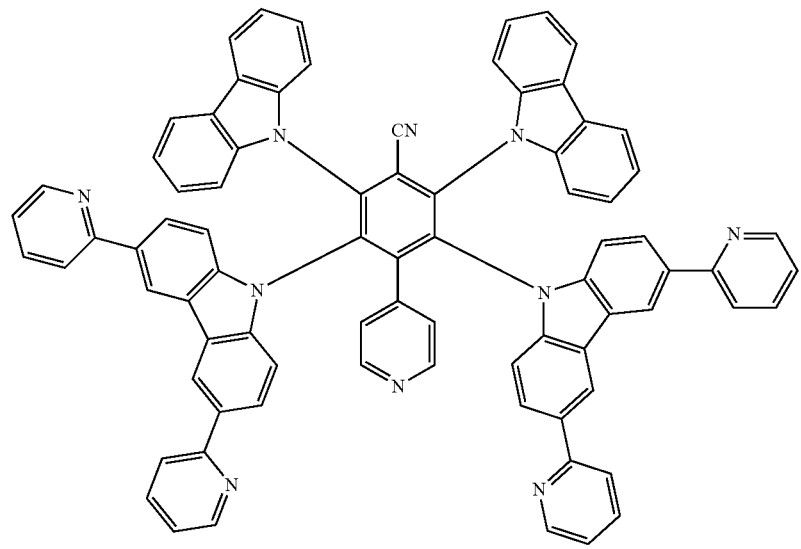
17
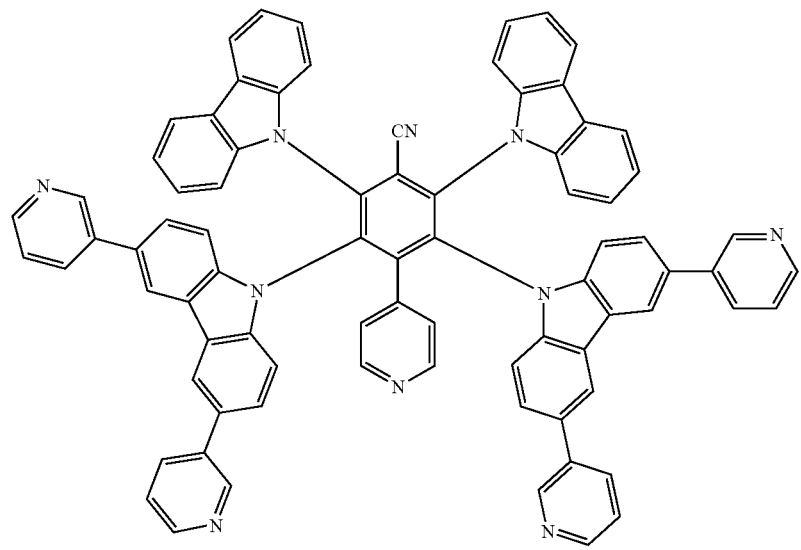

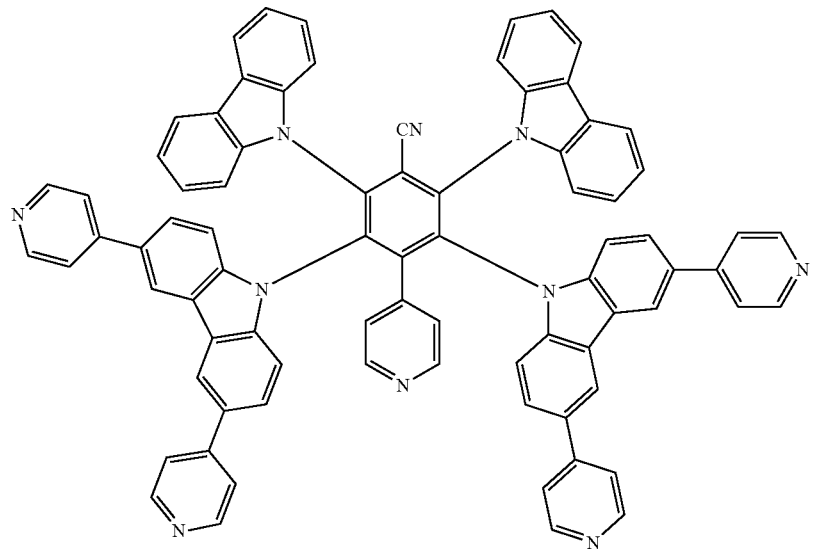
18
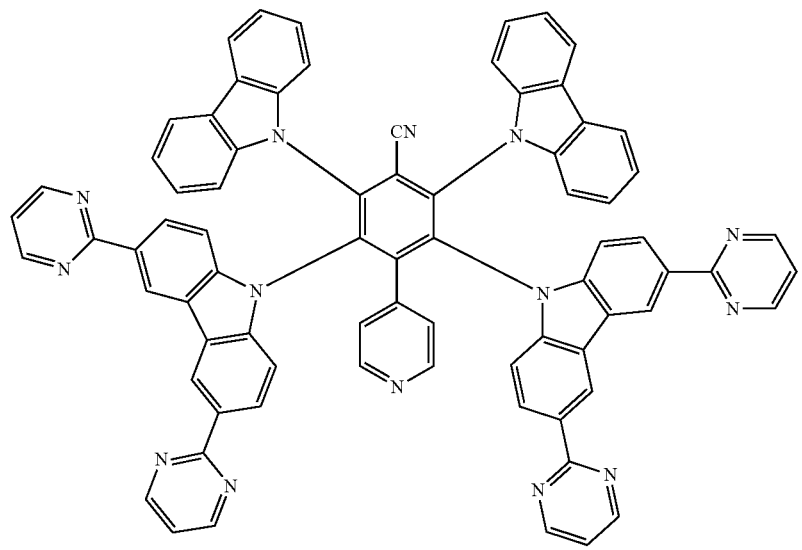
19
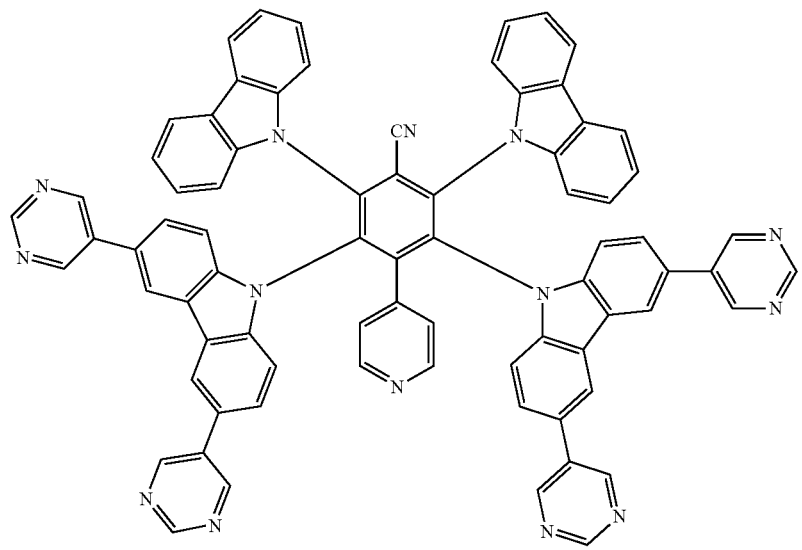
20

-continued
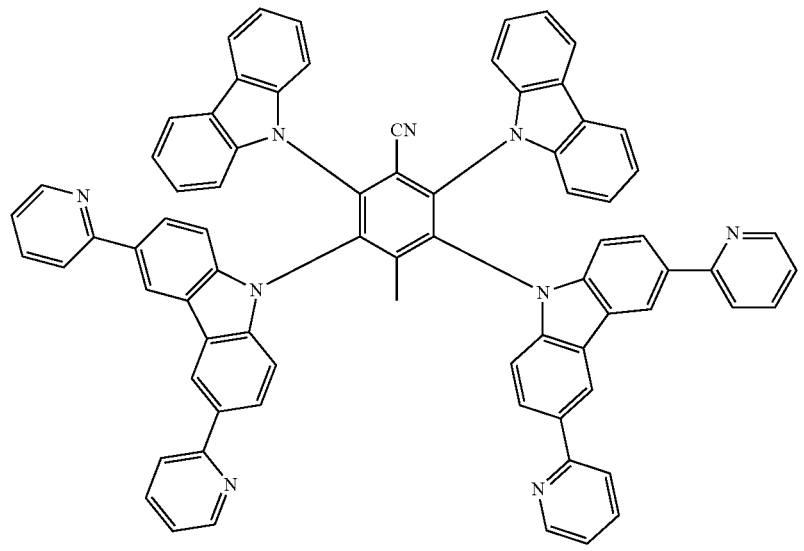
21
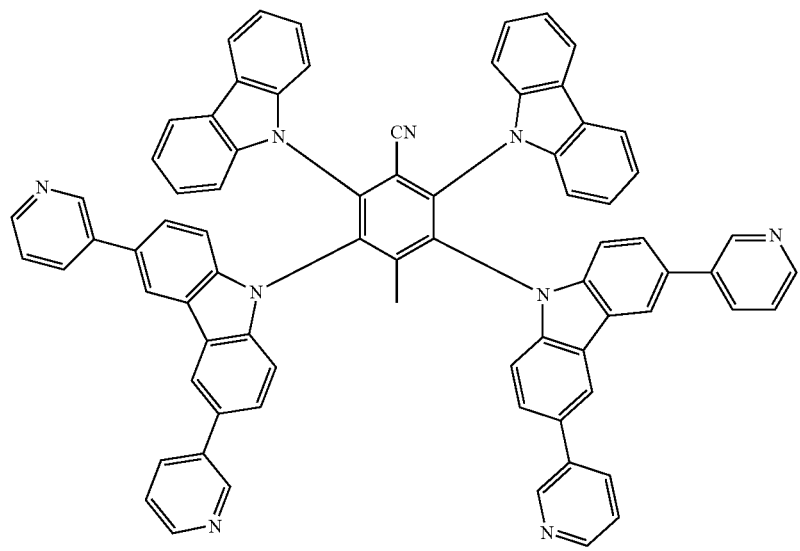
22
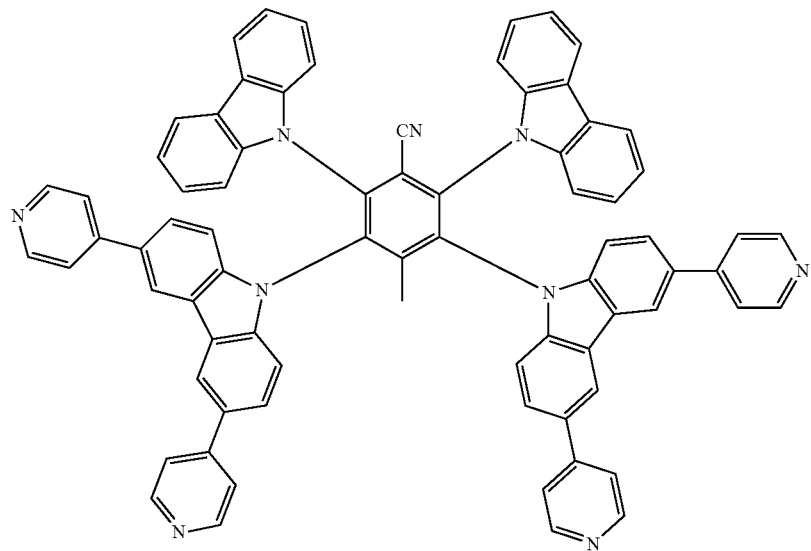
23

-continued
24
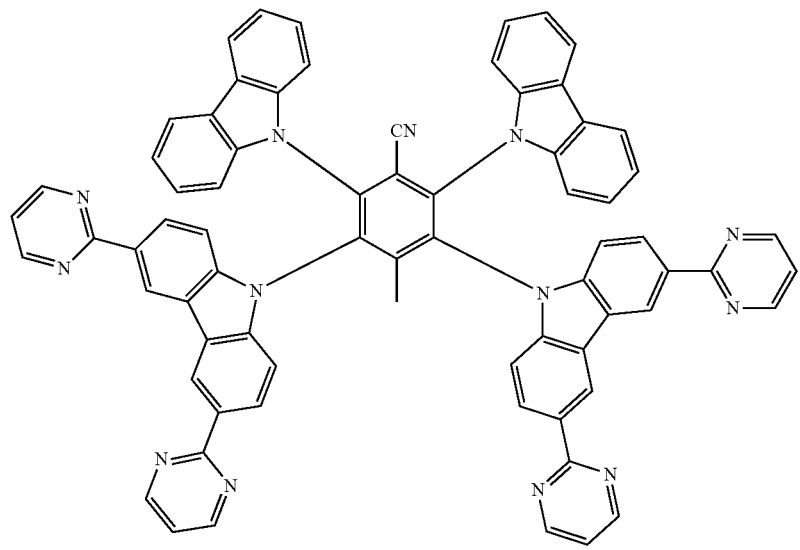
25
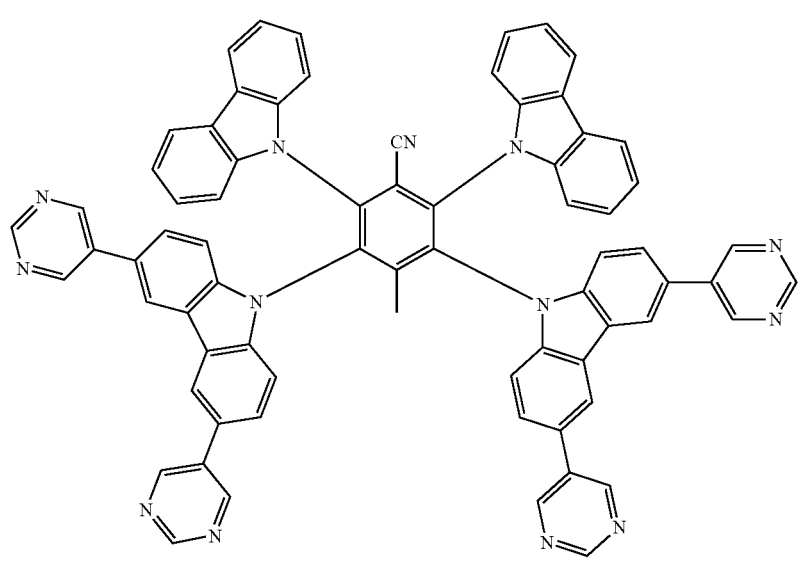
26
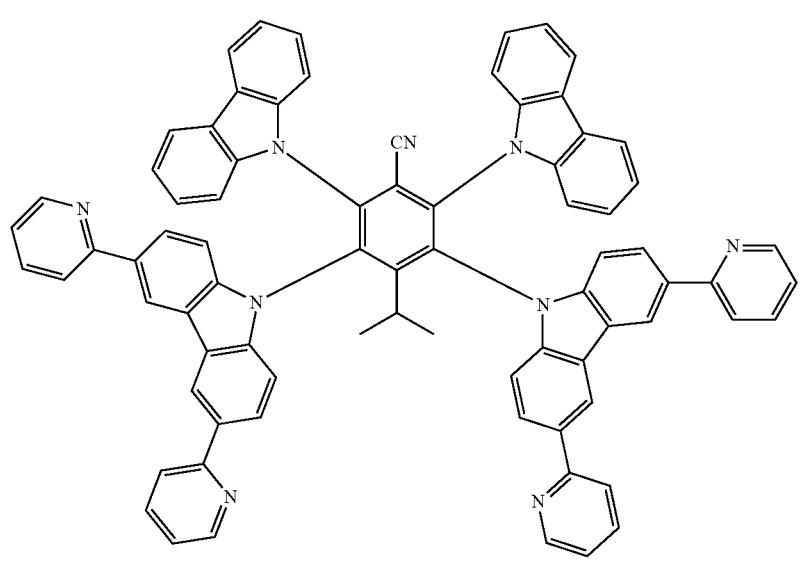

-continued
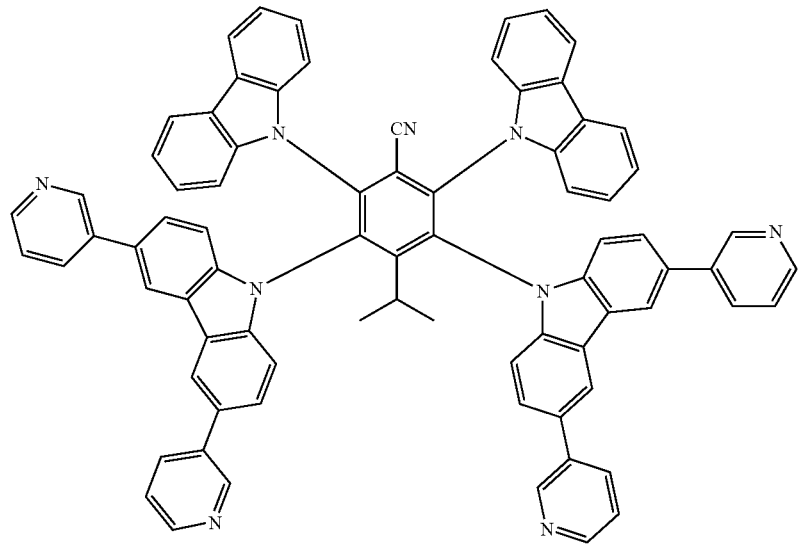
27
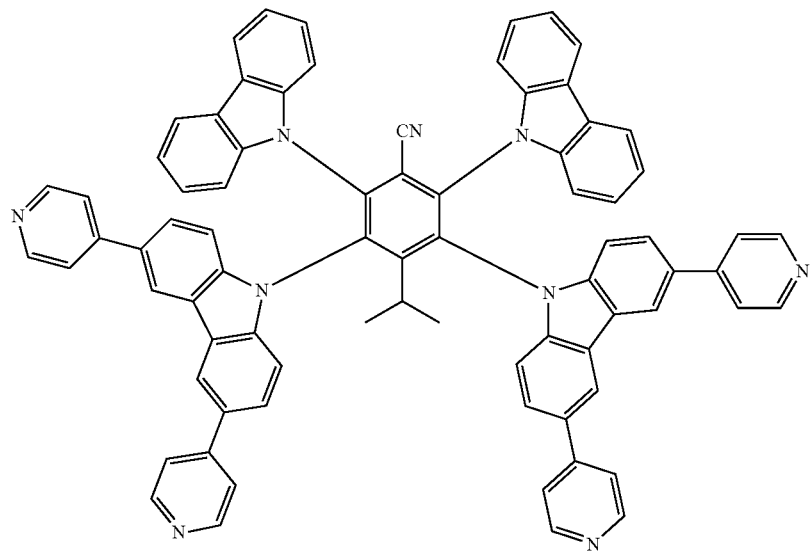
28
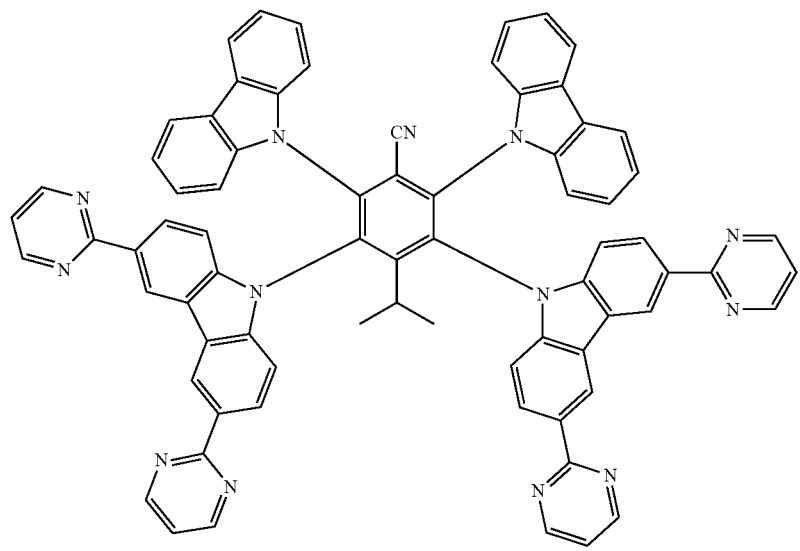
29

-continued
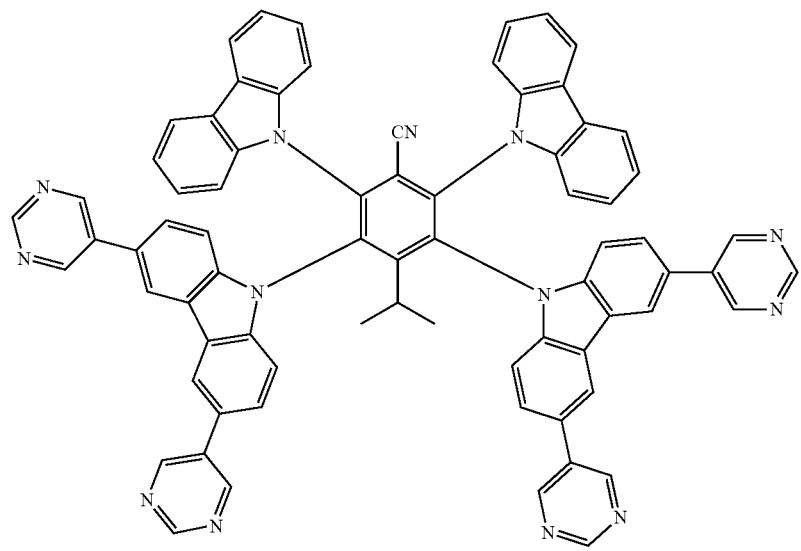
30
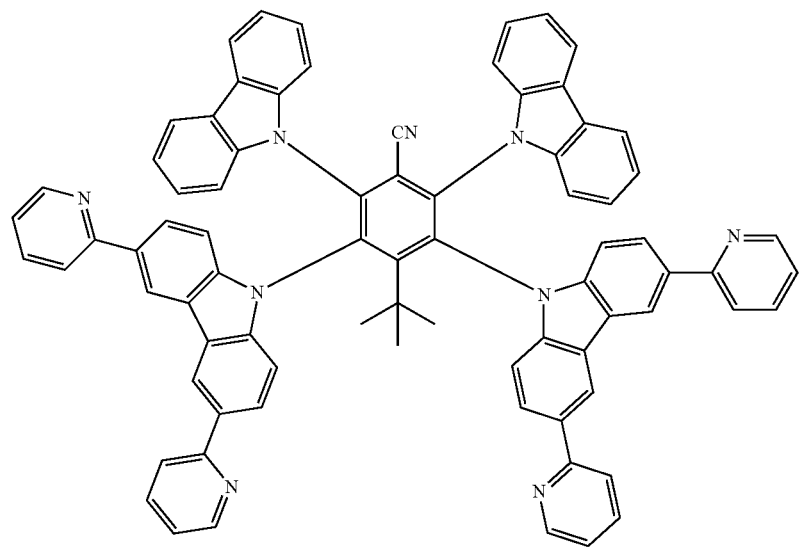
31
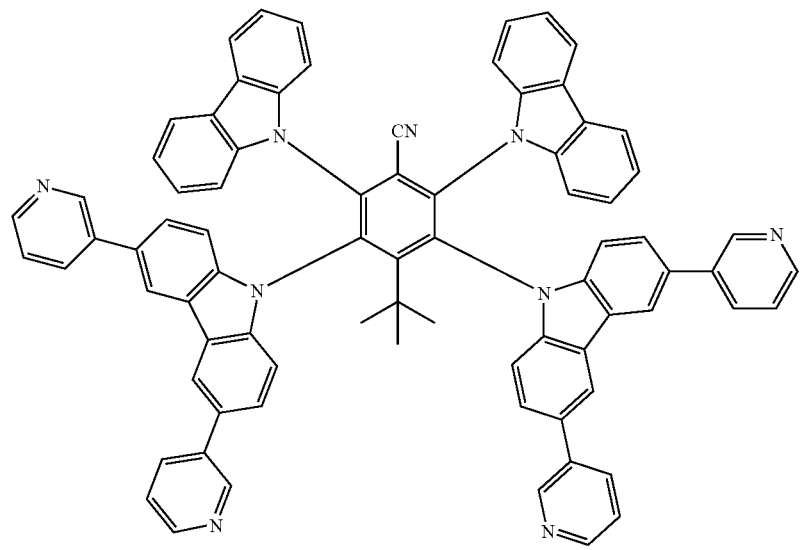
32

33
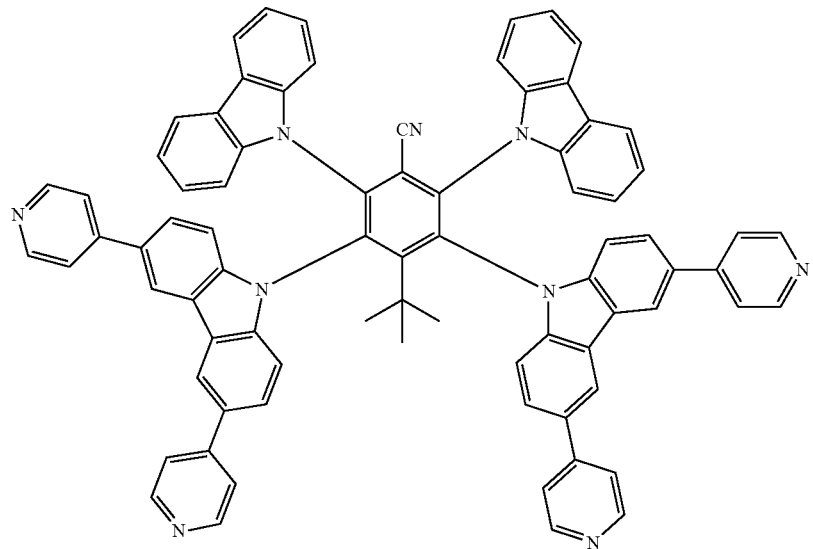
33
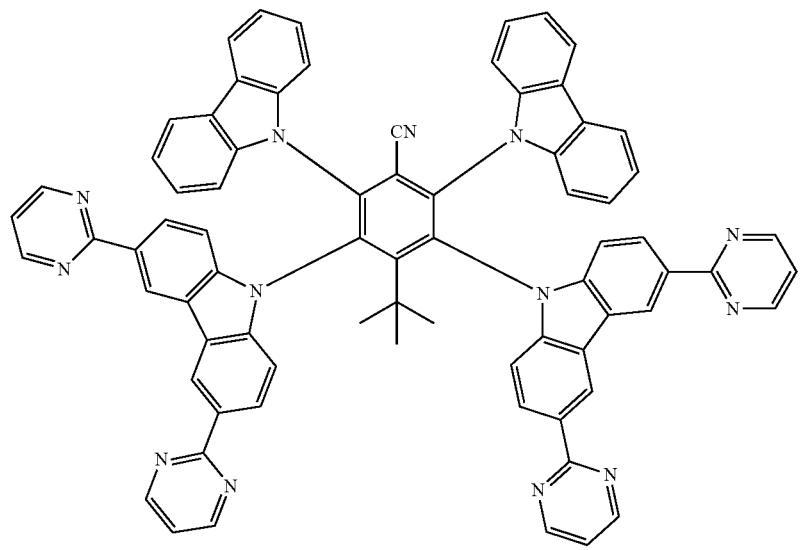
34
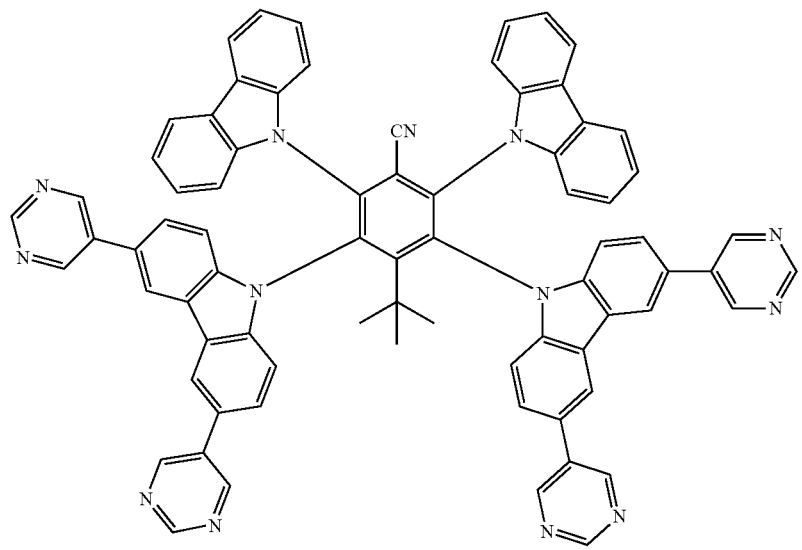
35

-continued
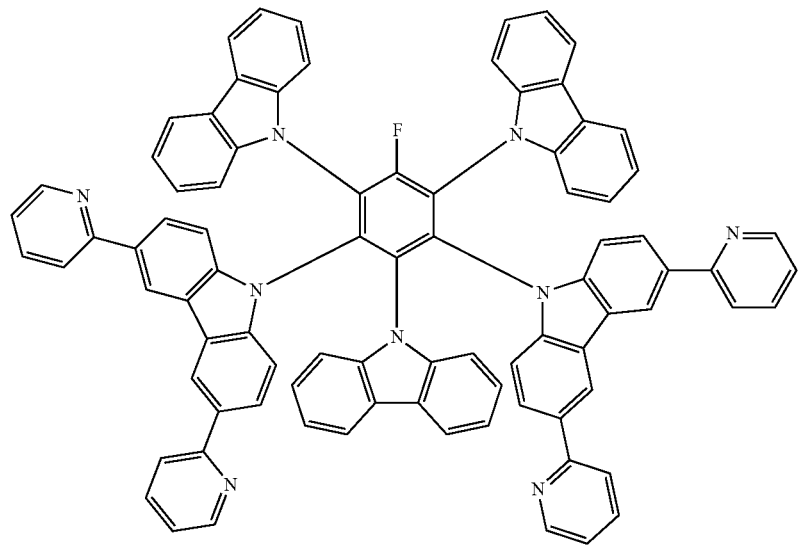
36
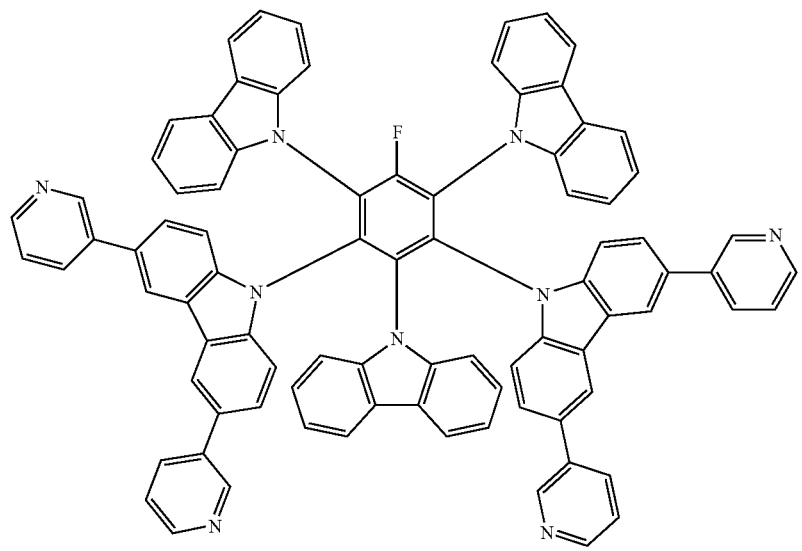
37
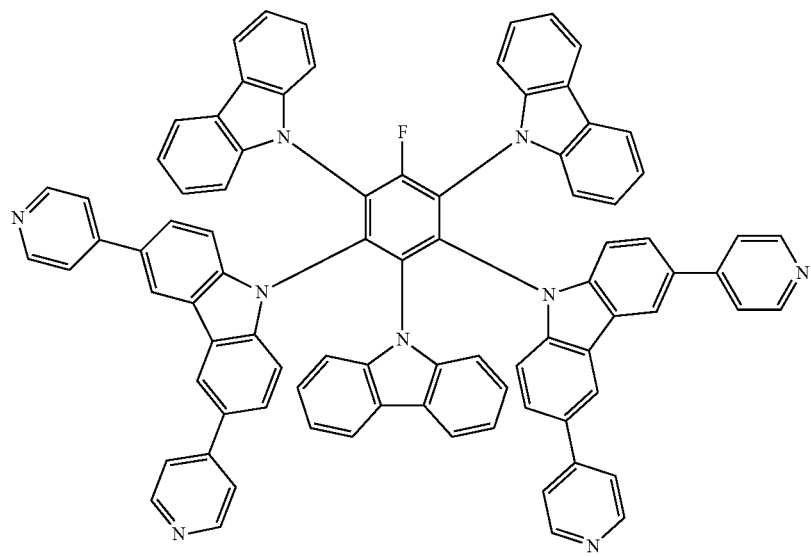
38

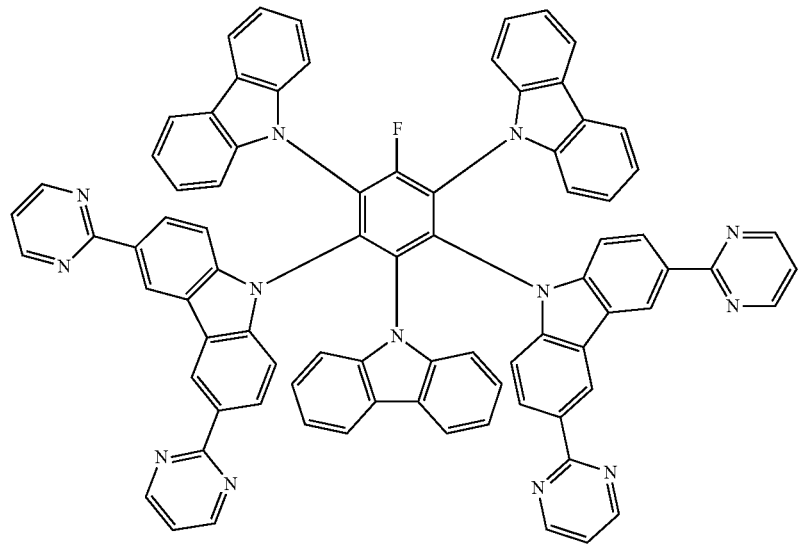
39
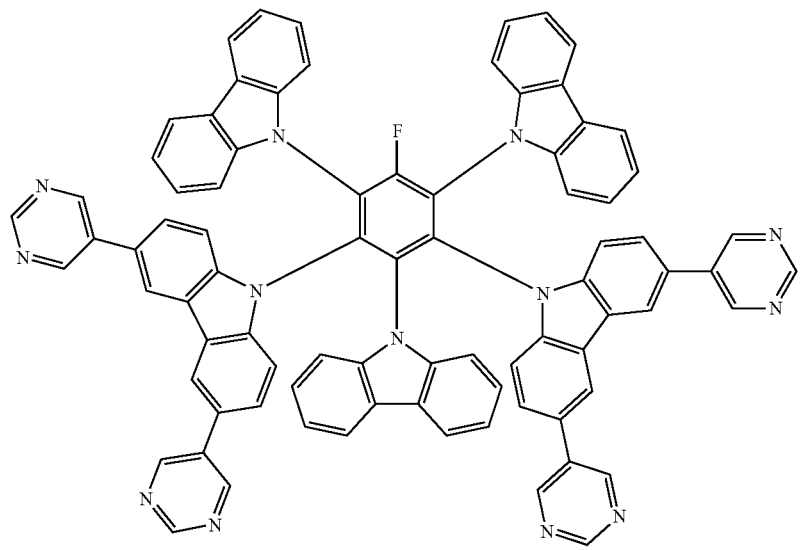
40
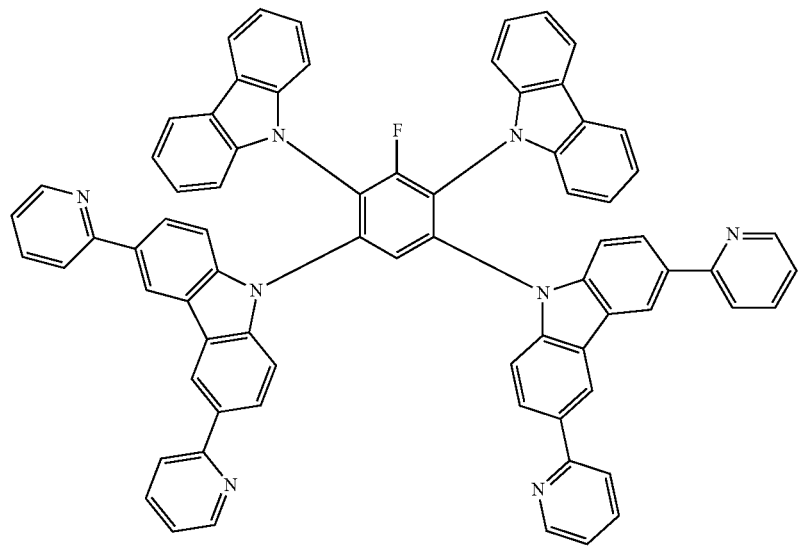
41

42
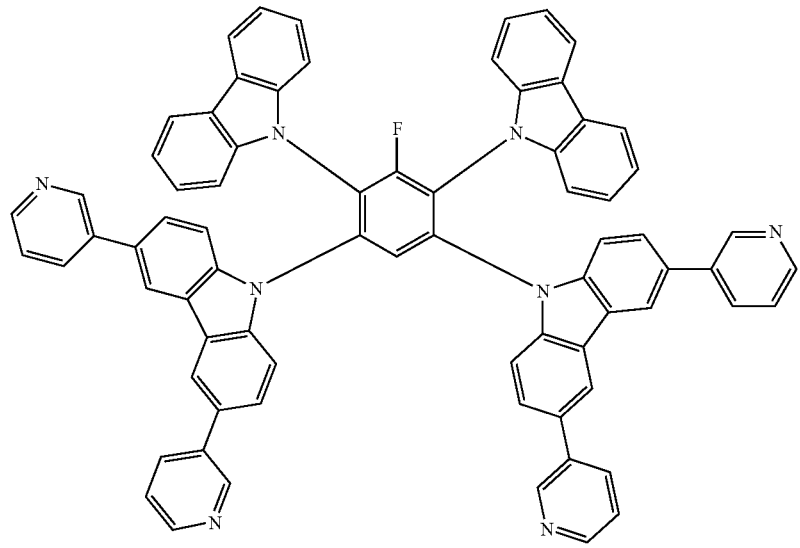
43
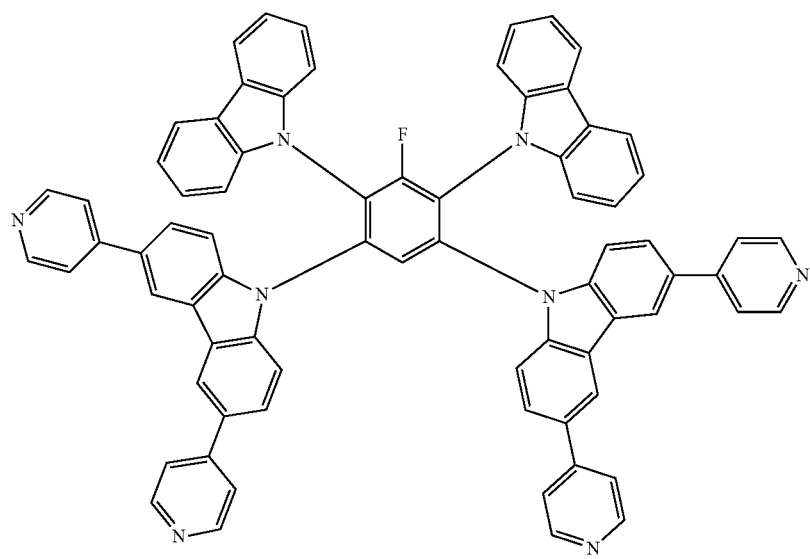
44
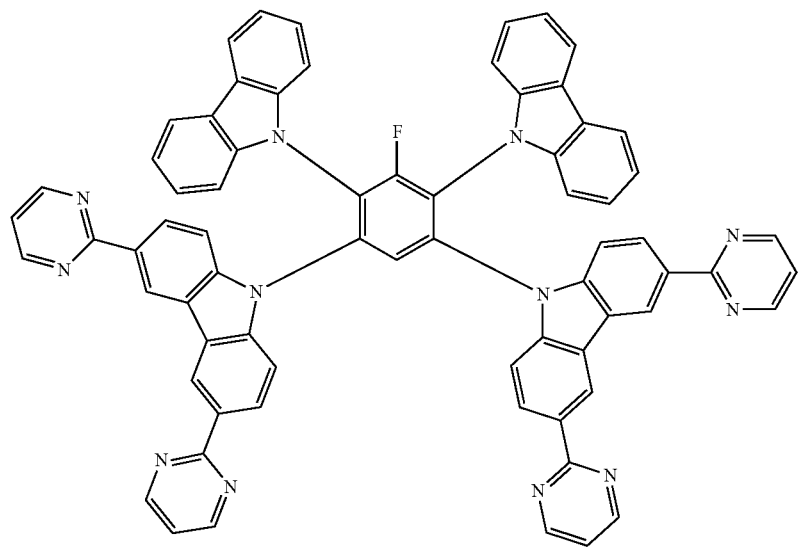

45
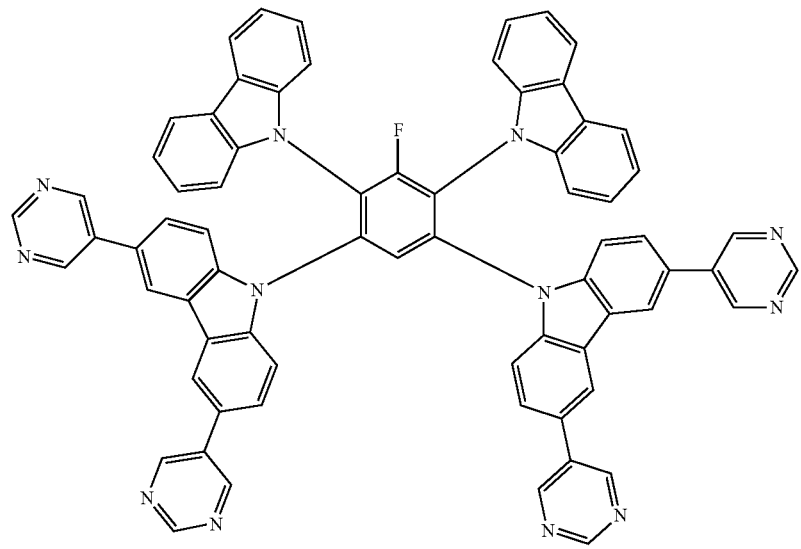
46
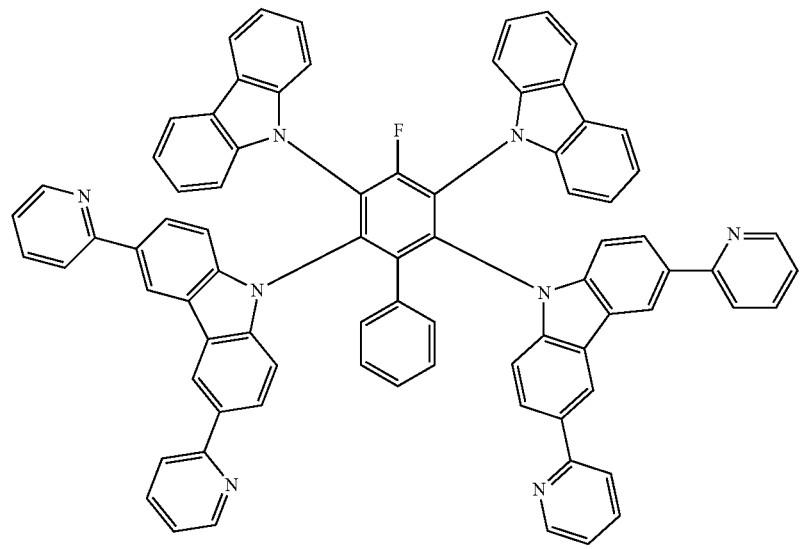
47
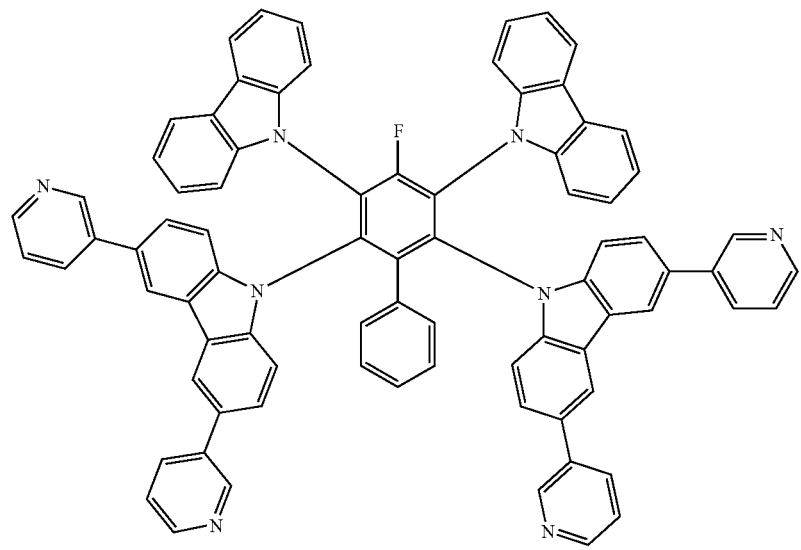

-continued
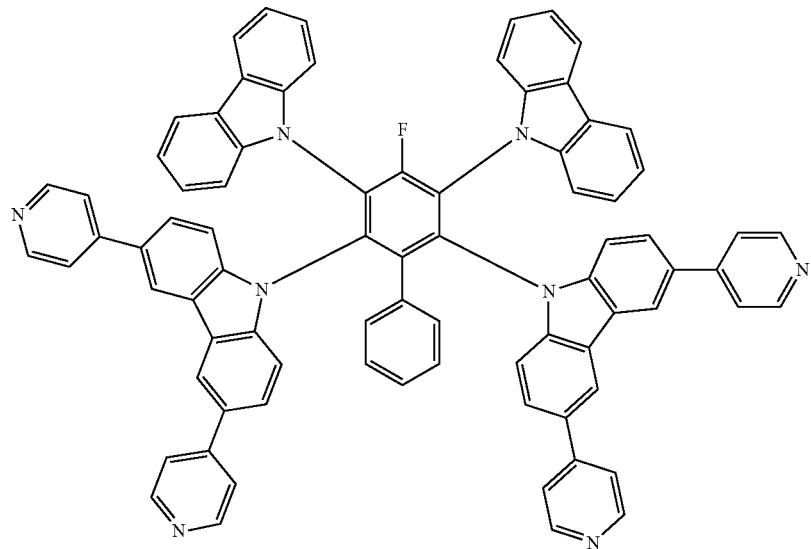
48
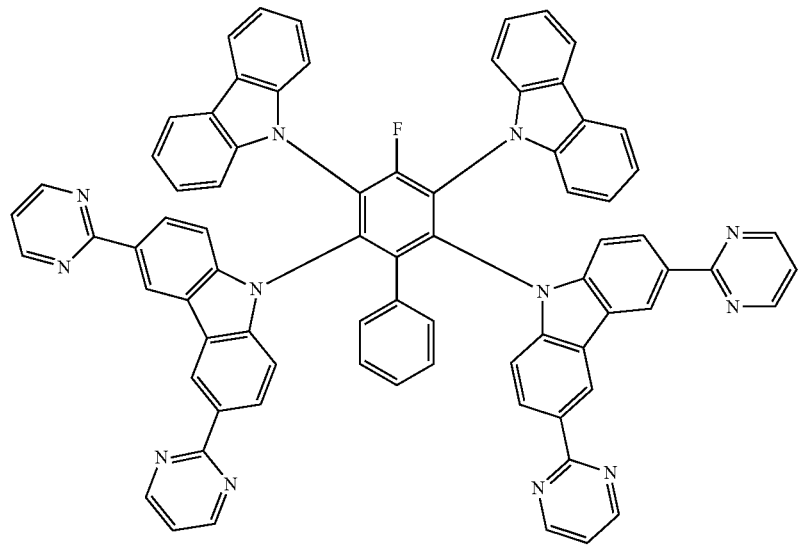
49
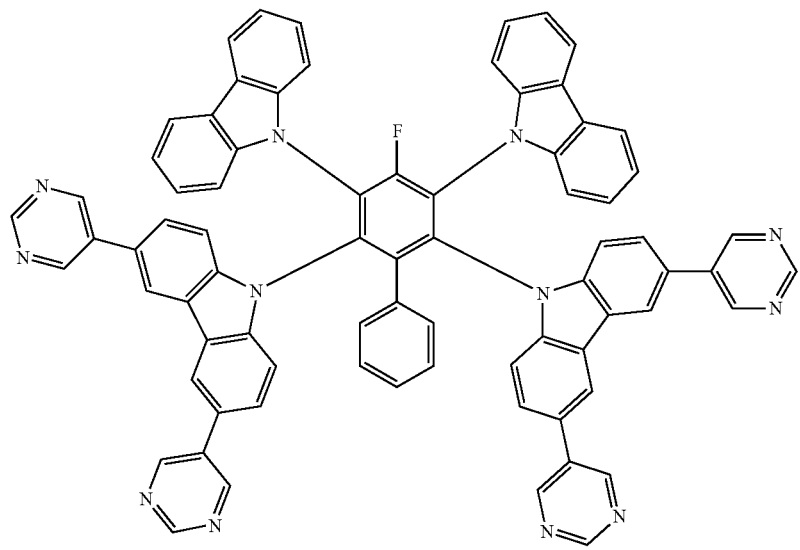
50

-continued
51
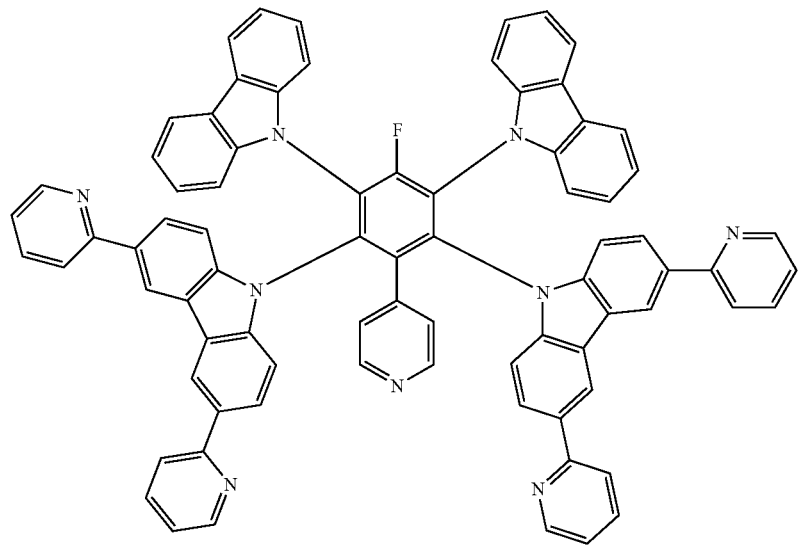
52
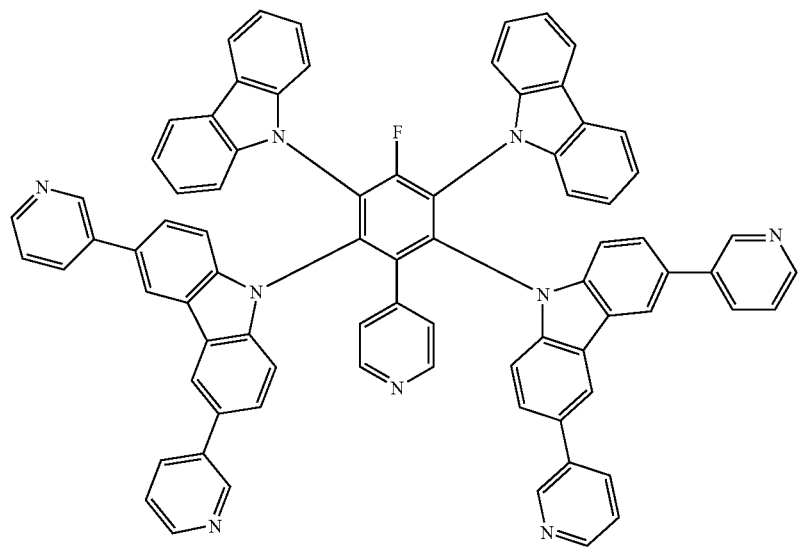
53
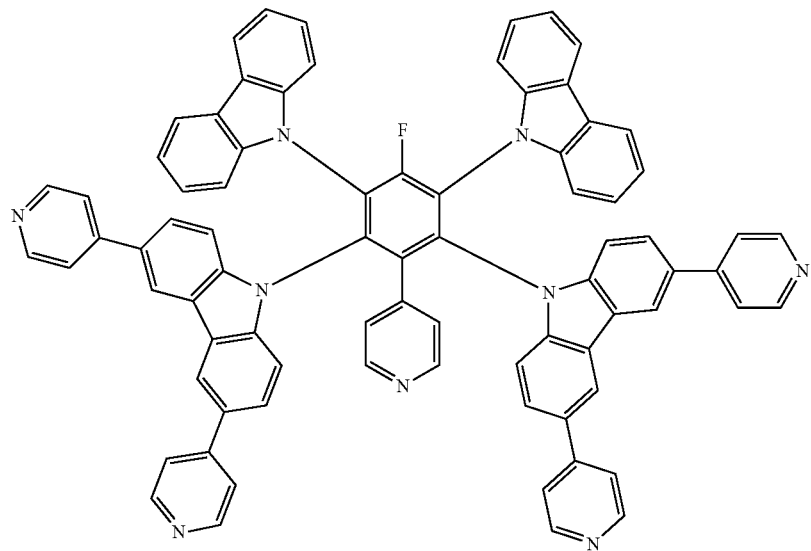

-continued
54
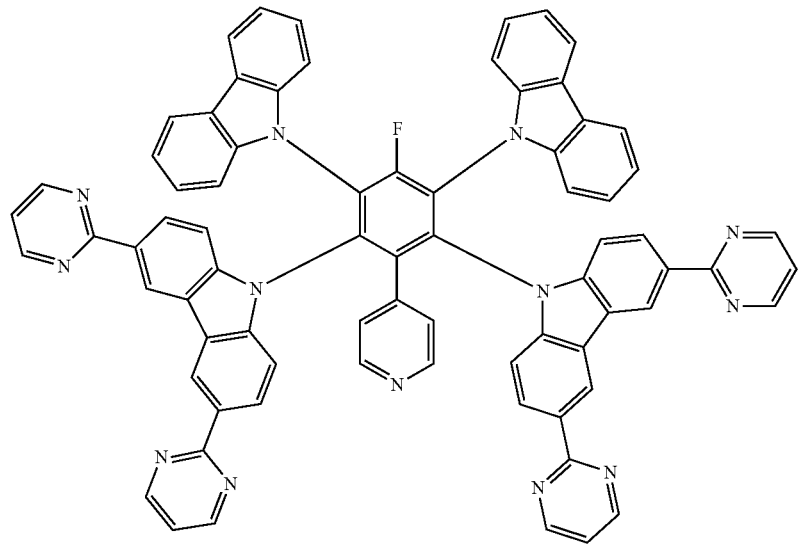
55
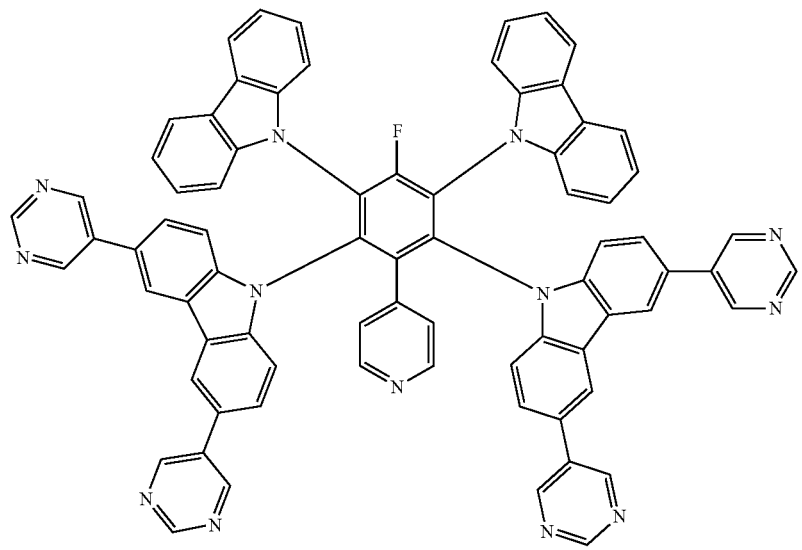
56
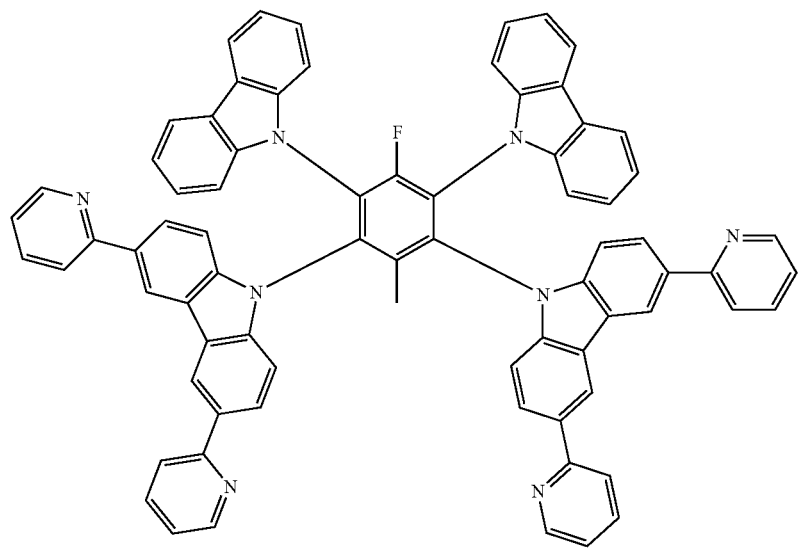

-continued
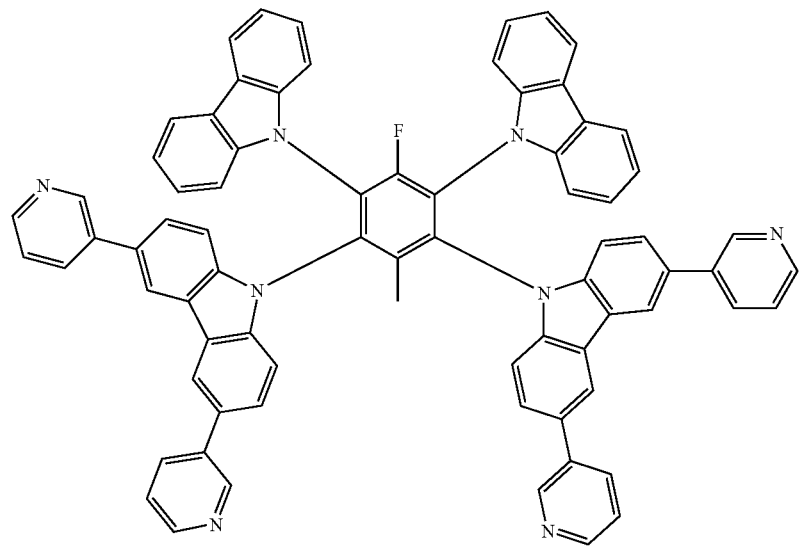
57
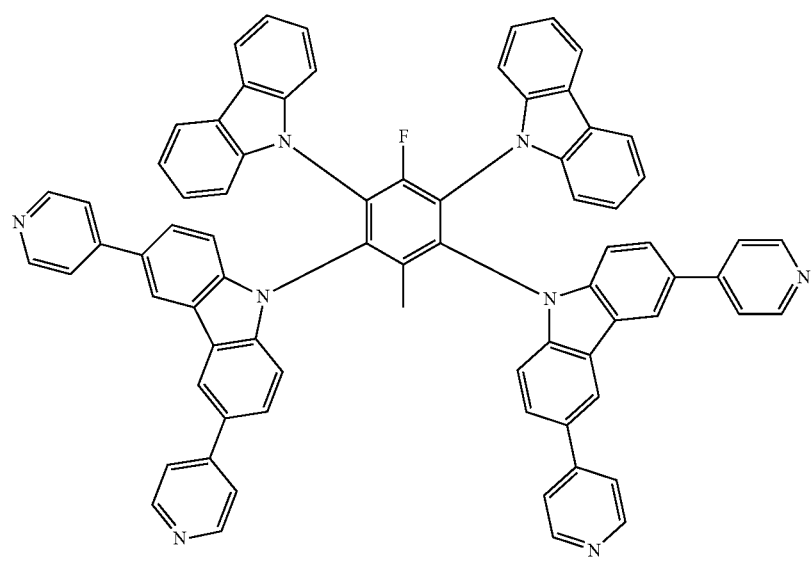
58
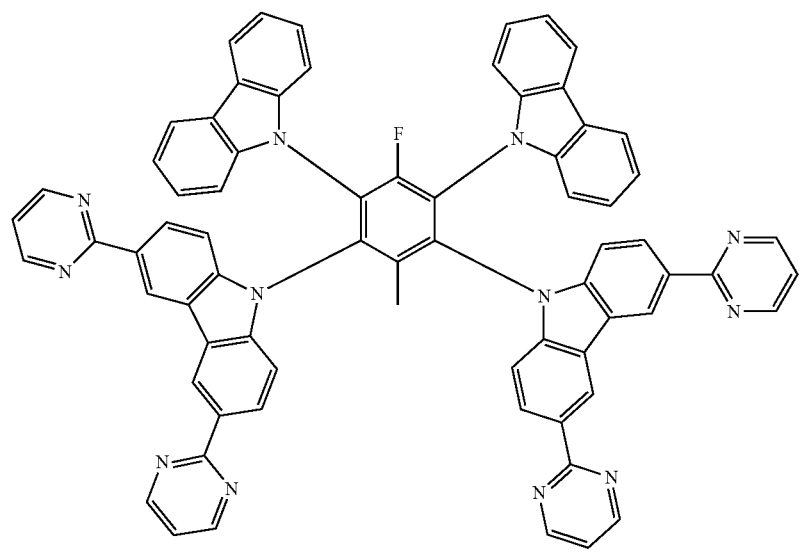
59

-continued
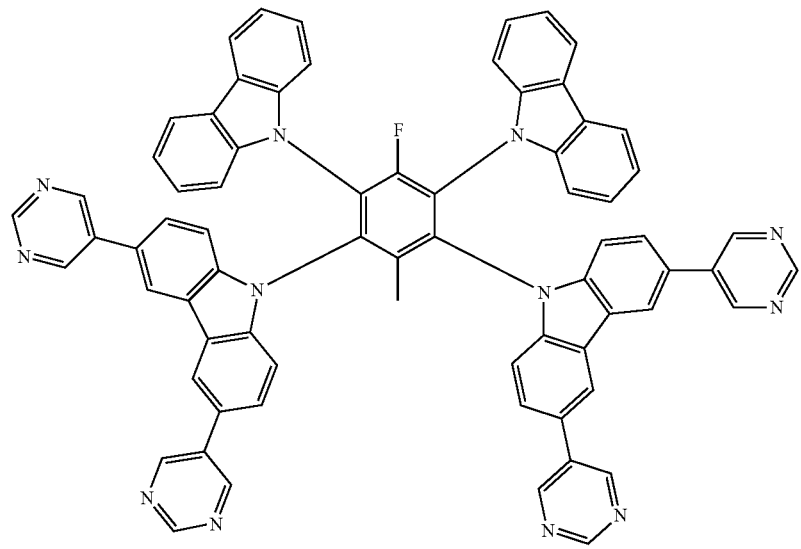
60
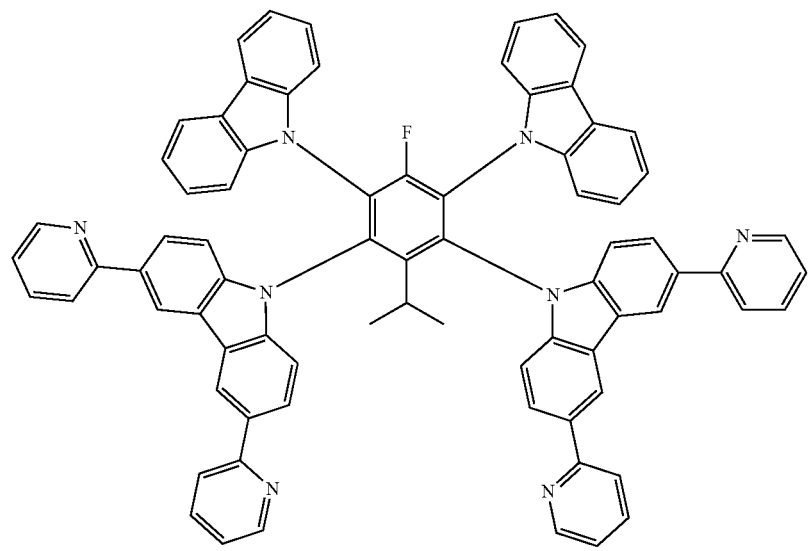
61
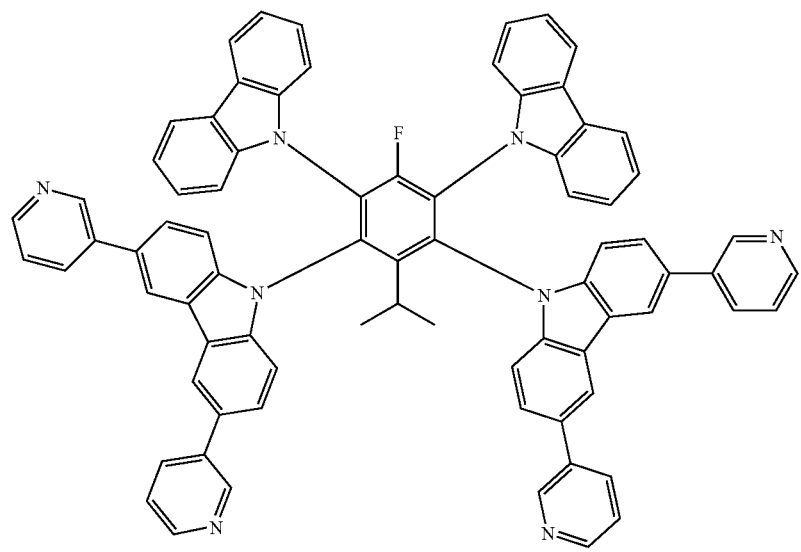
62

63
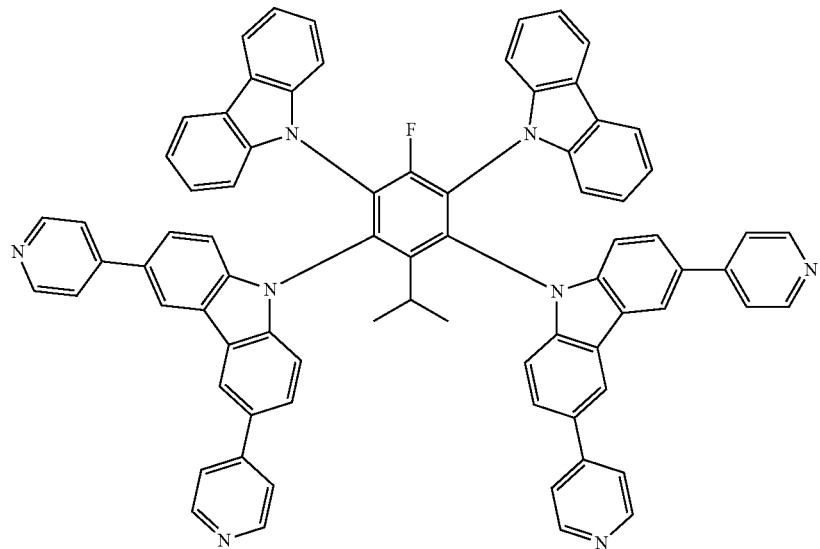
64
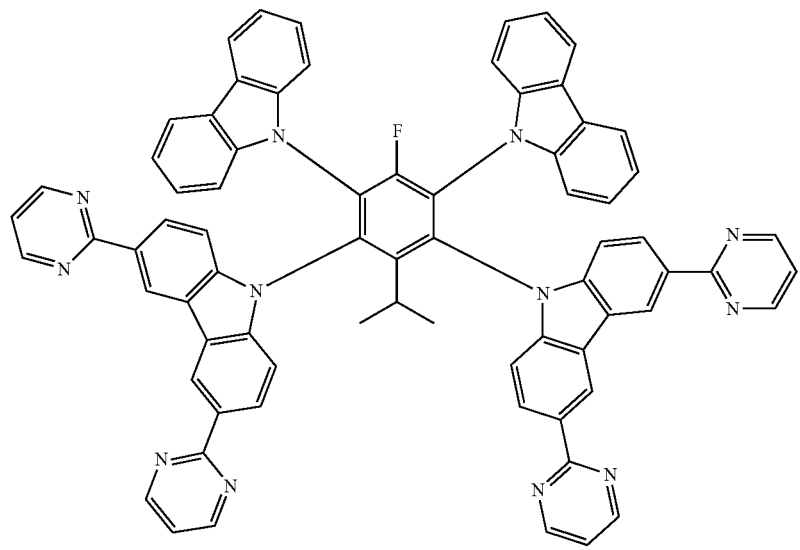
65
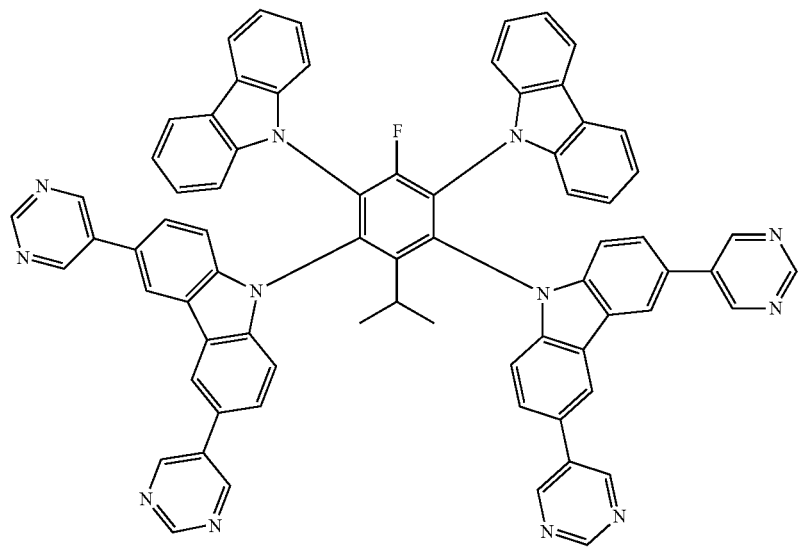

66
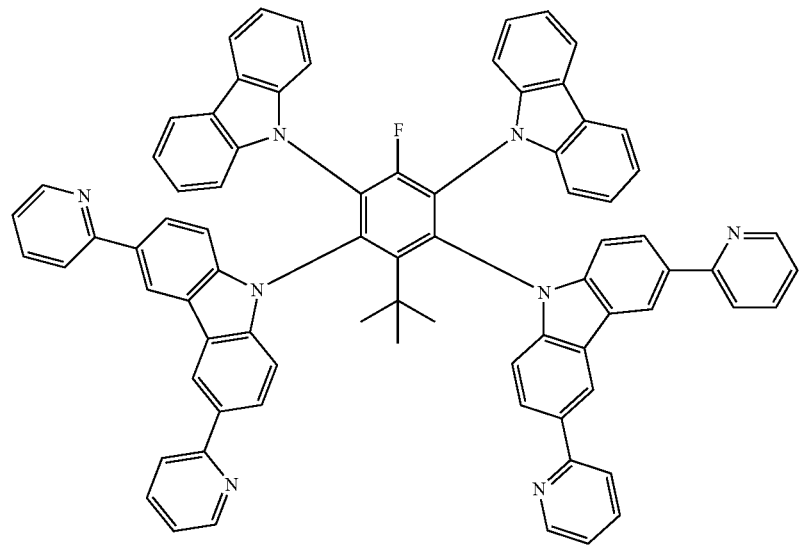
67
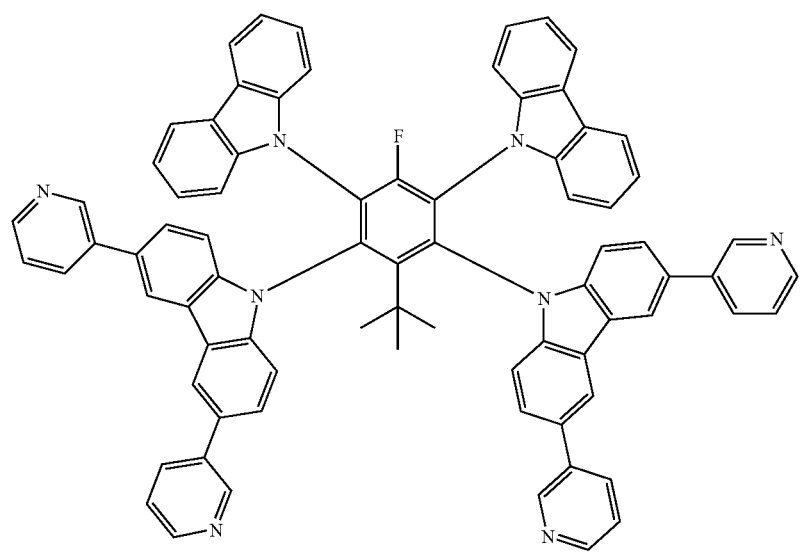
68
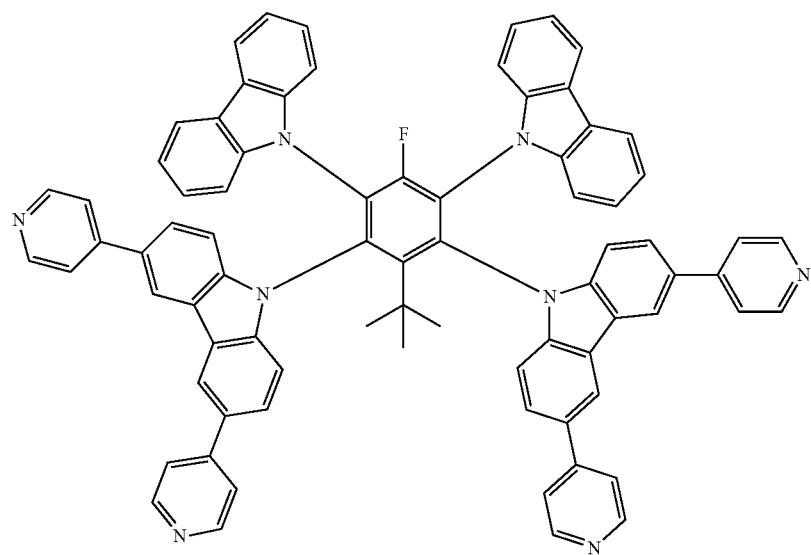

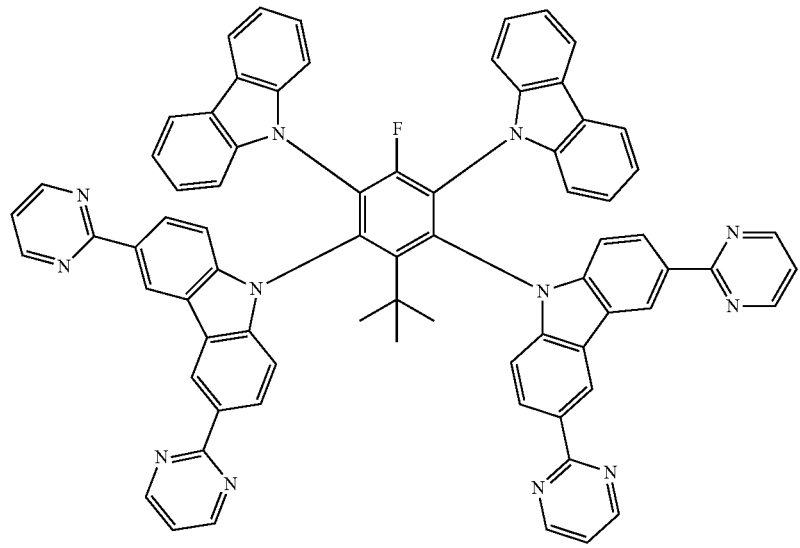
69
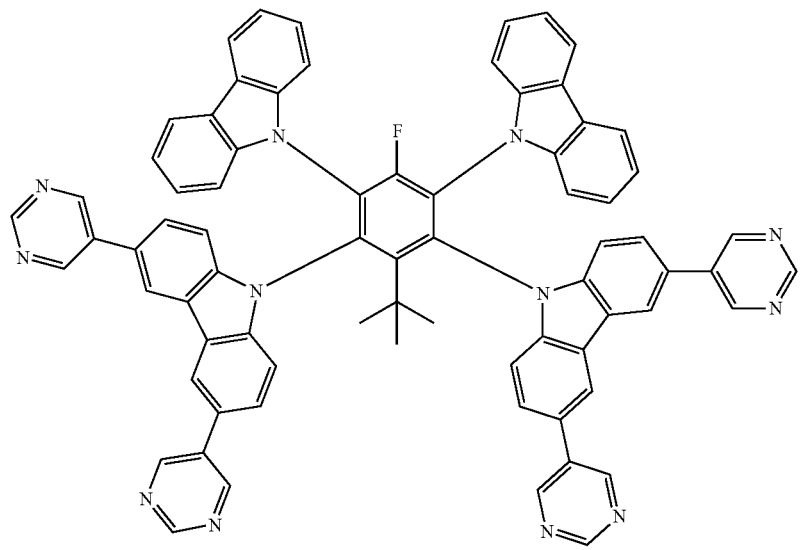
70
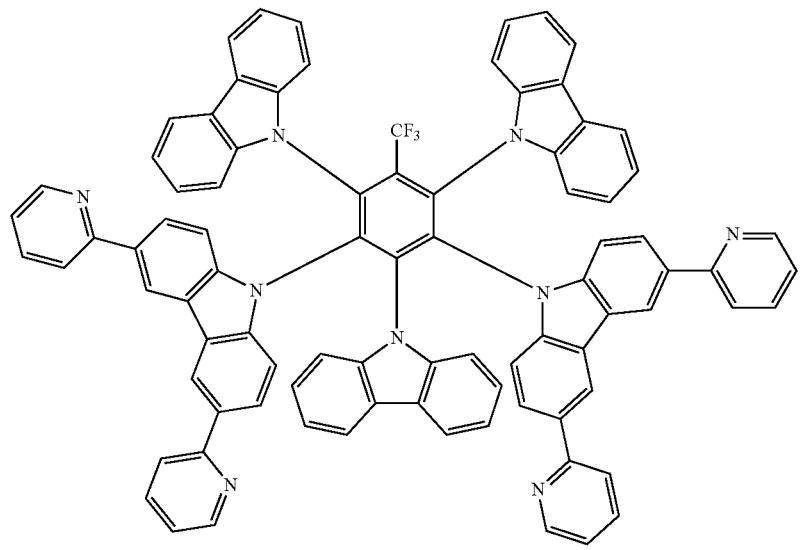
71

-continued
72
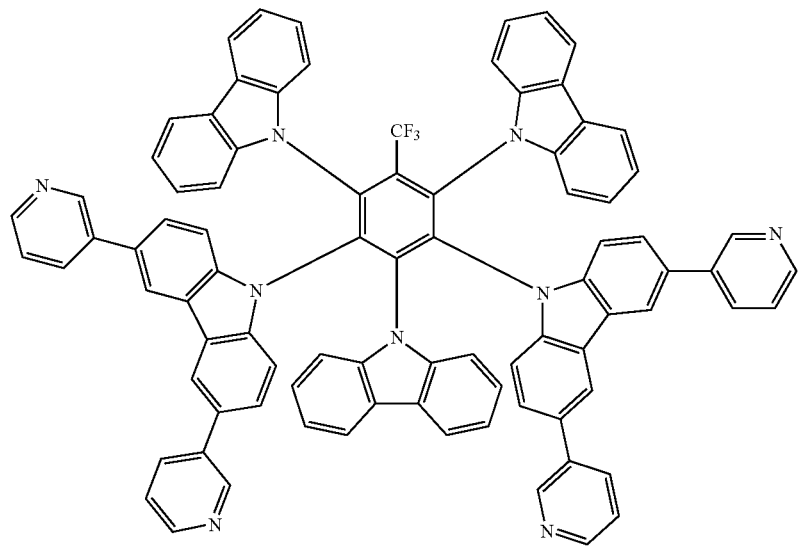
73
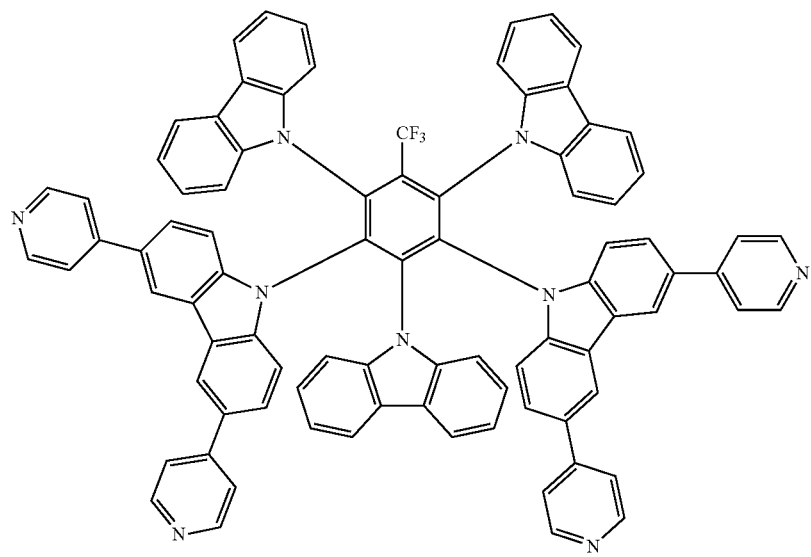
74
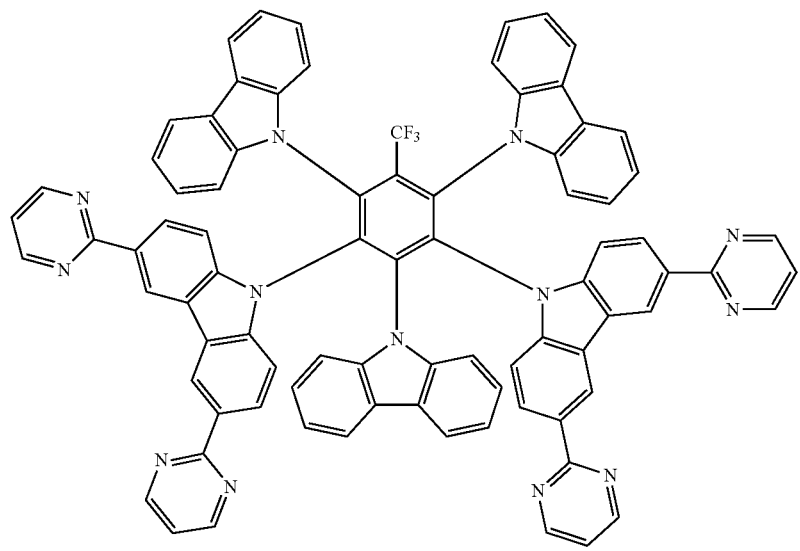

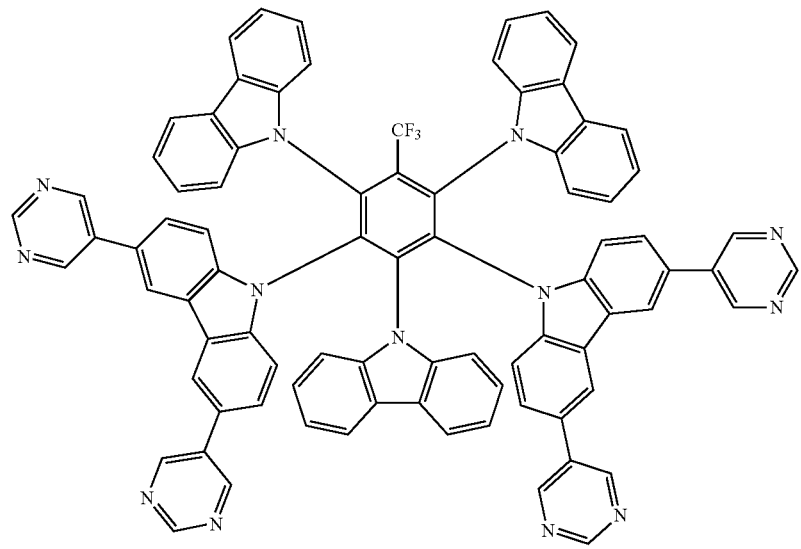
75
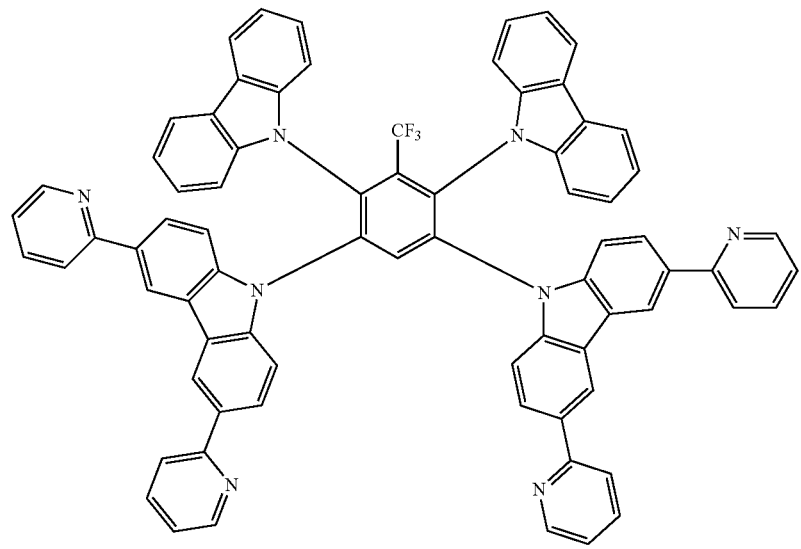
76
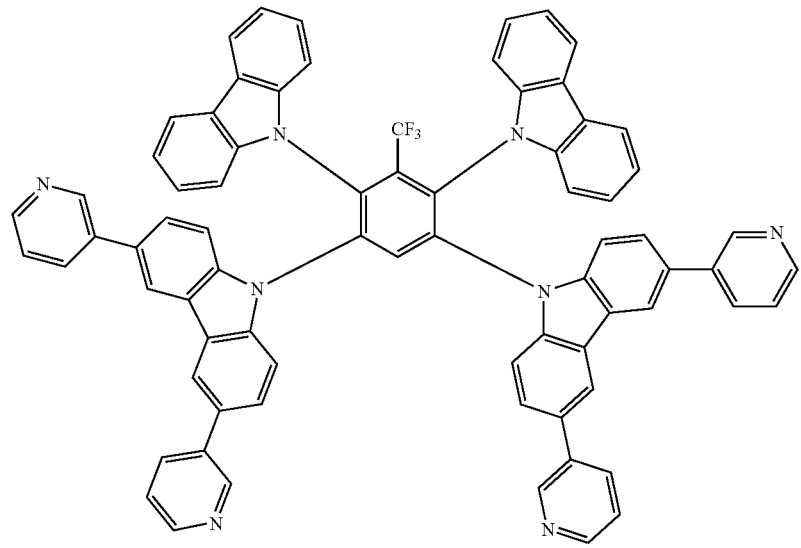
77

78
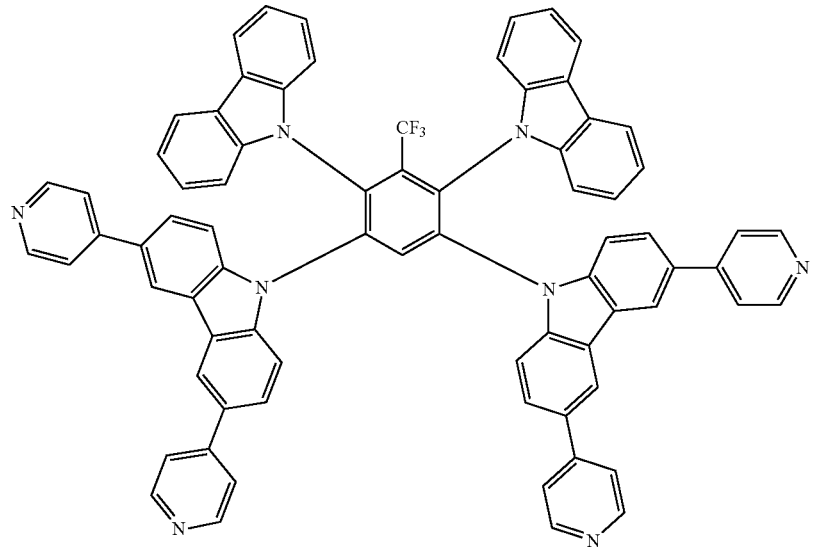
79
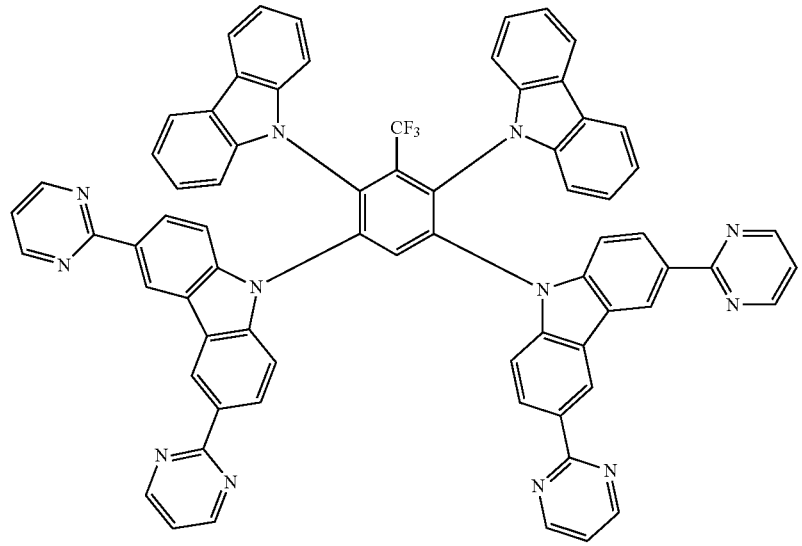
80
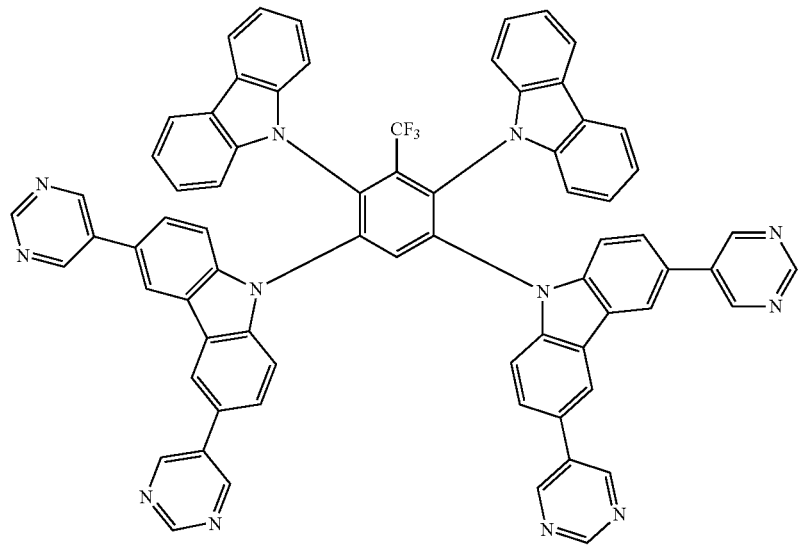

-continued
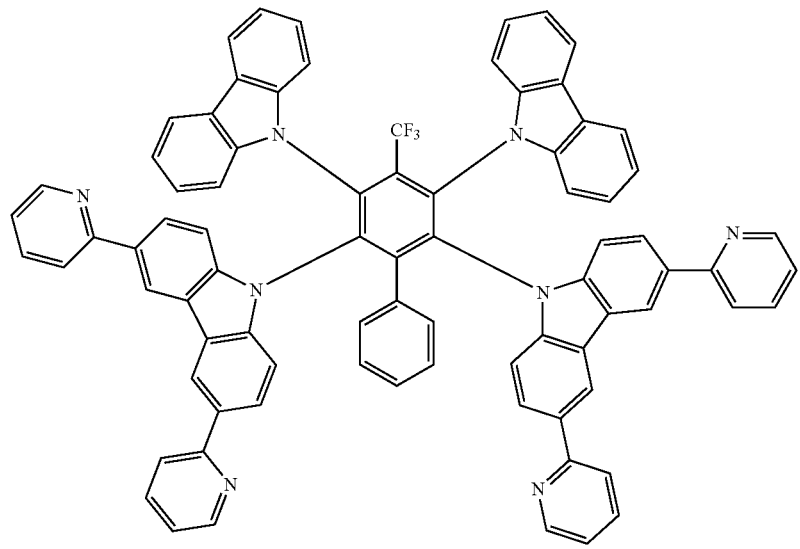
81
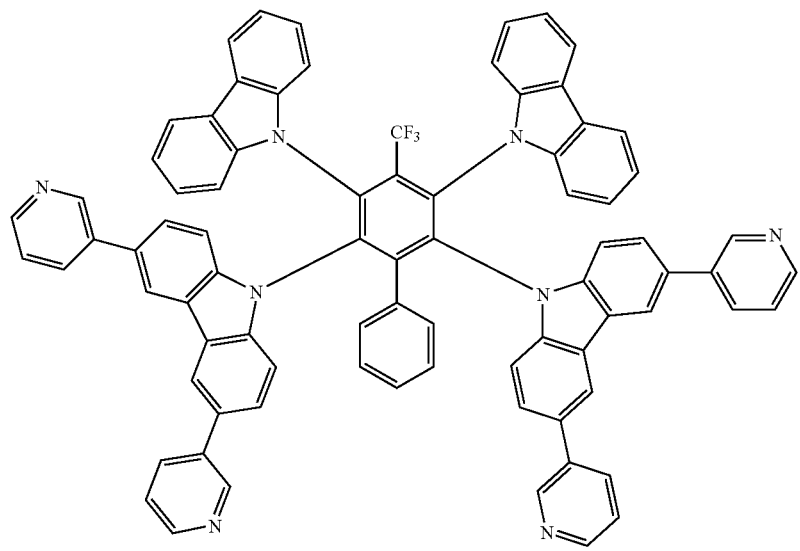
82
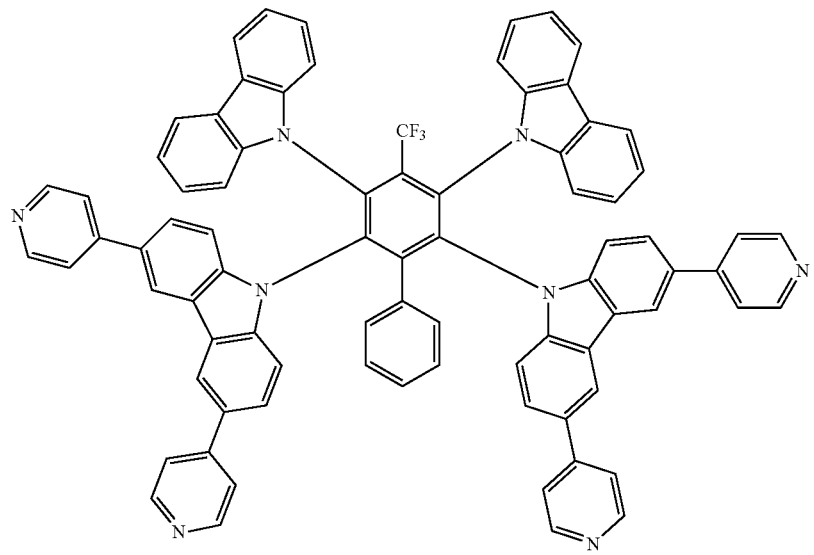
83

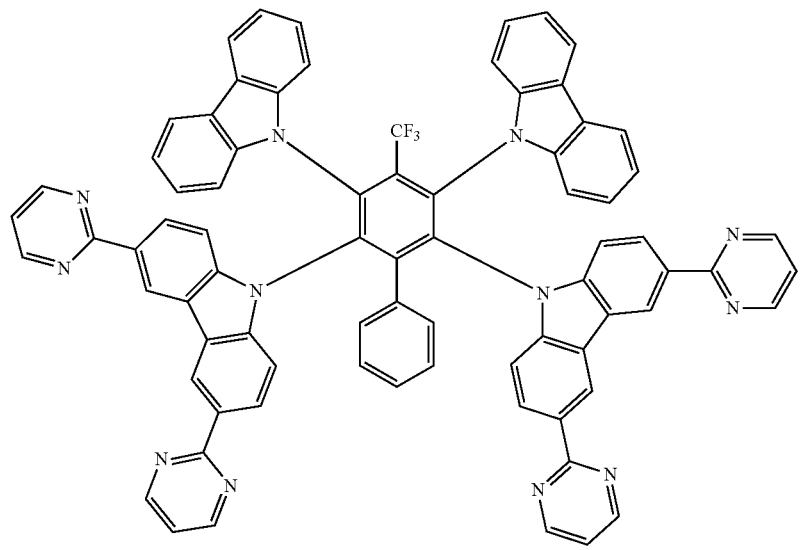
84
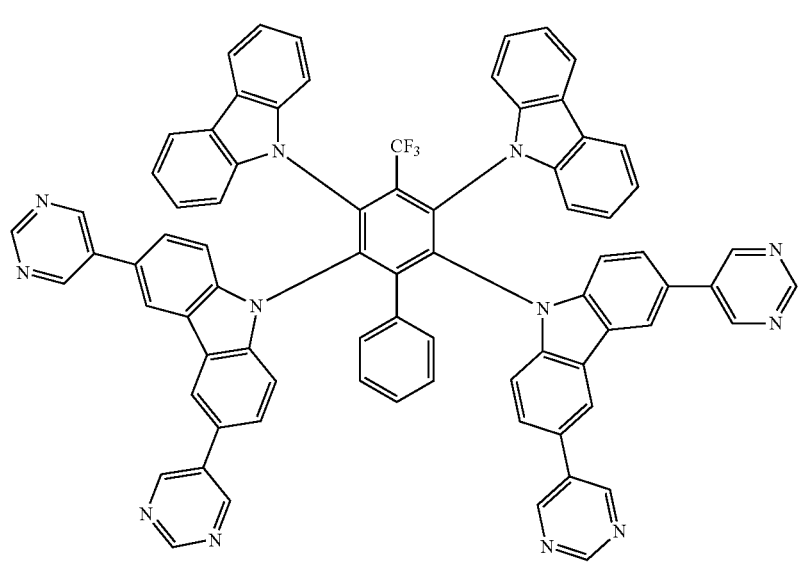
85
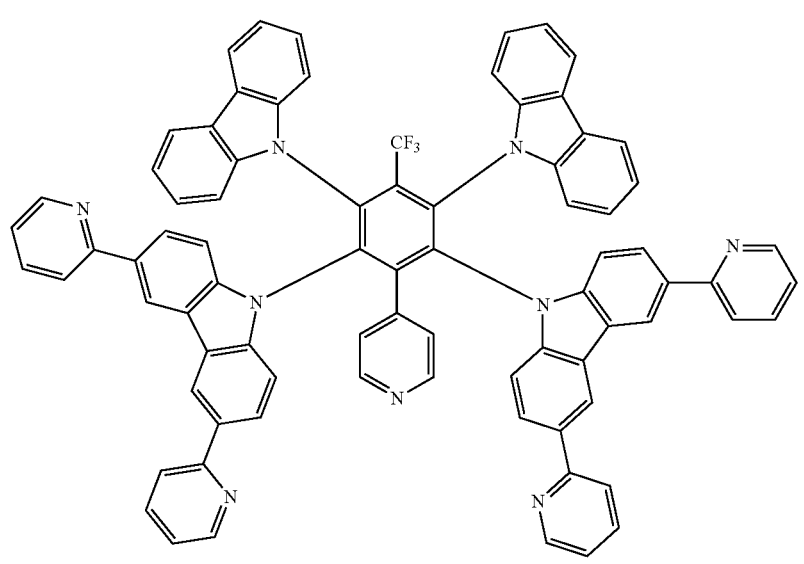
86

87
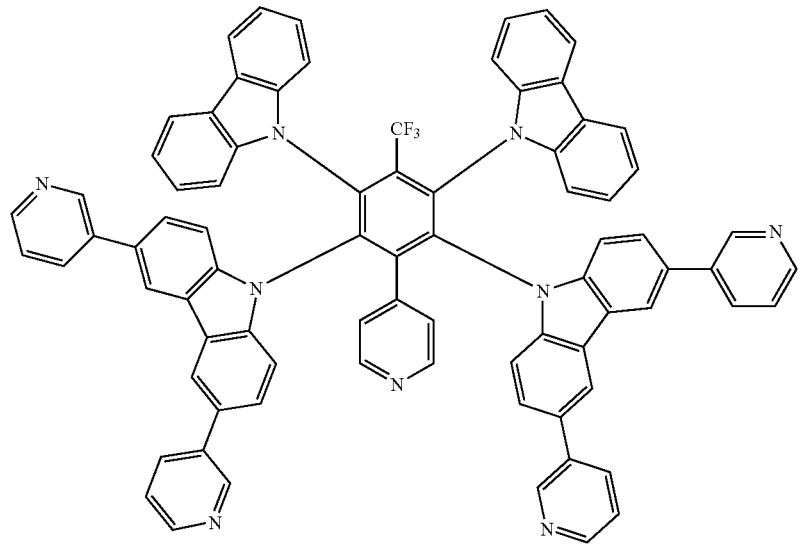
88
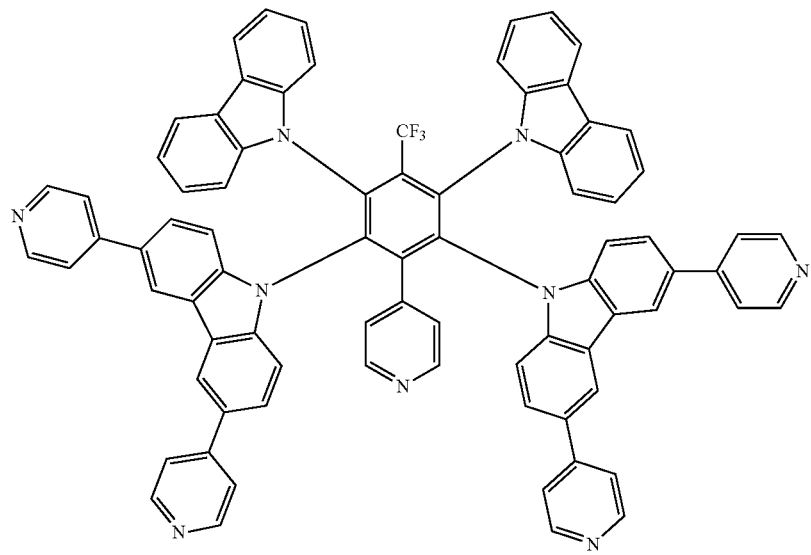
89
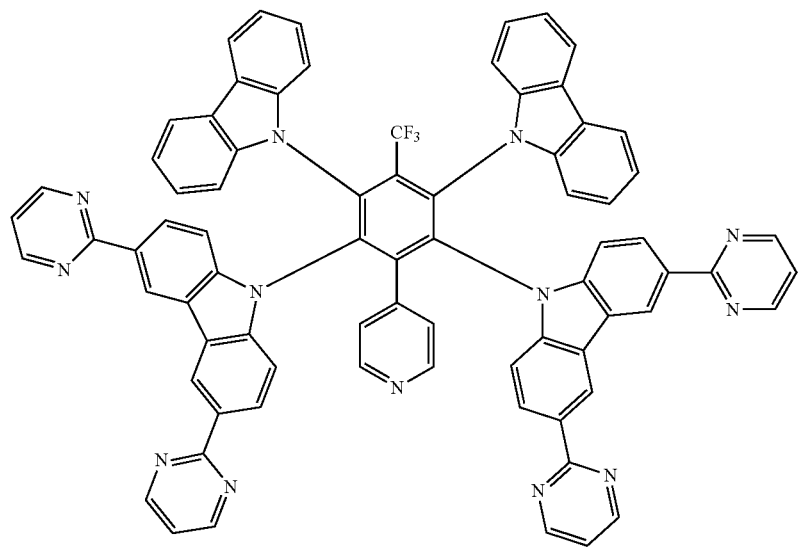

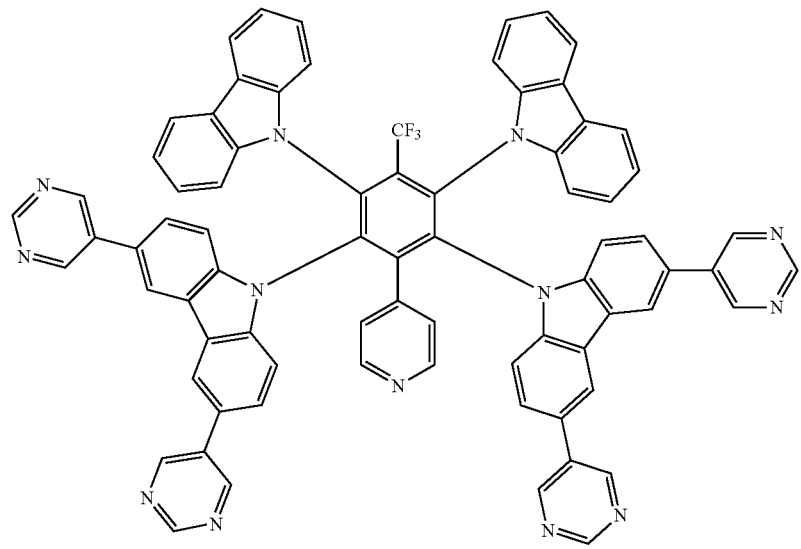
90
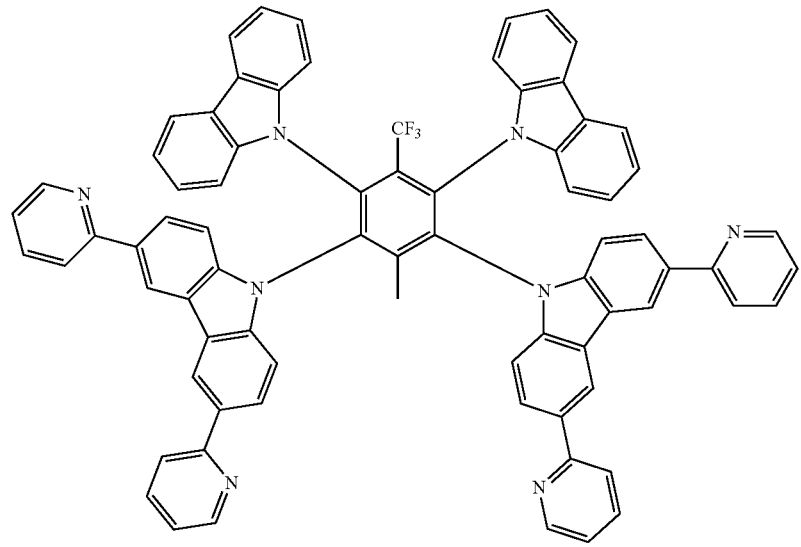
91
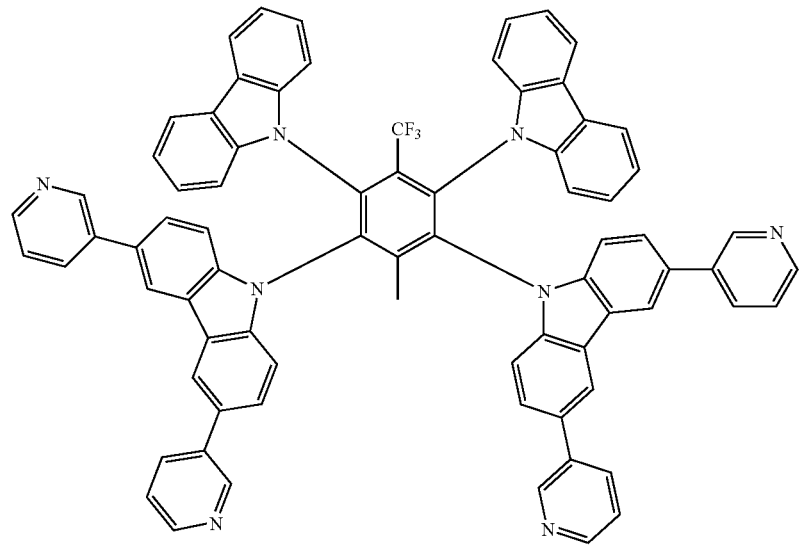
92

93
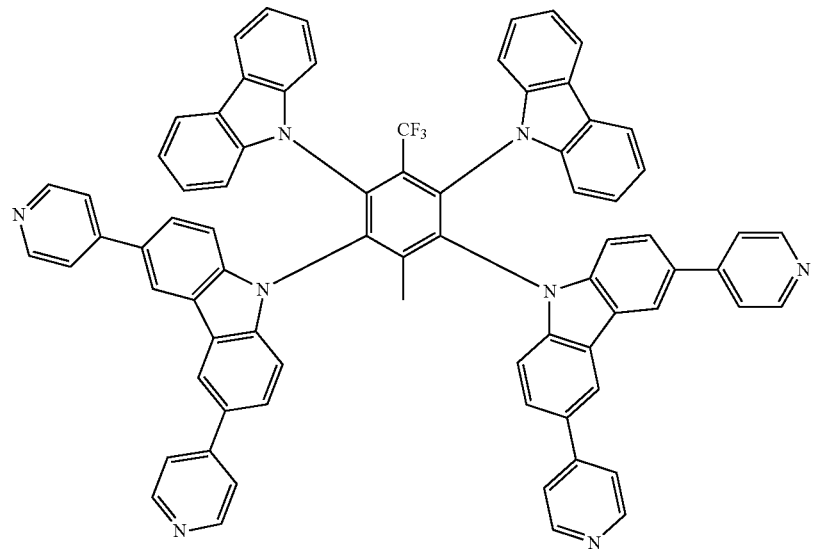
94
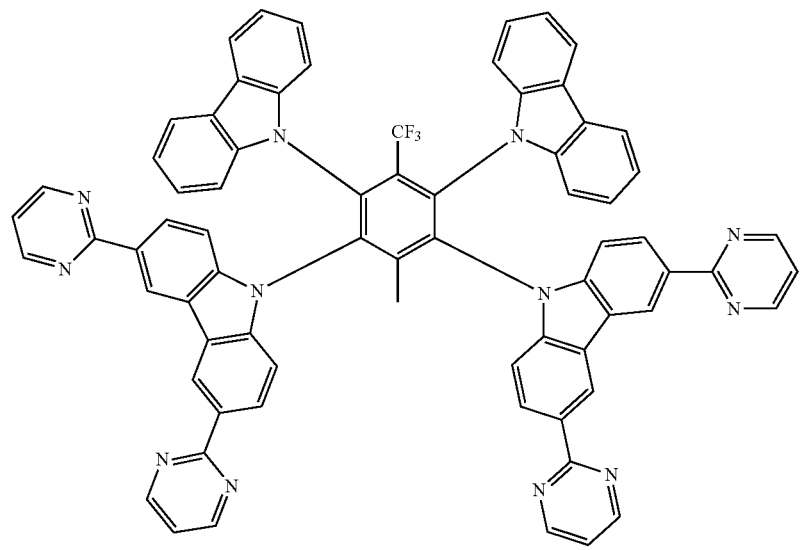
95
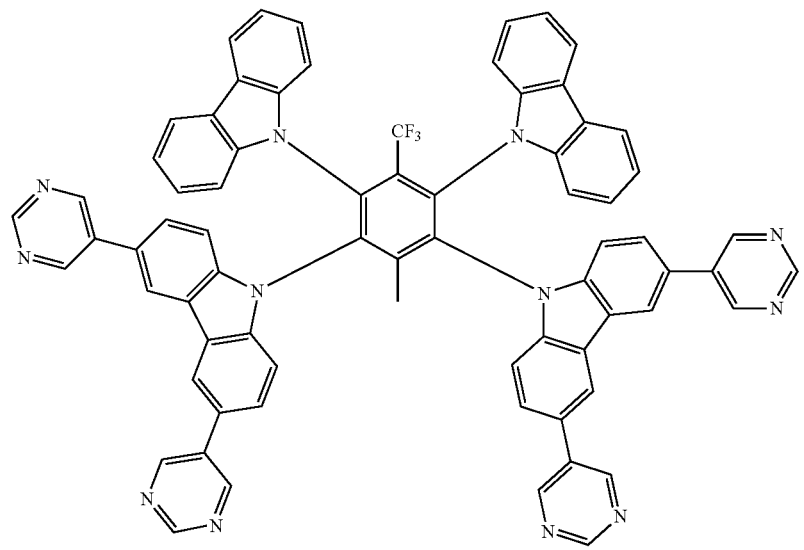

-continued
96
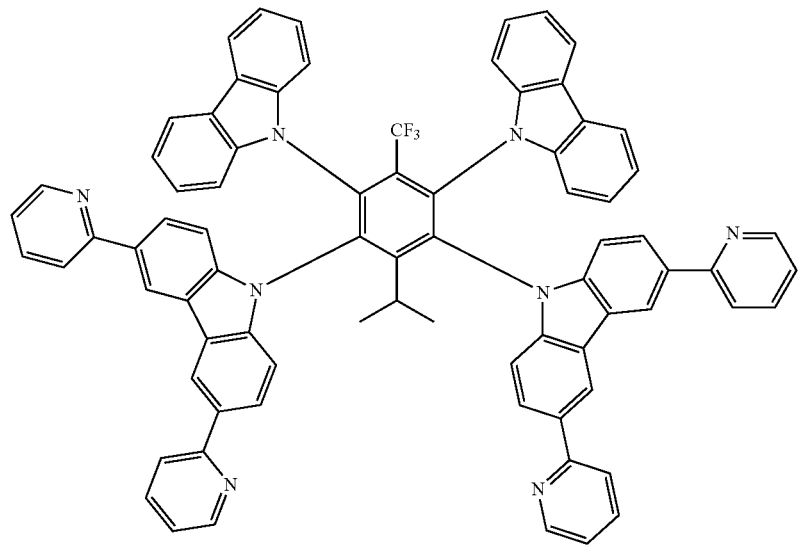
97
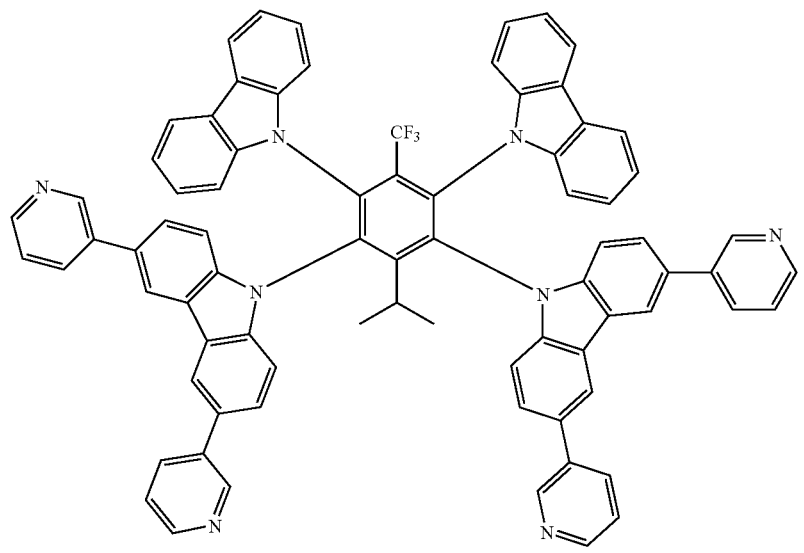
98
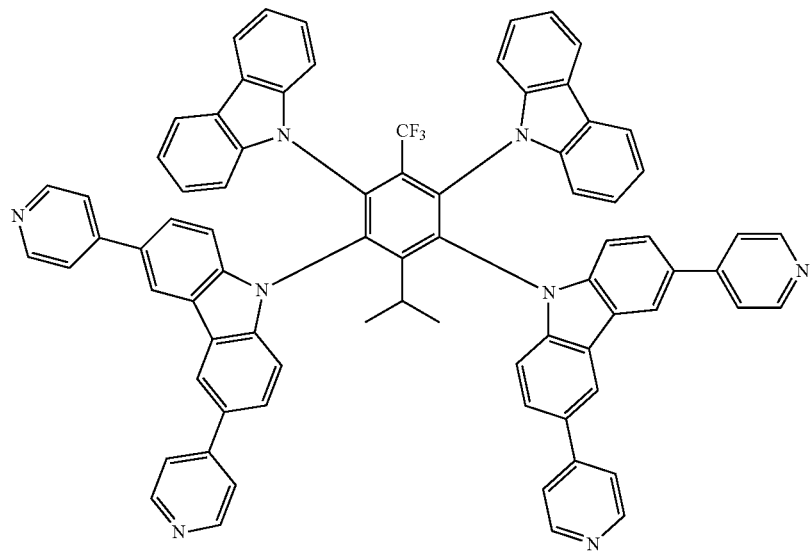

99
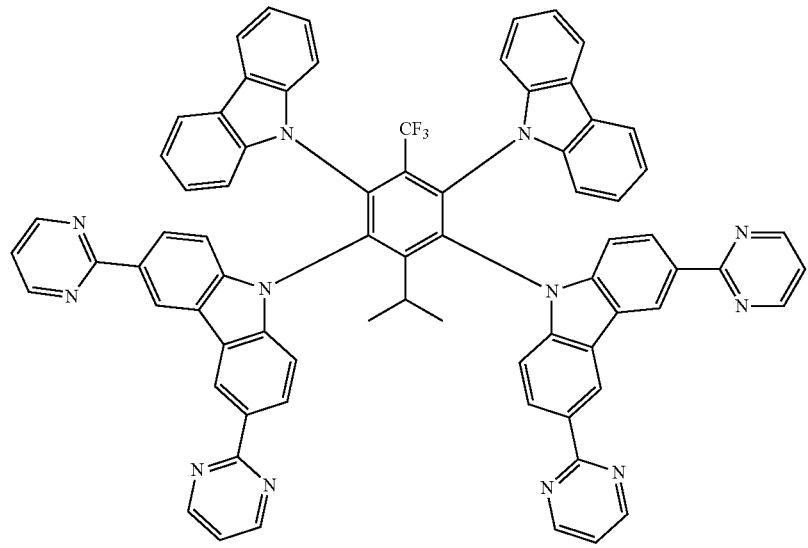
100
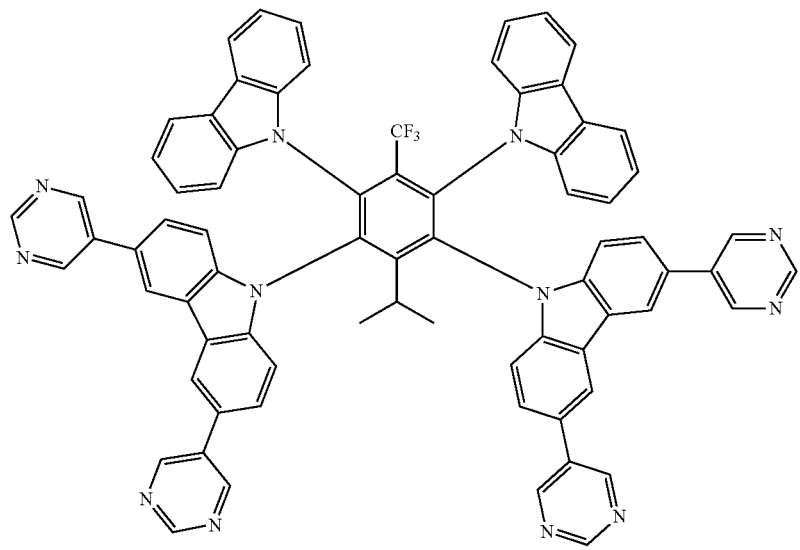
101
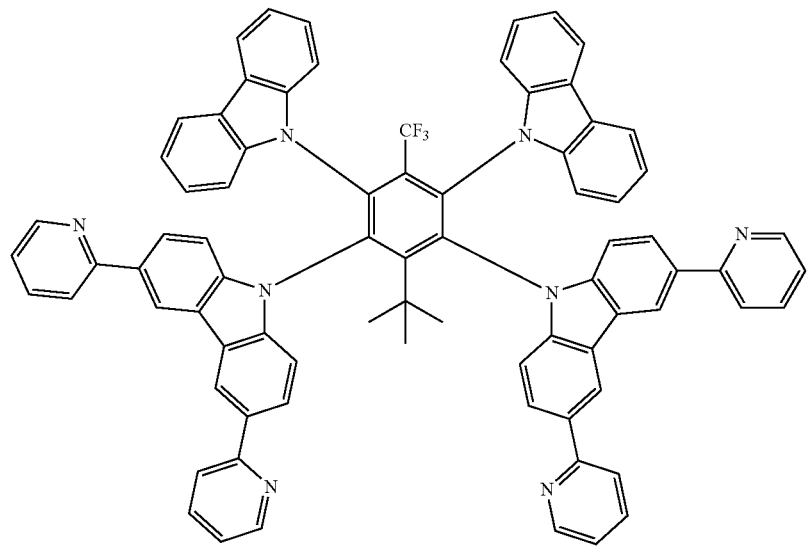

102
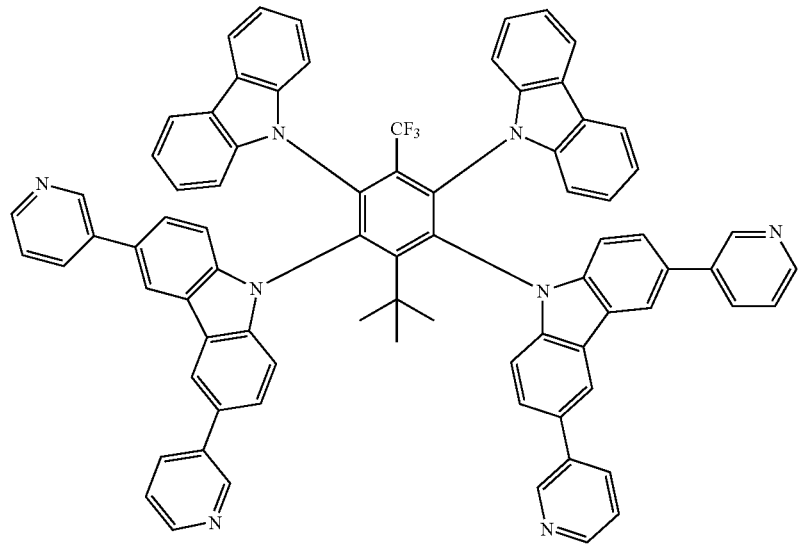
103
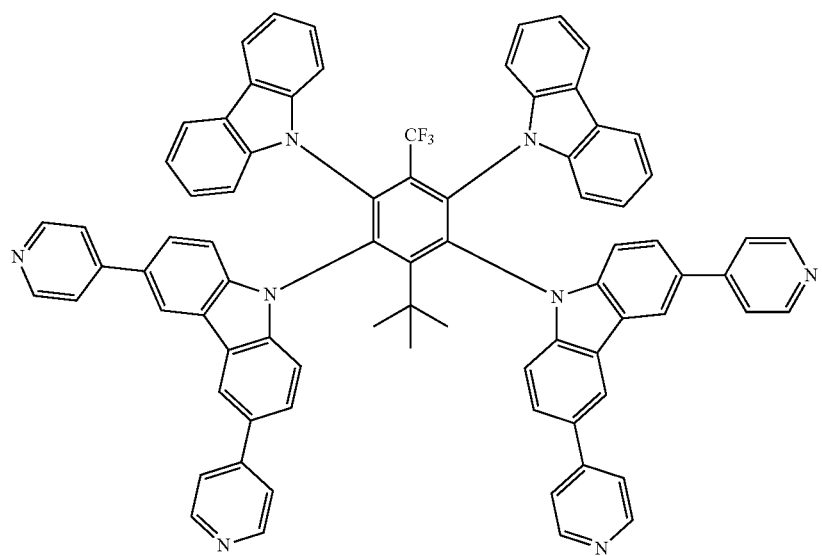
104
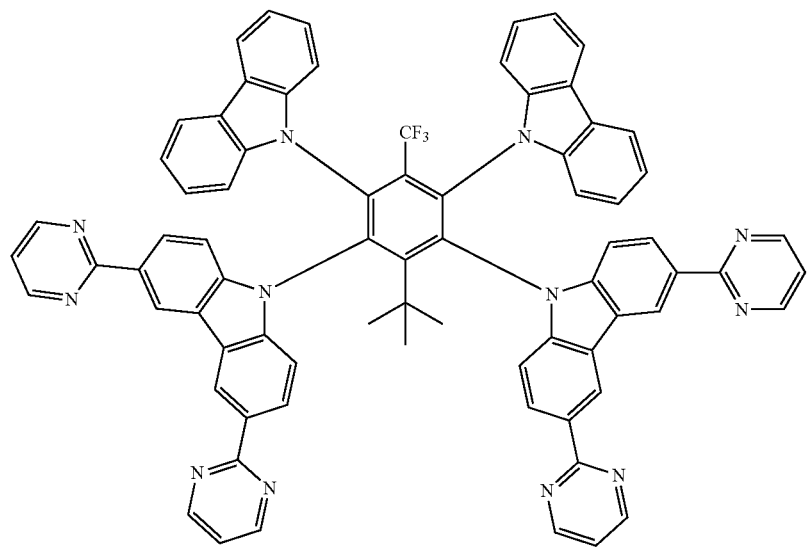

-continued

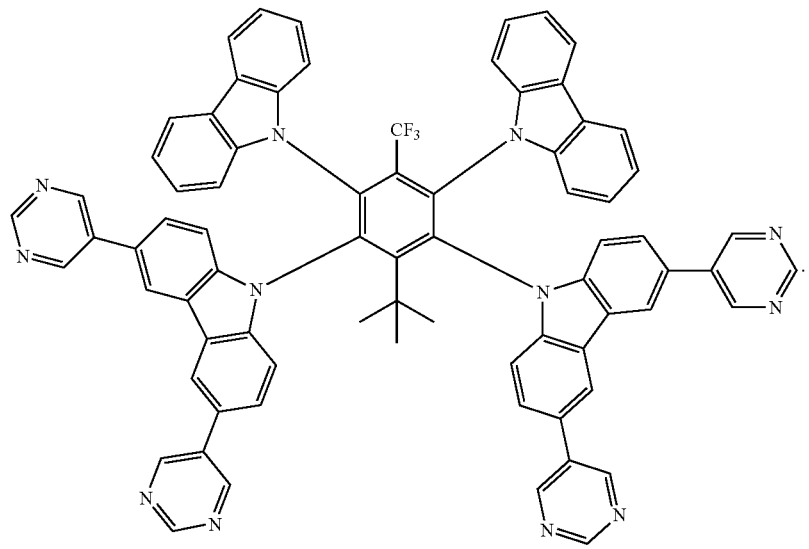

105

In the organic electroluminescence device 10 of an embodiment, the emission layer EML may emit delayed fluorescence. For example, the emission layer EML may emit thermally activated delayed fluorescence (TADF).

In some embodiments, the organic electroluminescence device 10 of an embodiment may include a plurality of emission layers. When the organic electroluminescence device 10 includes a plurality of emission layers, at least one emission layer EML may include the aromatic compound of an embodiment described above.

In an embodiment, the emission layer EML may include a host and a dopant, and may include the aromatic compound of an embodiment described above as a dopant. For example, in the organic electroluminescence device 10 of an embodiment, the emission layer EML may include a host for delayed fluorescence emission and a dopant for delayed fluorescence emission, and may include the aromatic compound of the above-described embodiment as a dopant for delayed fluorescence emission. The emission layer EML may include at least one of the aromatic compounds represented by Compound Group 1 described above as a thermally activated delayed fluorescence dopant.

In an embodiment, the emission layer EML may be a delayed fluorescence emission layer, and the emission layer EML may include any suitable host material and the aromatic compound of the above-described embodiment. For example, in an embodiment, the aromatic compound may be used as a TADF dopant.

Meanwhile, in an embodiment, the emission layer EML may include any suitable host material. For example, in an embodiment, the emission layer EML may include, as a host material, tris(8-hydroxyquinolinato)aluminum (Alq₃), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)triphenylamine (TCTA), 1,3,5-tris (N-phenylbenzimidazol-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis (triphenylsilyl)benzene (UGH2), hexaphenylcyclotrisiloxane (DPSiO3), octaphenylcyclotetrasiloxane (DPSiO4), 2,8-bis(diphenylphosphoryl)dibenzofuran (PPF), 3,3'-bis(N-carbazolyl)-1,1'-biphenyl(mCBP), and/or 1,3-bis(carbazol-9-yl)benzene (mCP). However, an embodiment of the present disclosure is not limited thereto, and in addition to the presented host materials, suitable delayed fluorescence host materials may be included.

Meanwhile, in the organic electroluminescence device 10 of an embodiment, the emission layer EML may further include any suitable dopant material. In an embodiment, the emission layer EML may further include, as a dopant, styryl derivatives (for example, 1,4-bis[2-(3-N-ethylcarbazoryl) vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalen-2-yl)vinyl) phenyl)-N-phenylbenzenamine (N-BDAVBi)), perylene and/or the derivatives thereof (for example, 2,5,8,11-tetra-t-butylperylene (TBP)), pyrene and/or the derivatives thereof (for example, 1,1-dipyrene, 1,4-dipyrenylbenzene, 1,4-bis(N,N-diphenylamino)pyrene), etc.

In some embodiments, the organic electroluminescence device 10 of an embodiment may include a plurality of emission layers. The plurality of emission layers may be sequentially stacked. For example, the organic electroluminescence device 10 including the plurality of emission layers may emit white light. The organic electroluminescence device including a plurality of emission layers may be an organic electroluminescence device having a tandem structure.

In the organic electroluminescence device 10 of an embodiment illustrated in FIGS. 1 to 4, the electron transport region ETR is provided on the emission layer EML. The electron transport region ETR may include at least one of a hole blocking layer HBL, an electron transport layer ETL, or an electron injection layer EIL, but an embodiment is not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of an electron injection layer EIL or an electron transport layer ETL, and may have a single layer structure formed of an electron injection material and an electron transport material. In some embodiments, the electron transport region ETR may have a single layer structure formed of a plurality of different materials, or may have a structure of an electron transport layer ETL/electron injection layer EIL, or a hole blocking layer HBL/electron transport layer ETL/electron injection layer EIL, where the layers are stacked in order from the emission layer EML, but is not limited thereto. The thickness of the electron transport region ETR may be, for example, from about 1000 Å to about 1,500 Å.

The electron transport region ETR may be formed using one or more suitable methods such as a vacuum deposition method, a spin coating method, a cast method, a Langmuir-Blodgett (LB) method, an inkjet printing method, a laser printing method, a laser induced thermal imaging (LITI) method, etc.

When the electron transport region ETR includes the electron transport layer ETL, the electron transport region ETR may include an anthracene-based compound. However, the present disclosure is not limited thereto, and the electron transport region may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate) (Bebq2), 9,10-di(naphthalen-2-yl)anthracene (ADN), 1,3-bis[3,5-di(pyridin-3-yl)phenyl]benzene (BmPyPhB), or a mixture thereof. The thickness of the electron transport layer ETL may be from about 100 Å to about 1,000 Å and may be, for example, from about 150 Å to about 500 Å. When the thickness of the electron transport layer ETL satisfies the above-described range, satisfactory (or suitable) electron transport properties may be obtained without a substantial increase in driving voltage.

When the electron transport region ETR includes the electron injection layer EIL, the electron transport region ETR may be a halogenated metal (such as LiF, NaCl, CsF, RbCl, RbI, and/or CuI), a lanthanide metal (such as Yb), a metal oxide (such as $Li_2O$ and/or BaO), and/or lithium quinolate (LiQ), but is not limited thereto. The electron injection layer EIL may also be formed of a mixture material of an electron transport material and an insulating organo-metal salt. The organo-metal salt may be a material having an energy band gap of about 4 eV or more. In some embodiments, the organo-metal salt may include, for example, metal acetates, metal benzoates, metal acetoacetates, metal acetylacetonates, and/or metal stearates. The thickness of the electron injection layer EIL may be from about 1 Å to about 100 Å, for example, from about 3 Å to about 90 Å. When the thickness of the electron injection layer EIL satisfies the above-described range, satisfactory (or suitable) electron injection properties may be obtained without a substantial increase in driving voltage.

The electron transport region ETR may include a hole blocking layer HBL. The hole blocking layer HBL may include, for example, at least one of 2,9-dimethyl-4,7-diphenyl-1,10-phenanthroline (BCP), bis[2-(diphenylphosphino)phenyl]ether oxide (DPEPO), or 4,7-diphenyl-1,10-phenanthroline (Bphen), but is not limited thereto.

The second electrode EL2 is provided on the electron transport region ETR. The second electrode EL2 may be a common electrode and/or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some embodiments, the second electrode EL2 may have a multi-layer structure including a reflective film or a transflective film formed of any of the above-described materials, and a transparent conductive film formed of ITO, IZO, ZnO, ITZO, etc.

In some embodiments, the second electrode EL2 may be connected with an auxiliary electrode. If the second electrode EL2 is connected with the auxiliary electrode, the resistance of the second electrode EL2 may decrease.

Meanwhile, the organic electroluminescence device 10 according to an embodiment may further include a capping layer CPL on the second electrode EL2.

The capping layer CPL may include, for example, a-NPD, NPB, TPD, m-MTDATA, $Alq_3$, CuPc, N4,N4,N4',N4'-tetra (biphenyl-4-yl) biphenyl-4,4'-diamine (TPD15), 4,4',4"-tris (carbazol-9-yl)triphenylamine (TCTA), N, N'-bis(naphthalen-1-yl), etc.

The organic electroluminescence device 10 according to an embodiment includes an aromatic compound of the above-described embodiment in the emission layer EML between the first electrode EL1 and the second electrode EL2, thereby providing good luminous efficiency and long life characteristics. In some embodiments, the aromatic compound according to an embodiment may be a thermally activated delayed fluorescence dopant, and the emission layer EML may include the aromatic compound of an embodiment to emit thermally activated delayed fluorescence, thereby obtaining good luminous efficiency characteristics.

Hereinafter, with reference to Examples and Comparative Examples, a compound according to an embodiment of this present disclosure and an organic electroluminescence device of an embodiment will be described in more detail.

However, examples shown below are illustrated only for the understanding of this present disclosure, and the scope of the present disclosure is not limited thereto.

EXAMPLES

1. Synthesis of Aromatic Compounds of Example

First, a process of synthesizing aromatic compounds according to these embodiments will be described in more detail by exemplifying a process of synthesizing Compounds 1, 2, 11, and 21. It will be understood, however, that a process of synthesizing an aromatic compound, which will be described hereinafter, is provided as an example, and thus a process of synthesizing a compound according to embodiments of the present disclosure is not limited to the Examples below.

(1) Synthesis of Compound 1

Compound 1 according to Example may be synthesized by, for example, Reaction Formulae 1-1 to 1-4 below.

Synthesis of Intermediate Compound A-1

Intermediate Compound A-1 was synthesized by Reaction Formula 1-1 below.

Reaction Formula 1-1

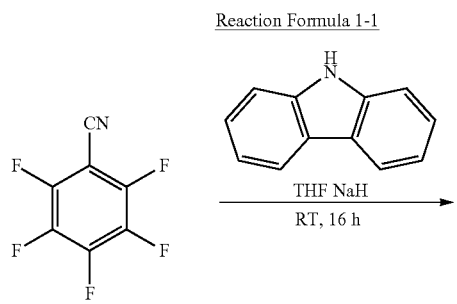

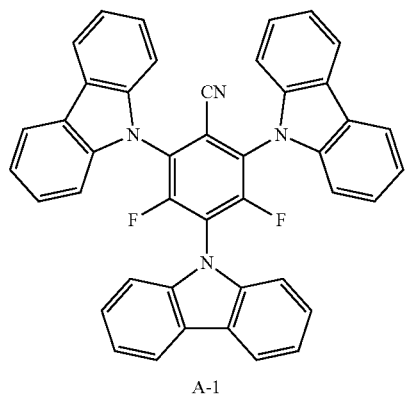

A-1

2,3,4,5,6-Pentafluorobenzonitrile (20.0 g, 103.6 mmol), carbazole (60.6 g, 362.5 mmol), and NaH (8.7 g, 362.5 mmol) were added to a three-neck flask, substituted with argon (Ar), and then tetrahydrofuran (THF, 1600 mL) was added and stirred at room temperature for 16 hours. After adding water to the reaction solution, an organic layer was extracted using THF, and dried with magnesium sulfate to remove the solvent. The obtained crude product was purified by silica gel column chromatography (hexane/toluene mixed solvent) and a recrystallization solvent (ethanol/toluene mixed solvent) to obtain a pale yellow solid (19.9 g, yield 30%). The obtained pale yellow solid was confirmed to have a molecular weight of 634 as measured by Fast Atom Bombardment Mass Spectrometry (FAB MS), and it was confirmed to be Intermediate Compound A-1, which is a target subject.

Synthesis of Intermediate Compound A-2

Intermediate Compound A-2 was synthesized by Reaction Formula 1-2 below.

Reaction Formula 1-2

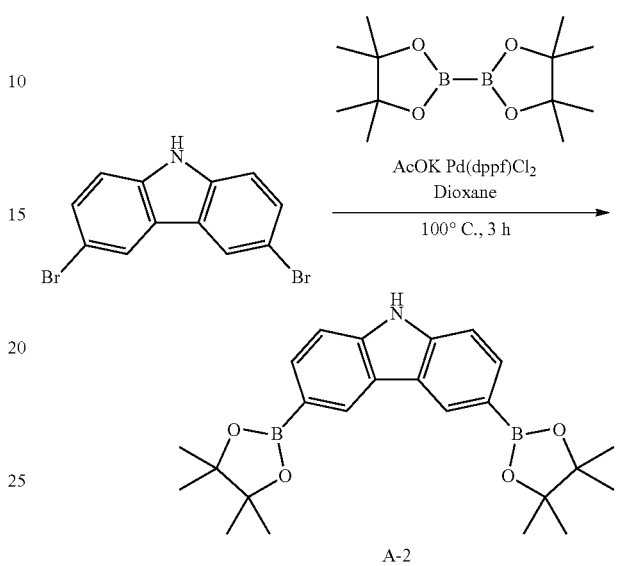

A-2

3,6-Dibromocarbazole (25.0 g, 76.9 mmol), bis(pinacolato)diboron (58.0 g, 230.1 mmol), [1,1'-bis(diphenylphosphino) ferrocene] dichloropalladium (II) (12.6 g, 15.4 mmol), and potassium acetate (90.0 g, 923 mmol) were added to a three-neck flask, substituted with argon (Ar), and then 1,4-Dioxane (500 mL) was added and stirred at 100° C. for 3 hours. After adding water to the reaction solution, an organic layer was extracted using dichloromethane, and dried with magnesium sulfate to remove the solvent. The obtained crude product was purified by silica gel column chromatography (hexane/toluene mixed solvent) and a recrystallization solvent (ethanol/toluene mixed solvent) to obtain a white solid (17.3 g, yield 54%). The obtained white solid was confirmed to have a molecular weight of 419 as measured by FAB MS, and it was confirmed to be Intermediate Compound A-2, which is a target subject.

Synthesis of Intermediate Compound A-3

Intermediate Compound A-3 was synthesized by Reaction Formula 1-3 below.

Reaction Formula 1-3

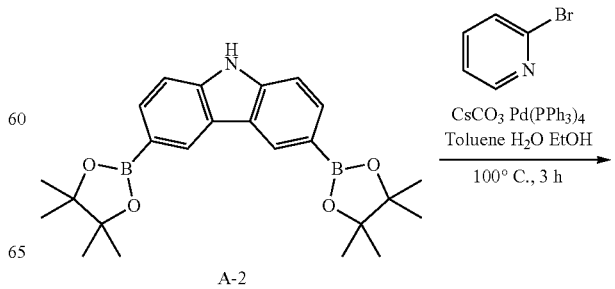

A-2

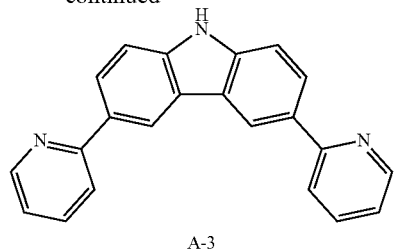

A-3

Intermediate Compound A-2 (15.0 g, 35.7 mmol), 2-bromopyridine (17.0 g, 107.4 mmol), tetrakis(triphenylphosphine)palladium(0) (18.6 g, 16.1 mmol), and cesium carbonate (104.9 g, 322.1 mmol) were added to a three-neck flask, substituted with argon (Ar), and then toluene (388 mL), ethanol (258 mL), and water (258 mL) were added and stirred at 100° C. for 3 hours. After adding water to the reaction solution, an organic layer was extracted using ethyl acetate, and dried with magnesium sulfate to remove the solvent. The obtained crude product was purified by silica gel column chromatography (hexane/toluene mixed solvent) and a recrystallization solvent (ethanol/toluene mixed solvent) to obtain a white solid (4.4 g, yield 38%). The obtained white solid was confirmed to have a molecular weight of 321 as measured by FAB MS, and it was confirmed to be Intermediate Compound A-3, which is a target subject.

Synthesis of Compound 1

Compound 1 was synthesized by Reaction Formula 1-4 below.

Reaction Formula 1-4

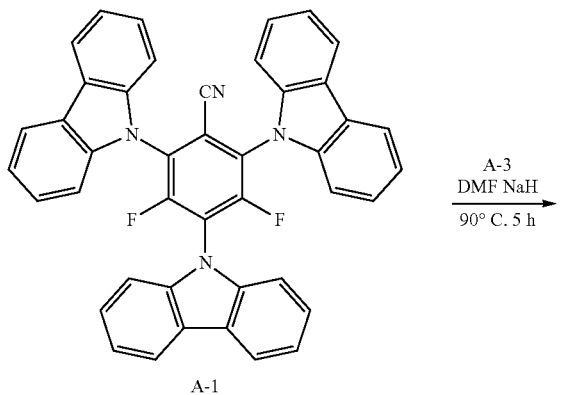

A-1

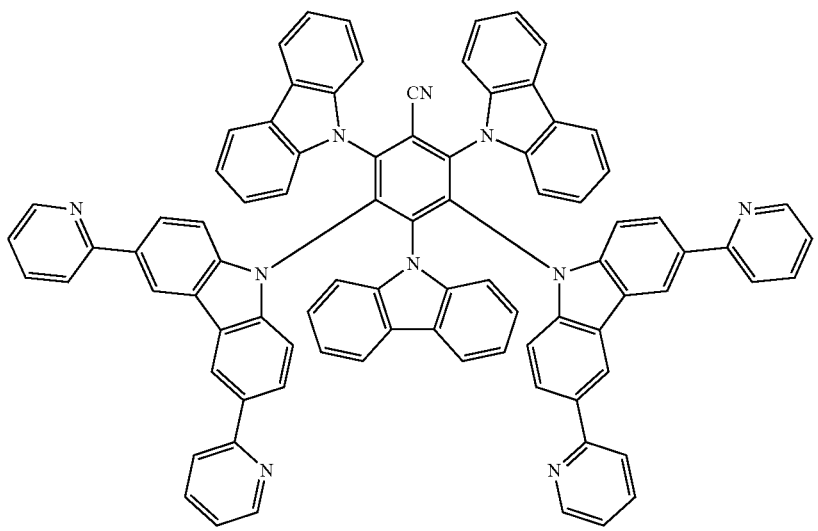

Compound 1

Intermediate Compound A-1 (3.0 g, 4.7 mmol), Intermediate Compound A-3 (3.8 g, 12.0 mmol), and NaH (0.3 g, 12.0 mmol) were added to a three-neck flask, substituted with argon (Ar), and then dimethylformamide (DMF, 75 mL) was added and stirred at 90° C. for 5 hours. After adding water to the reaction solution, an organic layer was extracted using dichloromethane, and dried with magnesium sulfate to remove the solvent. The obtained crude product was purified by silica gel column chromatography (hexane/toluene mixed solvent) and a recrystallization solvent (ethanol/toluene mixed solvent) to obtain of a pale yellow solid (3.5 g, yield 60%). The obtained pale yellow solid was confirmed to have a molecular weight of 1233 as measured by FAB MS, and it was confirmed to be Compound 1, which is a target subject.

(2) Synthesis of Compound 2

Compound 2 according to an embodiment, for example, may be synthesized by Reaction Formulae 2-1 and 2-2.

Synthesis of Intermediate Compound B

Intermediate Compound B was synthesized by Reaction Formula 2-1 below.

Reaction Formula 2-1

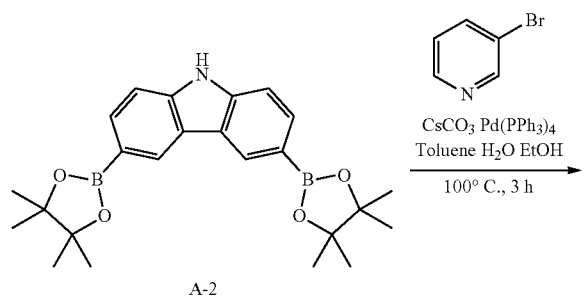

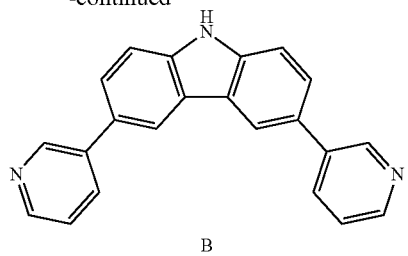

Intermediate Compound A-2 (15.0 g, 35.7 mmol), 3-bromopyridine (17.0 g, 107.4 mmol), tetrakis(triphenylphosphine)palladium(0) (18.6 g, 16.1 mmol), and Cesium carbonate (104.9 g, 322.1 mmol) were added to a three-neck flask, substituted with argon (Ar), and then toluene (388 mL), ethanol (258 mL), and water (258 mL) were added and stirred at 100° C. for 3 hours. After adding water to the reaction solution, an organic layer was extracted using ethyl acetate, and dried with magnesium sulfate to remove the solvent. The obtained crude product was purified by silica gel column chromatography (hexane/toluene mixed solvent) and a recrystallization solvent (ethanol/toluene mixed solvent) to obtain of a white solid (3.5 g, yield 31%). The obtained white solid was confirmed to have a molecular weight of 321 as measured by FAB MS, and it was confirmed to be Intermediate Compound B, which is a target subject.

Synthesis of Compound 2

Compound 2 was synthesized by Reaction Formula 2-2 below.

Reaction Formula 2-2

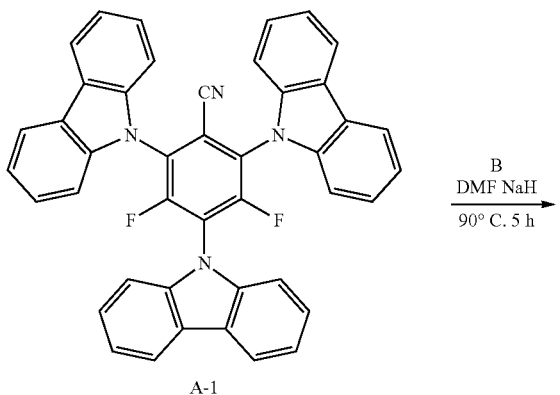

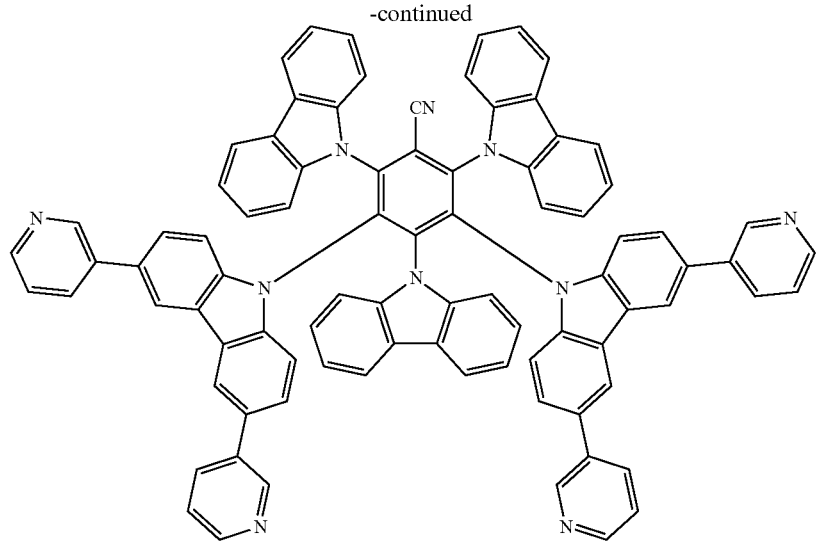

Compound 2

Intermediate Compound A-1 (3.0 g, 4.7 mmol), Intermediate Compound B (3.8 g, 12.0 mmol), and NaH (0.3 g, 12.0 mmol) were added to a three-neck flask, substituted with argon (Ar), and then dimethylformamide (DMF, 75 mL) was added and stirred at 90° C. for 5 hours. After adding water to the reaction solution, an organic layer was extracted using dichloromethane, and dried with magnesium sulfate to remove the solvent. The obtained crude product was purified by silica gel column chromatography (hexane/toluene mixed solvent) and a recrystallization solvent (ethanol/toluene mixed solvent) to obtain of a pale yellow solid (2.5 g, yield 43%). The obtained pale yellow solid was confirmed to have a molecular weight of 1233 as measured by FAB MS, and it was confirmed to be Compound 2, which is a target subject.

(3) Synthesis of Compound 11

Compound 11 according to an embodiment, for example, may be synthesized by Reaction Formulae 3-1 to 3-3 below.

Synthesis of Intermediate Compound C-1

Intermediate Compound C-1 was synthesized by Reaction Formula 3-1 below.

Reaction Formula 3-1

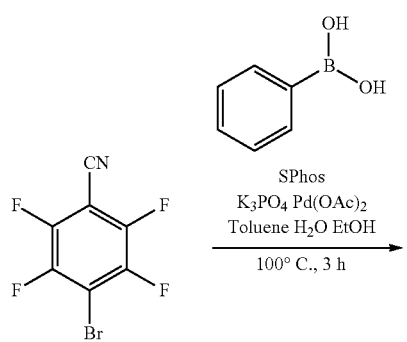

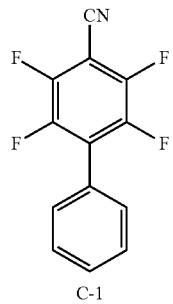

C-1

4-bromotetrafluorobenzonitrile (10.0 g, 39.4 mmol), phenylboronic acid (5.8 g, 47.3 mmol), palladium (II) acetate (18.6 g, 16.1 mmol), tripotassium phosphate (16.7 g, 78.8 mmol), and SPhos (2-dicyclohexylphosphino-2',6'-dimethoxybiphenyl) (1.6 g, 3.9 mmol) were added to a three-neck flask, substituted with argon (Ar), and then toluene (394 mL), ethanol (16 mL), and water (16 mL) were added and stirred at 100° C. for 3 hours. After adding water to the reaction solution, an organic layer was extracted using ethyl acetate, and dried with magnesium sulfate to remove the solvent. The obtained crude product was purified by silica gel column chromatography (hexane/toluene mixed solvent) and a recrystallization solvent (ethanol/toluene mixed solvent) to obtain of a white solid (7.0 g, yield 62%). The obtained white solid was confirmed to have a molecular weight of 287 as measured by FAB MS, and it was confirmed to be Intermediate Compound C-1, which is a target subject.

Synthesis of Intermediate Compound C-2
Intermediate Compound C-2 was synthesized by Reaction Formula 3-2 below.

Reaction Formula 3-2

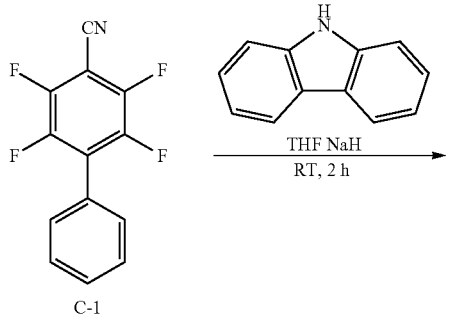

C-1

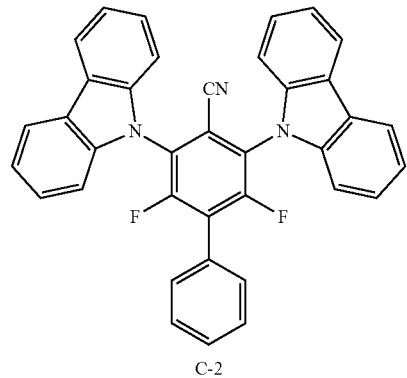

C-2

Intermediate Compound C-1 (7.0 g, 27.9 mmol), carbazole (9.3 g, 55.7 mmol), and NaH (1.3 g, 55.7 mmol) were added to a three-neck flask, substituted with argon (Ar), and then THF (450 mL) was added and stirred at room temperature for 2 hours. After adding water to the reaction solution, an organic layer was extracted using toluene, and dried with magnesium sulfate to remove the solvent. The obtained crude product was purified by silica gel column chromatography (hexane/toluene mixed solvent) and a recrystallization solvent (ethanol/toluene mixed solvent) to obtain of a pale yellow solid (5.5 g, yield 36%). The obtained pale yellow solid was confirmed to have a molecular weight of 545 as measured by FAB MS, and it was confirmed to be Intermediate Compound C-2, which is a target subject.

Synthesis of Compound 11
Compound 11 was synthesized by Reaction Formula 3-3 below.

Reaction Formula 3-3

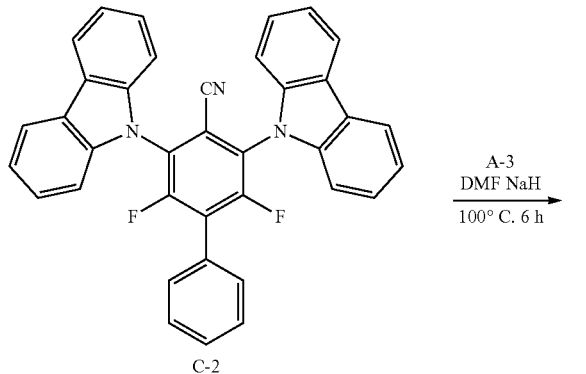

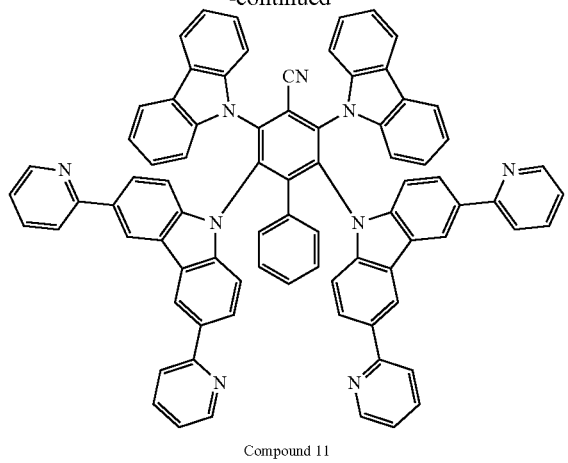

Compound 11

Intermediate Compound C-2 (7.0 g, 12.8 mmol), Intermediate Compound A-3 (10.3 g, 32.1 mmol), and NaH (0.8 g, 32.1 mmol) were added to a three-neck flask, substituted with argon (Ar), and then DMF (200 mL) was added and stirred at 100° C. for 6 hours. After adding water to the reaction solution, an organic layer was extracted using dichloromethane, and dried with magnesium sulfate to remove the solvent. The obtained crude product was purified by silica gel column chromatography (hexane/toluene mixed solvent) and a recrystallization solvent (ethanol/toluene mixed solvent) to obtain of a pale yellow solid (9.8 g, yield 67%). The obtained pale yellow solid was confirmed to have a molecular weight of 1148 as measured by FAB MS, and it was confirmed to compound 11, which is a target subject.

(4) Synthesis of Compound 21
Compound 21 according to an embodiment, may be synthesized by, for example, Reaction Formulae 4-1 and 4-2 below.

Synthesis of Intermediate Compound D
Intermediate Compound D was synthesized by Reaction Formula 4-1 below.

Reaction Formula 4-1

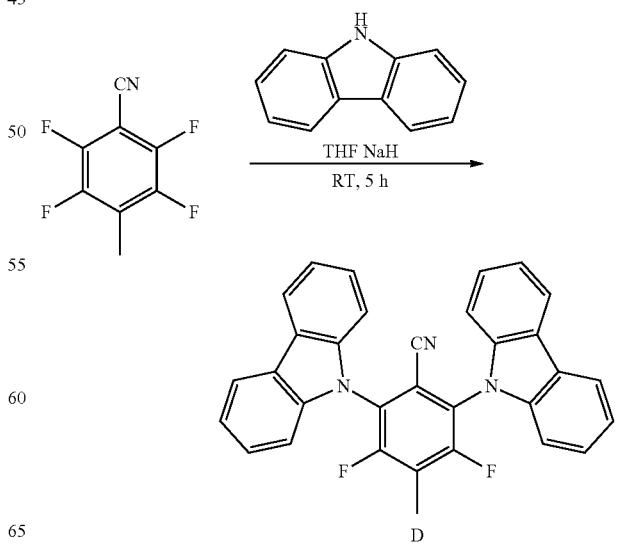

D 2,3,5,6-tetrafluoro-4-methylbenzonitrile (10.0 g, 52.9 mmol), carbazole (17.7 g, 105.8 mmol), and NaH (2.5 g, 105.8 mmol) were added to a three-neck flask, substituted with argon (Ar), and then THF (800 mL) was added and stirred at room temperature for 5 hours. After adding water to the reaction solution, an organic layer was extracted using toluene, and dried with magnesium sulfate to remove the solvent. The obtained crude product was purified by silica gel column chromatography (hexane/toluene mixed solvent) and a recrystallization solvent (ethanol/toluene mixed solvent) to obtain of a pale yellow solid (5.2 g, yield 45%). The obtained pale yellow solid was confirmed to have a molecular weight of 483 as measured by FAB MS, and it was confirmed to Intermediate Compound D, which is a target subject.

Synthesis of Compound 21

Compound 21 was synthesized by Reaction Formula 4-2 below.

Reaction Formula 4-2

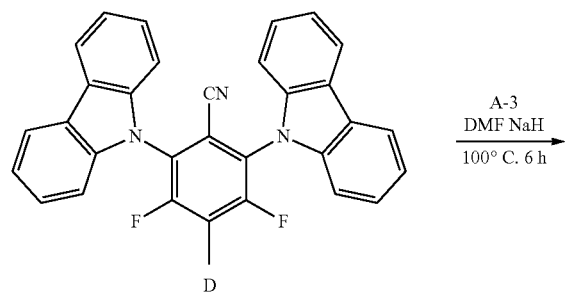

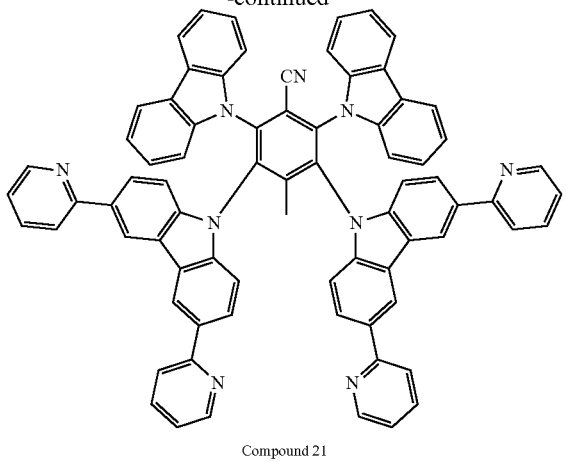

Compound 21

Intermediate Compound D (5.0 g, 9.2 mmol), Intermediate Compound A-3 (7.4 g, 22.9 mmol), and NaH (0.6 g, 22.9 mmol) were added to a three-neck flask, substituted with argon (Ar), and then DMF (200 mL) was added and stirred at 100° C. for 6 hours. After adding water to the reaction solution, an organic layer was extracted using toluene, and dried with magnesium sulfate to remove the solvent. The obtained crude product was purified by silica gel column chromatography (hexane/toluene mixed solvent) and a recrystallization solvent (ethanol/toluene mixed solvent) to obtain of a pale yellow solid (4.1 g, yield 64%). The obtained pale yellow solid was confirmed to have a molecular weight of 1088 as measured by FAB MS, and it was confirmed to Compound 21, which is a target subject.

2. Evaluation of the Energy Level of Compounds

Table 2 below shows the lowest singlet excitation energy level (S1 level) and the lowest triplet excitation energy level (T1 level) of Compounds 1, 2, 11 and 21 and Comparative Example Compounds N1 to N3 below, and ΔEST values.

The Compounds used in Comparative Examples 1 to 3 are shown in Table 1.

TABLE 1

| Comparative Example N1 | |
|---|---|

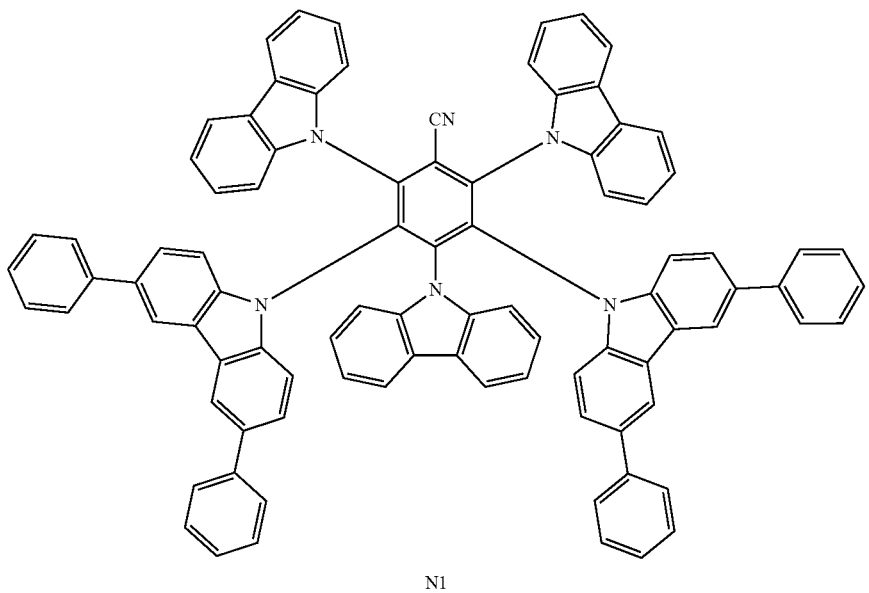 [SMILES: N#Cc1c(-n2c3ccccc3c3ccccc32)c(-n2c3ccc(-c4ccccc4)cc3c3cc(-c4ccccc4)ccc32)c(-n2c3ccccc3c3ccccc32)c(-n2c3ccc(-c4ccccc4)cc3c3cc(-c4ccccc4)ccc32)c1-n1c2ccccc2c2ccccc21 ; "N1"]

N1

TABLE 1-continued

Comparative Example N2

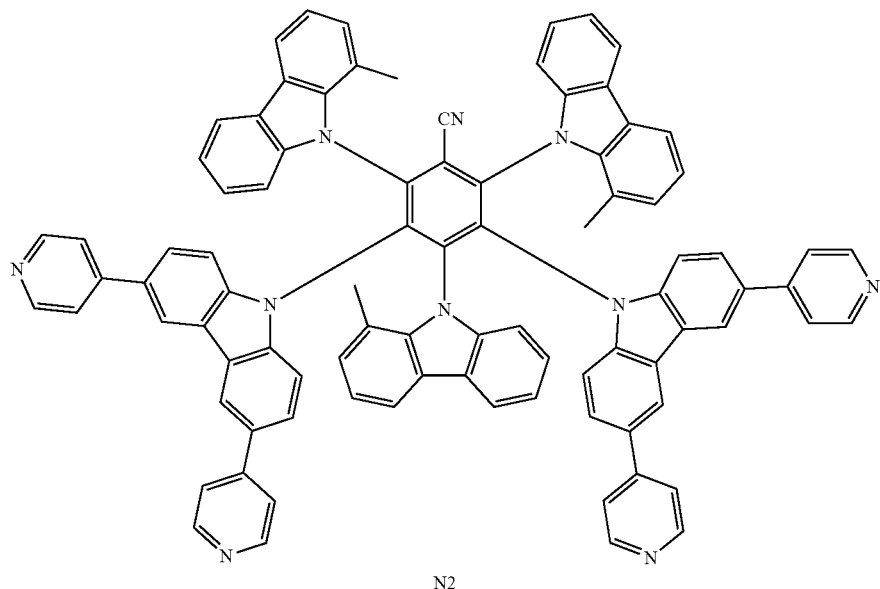 [SMILES: Cc1cccc2c3ccccc3n(-c3c(C#N)c(-n4c5ccccc5c5cccc(C)c54)c(-n4c5ccc(-c6ccncc6)cc5c5cc(-c6ccncc6)ccc54)c(-n4c5ccccc5c5cccc(C)c54)c3-n3c4ccc(-c5ccncc5)cc4c4cc(-c5ccncc5)ccc43)c12 ; "N2"]

N2

Comparative Example N3

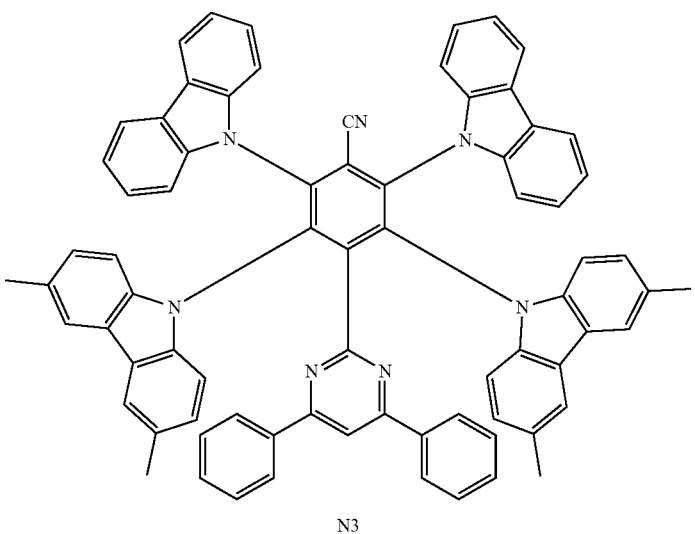

N3

The energy level values in Table 2 were calculated by an ab initio molecular orbital method. Specifically, it was calculated by B3LYP/6-31 G (d) using Gaussian 09 from Gaussian. ΔEST indicates the difference between the lowest singlet excitation energy level (S1 level) and the lowest triplet excitation energy level (Ti level).

TABLE 2

| Type of Compound | S1 level (eV) | T1 level (eV) | ΔEST (eV) |
| --- | --- | --- | --- |
| Compound 1 | 2.64 | 2.48 | 0.16 |
| Compound 2 | 2.67 | 2.50 | 0.17 |
| Compound 11 | 2.73 | 2.64 | 0.09 |
| Compound 21 | 2.85 | 2.76 | 0.09 |
| Comparative Compound N1 | 2.60 | 2.46 | 0.14 |
| Comparative Compound N2 | 2.61 | 2.51 | 0.10 |
| Comparative Compound N3 | 2.68 | 2.59 | 0.09 |

Referring to the results in Table 2, Example Compounds 1, 2, 11, and 21 have a $\Delta E_{ST}$ value of 0.25 eV or less. Given that, it is believed that Compounds 1, 2, 11 and 21 may be used as a thermally activated delayed fluorescence dopant material. Comparative Example Compounds N1 to N3 also have low $\Delta E_{ST}$ values, and it is believed they may be used as a thermally activated delayed fluorescence dopant material.

3. Evaluation of Luminous Properties of Compounds

Fluorescence properties were evaluated using a V-670 spectrometer from JASCO. Using PPF shown below as a host material and Compounds 1, 2, 11, 21 and Comparative Example Compounds N1 to N3 as dopant materials, respectively, an organic layer was formed on a quartz glass after deposition.

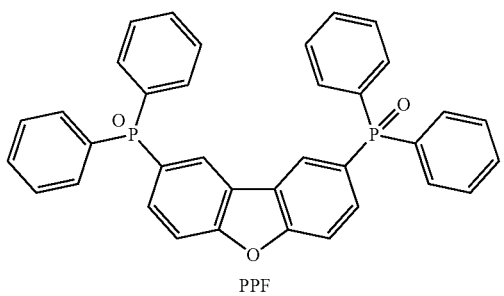

PPF

The ratio of the deposited host and dopant was 80:20. The fluorescence emission spectrum was measured in regard to the manufactured organic layer. Fluorescence quantum yield was measured using a ILF-835 integrating sphere system from JASCO.

Table 3 below shows the fluorescence emission characteristics of Examples and Comparative Examples, and $\lambda_{max}$ in the evaluation of fluorescence emission characteristics indicates an emission center wavelength representing the maximum emission intensity at the emission peak.

TABLE 3

| Example | Dopant Material | $\lambda_{max}$ (nm) | Fluorescence Quantum Yield (%) |
|---|---|---|---|
| Example 1 | Compound 1 | 470 | 75.1 |
| Example 2 | Compound 2 | 469 | 72.6 |
| Example 3 | Compound 11 | 463 | 76.0 |
| Example 4 | Compound 21 | 459 | 74.2 |
| Comparative Example 1 | Comparative Compound N1 | 495 | 80.0 |
| Comparative Example 2 | Comparative Compound N2 | 496 | 73.2 |
| Comparative Example 3 | Comparative Compound N3 | 485 | 65.0 |

Referring to the results in Table 3, Examples 1 to 4 and Comparative Examples 1 and 2 have similar values in fluorescence quantum yield. It is seen that the emission center wavelength, $\lambda_{max}$ of Examples 1 to 4, is in the short wavelength region, as compared with the center wavelength of Comparative Examples 1 to 3. That is, the results of Table 3 indicate that the Compounds 1, 2, 11 and 21 emit blue light in the short wavelength region as compared with the Comparative Example Compounds.

4. Manufacture and Evaluation of Organic Electroluminescence Devices (Manufacture of Organic Electroluminescence Devices)

An organic electroluminescence device of an embodiment including compounds of an embodiment in an emission layer was manufactured by the following method. Organic electroluminescence devices of Examples 1 to 4 were manufactured using Compounds 1, 2, 11, and 21, respectively, of the above-described Examples as dopant materials for the emission layer. Organic electroluminescence devices of Comparative Examples 1 to 3 were manufactured using Comparative Example Compounds N1 to N3, respectively, as dopant materials for the emission layer.

An ITO having a thickness of 1500 Å was patterned on a glass substrate, washed with ultrapure water, and ozone-treated after irradiating with UV for 10 minutes. Thereafter, HAT-CN was deposited to a thickness of 100 Å to form a hole injection layer, and a-NPD was deposited to a thickness of 400 Å to form a hole transport layer. Then, mCP was deposited to a thickness of 50 Å to form an electron blocking layer.

Next, mCBP and the Example Compounds or the Comparative Example Compounds, respectively, were co-deposited at 1:99 on the electron blocking layer to form an emission layer having a thickness of 200 Å. That is, the emission layers formed by co-deposition in Examples 1 to 4 were deposited by mixing the Compounds 1, 2, 11, and 21 with mCBP, respectively, and the emission layers in Comparative Examples 1 to 3 were deposited by mixing Comparative Example Compounds N1 to N3 with mCBP, respectively.

An electron transport layer having a thickness of 300 Å was formed of 2,2',2"-(1,3,5-Benzinetriyl)-tris(1-phenyl-1-H-benzimidazole) (TPBi) on the emission layer. Thereafter, an electron injection layer having a thickness of 50 Å was formed of LiF. Then, a second electrode having a thickness of 1000 Å was formed of aluminum (Al).

In an embodiment, the hole injection layer, the hole transport layer, the electron blocking layer, the emission layer, the electron transport layer, the electron injection layer, and the second electrode were formed using a vacuum deposition apparatus.

(Evaluation of Organic Electroluminescence Device Characteristics)

Table 4 shows the evaluation results of the organic electroluminescence devices of Examples 1 to 4 and Comparative Examples 1 to 3. $\lambda$max, which is an emission center wavelength, luminous efficiency, and lifetime of the organic electroluminescence devices were compared. In the characteristics evaluation results of the Examples and Comparative Examples shown in Table 4, voltage and current density were measured using a source meter (2400 series from Keithley Instruments), and luminance and external quantum efficiency were measured using an external quantum efficiency measuring apparatus (C9920-12 from HAMAMATSU Photonics). Luminous efficiency represents current efficiency values for the current density of 10 mA/cm$^2$ and lifetime represents the half-lifetime at 1.0 mA/cm$^2$.

In Table 4, luminous efficiency and lifetime were compared and shown by relative values. The luminous efficiency and lifetime in Comparative Example 1 were set at 1, and the luminous efficiency and lifetime of Comparative Examples and Examples were shown in a relative sense.

TABLE 4

| Example | Dopant Material | $\lambda_{max}$ (nm) | Luminous efficiency | Lifetime |
|---|---|---|---|---|
| Example 1 | Compound 1 | 475 | 1.25 | 2.50 |
| Example 2 | Compound 2 | 470 | 1.10 | 2.20 |
| Example 3 | Compound 11 | 466 | 1.15 | 2.30 |
| Example 4 | Compound 21 | 463 | 1.20 | 2.15 |
| Comparative Example 1 | Comparative Compound N1 | 497 | 1.00 | 1.00 |
| Comparative Example 2 | Comparative Compound N2 | 499 | 0.82 | 0.95 |
| Comparative Example 3 | Comparative Compound N3 | 488 | 0.76 | 0.57 |

Referring to the results of Table 4, it is confirmed that the organic electroluminescence devices of Examples 1 to 4 have good luminous efficiency and long life device characteristics when compared to the organic electroluminescence devices of Comparative Examples 1 to 3. Further, the organic electroluminescence devices of Examples 1 to 4 have the maximum emission λmax in the short wavelength region when compared with the organic electroluminescence devices of Comparative Examples 1 to 3, and thus it is seen that the organic electroluminescence devices of Examples 1 to 4 emit deep blue light, which is short blue light, when compared with Comparative Examples 1 to 3.

It is believed that the Example Compounds include a nitrogen-containing ring group in the carbazole group to weaken the electron donating of the carbazole group, thereby emitting short, deep blue light. In addition, the inclusion of a nitrogen-containing ring group expands the conjugate range of the carbazole group, and thus the nitrogen-containing ring group contributes to the stability of the compounds by forming an intramolecular hydrogen bond or an intermolecular hydrogen bond.

Meanwhile, Comparative Example Compound N2 includes a nitrogen-containing ring group attached to the carbazole group, similar to the compound of the present disclosure, but has a long wavelength value when compared to the Example Compounds. It is believed that an electron withdrawing methyl group that is substituted on a carbazole group that does not include a nitrogen-containing ring group, may make the wavelength longer. In addition, the steric distortion of the compound is generated due to the methyl group, and the stability of the compound is reduced, and thus the device lifetime is lower than that of the Example Compounds.

Referring to the evaluation results of the Examples Compounds and the Examples of the organic electroluminescence device, it is seen that the compounds of an embodiment may be used as a luminous material that emits deep blue light and has a long life characteristic. In addition, it is seen that the organic electroluminescence device of an embodiment that includes the compound of an embodiment to emit deep blue light, has good efficiency and long life characteristics.

The aromatic compound of an embodiment may include a nitrogen-containing ring group attached to the carbazole group that is directly bonded to a benzene ring, and may be used as a material that emits deep blue light while having a long life characteristic. The organic electroluminescence device including the aromatic compound of an embodiment may emit deep blue light while having good luminous efficiency and long life device characteristics.

An organic electroluminescence device of an embodiment may have improved device characteristics such as high efficiency and long life in a blue wavelength region.

An aromatic compound of an embodiment may be included in an emission layer of the organic electroluminescence device to provide the organic electroluminescence device having high efficiency.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the present disclosure has been described with reference to example embodiments of the present disclosure, it will be understood that the present disclosure should not be limited to these embodiments, but that various changes and modifications can be made by those skilled in the art without departing from the spirit and scope of the present disclosure.

Accordingly, the technical scope of the present disclosure is not intended to be limited to the contents set forth in the detailed description of the specification, but is intended to be defined by the appended claims and their equivalents.

What is claimed is:

1. An organic electroluminescence device, comprising:
a first electrode;
a second electrode on the first electrode; and
an emission layer between the first electrode and the second electrode, the emission layer comprising an aromatic compound,
wherein the first electrode and the second electrode each independently comprise a transmissive electrode, a transflective electrode or a reflective electrode, the transmissive electrode comprising at least one selected from indium tin oxide, indium zinc oxide, zinc oxide and indium tin zinc oxide, and the transflective and reflective electrode each independently comprising at least one selected from Ag, Mg, Cu, Al, Pt, Pd, Au, Ni, Nd, Ir, Cr, Li, Ca, LiF/Ca, LiF/Al, Mo, Ti, a compound thereof, and a mixture thereof,
wherein the aromatic compound comprises:
a benzene ring;
two unsubstituted carbazole groups directly bonded to the benzene ring;
two substituted carbazole groups directly bonded to the benzene ring and each substituted with a nitrogen-containing ring group that is a pyridine group or a pyrimidine group; and
a substituent directly bonded to the benzene ring and is a cyano group, a fluorine, or a C1-C10 alkyl group substituted with a fluorine.

2. The organic electroluminescence device of claim 1, wherein the emission layer is to emit delayed fluorescence.

3. The organic electroluminescence device of claim 1, wherein the two unsubstituted carbazole groups are bonded to the benzene ring to be symmetric with each other with respect to the substituent directly bonded to the benzene ring, and
the two substituted carbazole groups are bonded to the benzene ring to be symmetric with each other with respect to the substituent directly bonded to the benzene ring.

4. The organic electroluminescence device of claim 1, wherein the substituent directly bonded to the benzene ring and each of the two unsubstituted carbazole groups are bonded to the benzene ring at ortho-positions respectively, and
the substituent directly bonded to the benzene ring and each of the two substituted carbazole groups are bonded to the benzene ring at meta-positions respectively.

5. The organic electroluminescence device of 1, wherein the emission layer comprises at least one of the compounds of Compound Group 1:

Compound Group 1
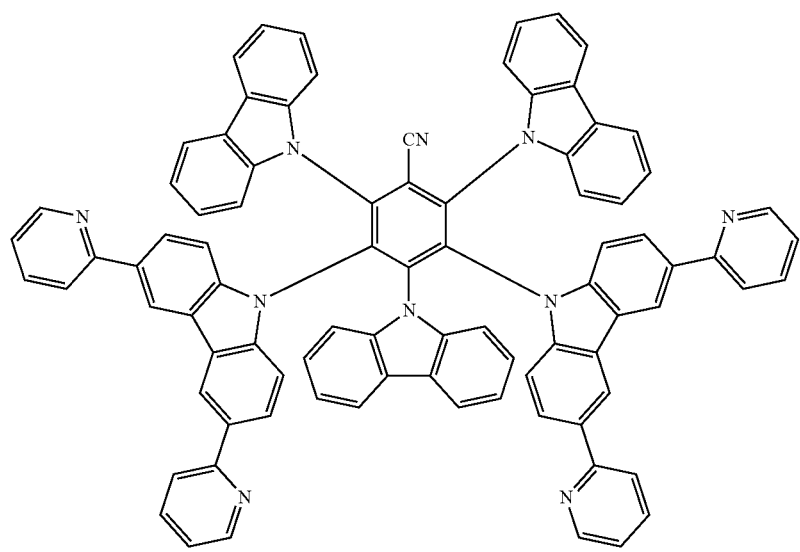
1
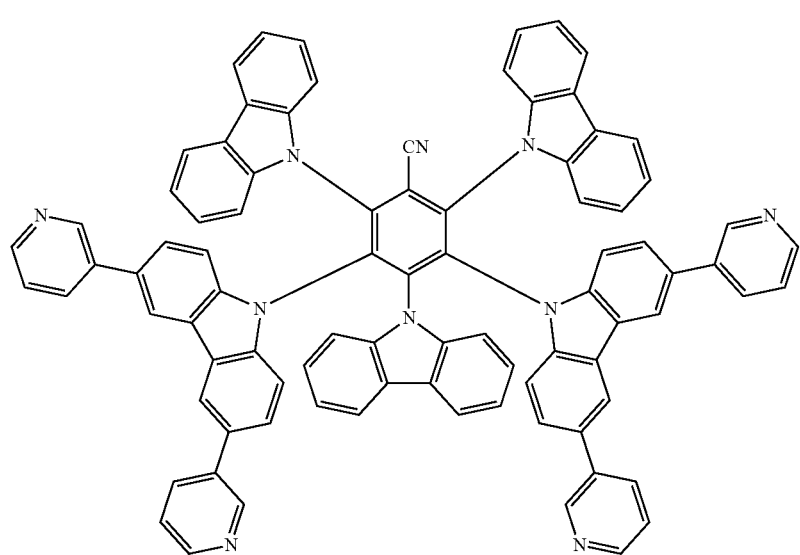
2

3
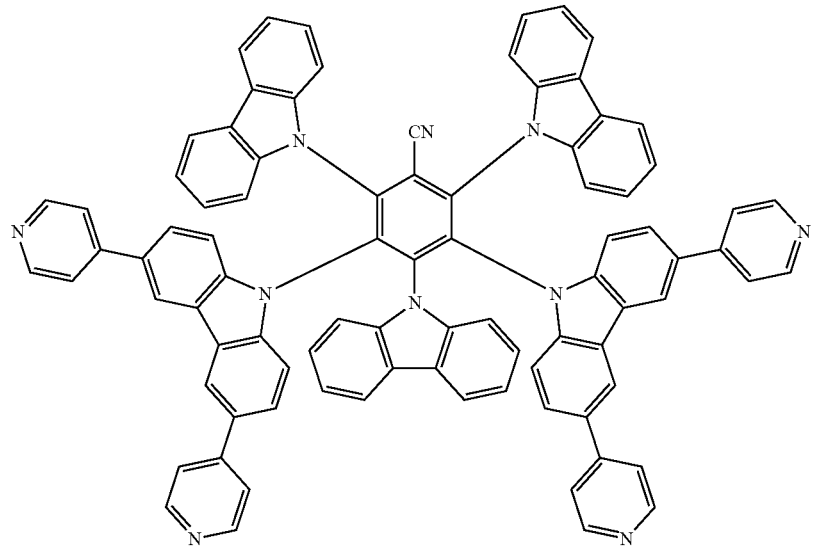
4
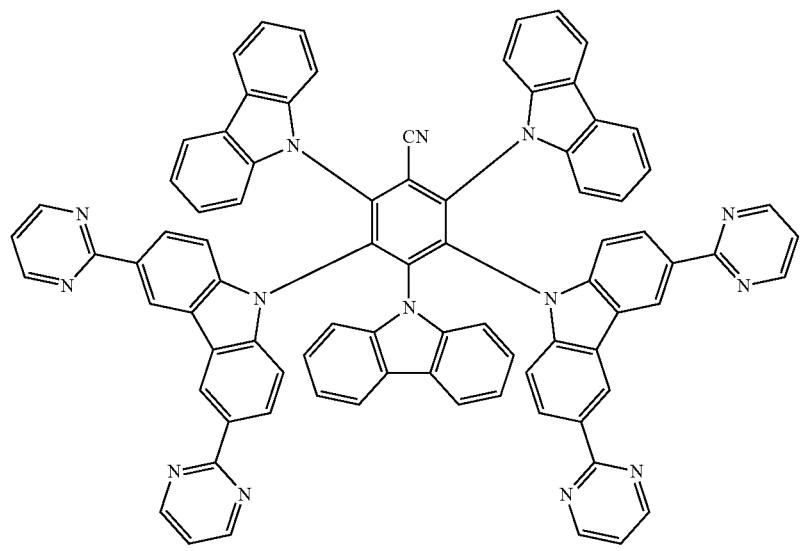
5
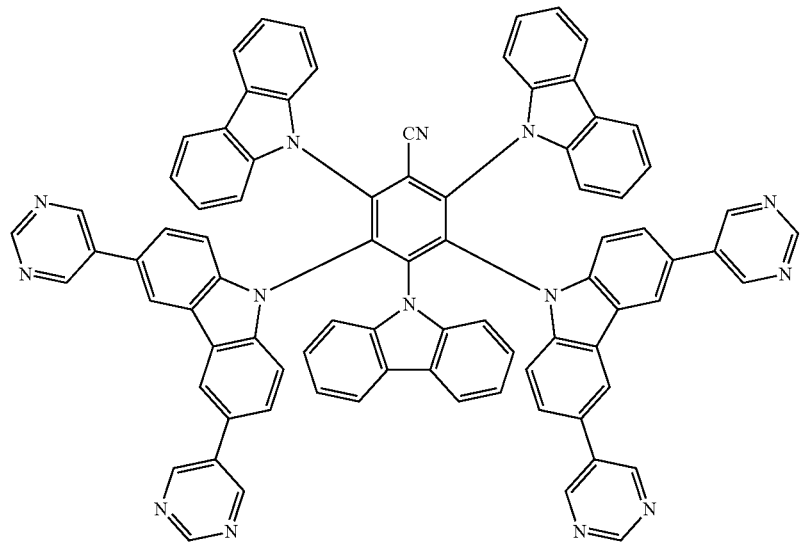

6
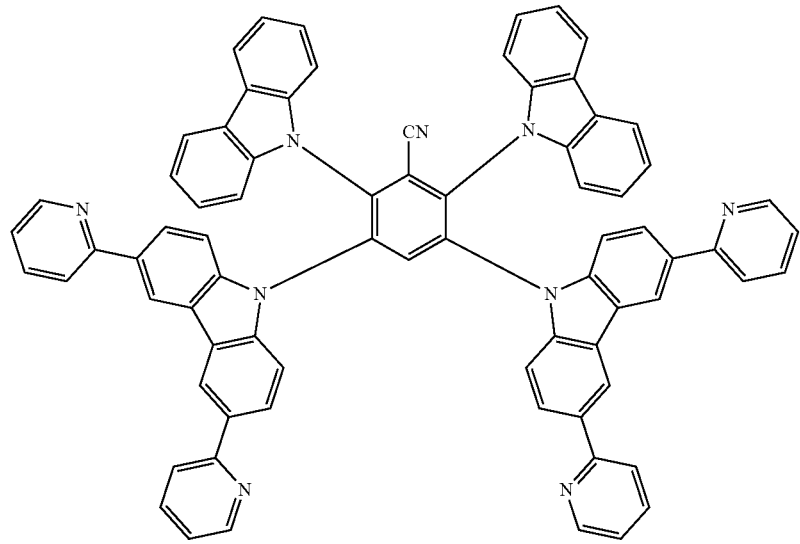
7
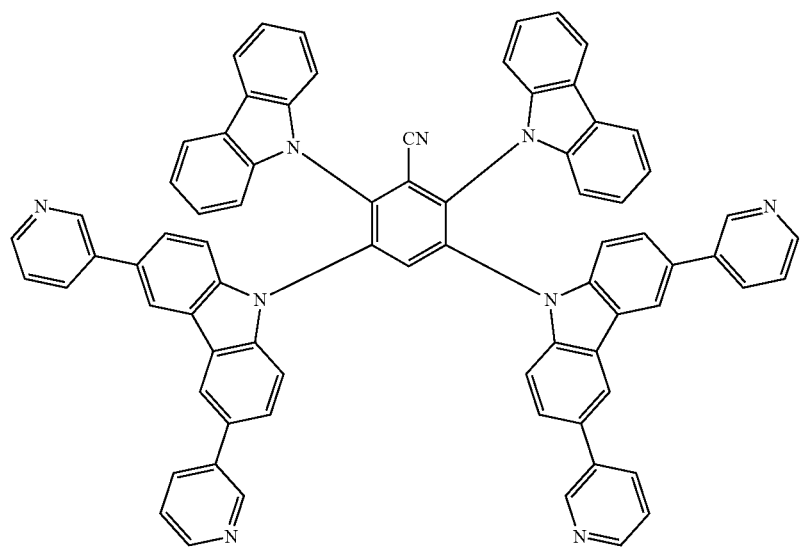
8
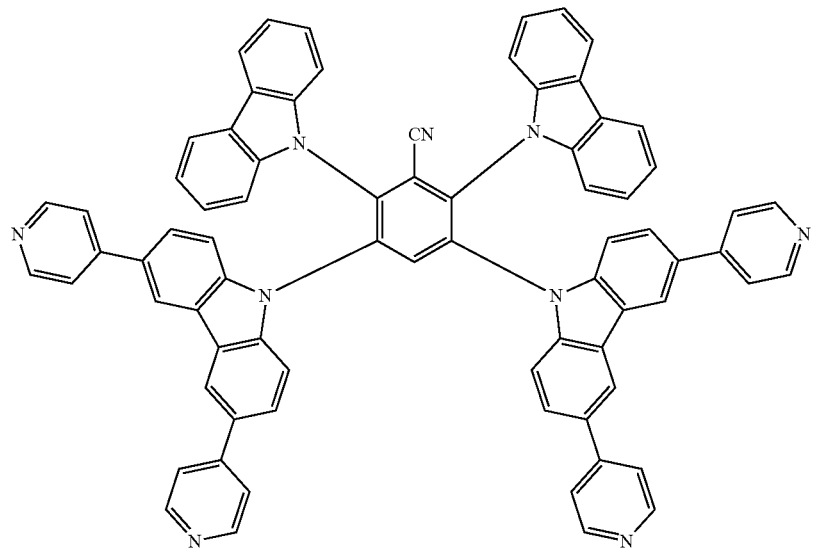

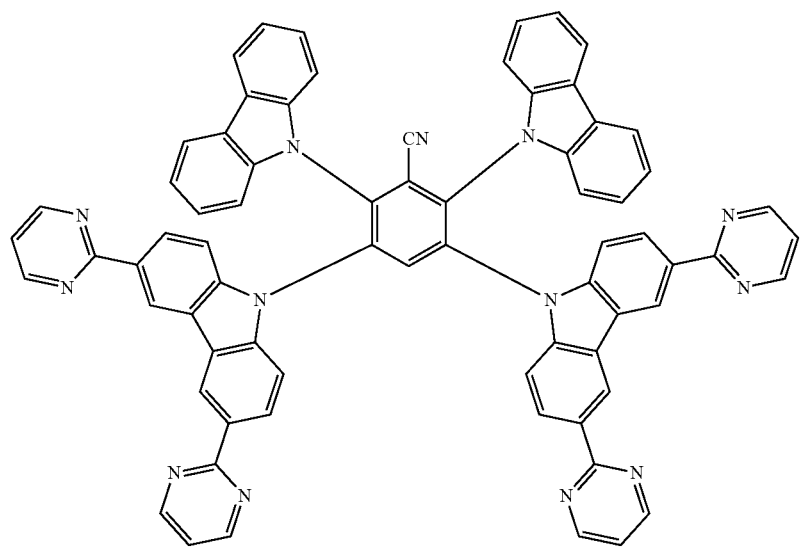
9
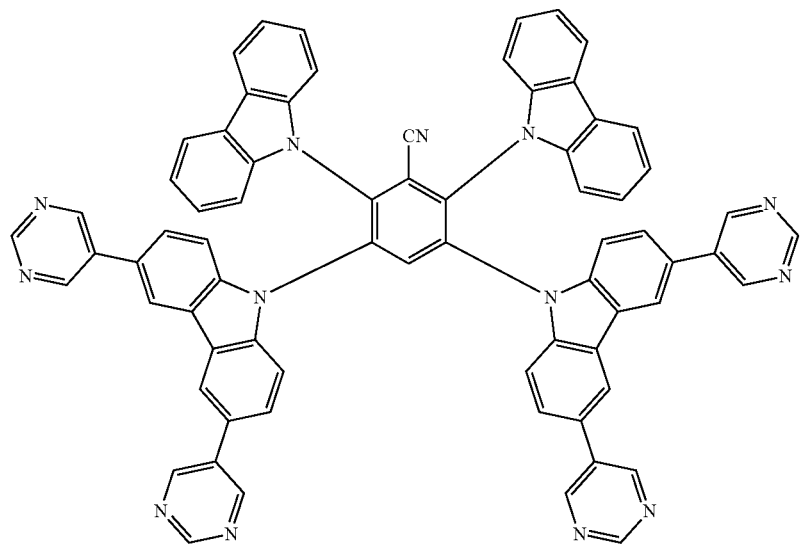
10
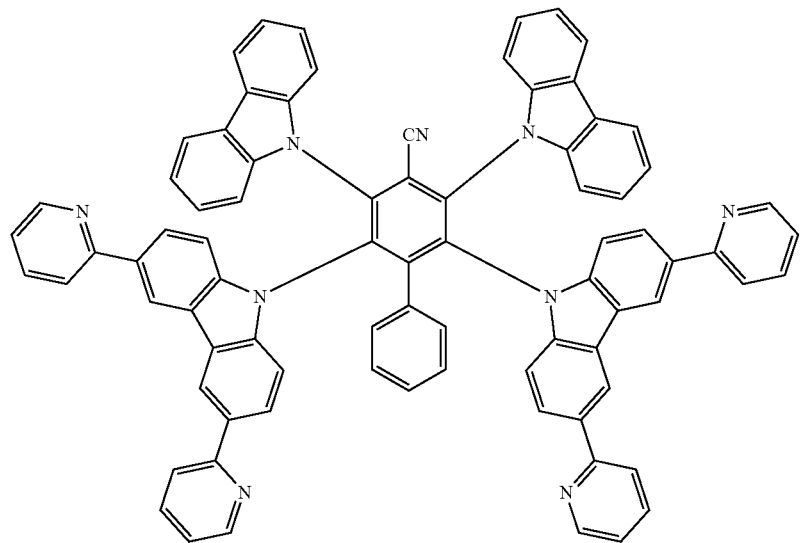
11

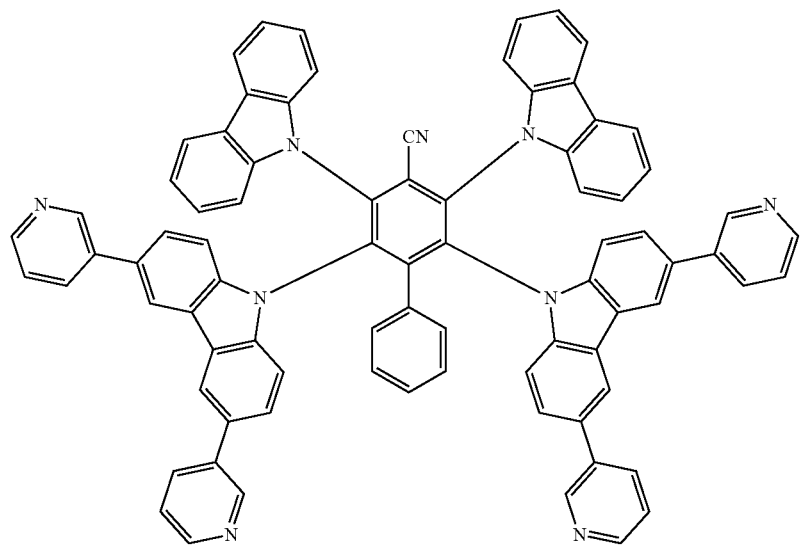
12
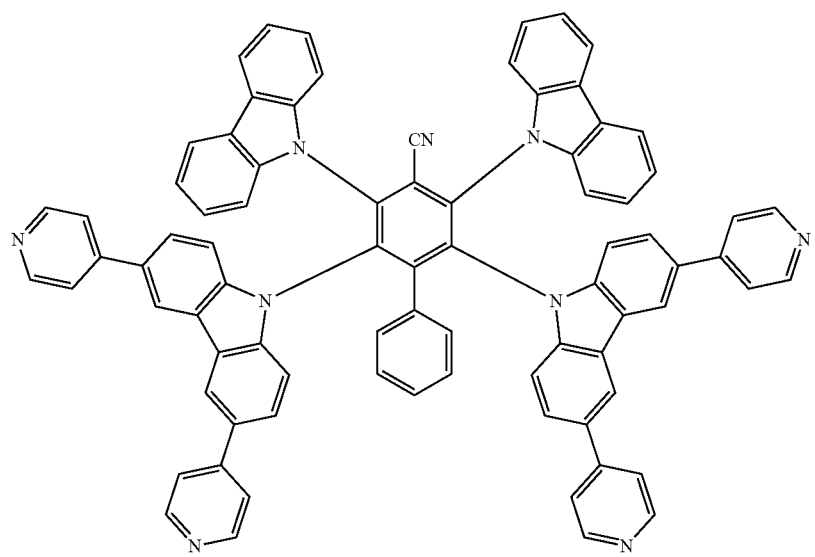
13
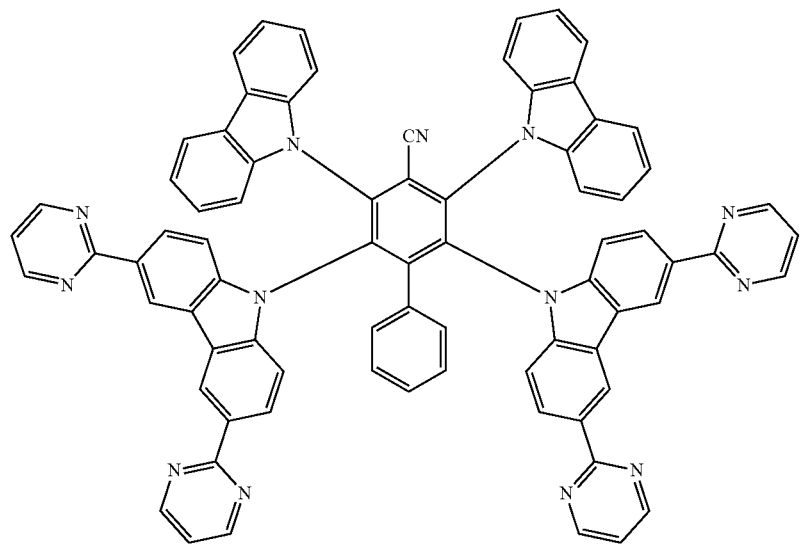
14

-continued
15
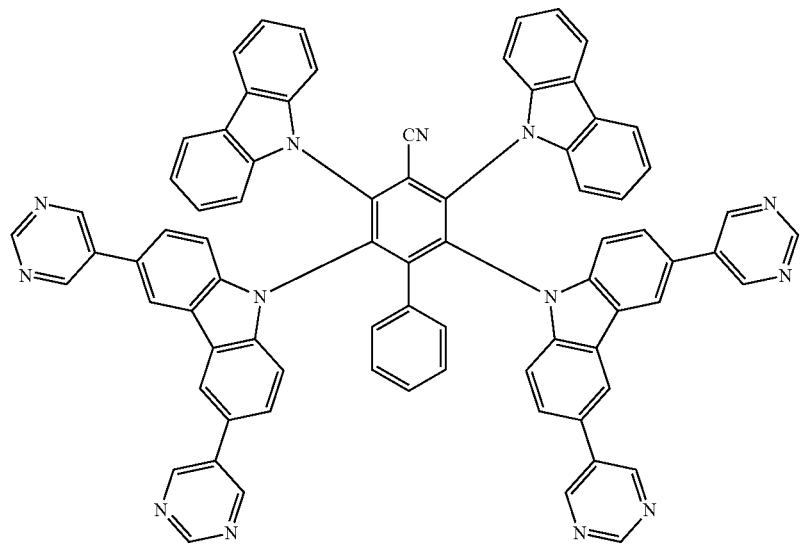
16
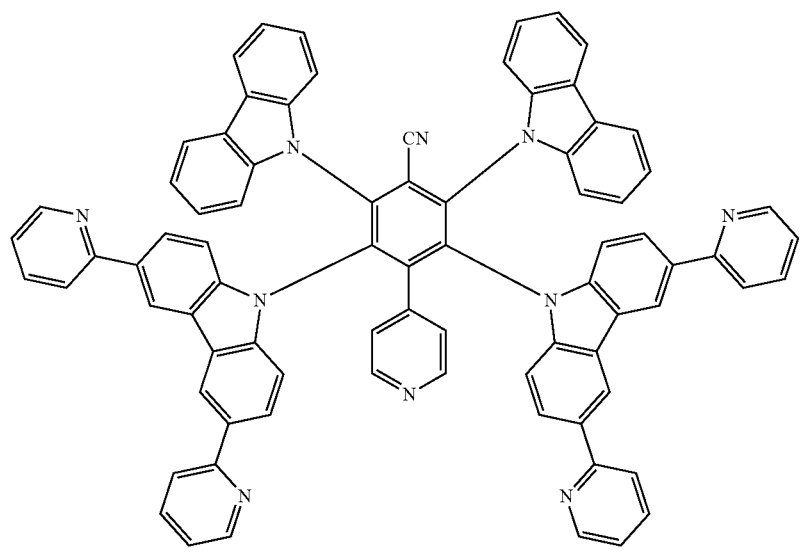
17
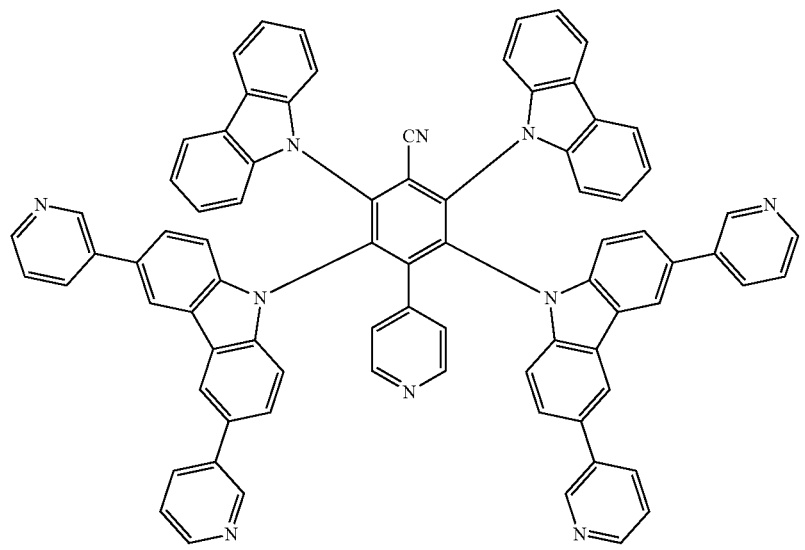

-continued
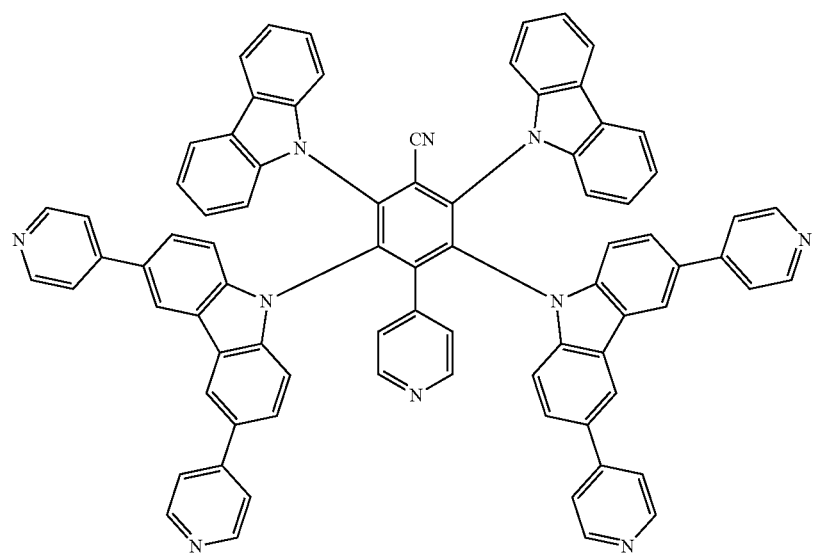
18
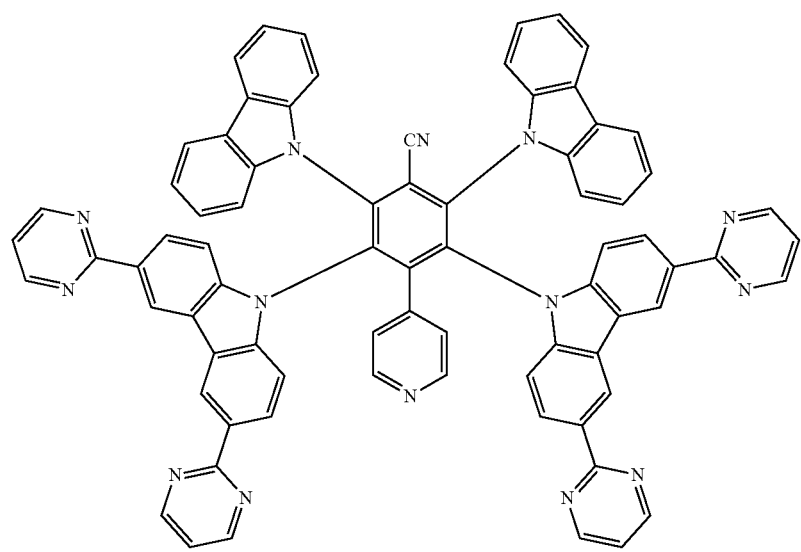
19
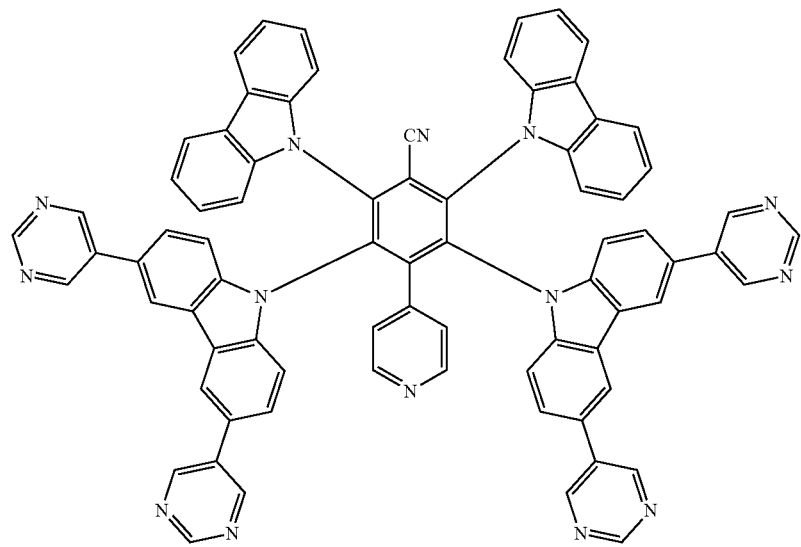
20

-continued
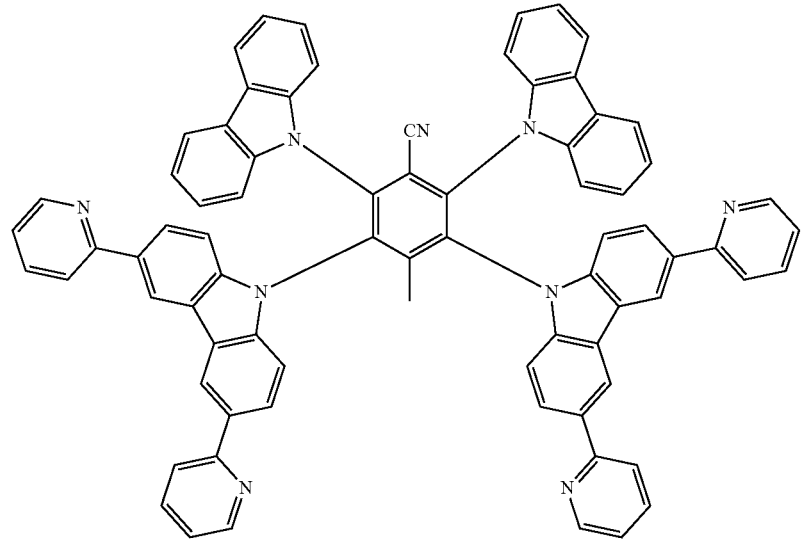
21
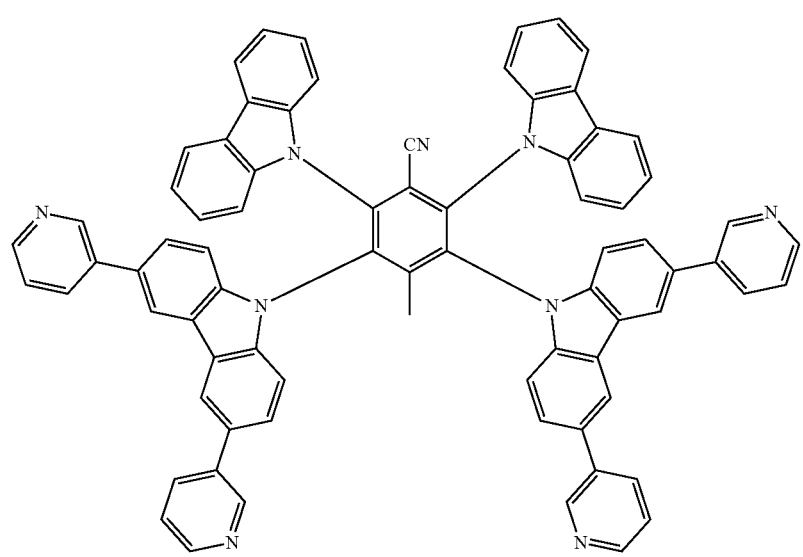
22
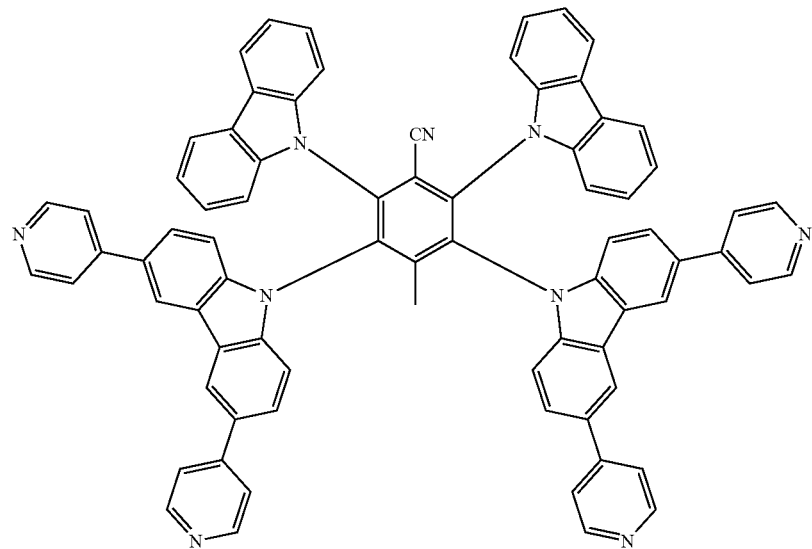
23

-continued
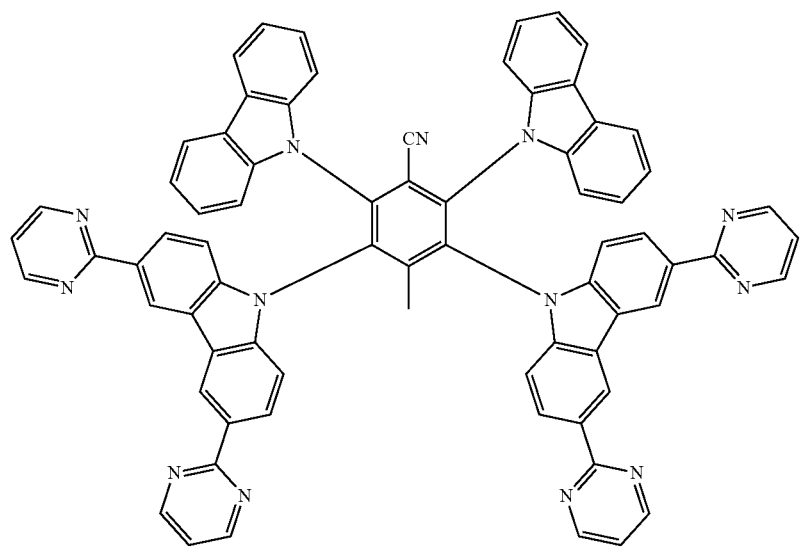
24
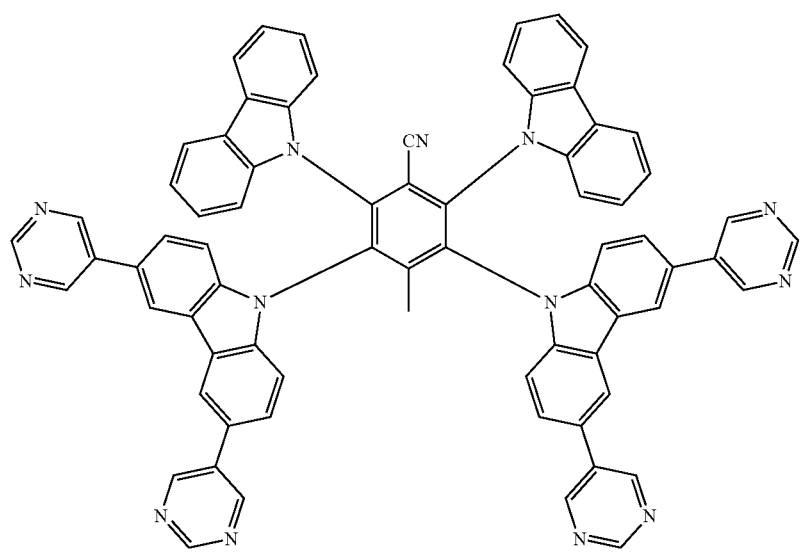
25
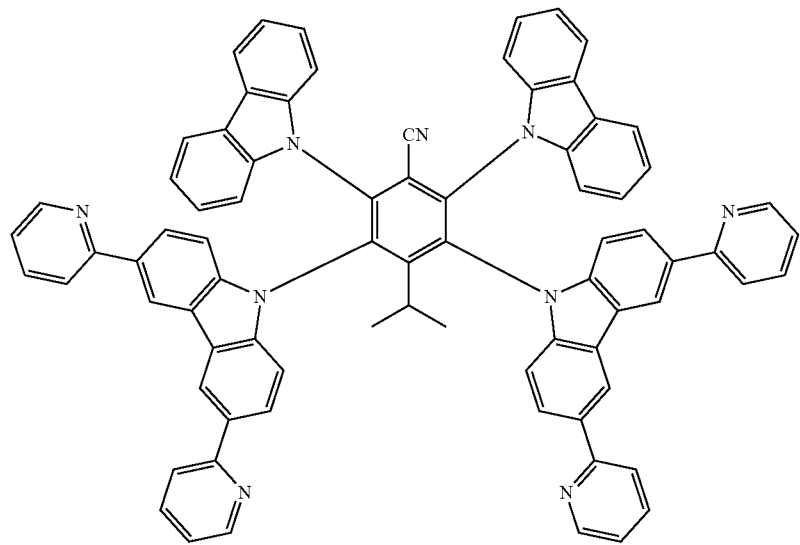
26

-continued
27
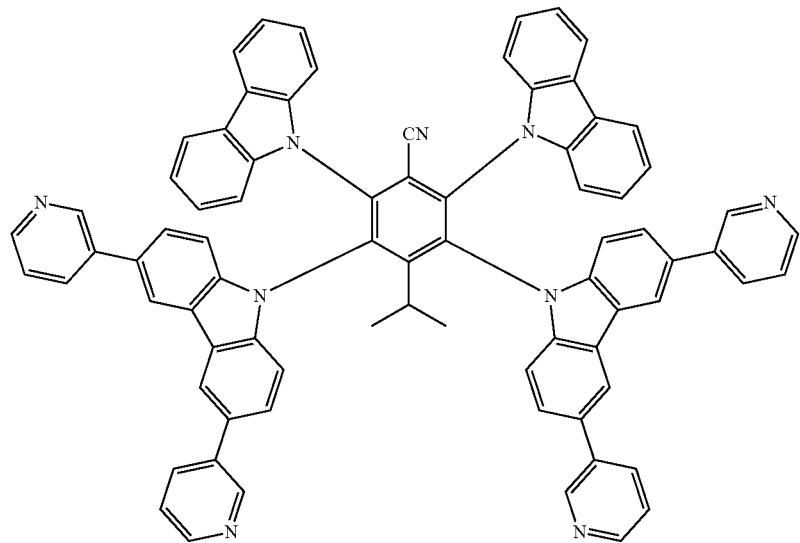
28
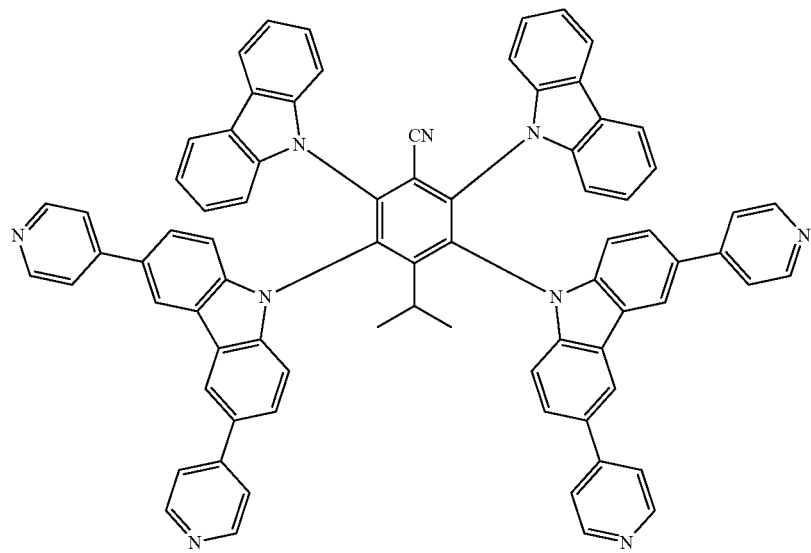
29
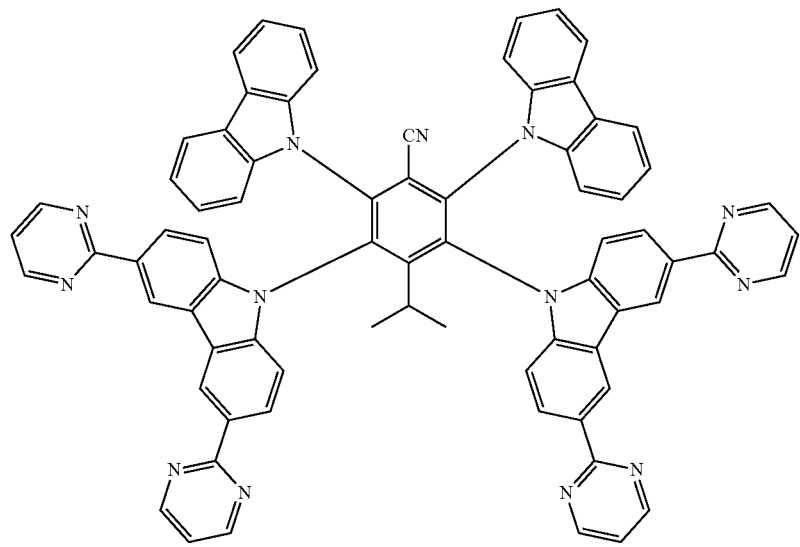

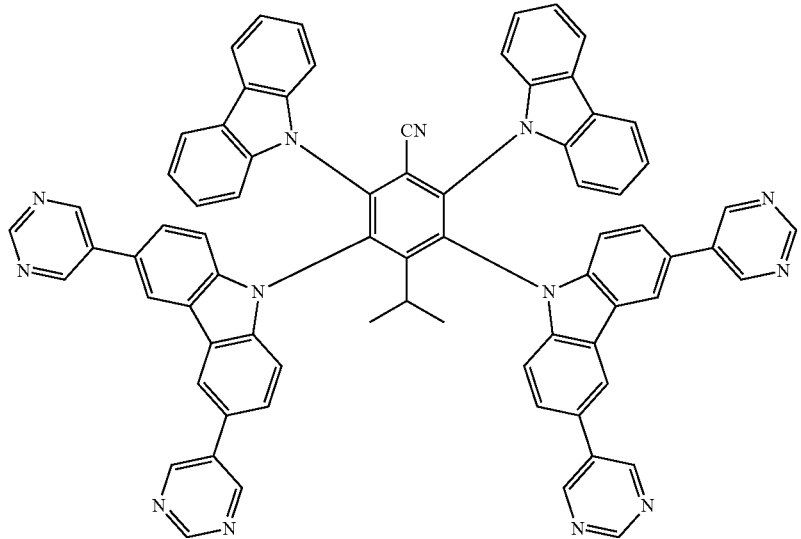
30
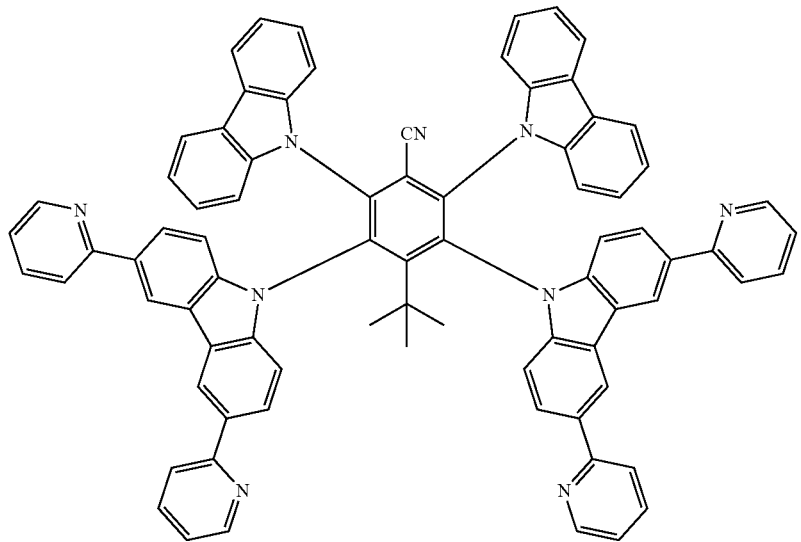
31
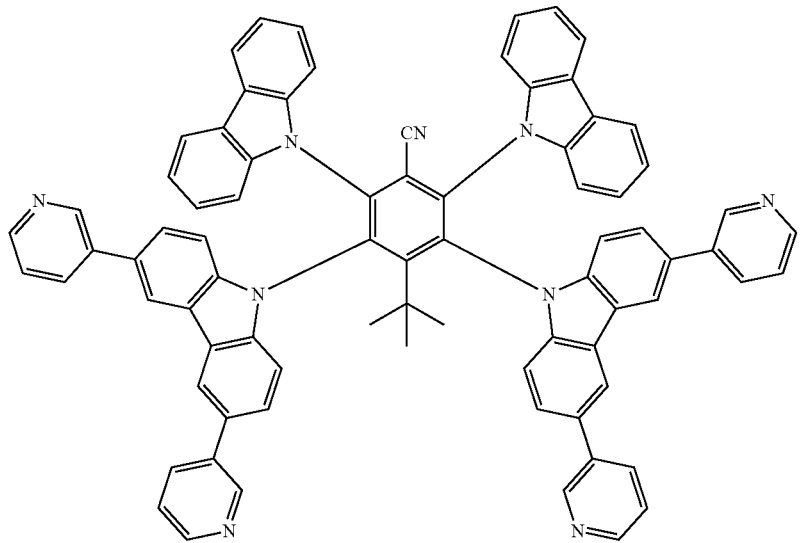
32

-continued
33
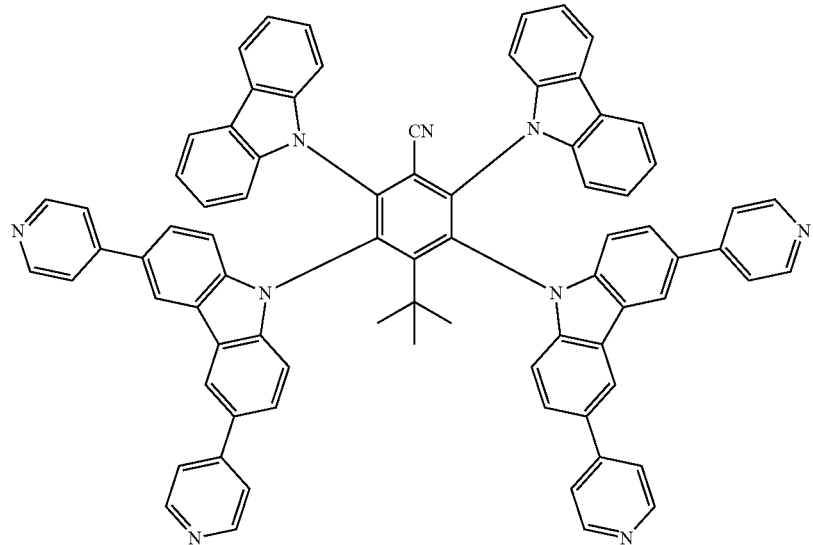
34
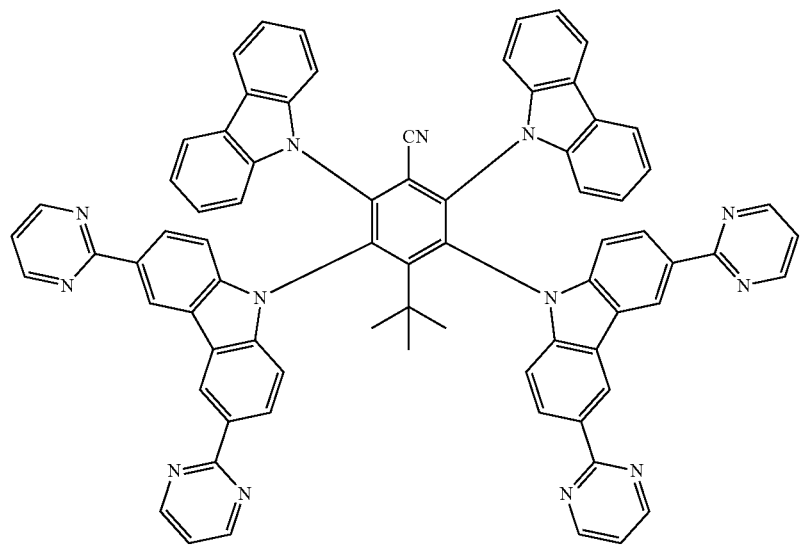
35
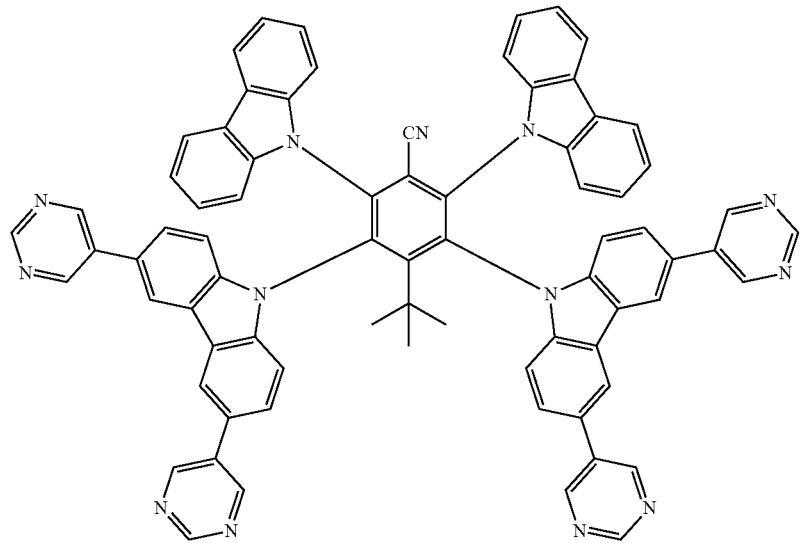

-continued
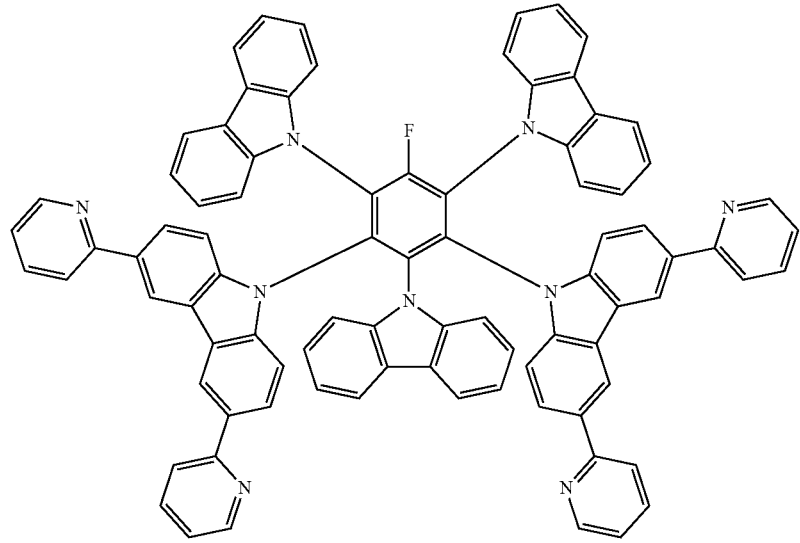
36
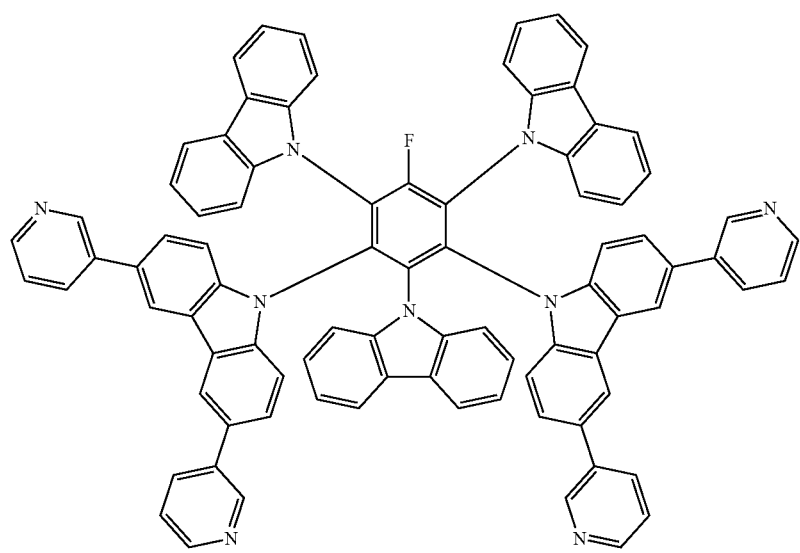
37
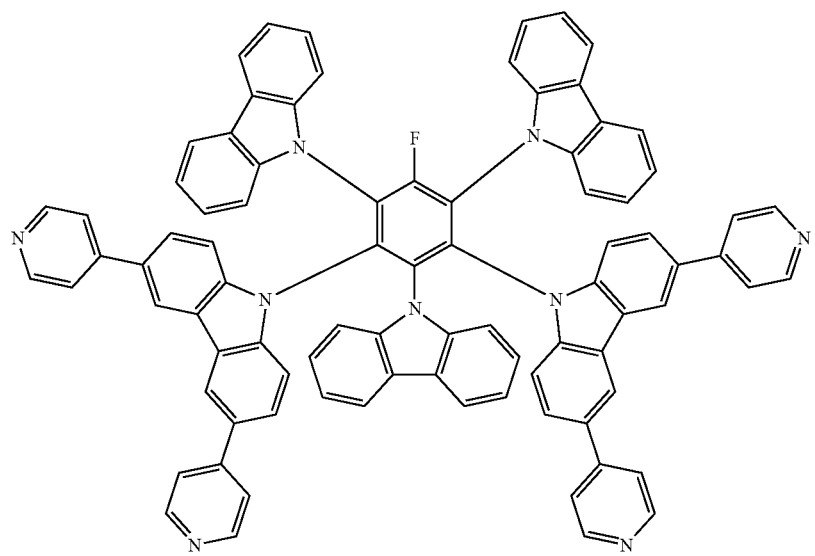
38

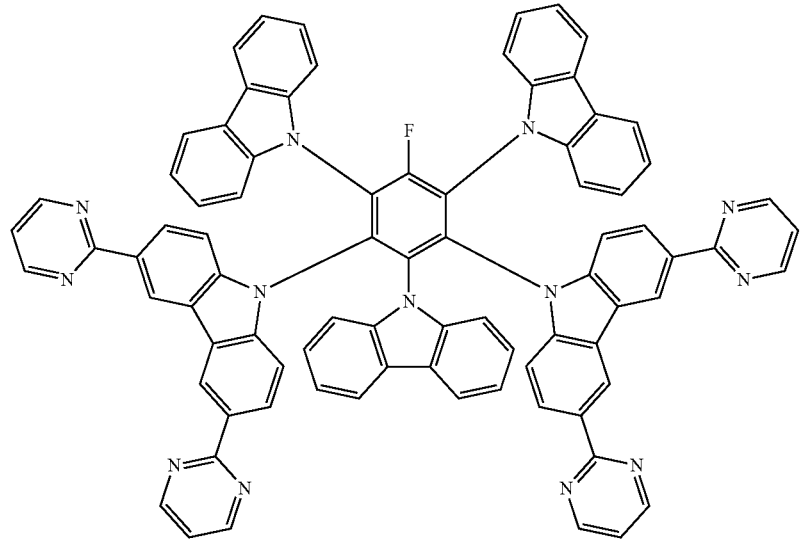
39
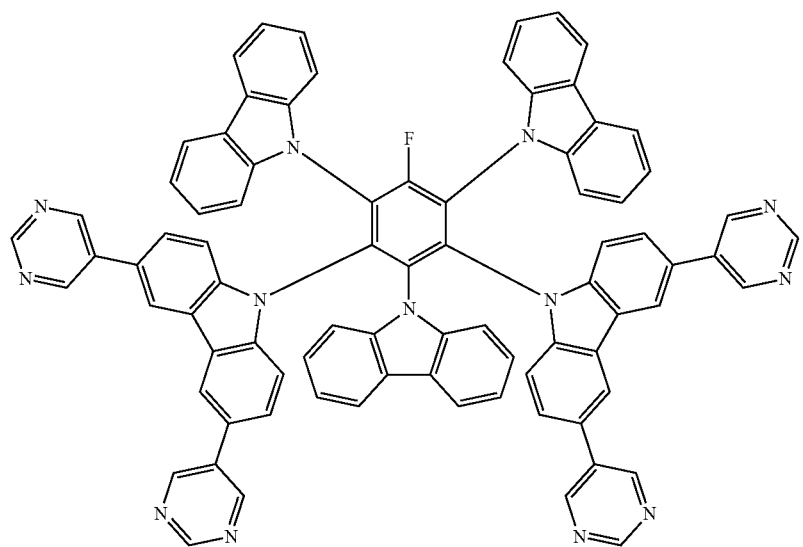
40
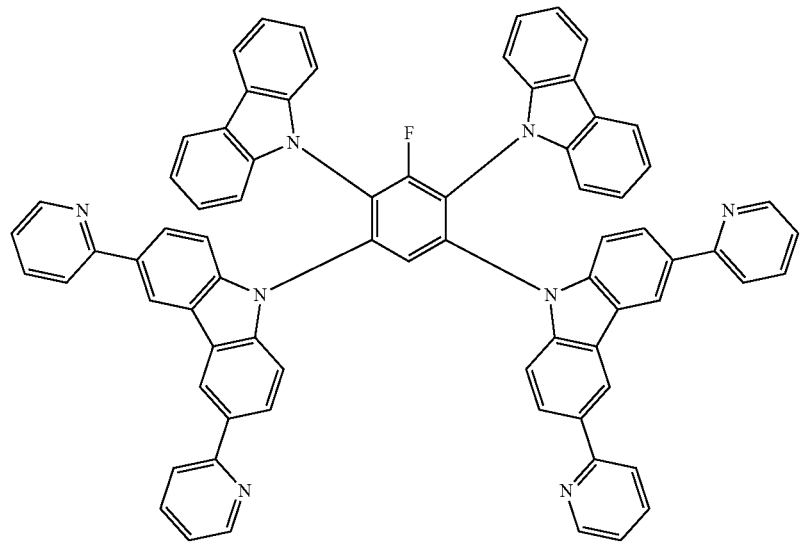
41

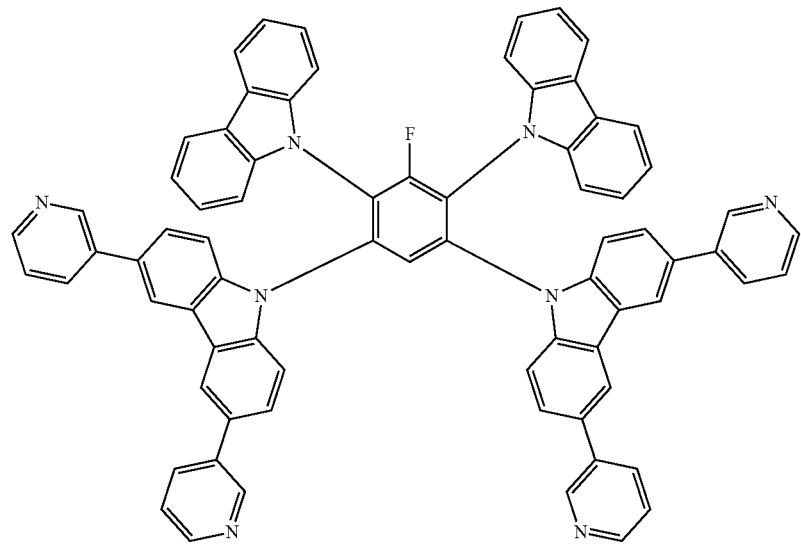
42
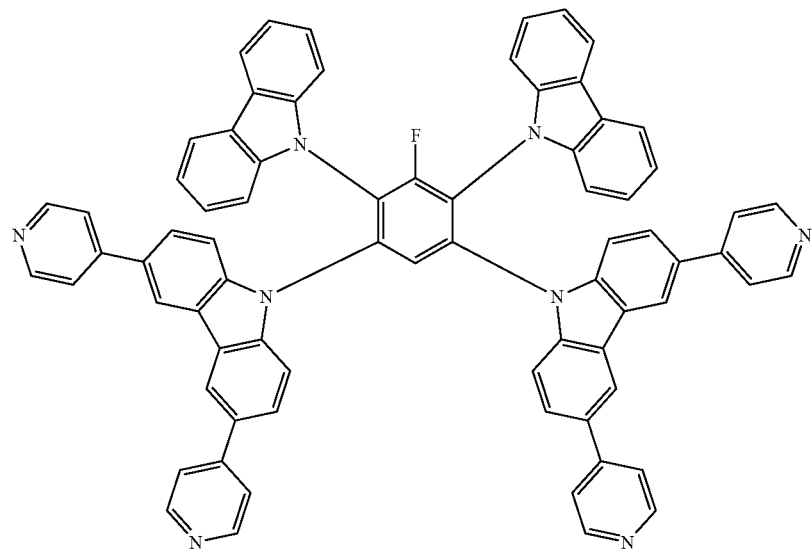
43
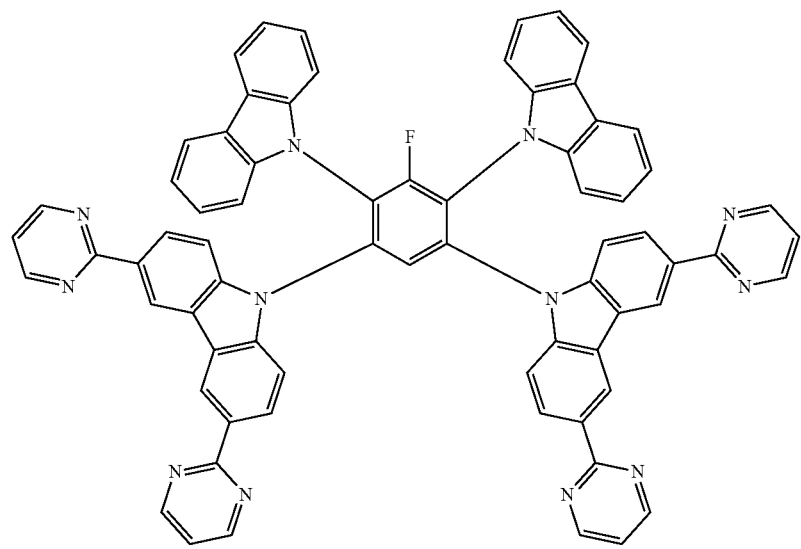
44

45
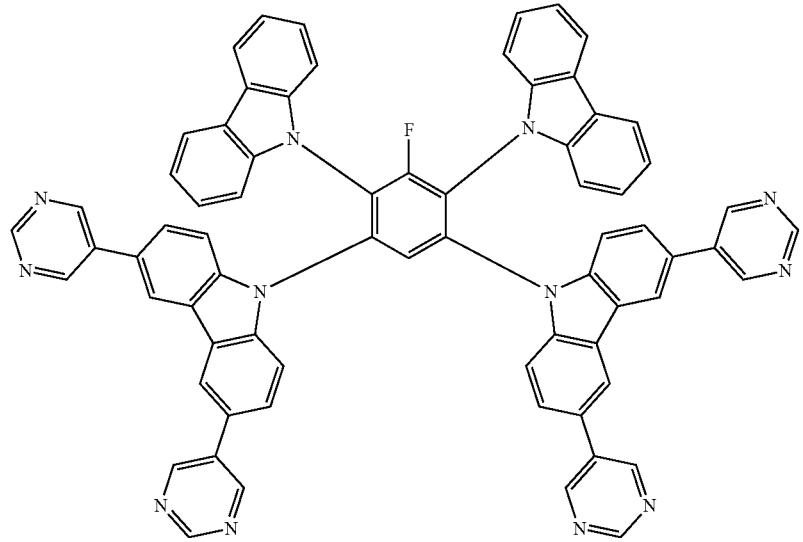
46
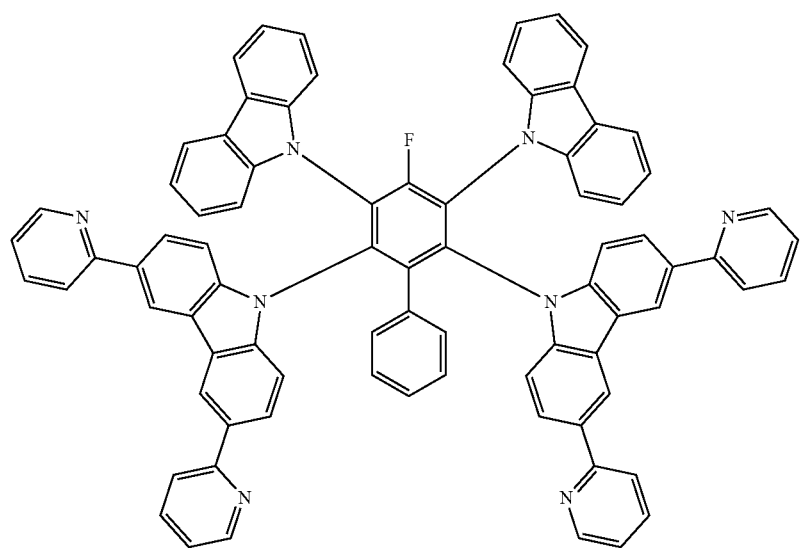
47
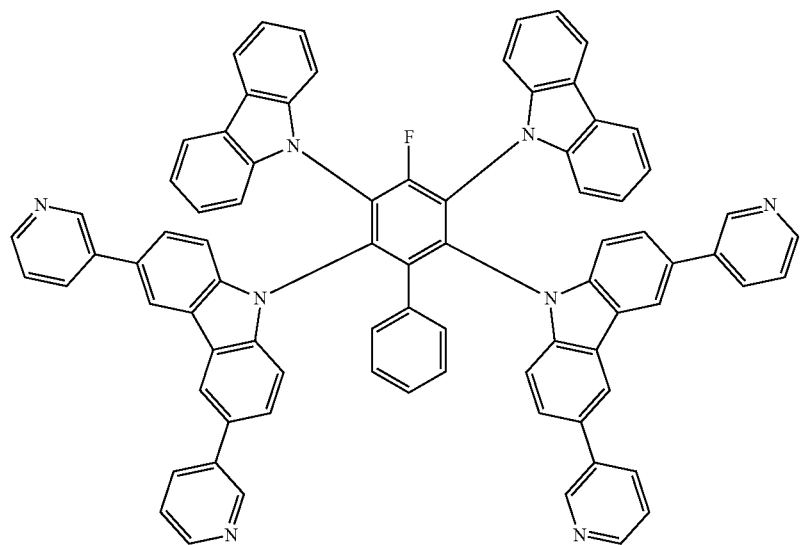

-continued
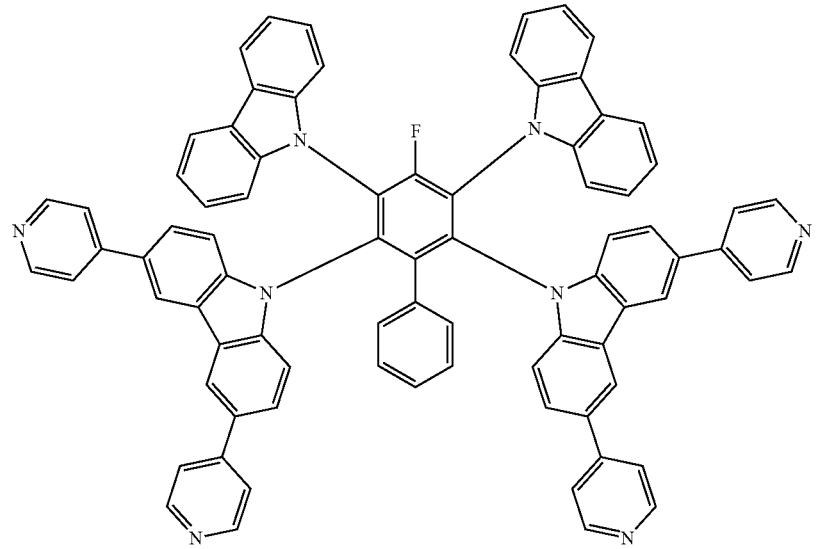
48
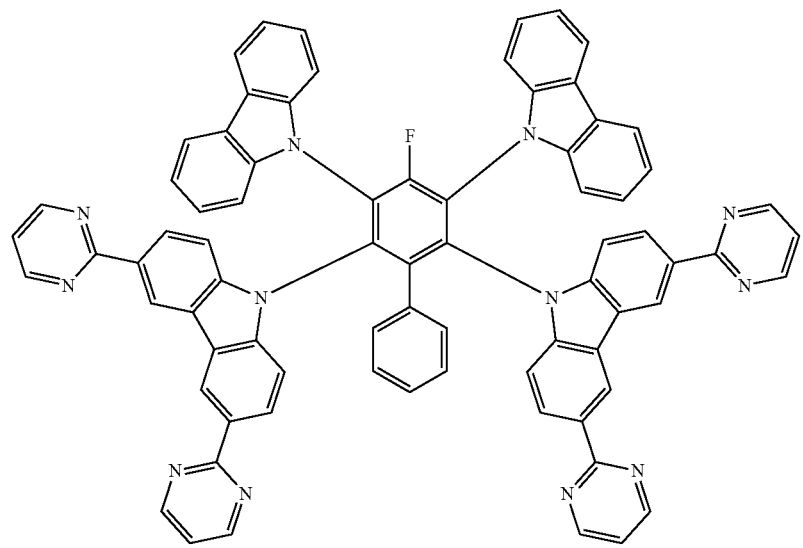
49
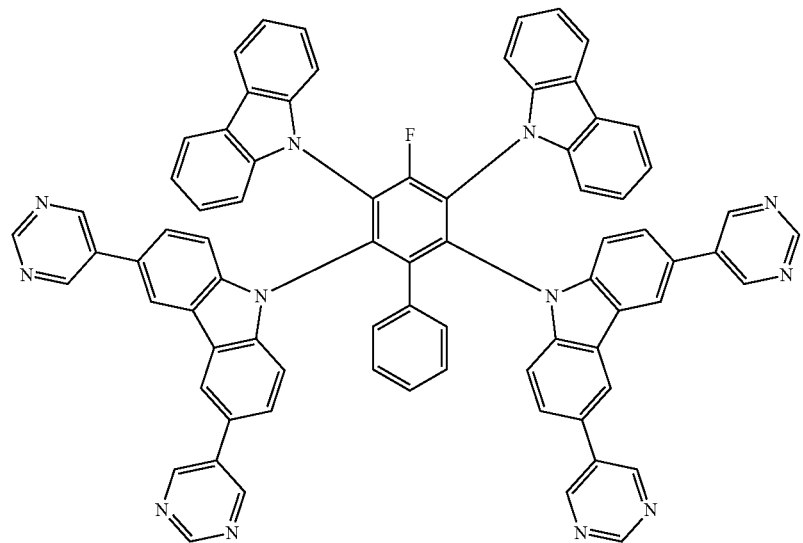
50

51
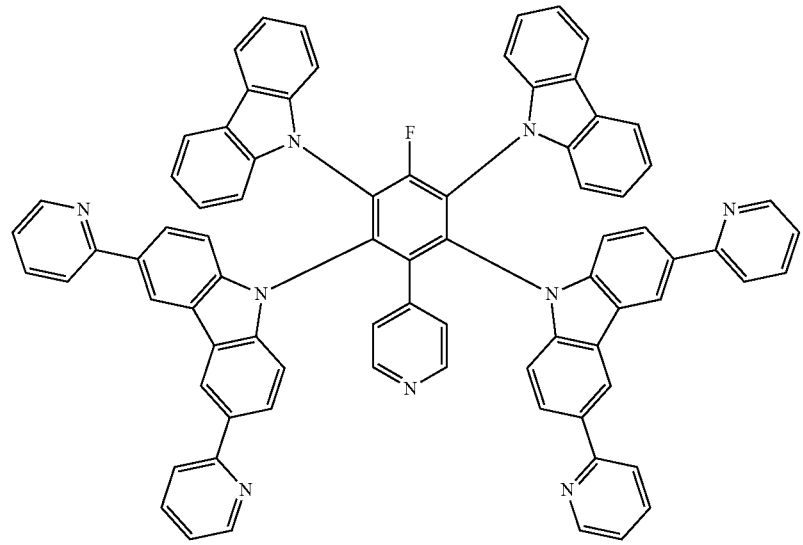
52
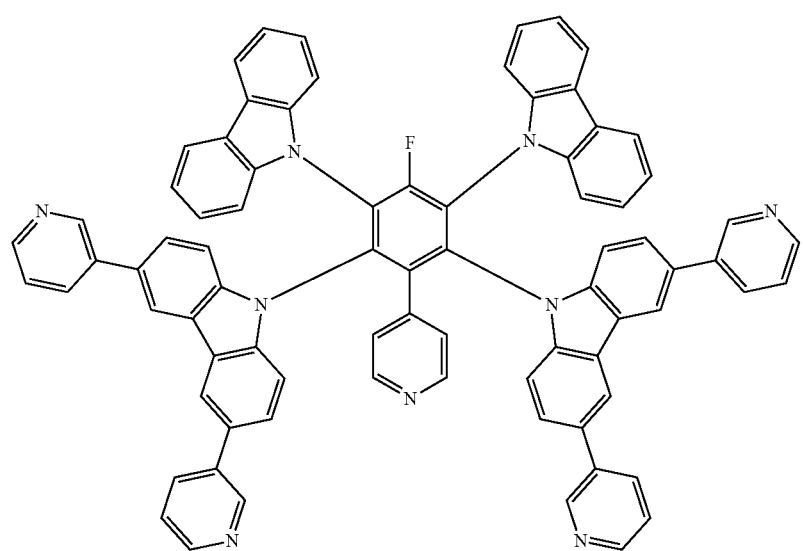
53
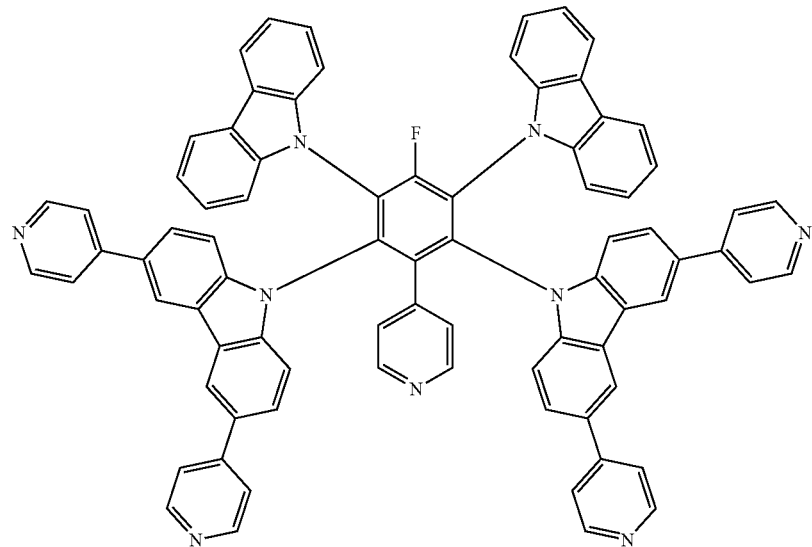

-continued
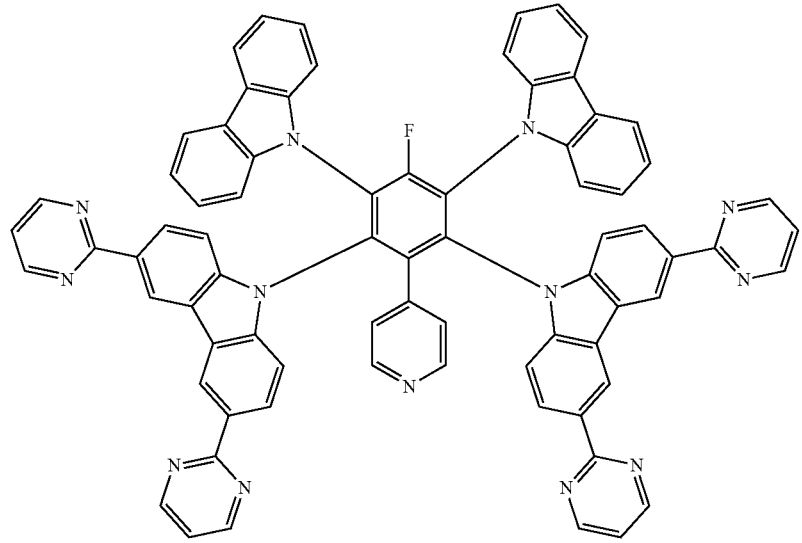
54
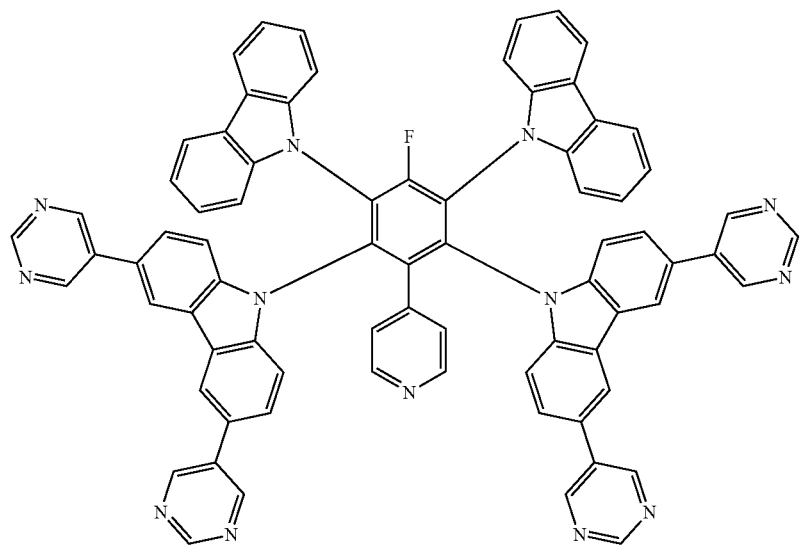
55
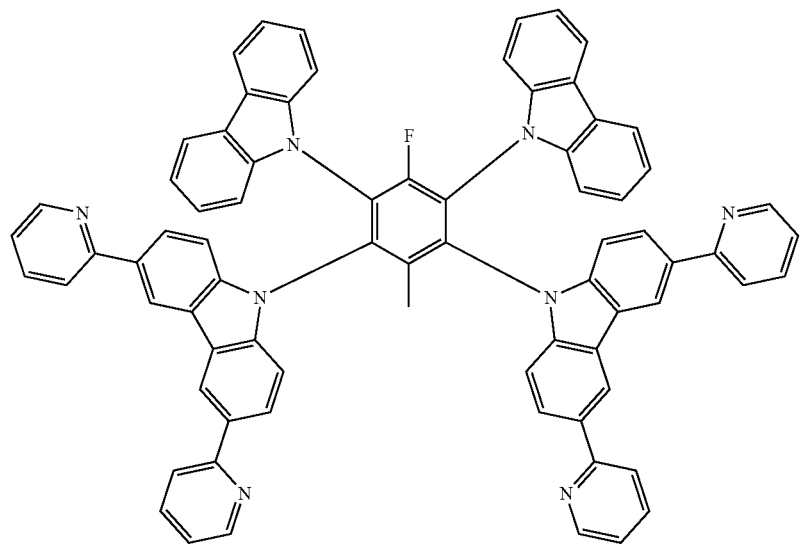
56

-continued
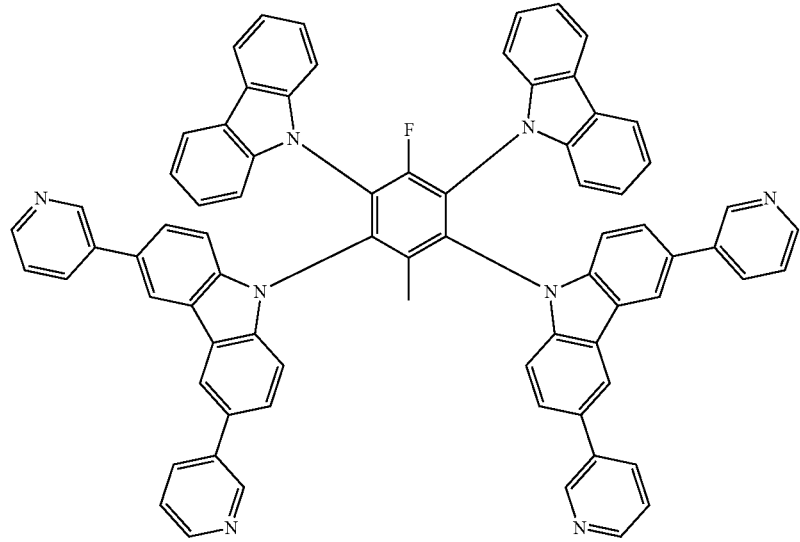
57
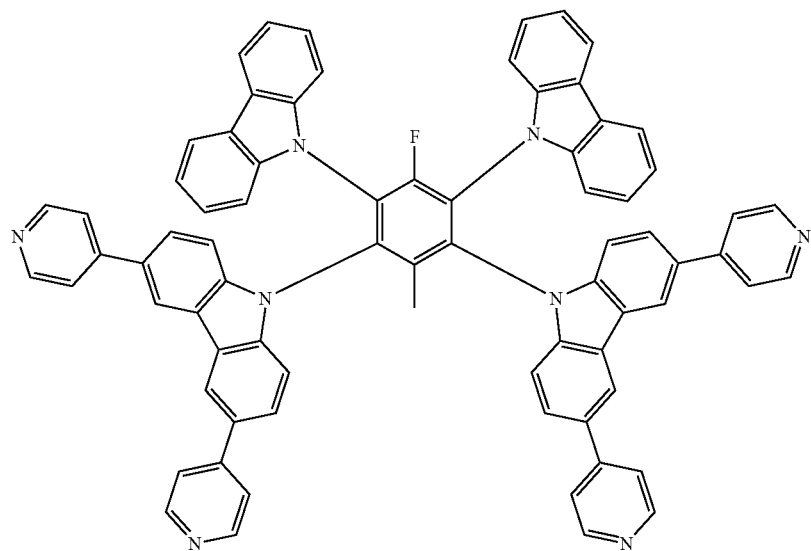
58
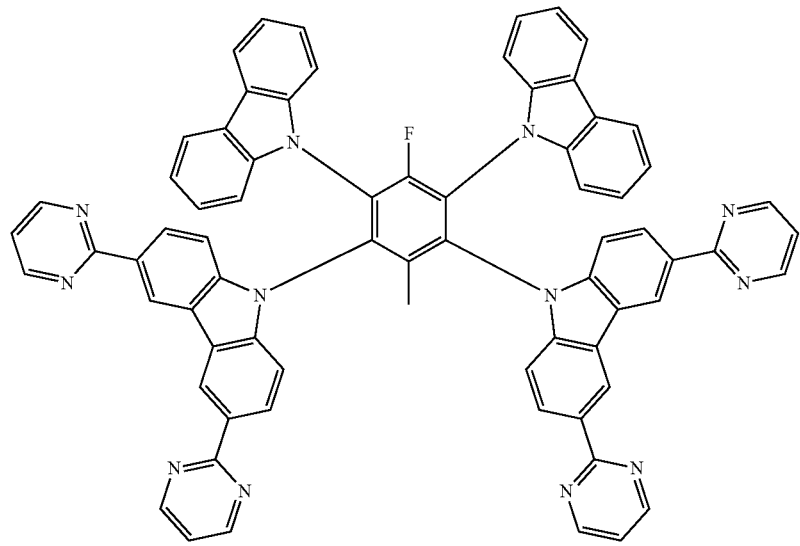
59

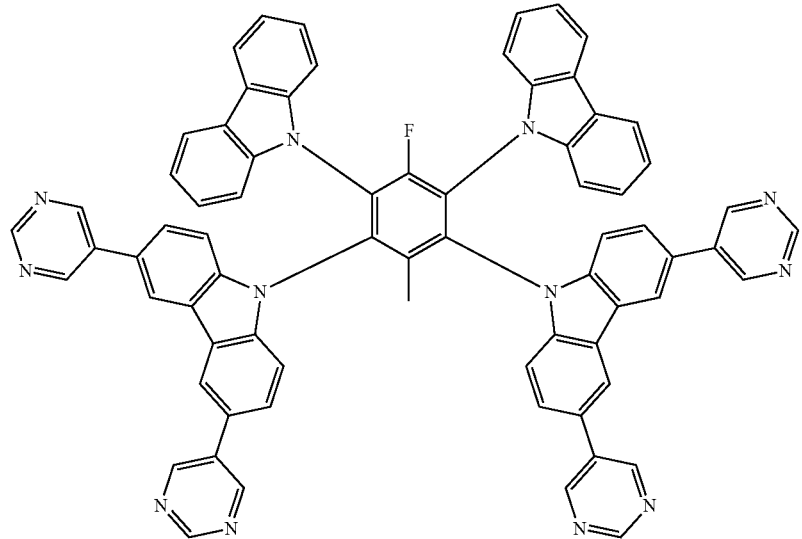
60
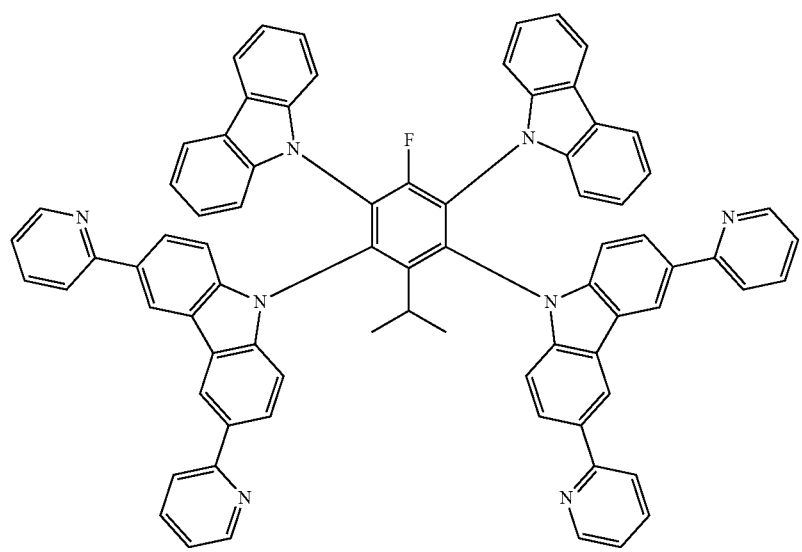
61
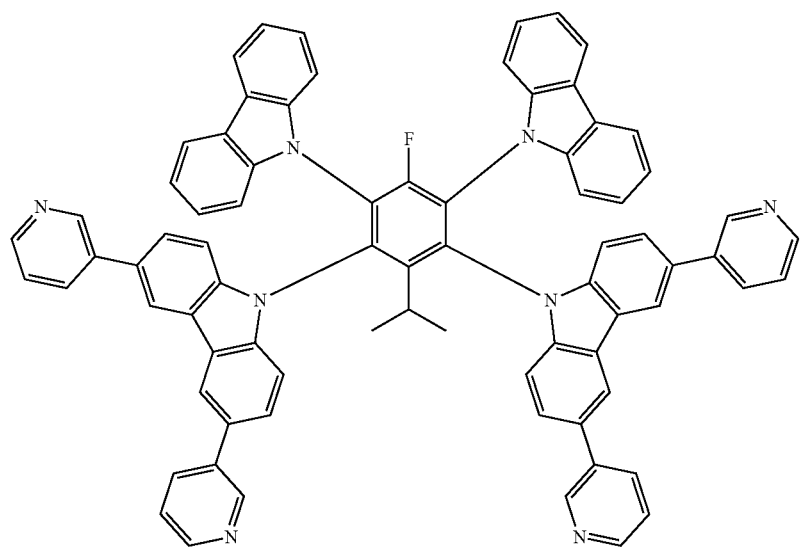
62

-continued
63
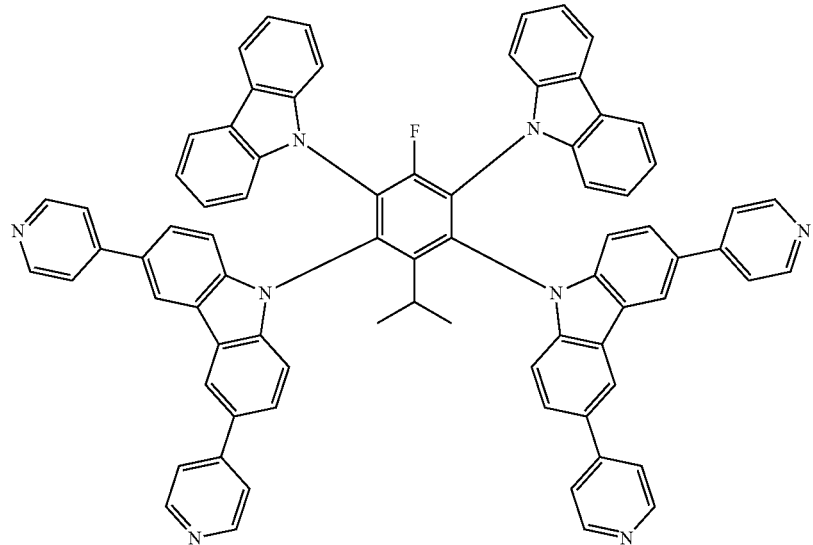
64
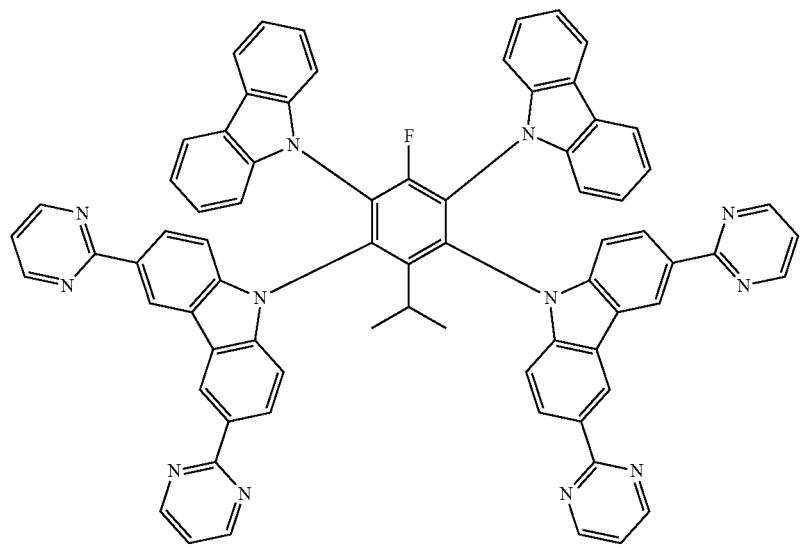
65
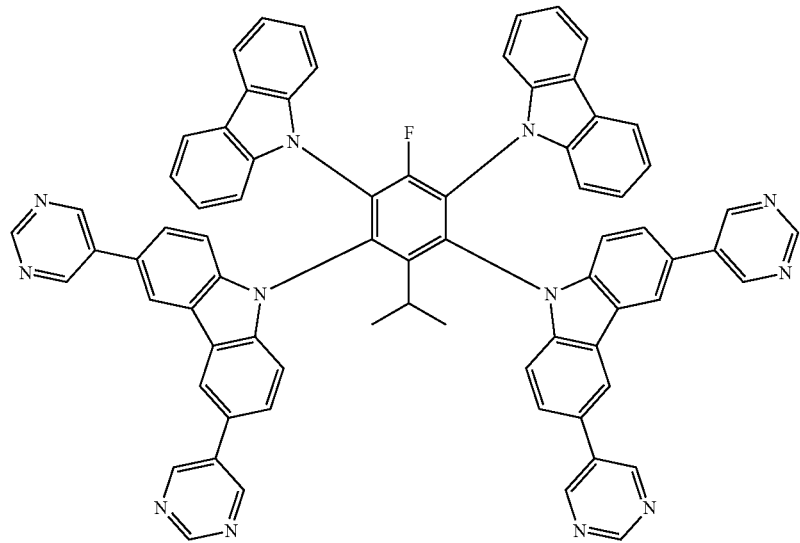

-continued
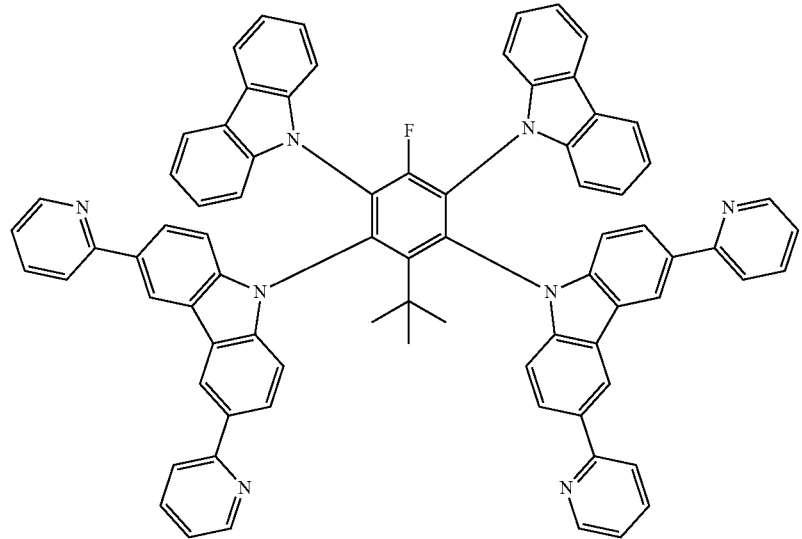
66
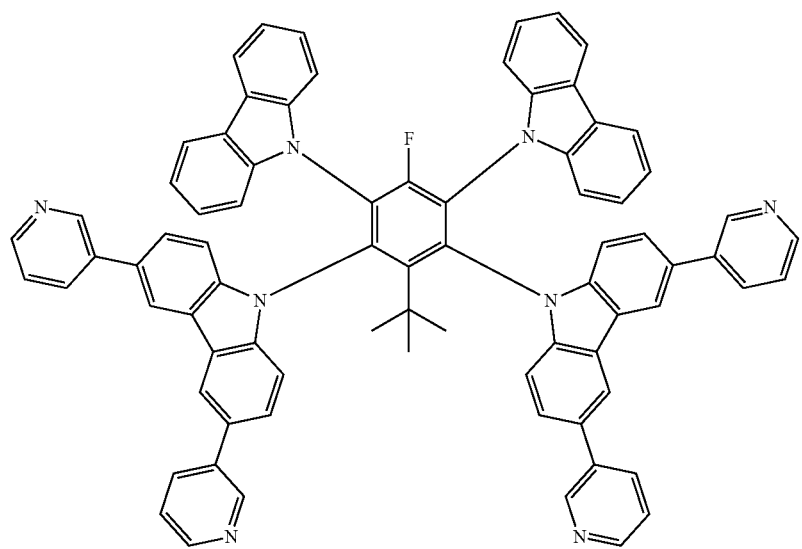
67
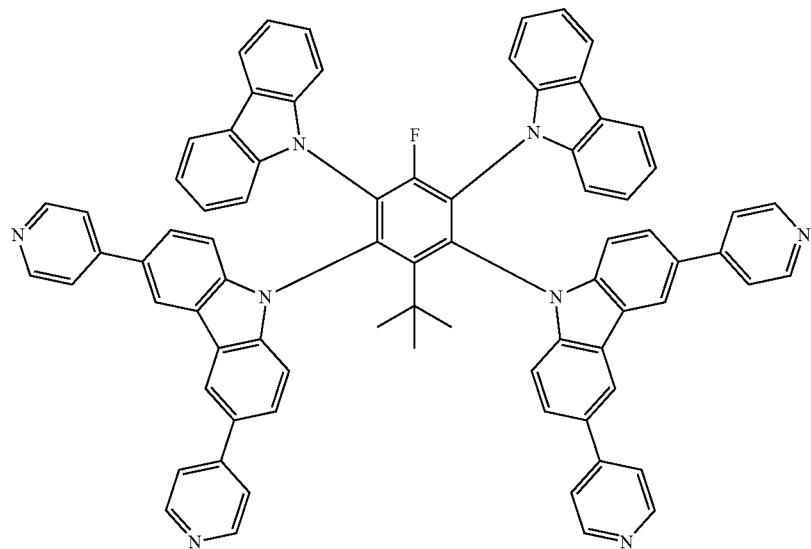
68

-continued
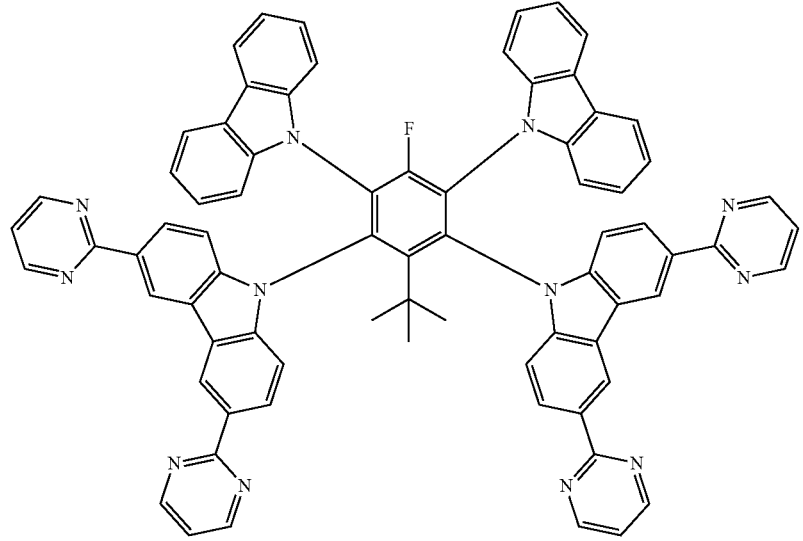
69
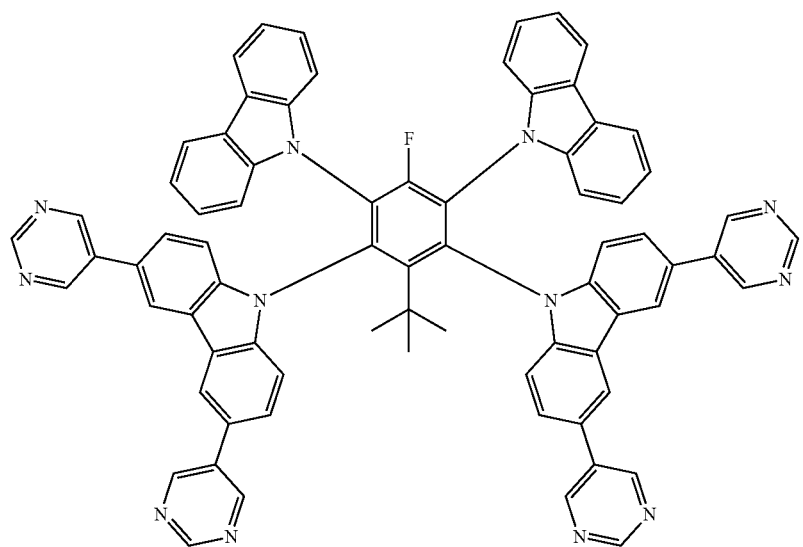
70
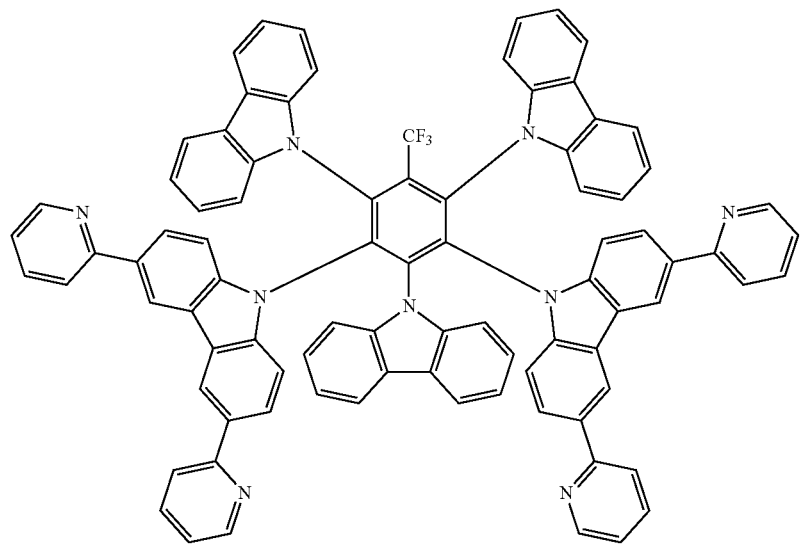
71

-continued
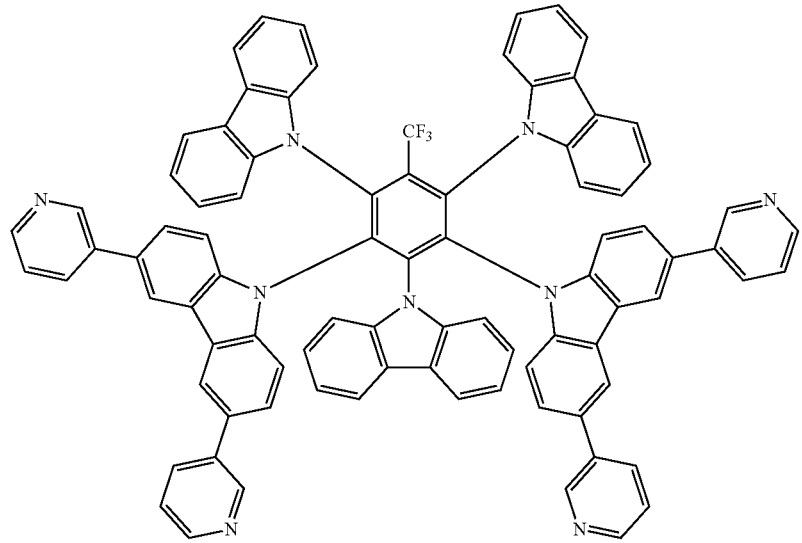
72
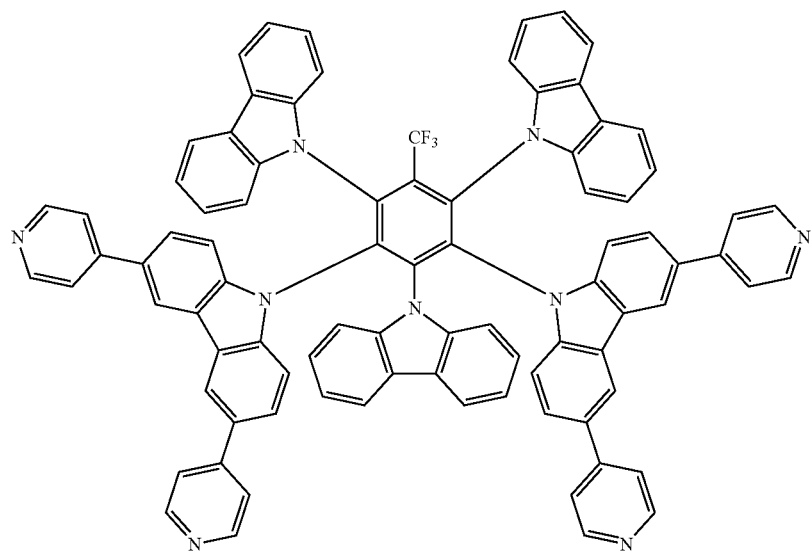
73
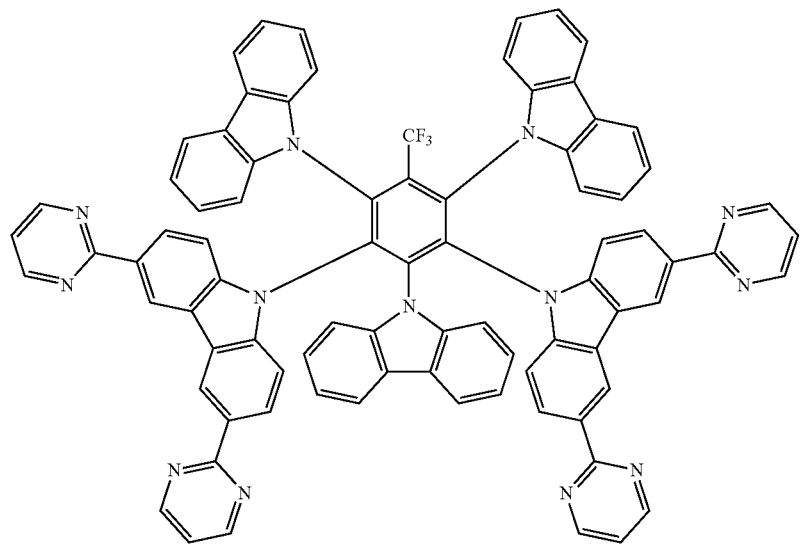
74

75
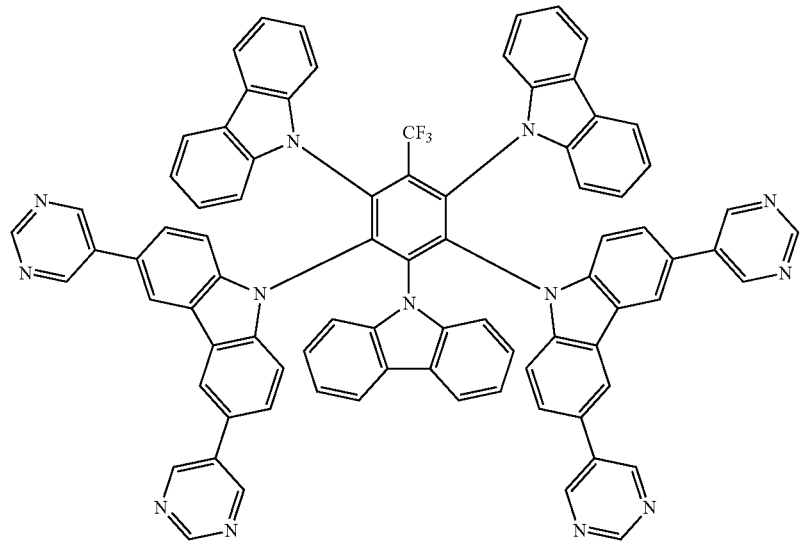
76
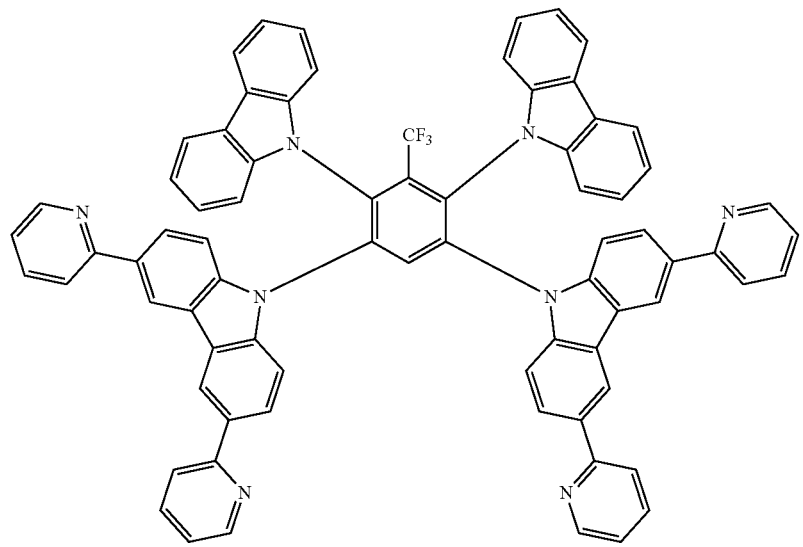
77
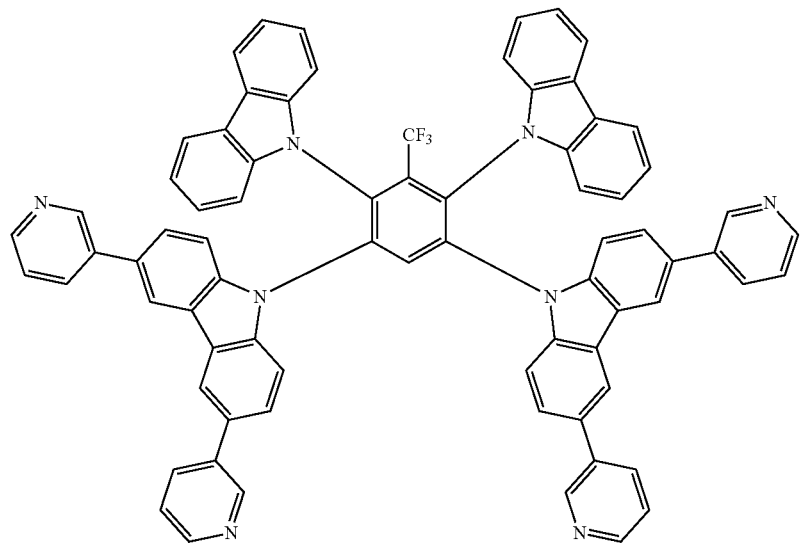

78
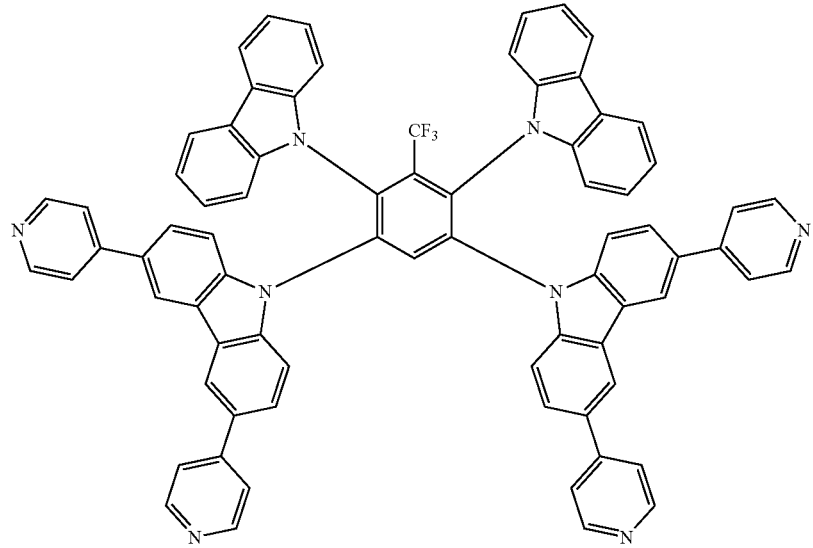
79
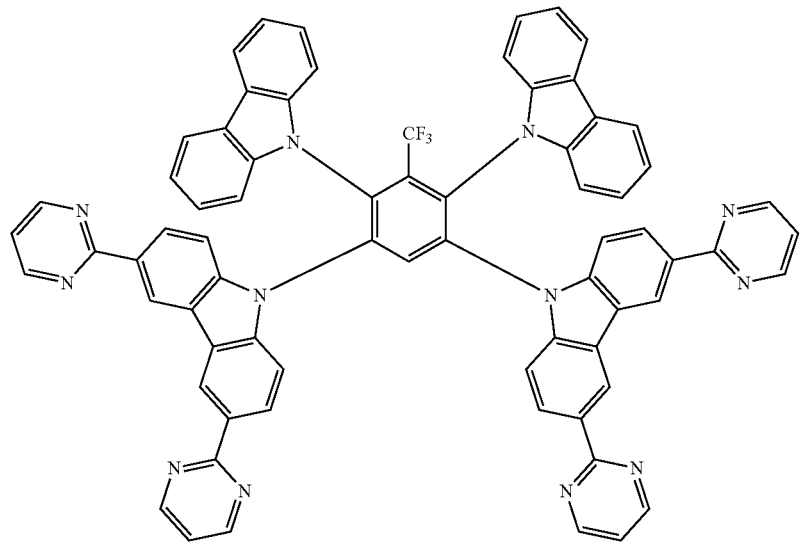
80
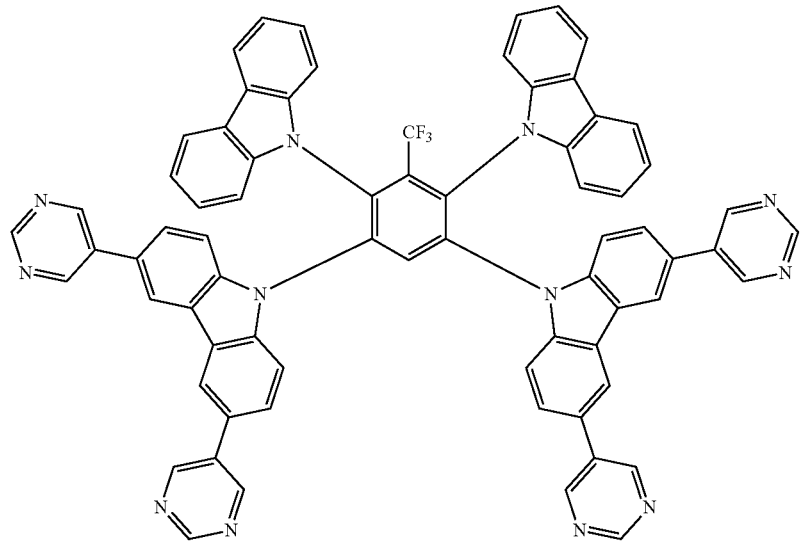

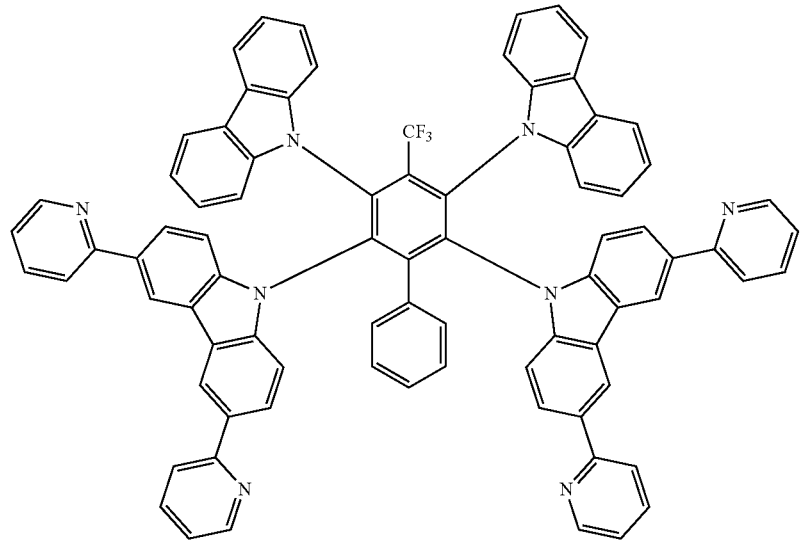
81
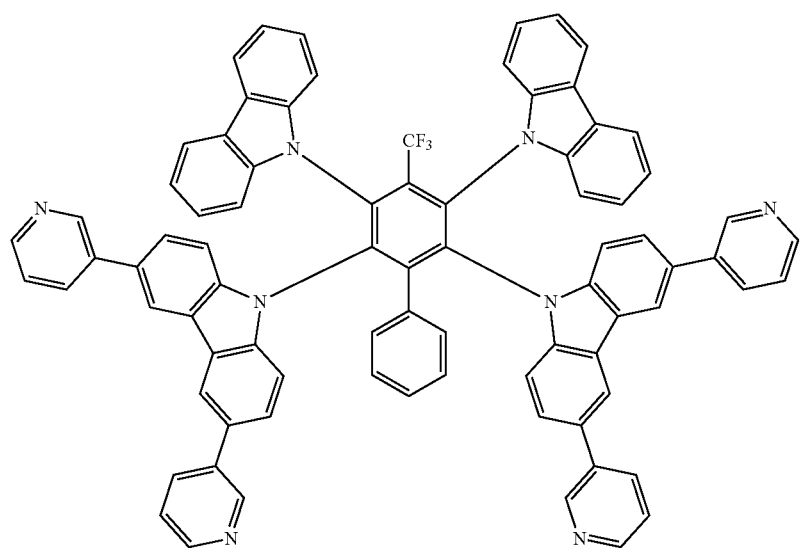
82
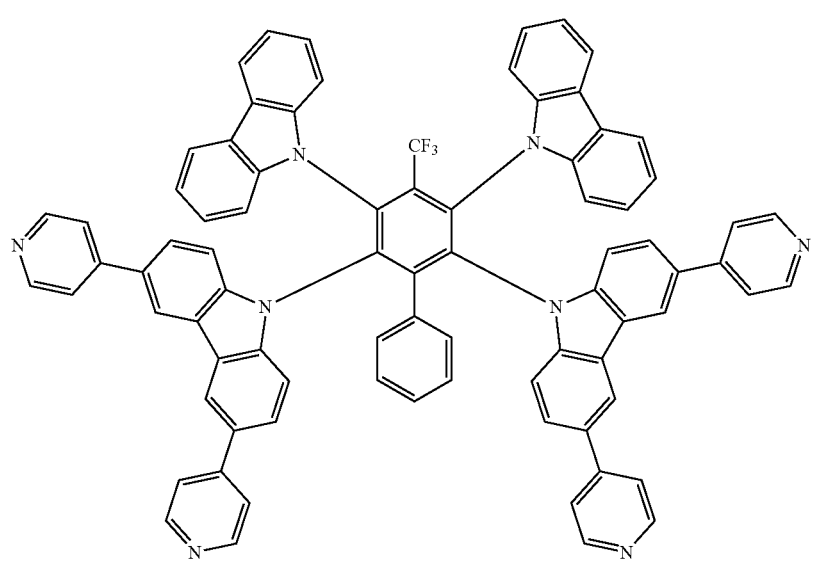
83

84
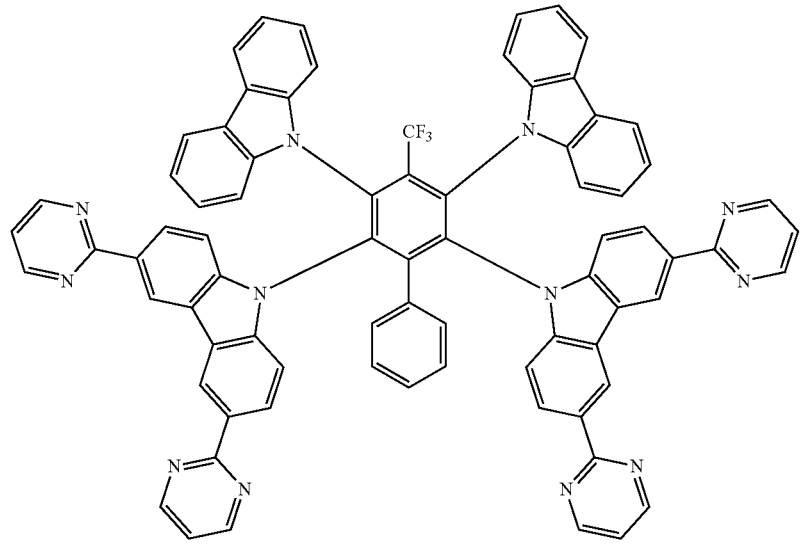
85
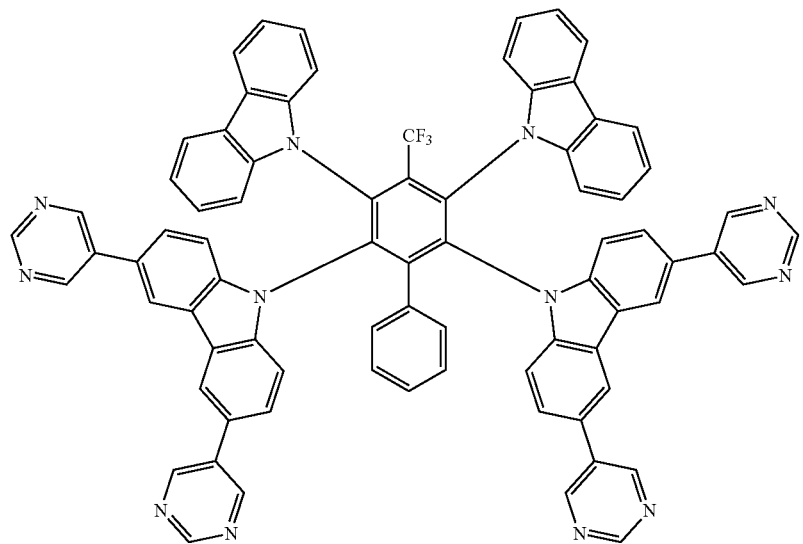
86
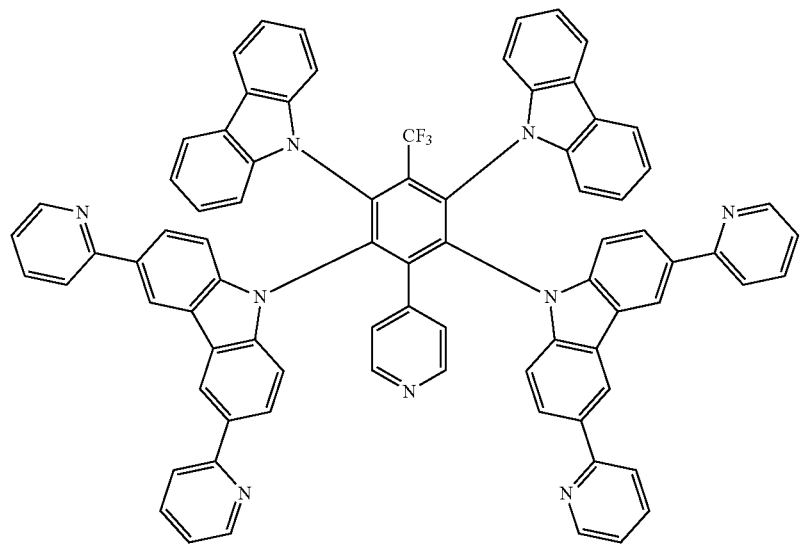

-continued
87
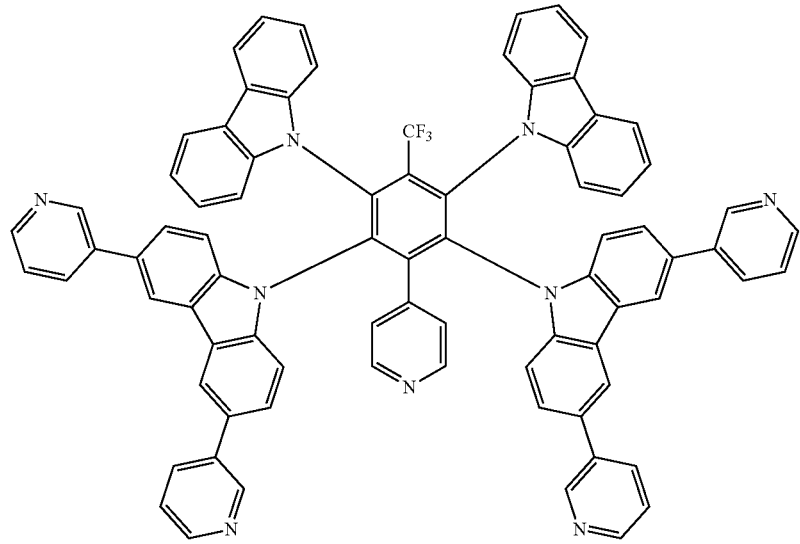
88
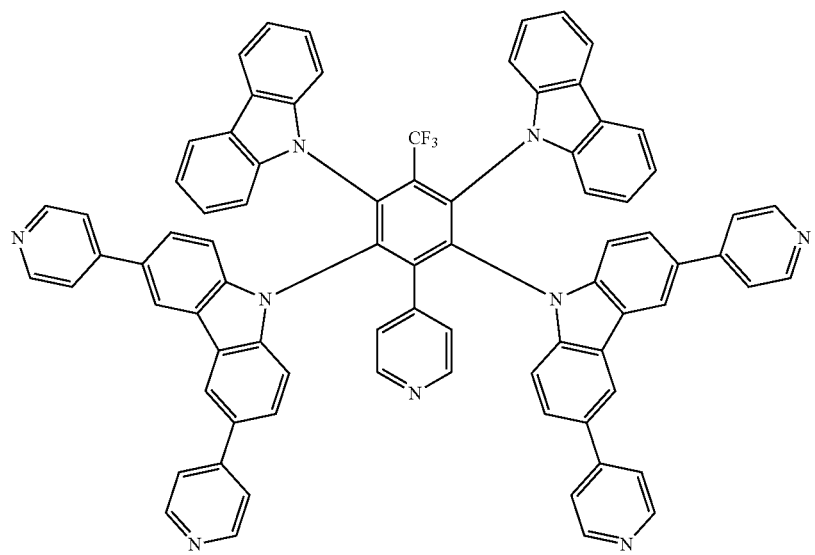
89
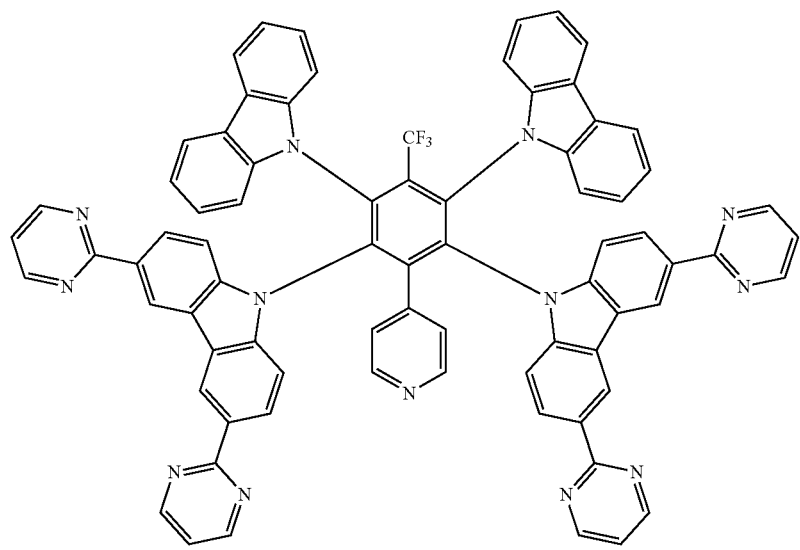

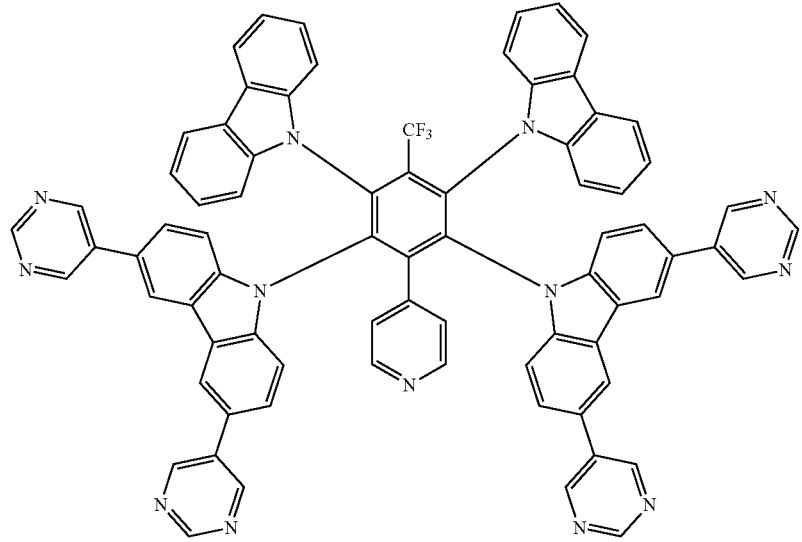
90
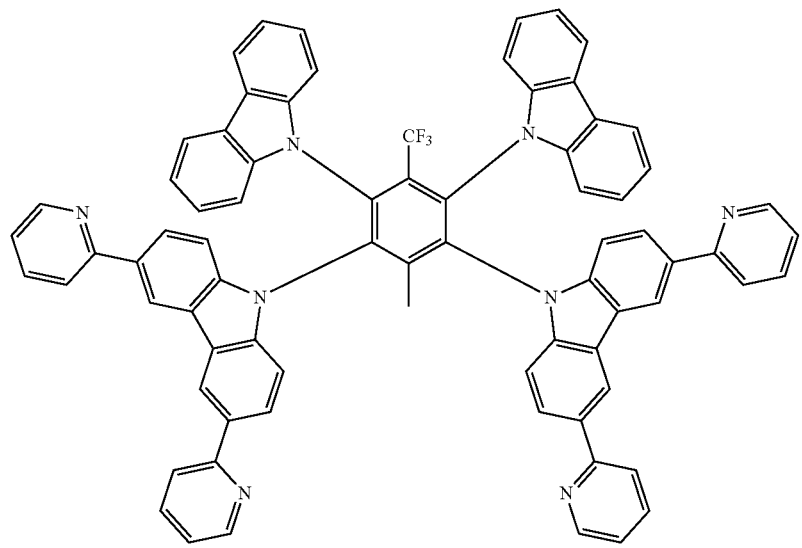
91
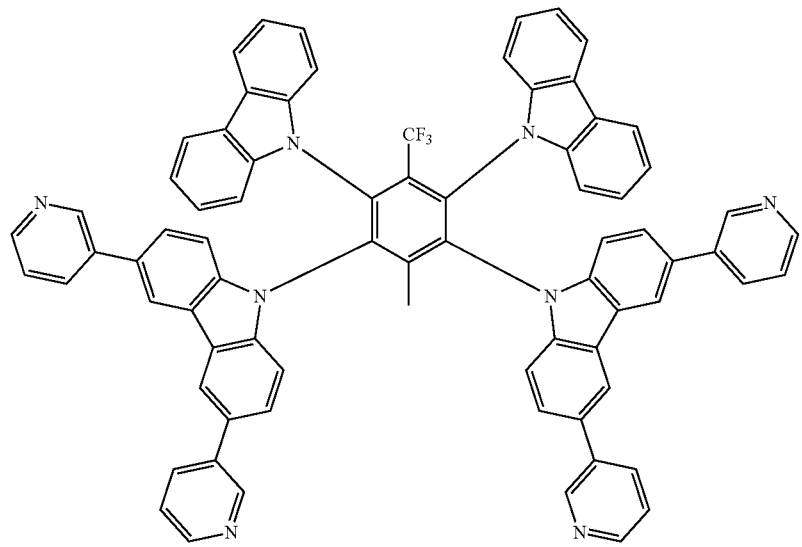
92

-continued
93
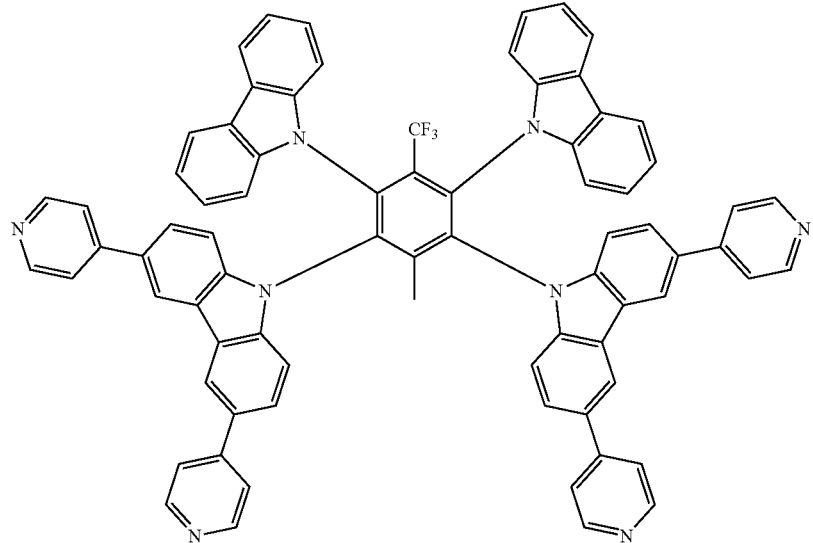
94
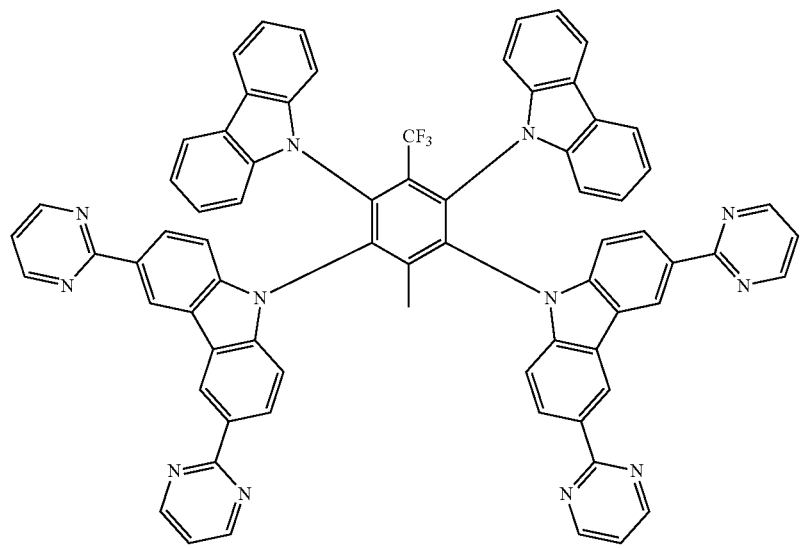
95
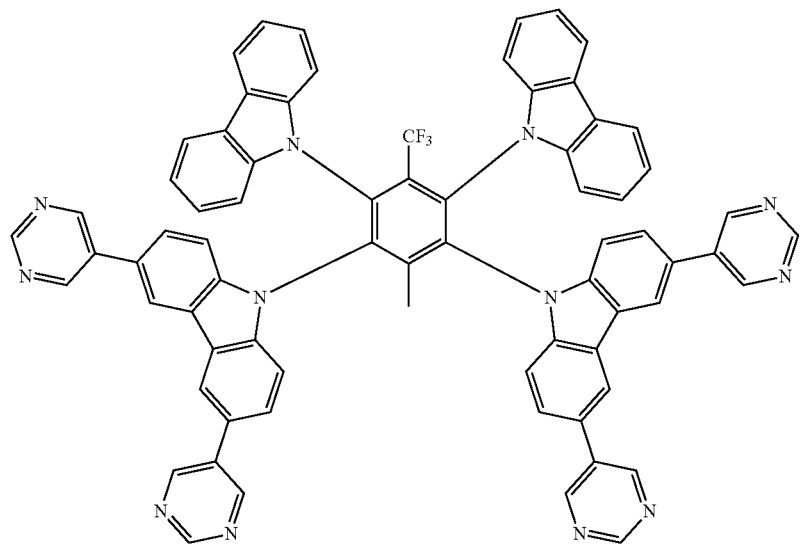

96
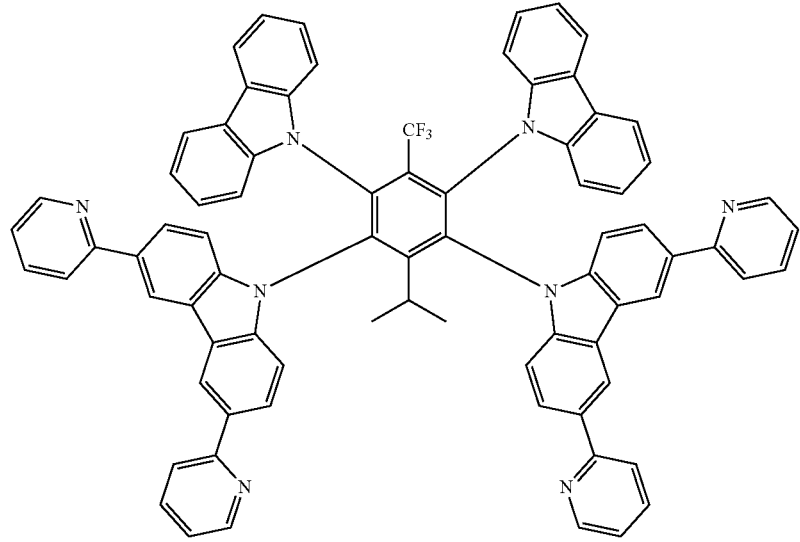
97
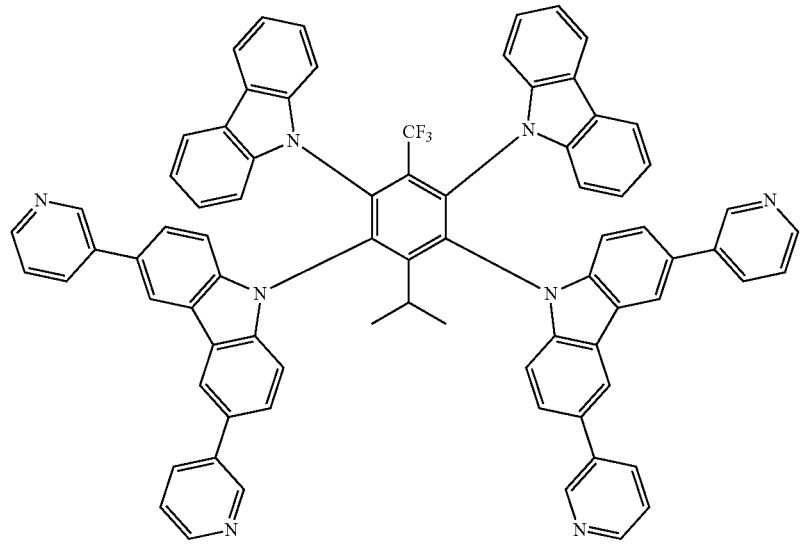
98
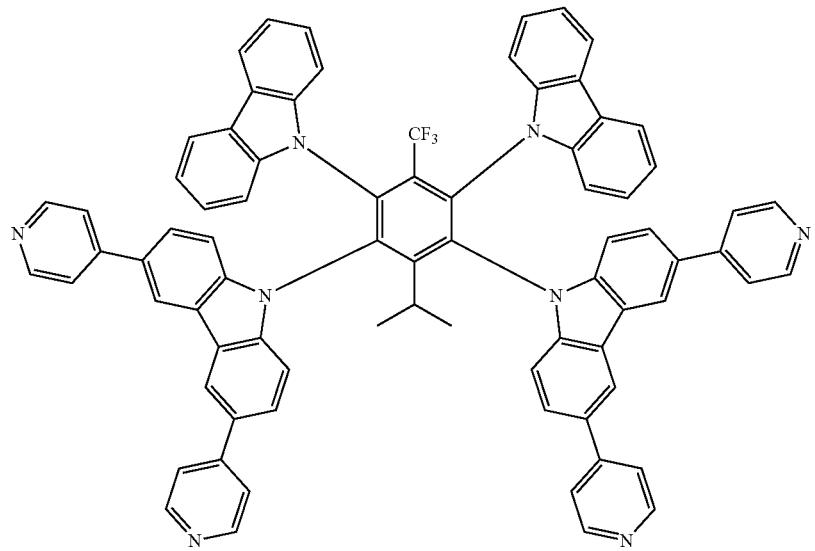

99
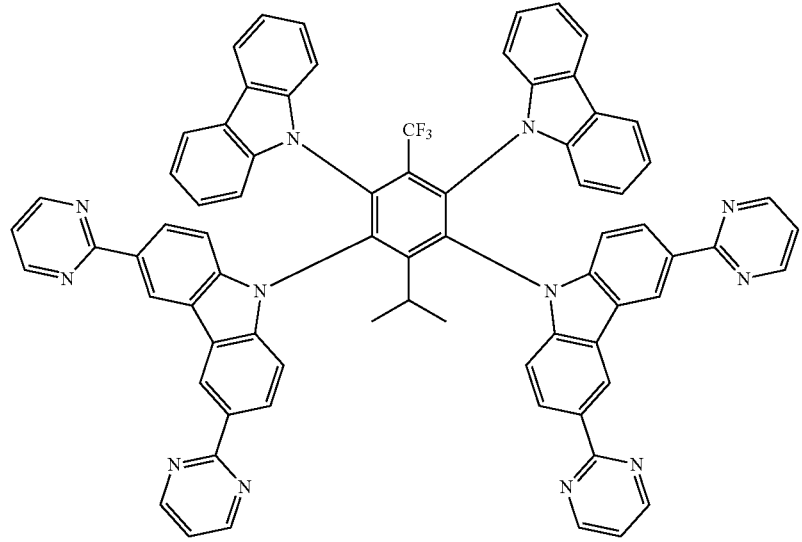
100
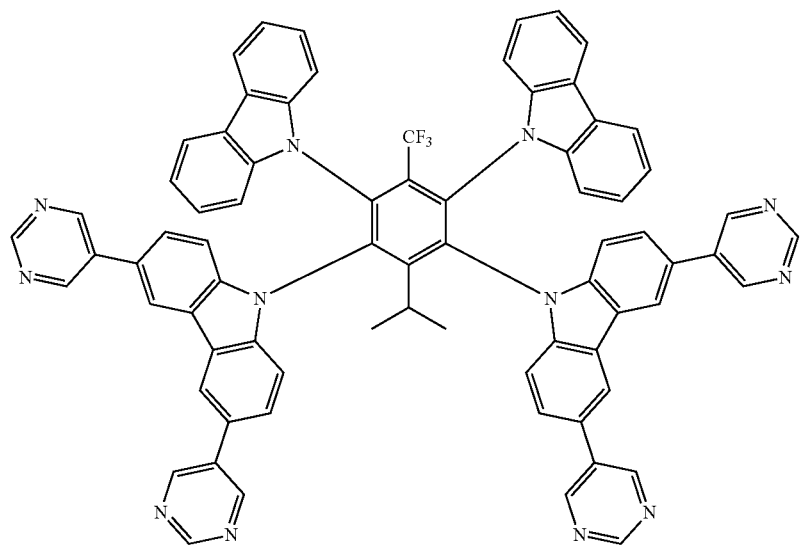
101
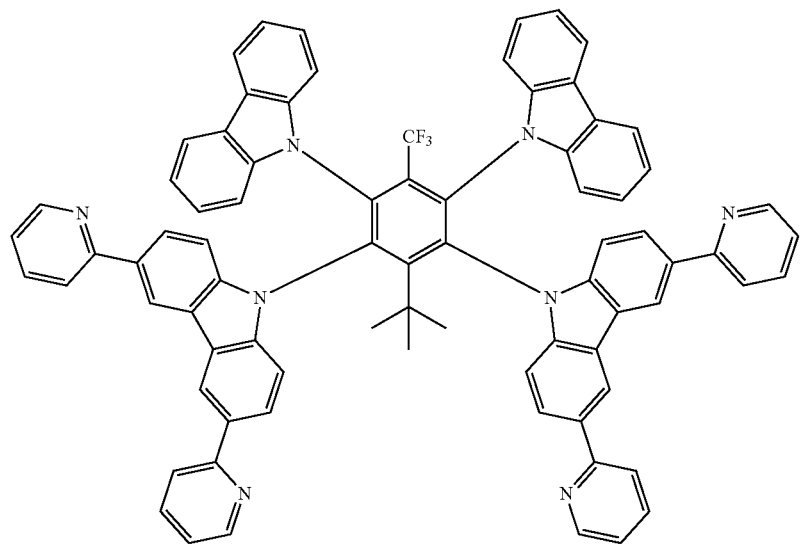

-continued
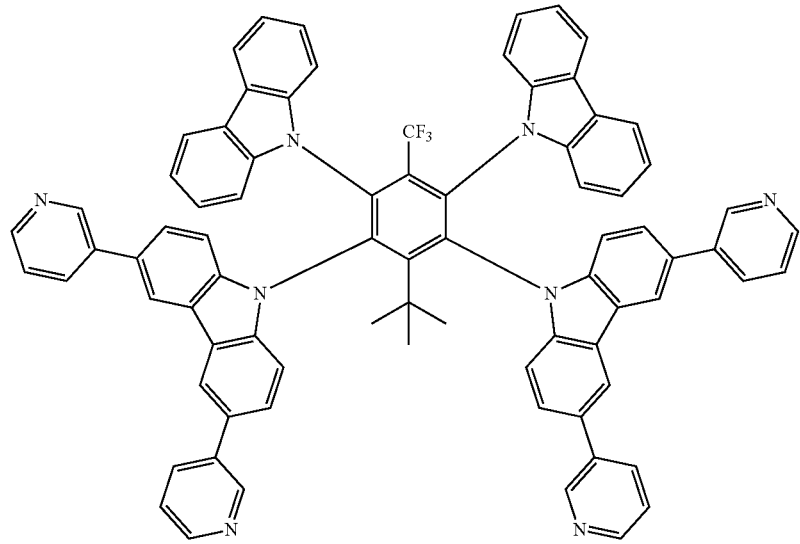
102
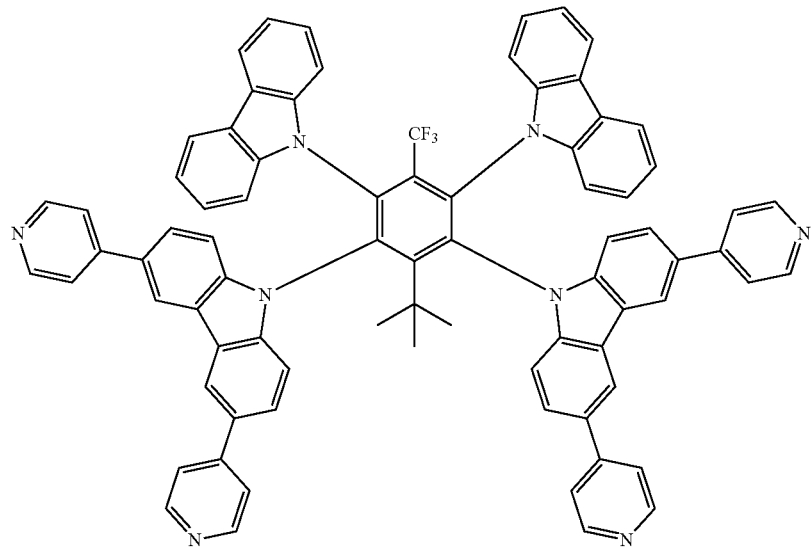
103
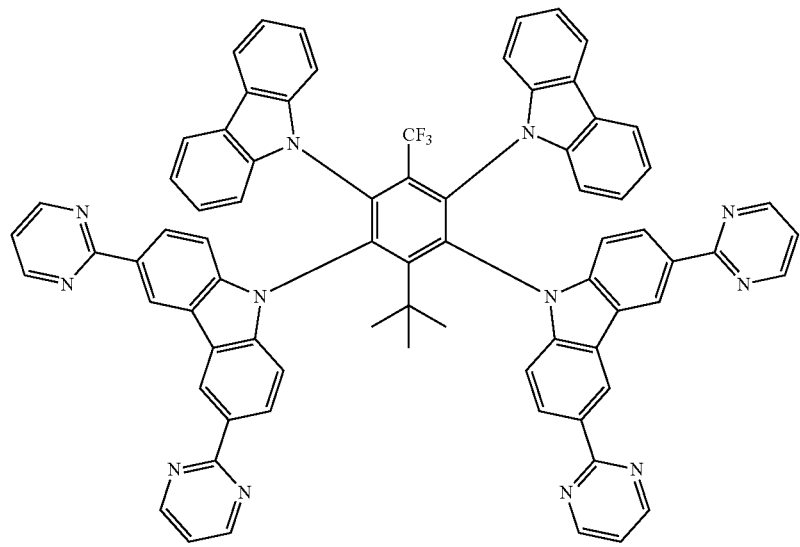
104

-continued

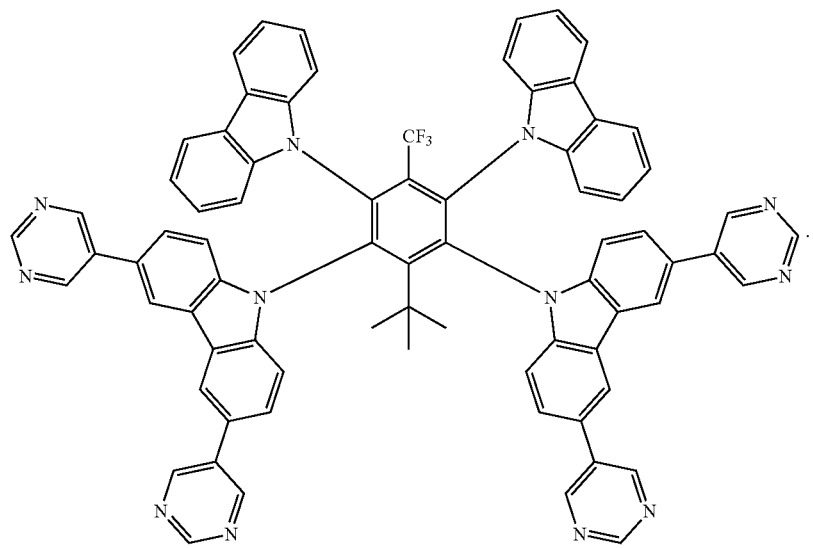

105

6. An organic electroluminescence device, comprising:
a first electrode;
a second electrode on the first electrode; and
an emission layer between the first electrode and the second electrode,
wherein the first electrode and the second electrode each independently comprise a transmissive electrode, a transflective electrode or a reflective electrode, the transmissive electrode comprising at least one selected from indium tin oxide, indium zinc oxide, zinc oxide and indium tin zinc oxide, and the transflective and reflective electrode each independently comprising at least one selected from Ag, Mg, Cu, Al, Pt, Pd, Au, Ni, Nd, Ir, Cr, Li, Ca, LiF/Ca, LiF/Al, Mo, Ti, a compound thereof, and a mixture thereof,
wherein the emission layer comprises an aromatic compound represented by Formula 1:

Formula 1

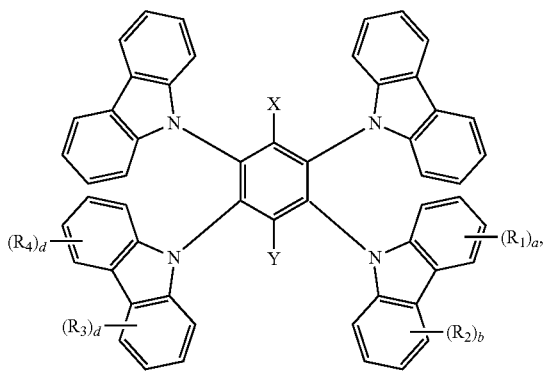

wherein in Formula 1,
X is a cyano group, a fluorine, or a C1-C10 alkyl group substituted with a fluorine,
Y is a hydrogen atom, a deuterium atom, a halogen atom, a cyano group, an unsubstituted heteroaryl group having 3 to 20 ring-forming carbon atoms and at least one ring-forming nitrogen atom, a substituted or unsubstituted aryl group having 6 to 30 ring-forming carbon atoms, or a substituted or unsubstituted alkyl group having 1 to 20 carbon atoms,
a to d are each independently an integer of 1 to 4, and
at least one of $R_1$ to $R_4$ is represented by Formula 2 and the remaining ones of $R_1$ to $R_4$ are each independently a hydrogen atom, a deuterium atom, or a substituted or unsubstituted alkyl group having 1 to 4 carbon atoms, Formula 2

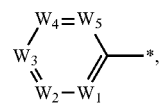

wherein in Formula 2,
at least one of $W_1$ to $W_5$ is a nitrogen atom and the remaining ones of $W_1$ to $W_5$ are each independently $CR_5$, and
$R_5$ is a hydrogen atom, a deuterium atom, or a substituted or unsubstituted alkyl group having 1 to 4 carbon atoms.

7. The organic electroluminescence device of claim 6, wherein Formula 2 is represented by Formula 2-1 or Formula 2-2:

Formula 2-1

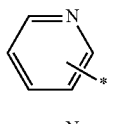

Formula 2-2

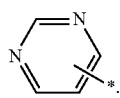

8. The organic electroluminescence device of claim 6, wherein the aromatic compound represented by Formula 1 is laterally symmetric with respect to Y.

9. The organic electroluminescence device of claim 6, wherein the emission layer comprises at least one of the compounds of Compound Group 1:
Compound Group 1
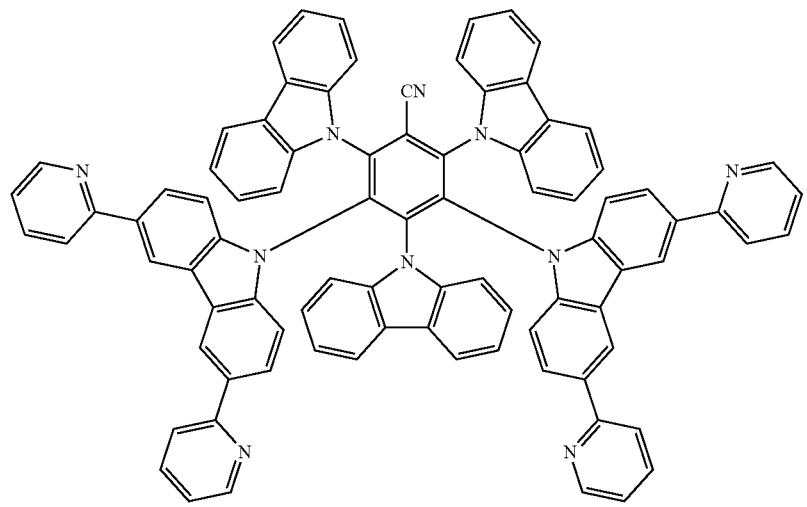
1
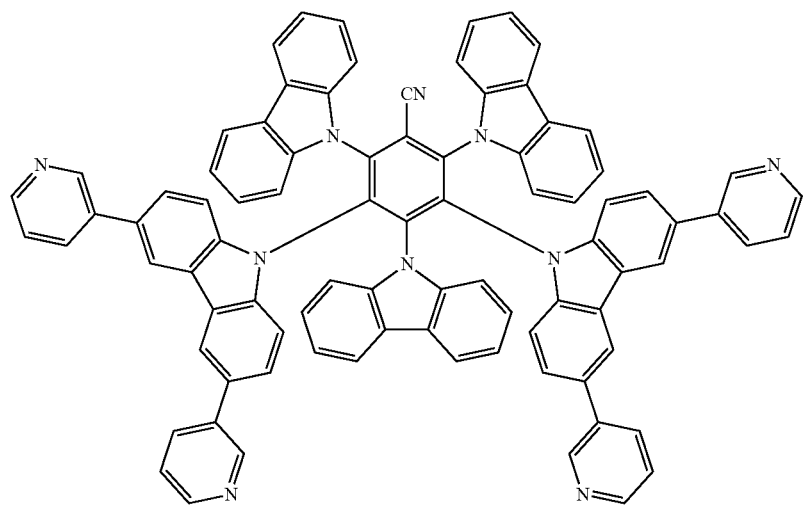
2
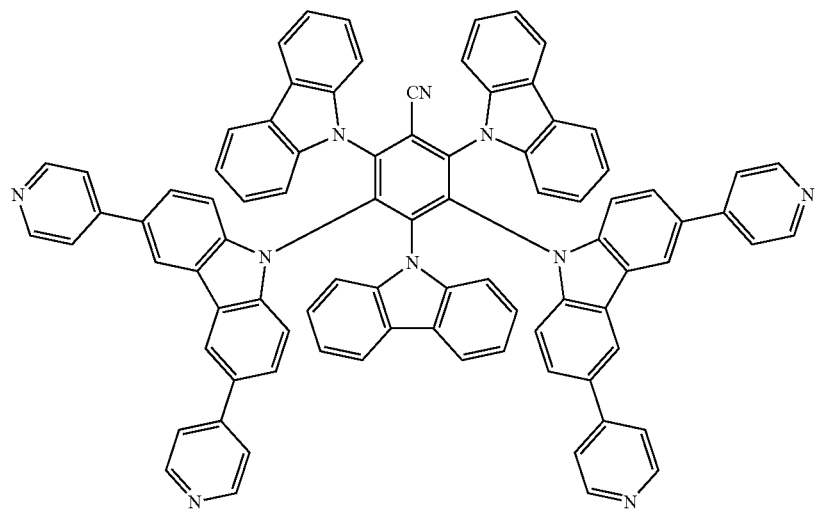
3

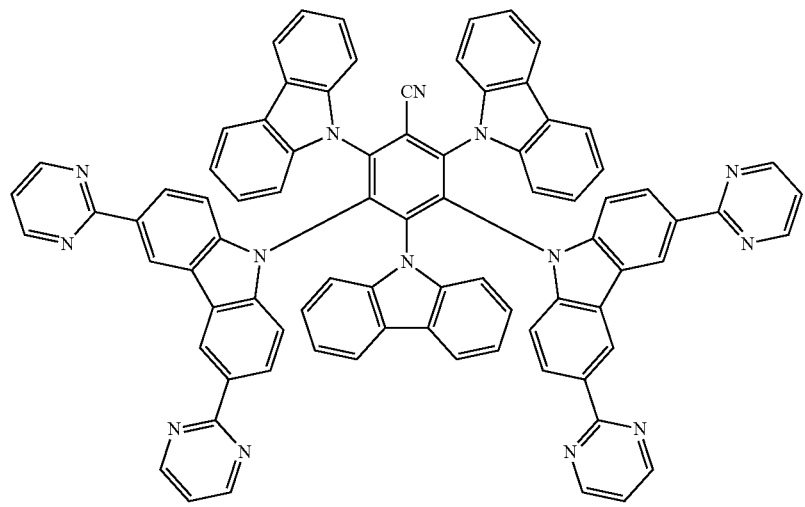
4
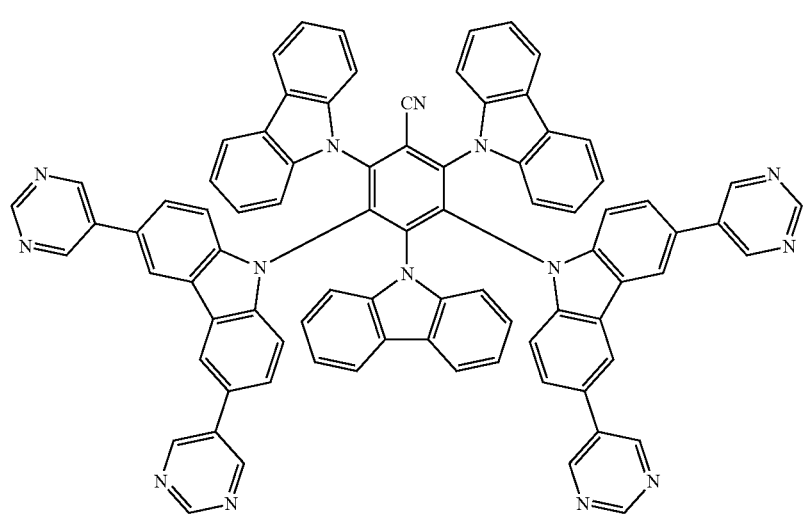
5
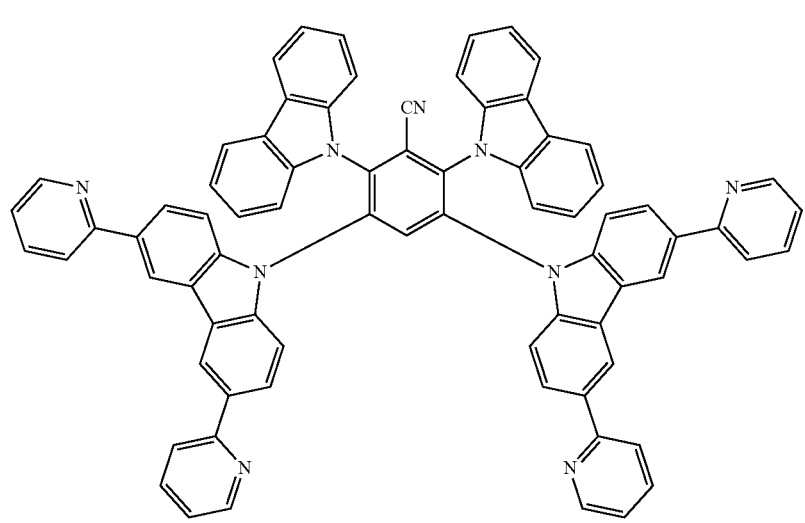
6

7
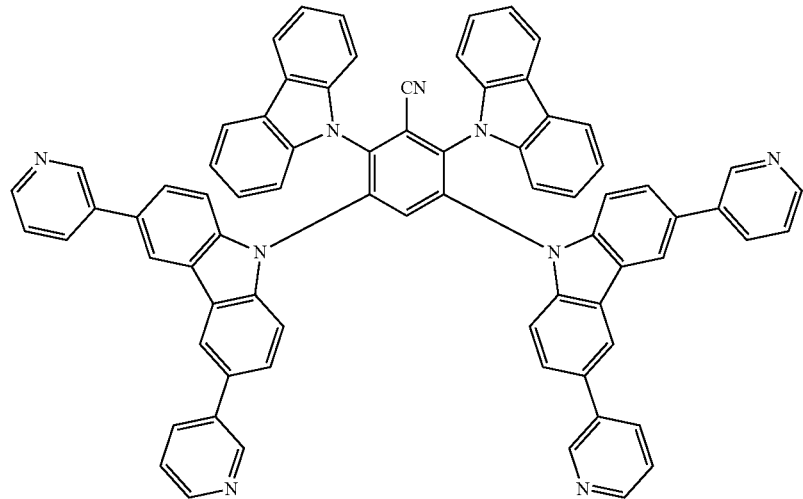
8
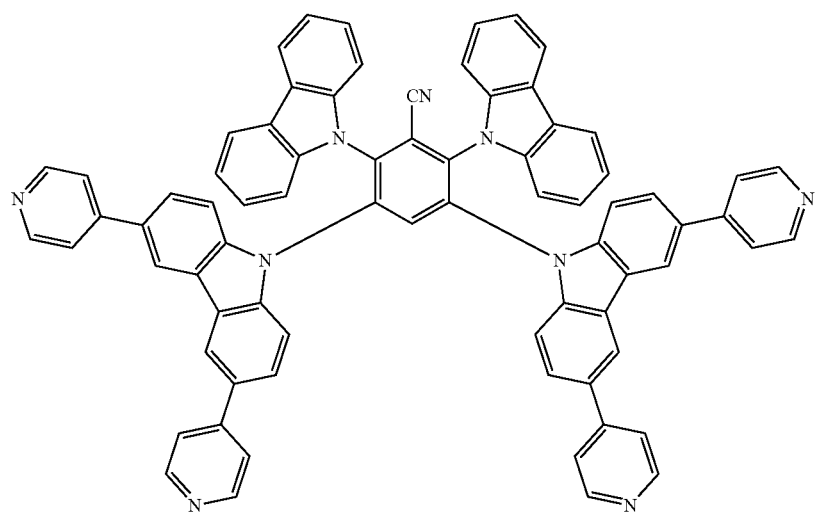
9
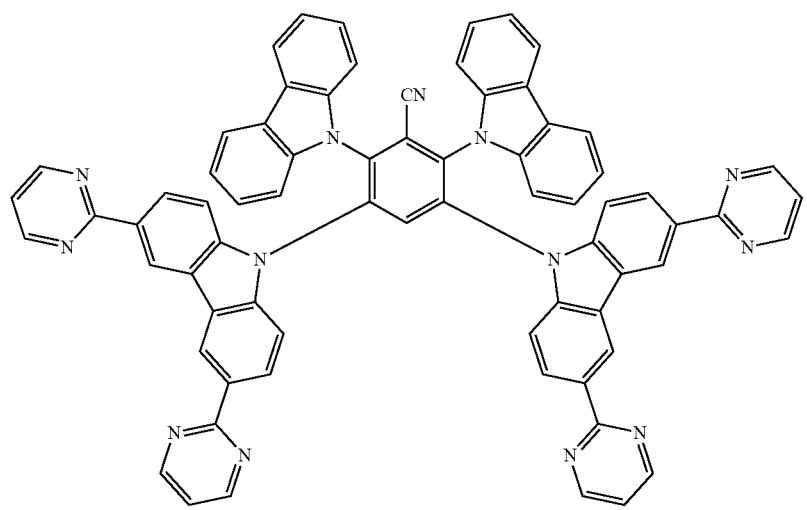

-continued
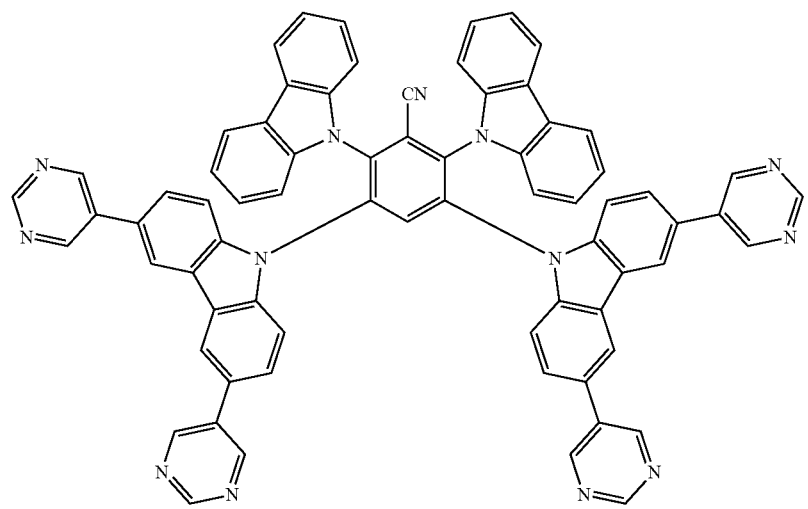
10
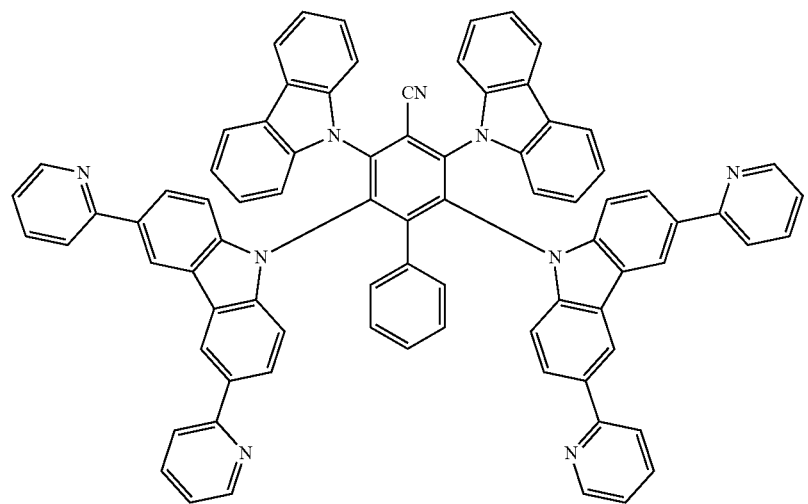
11
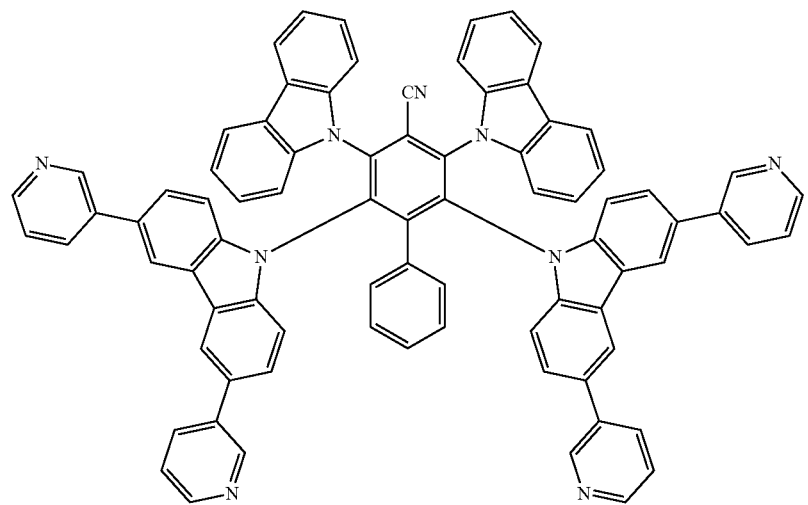
12

13
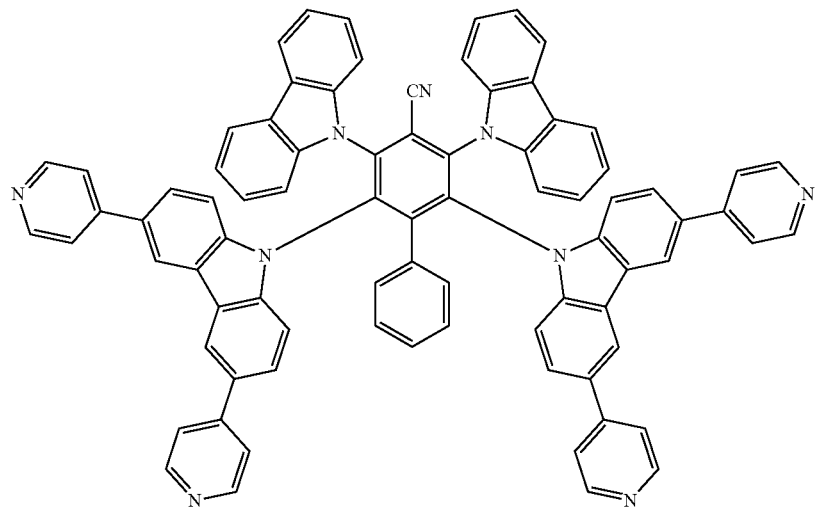
14
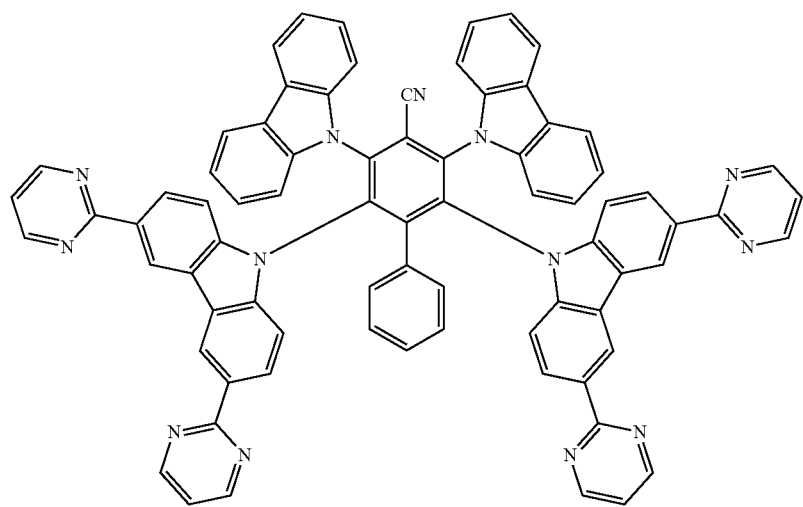
15
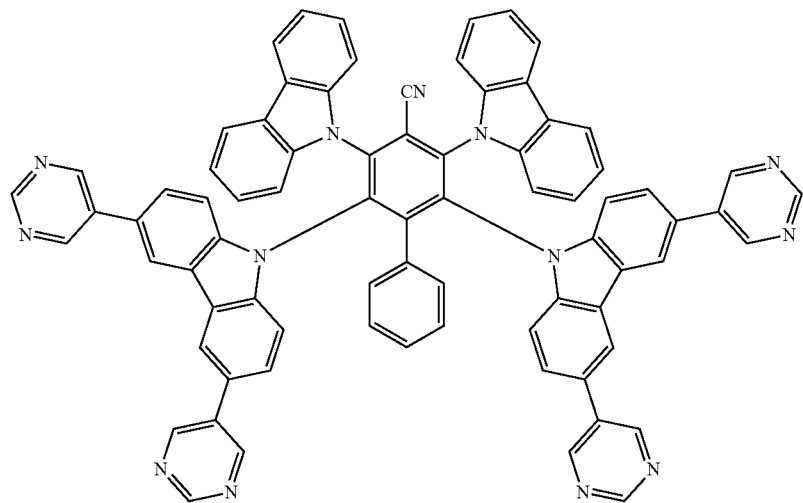

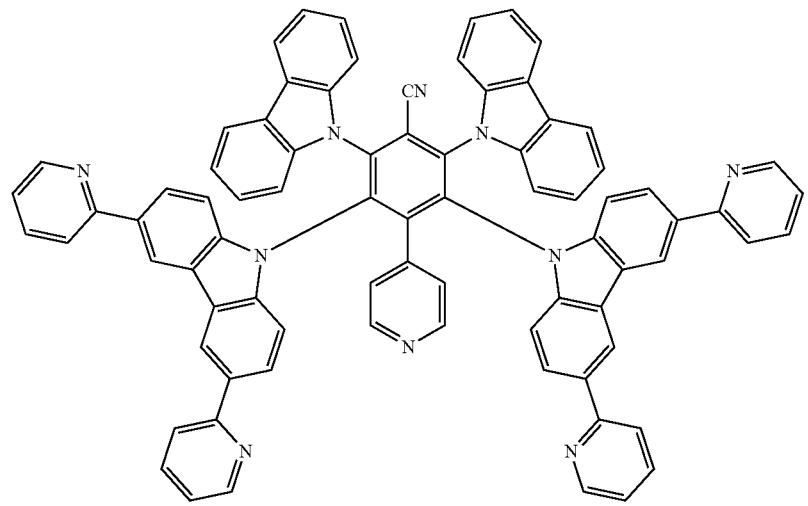
16
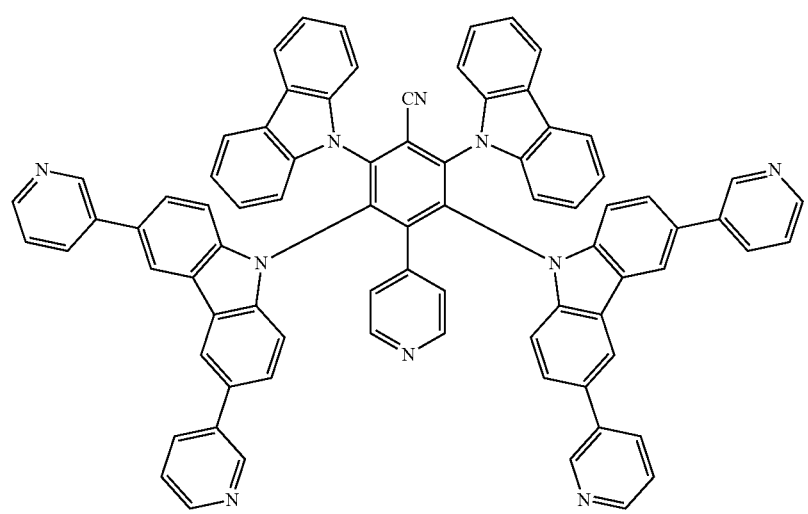
17
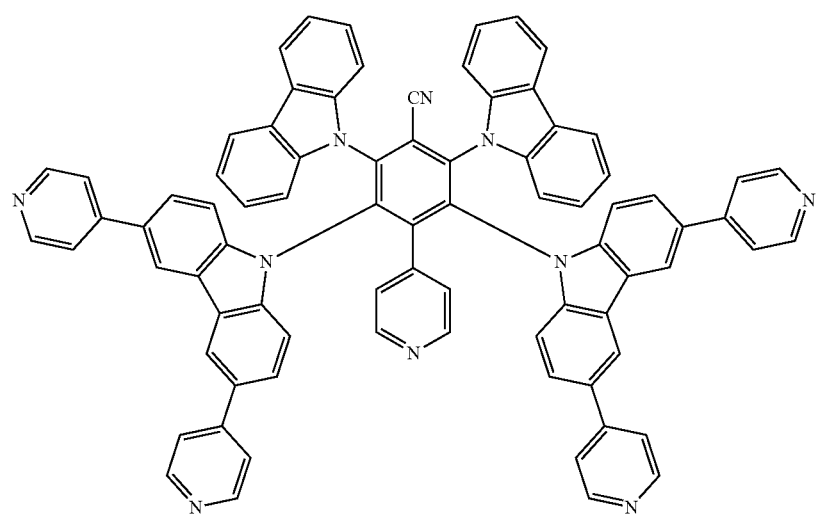
18

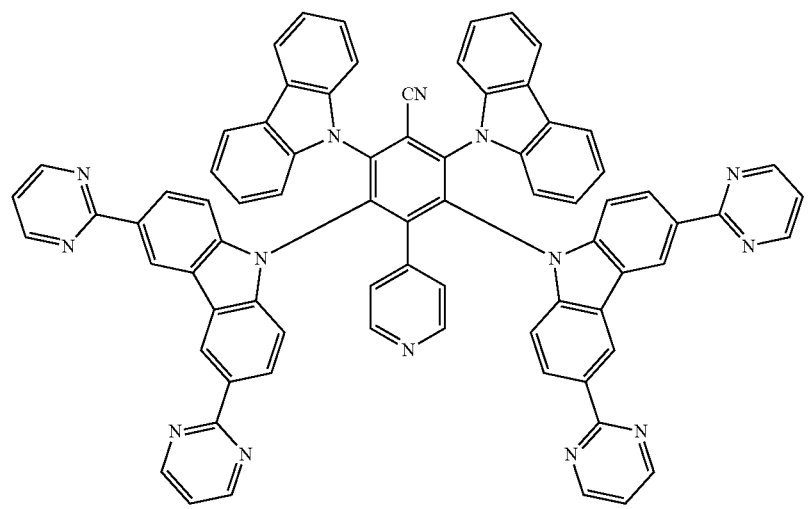
19
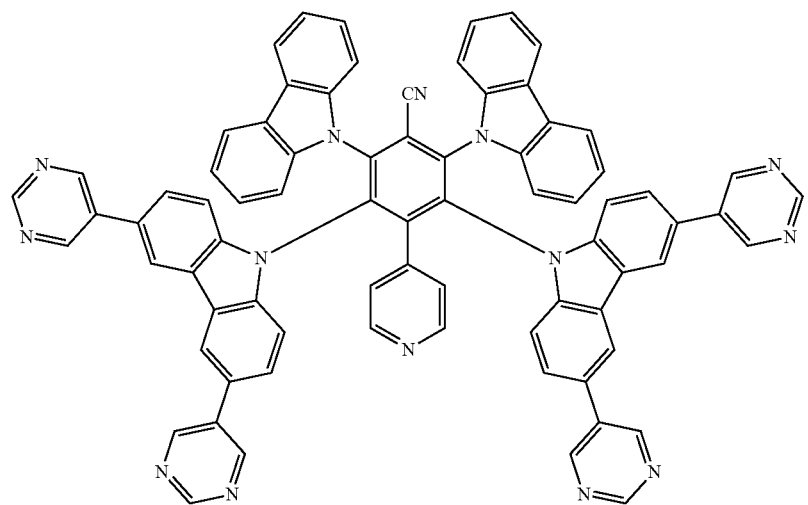
20
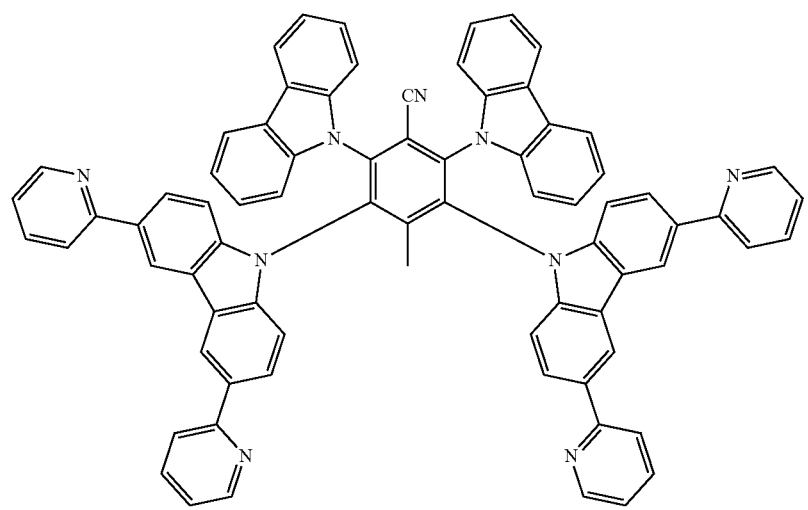
21

22
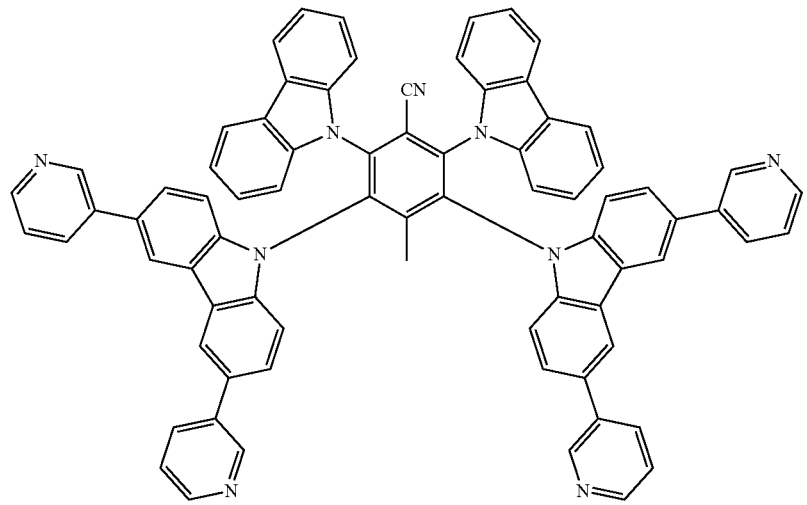
23
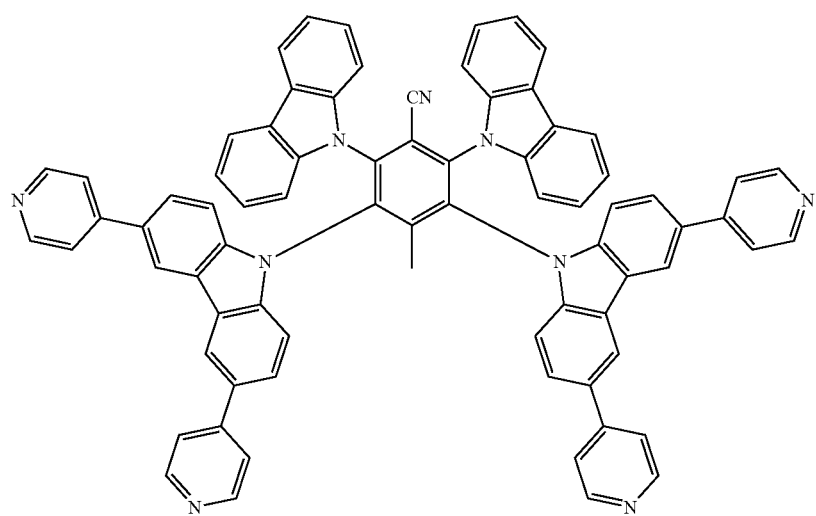
24
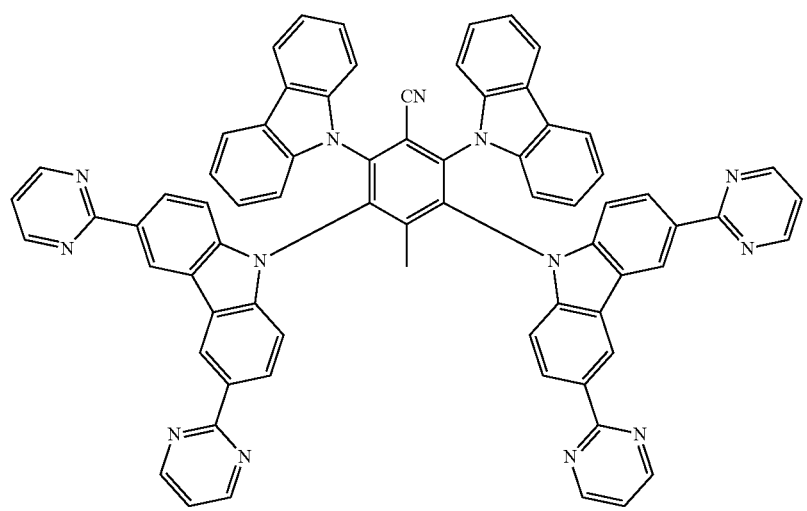

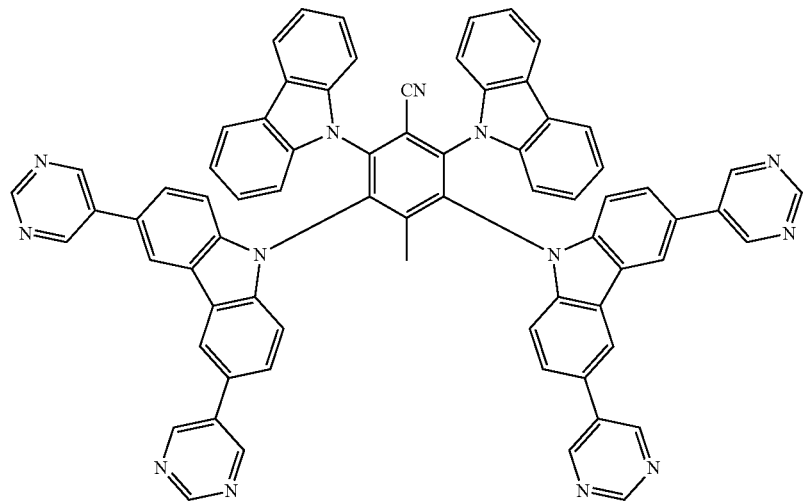
25
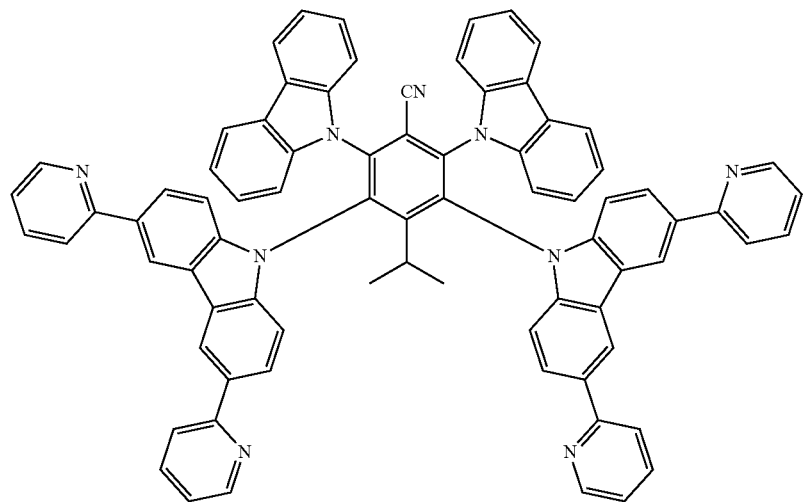
26
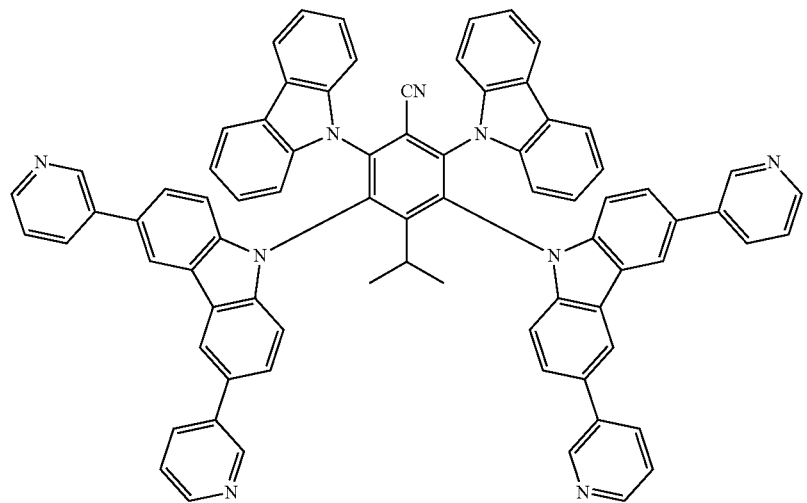
27

28
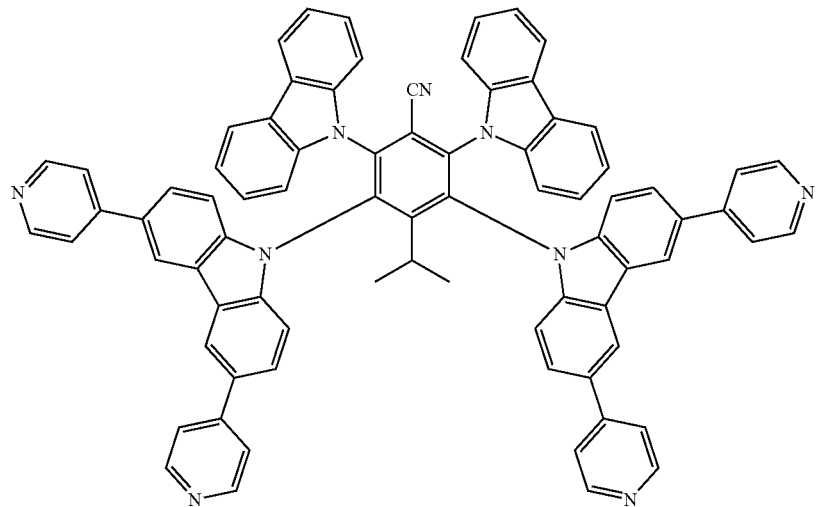
29
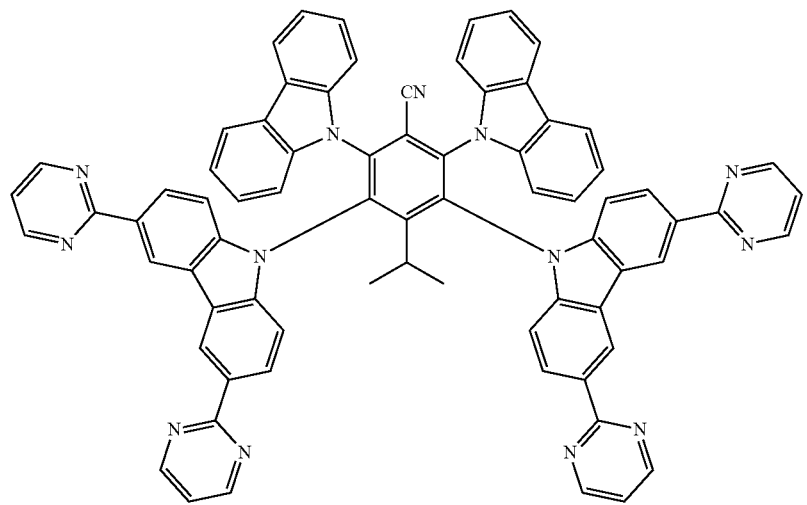
30
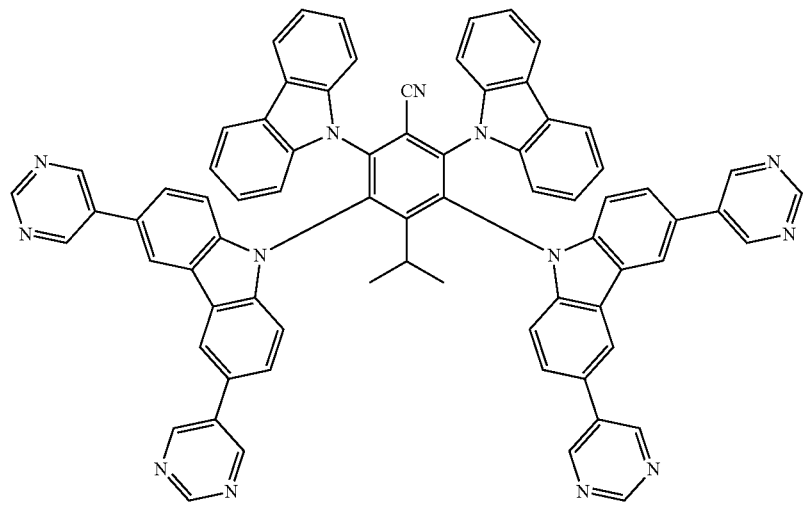

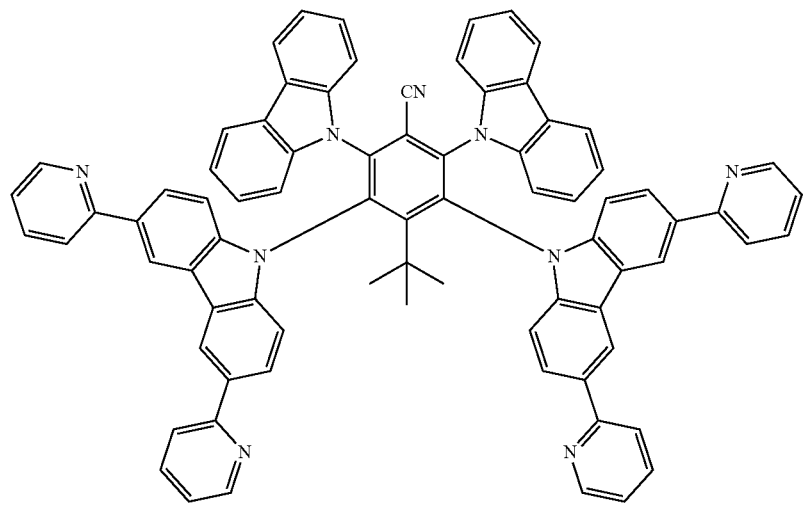
31
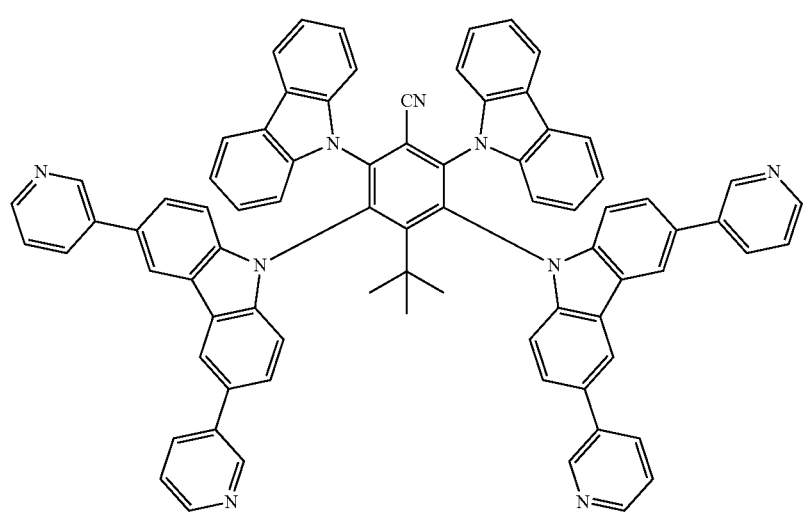
32
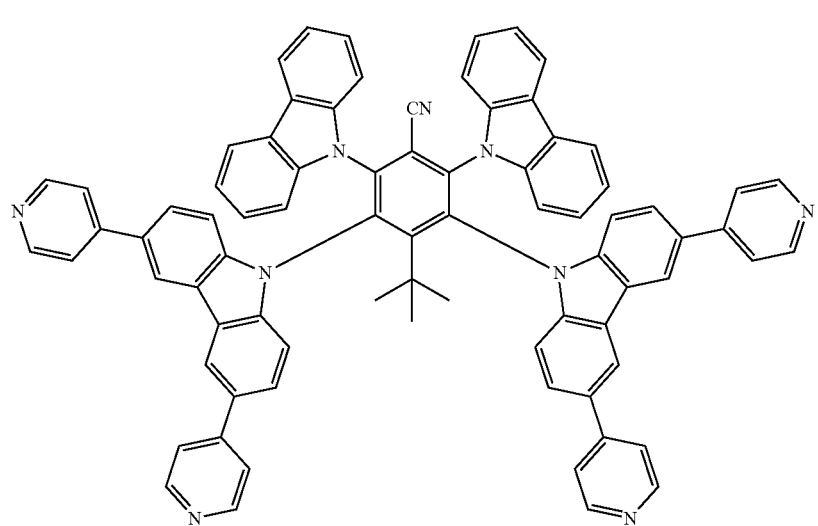
33

34
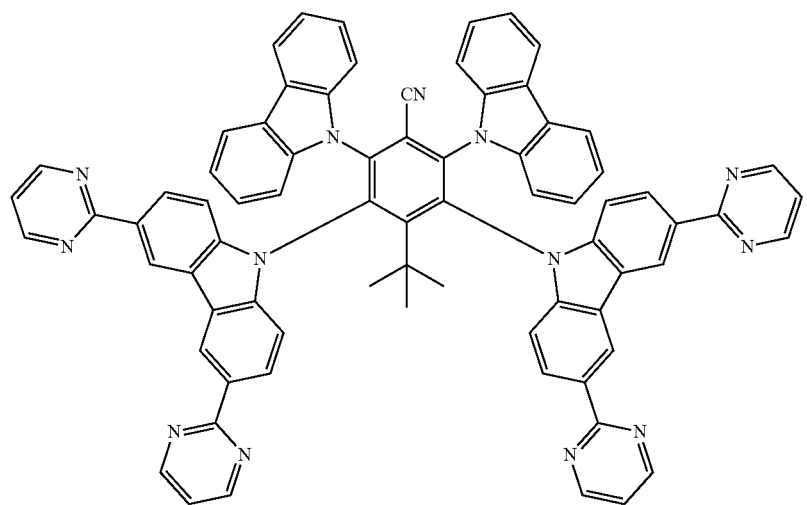
35
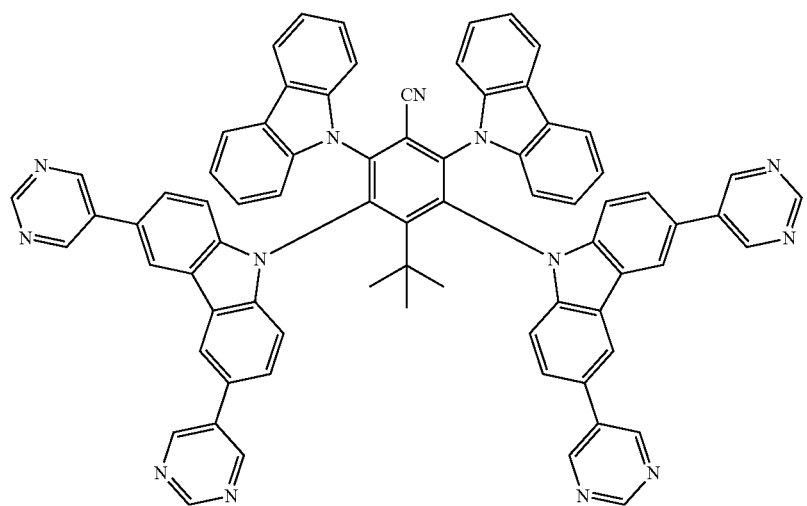
36
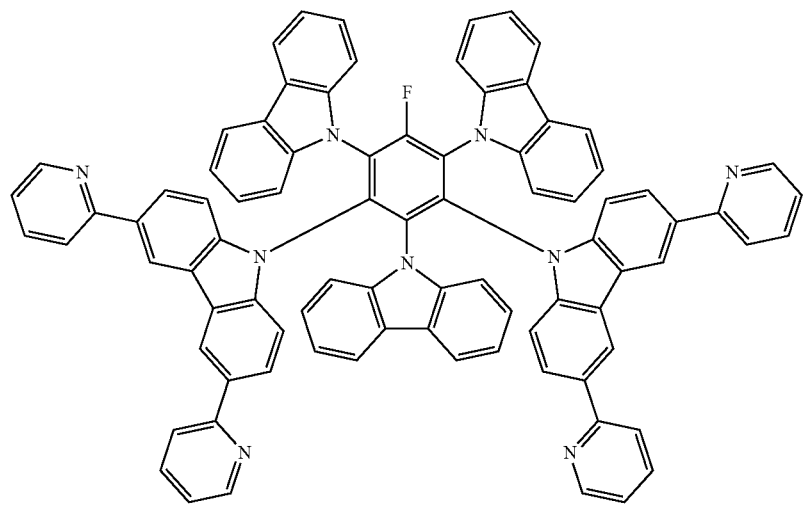

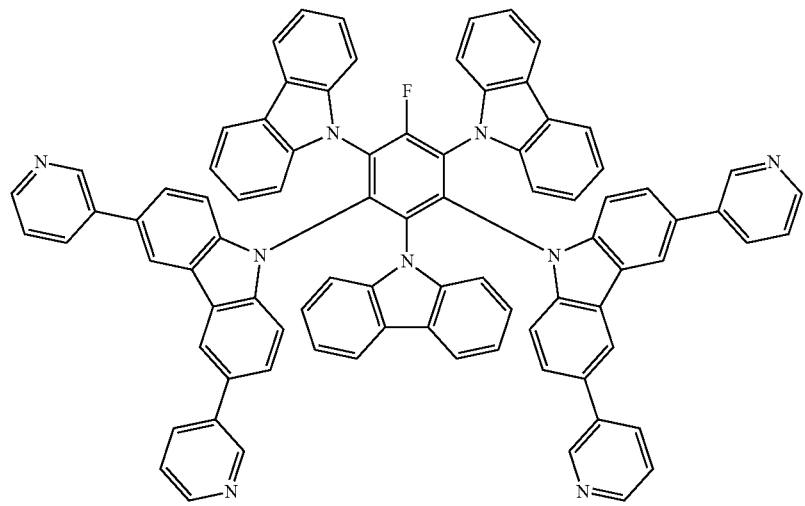
37
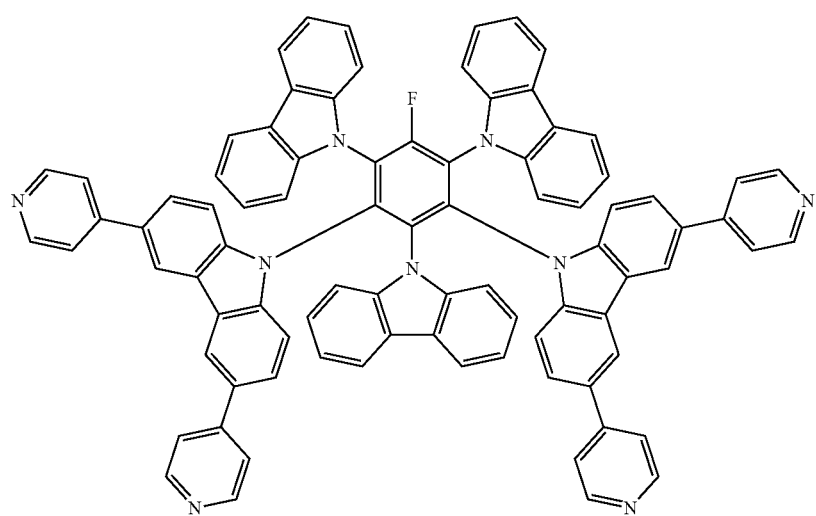
38
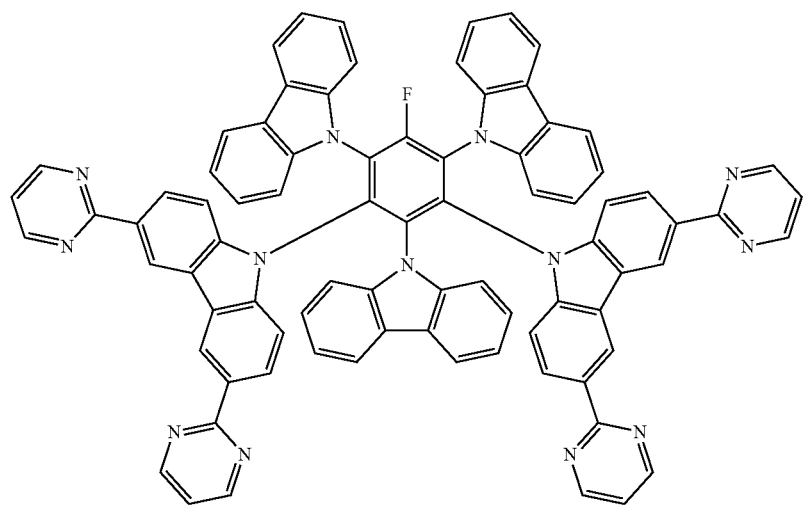
39

40
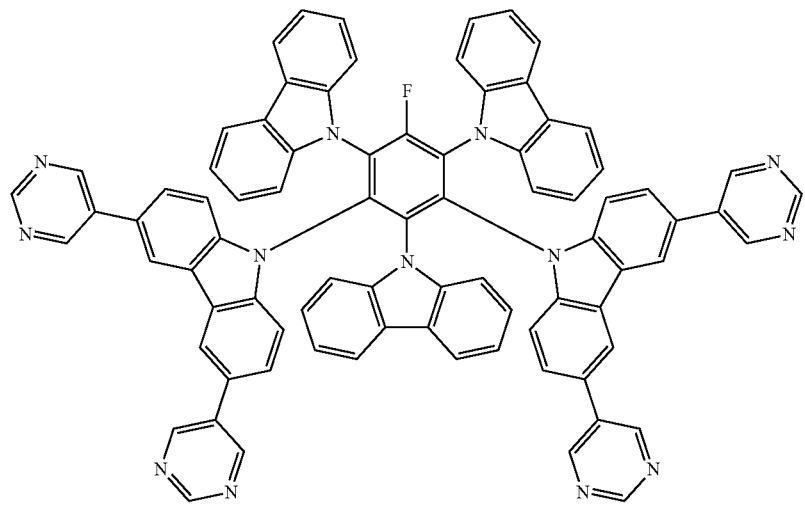
41
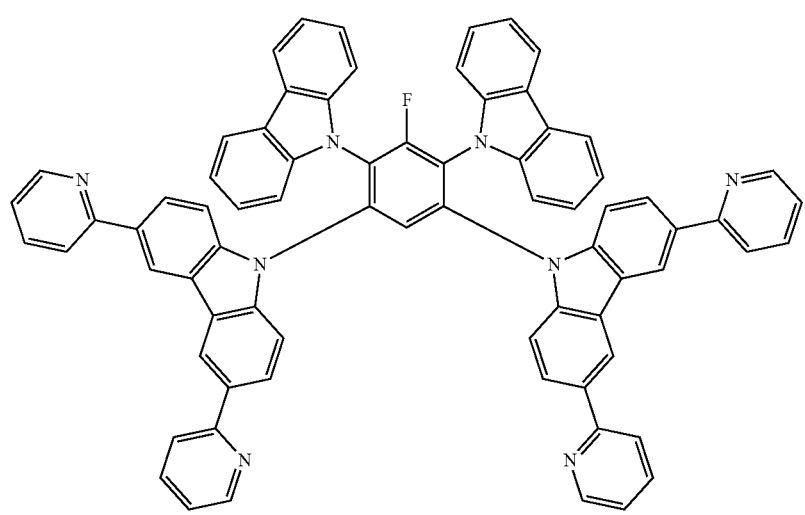
42
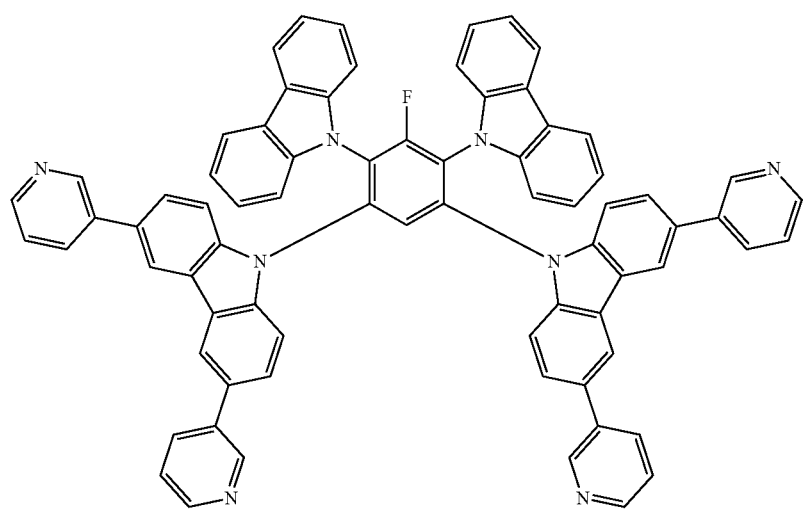

-continued
43
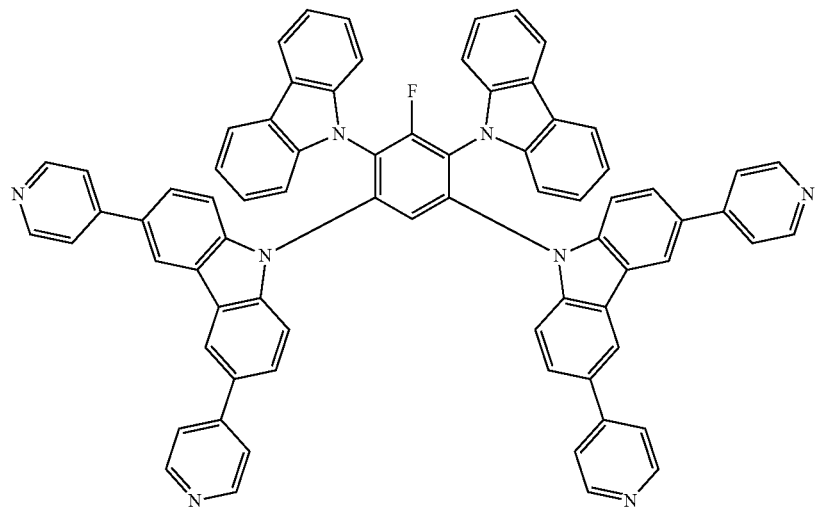
44
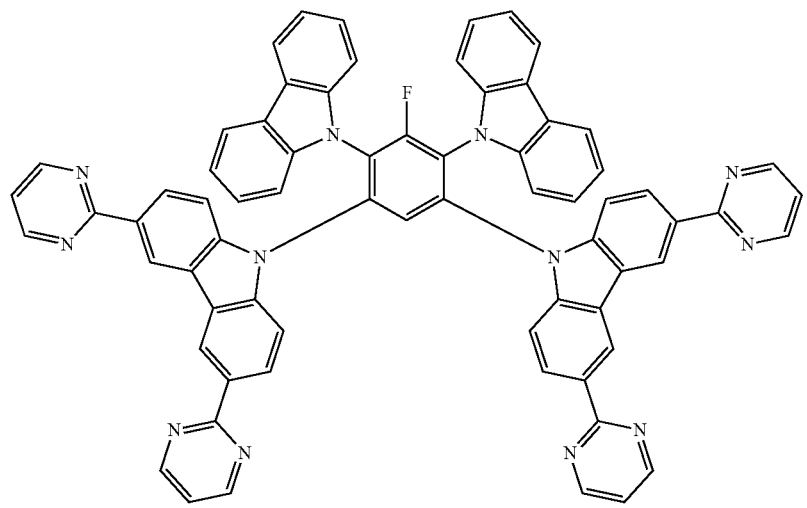
45
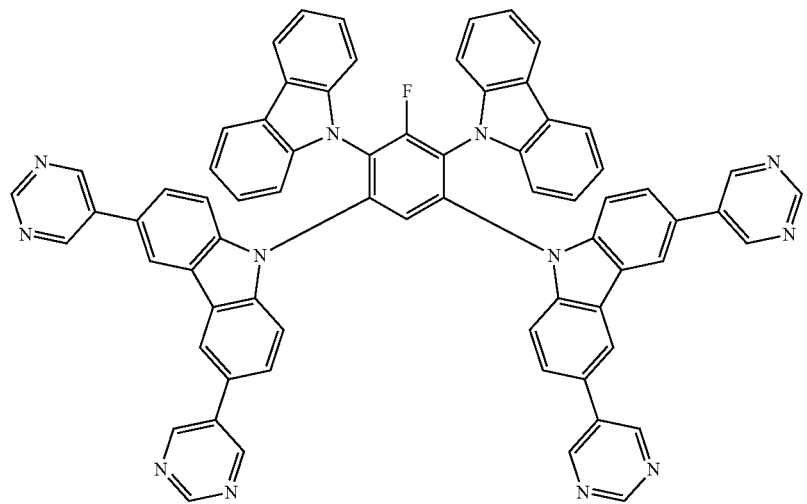

46
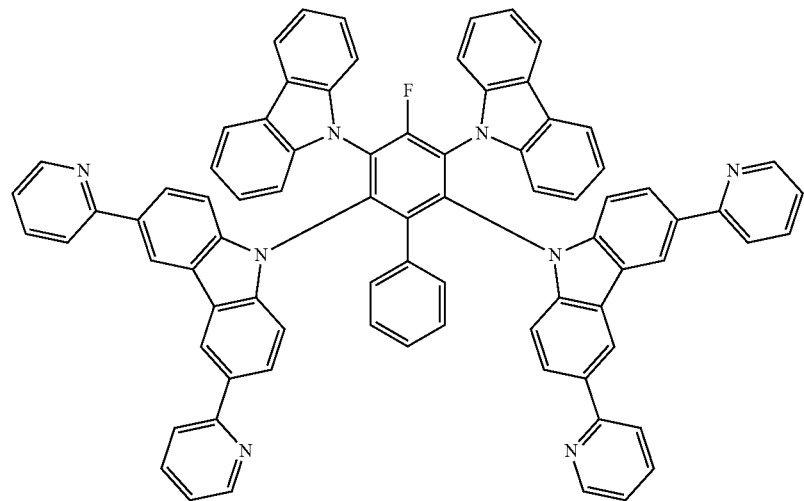
47
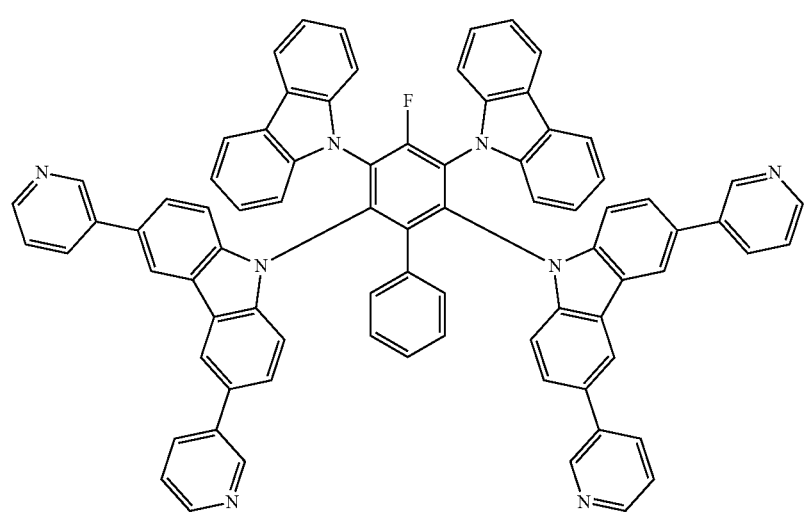
48
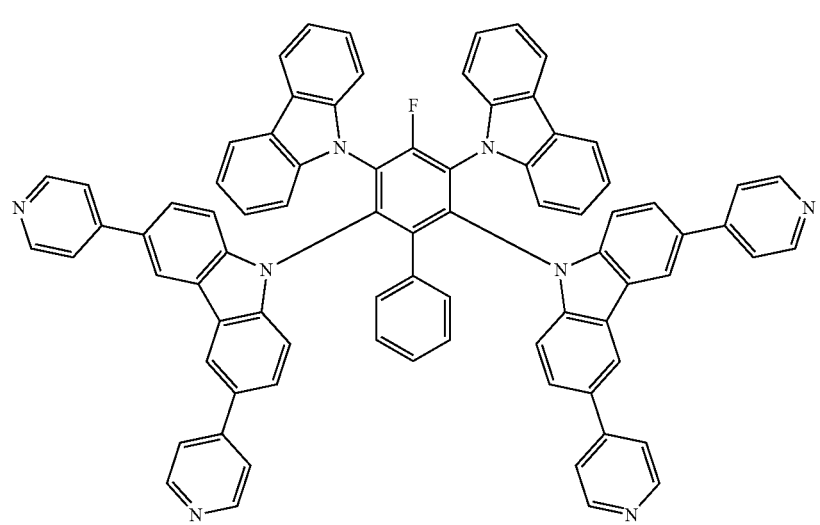

49
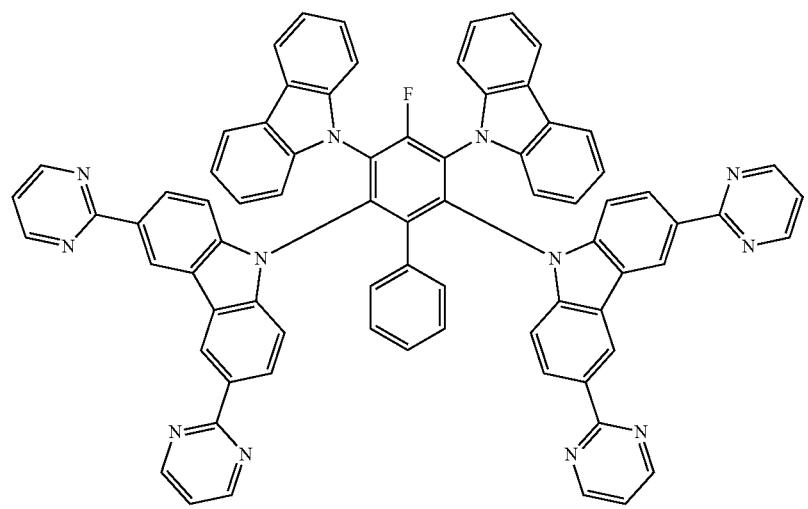
50
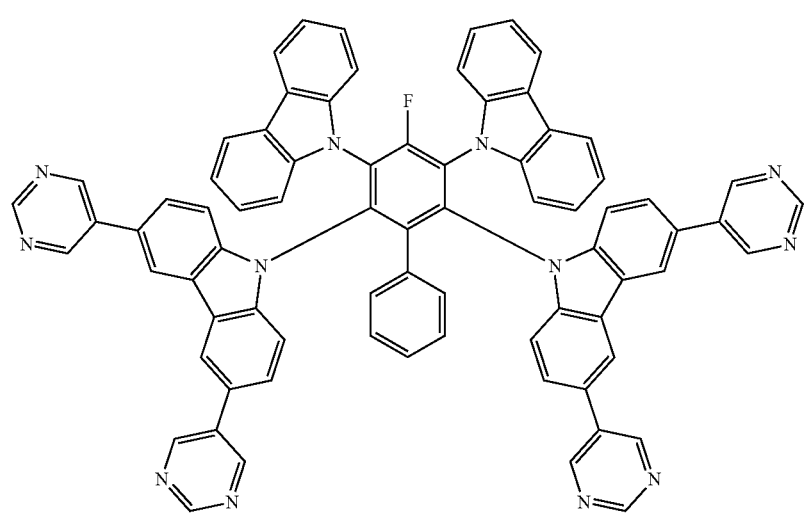
51
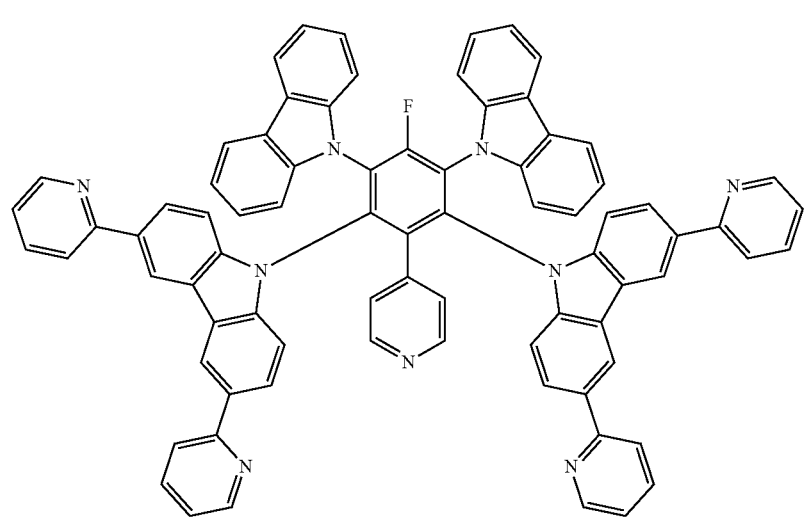

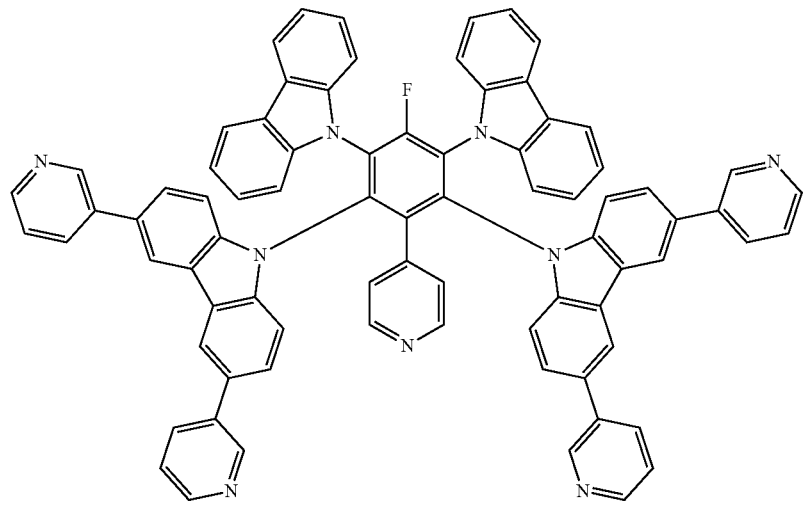
52
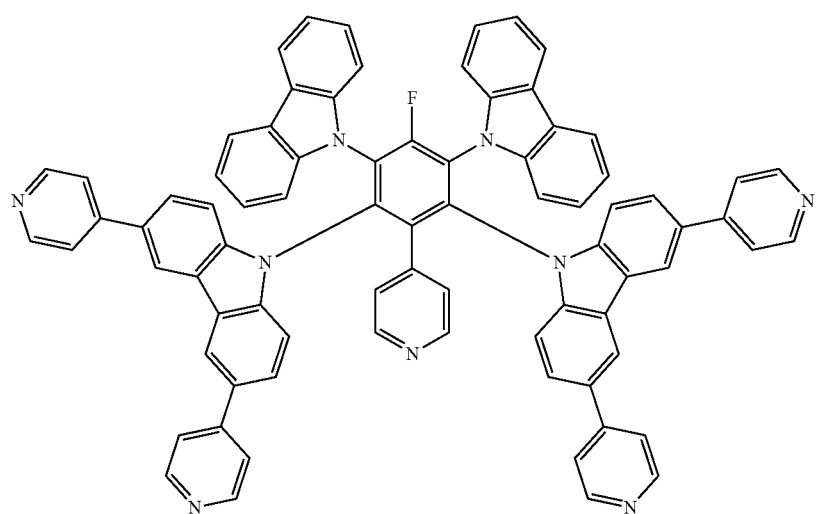
53
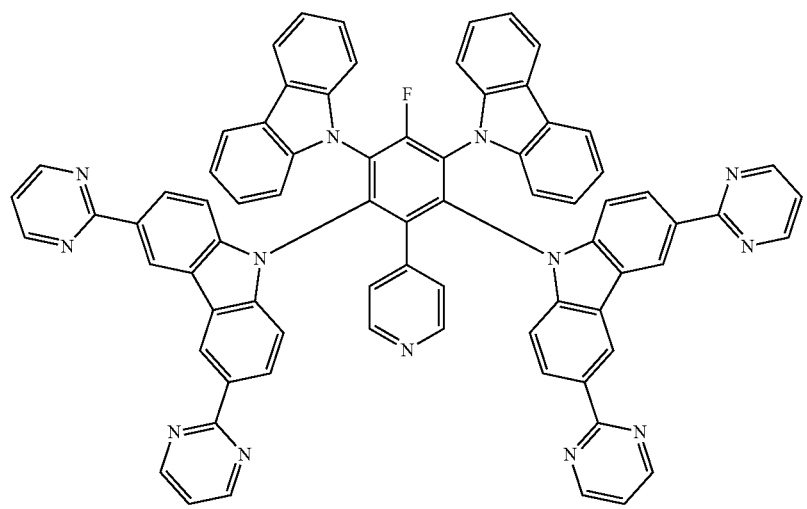
54

55
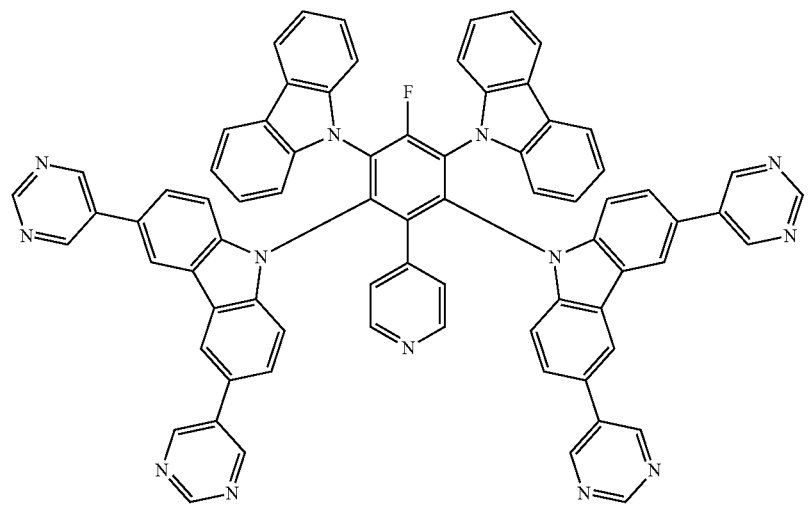
56
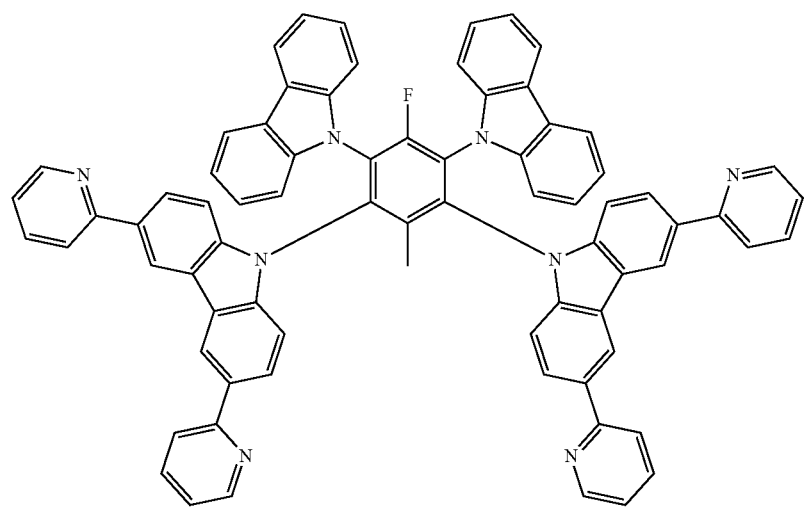
57
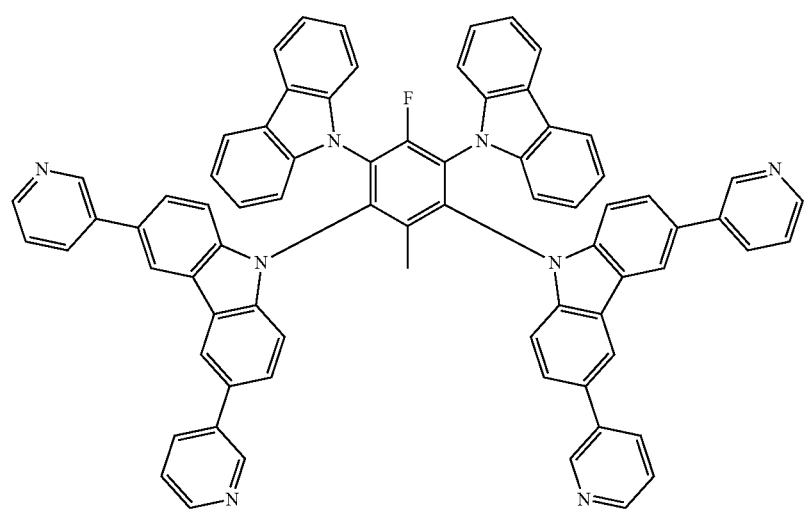

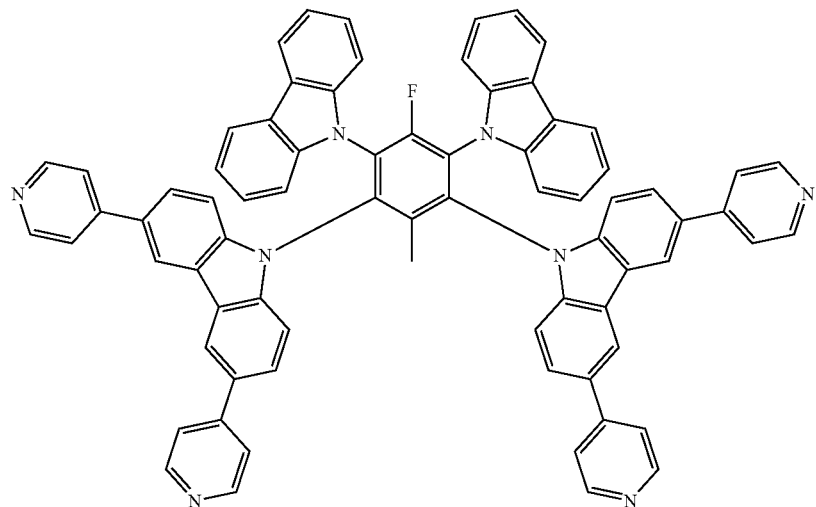
58
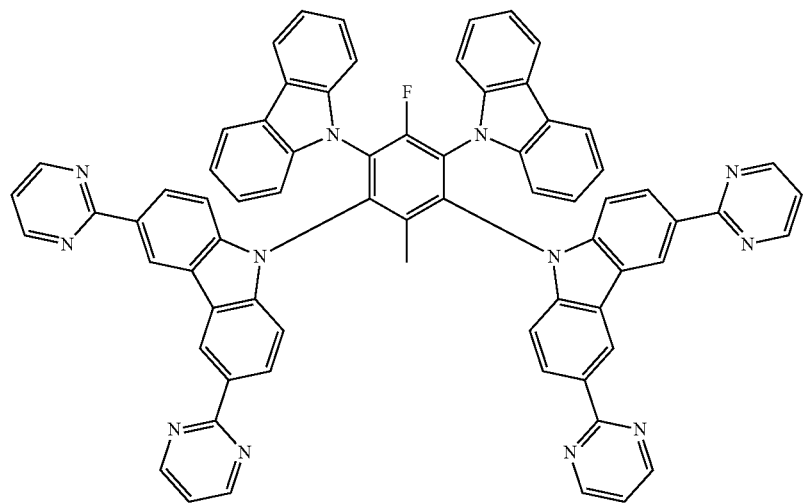
59
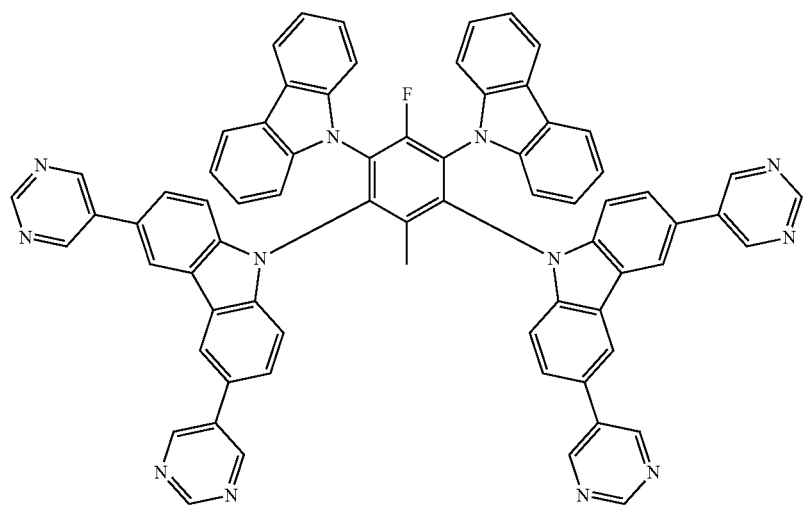
60

61
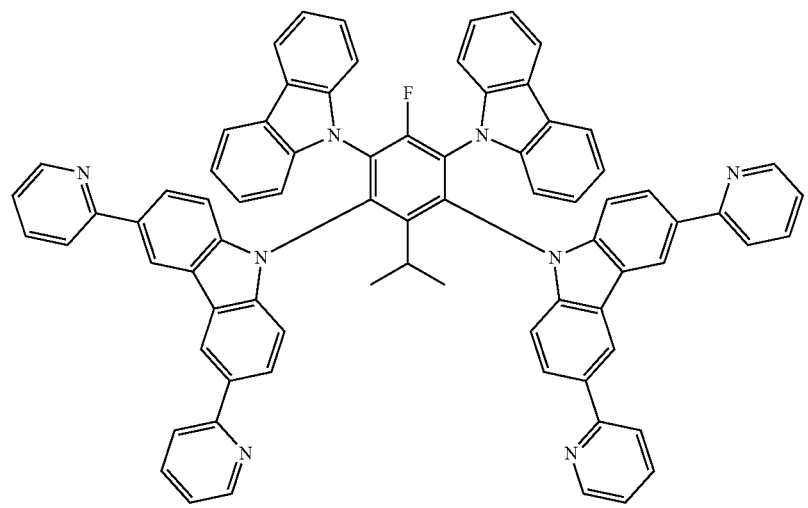
62
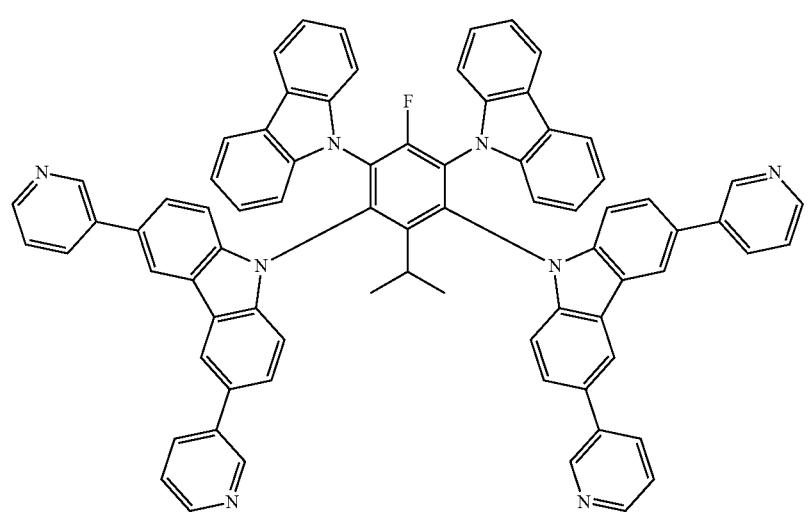
63
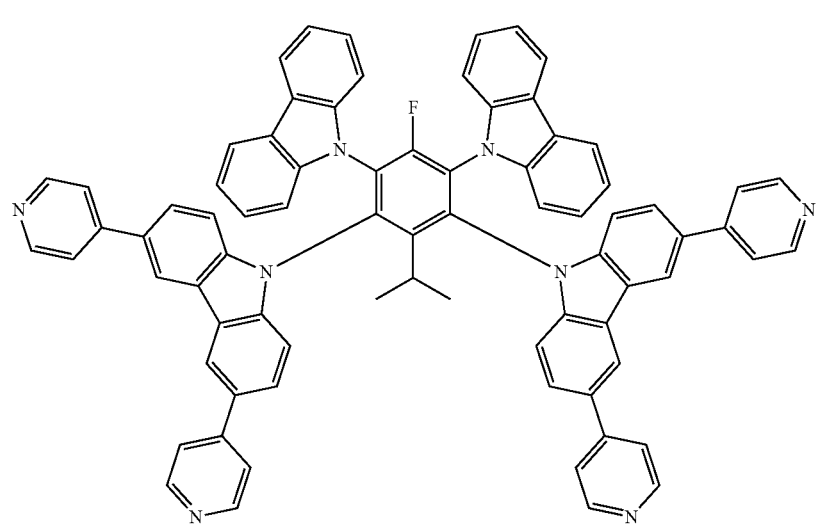

64
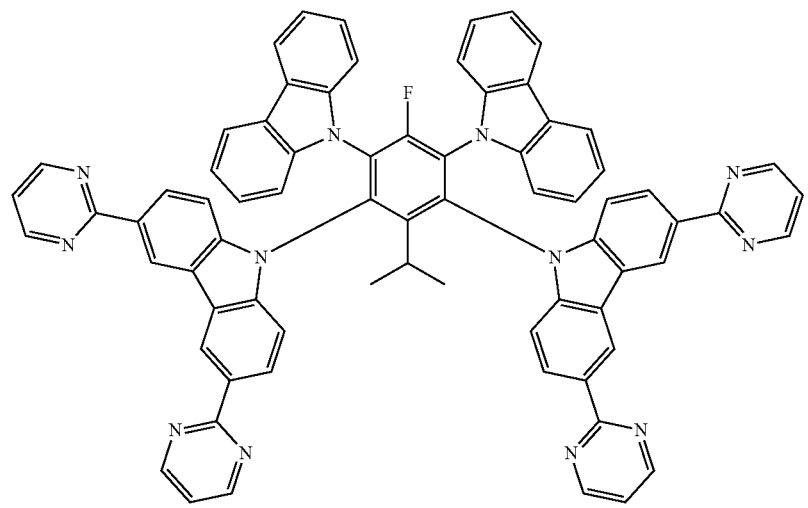
65
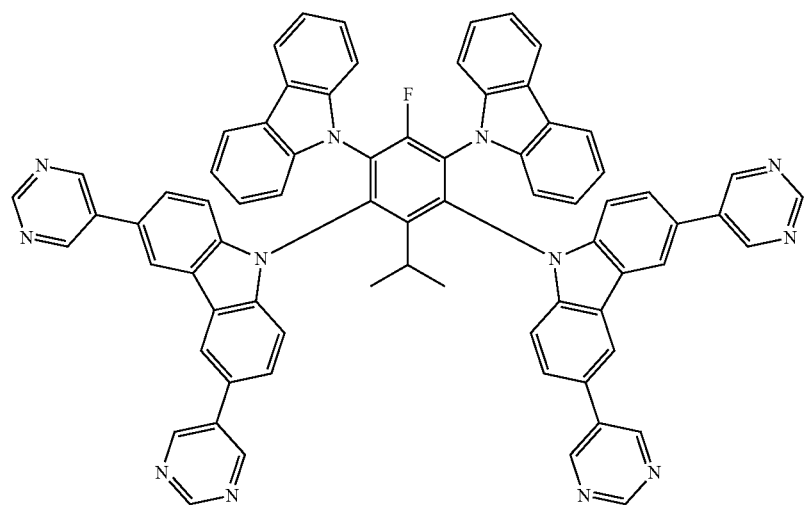
66
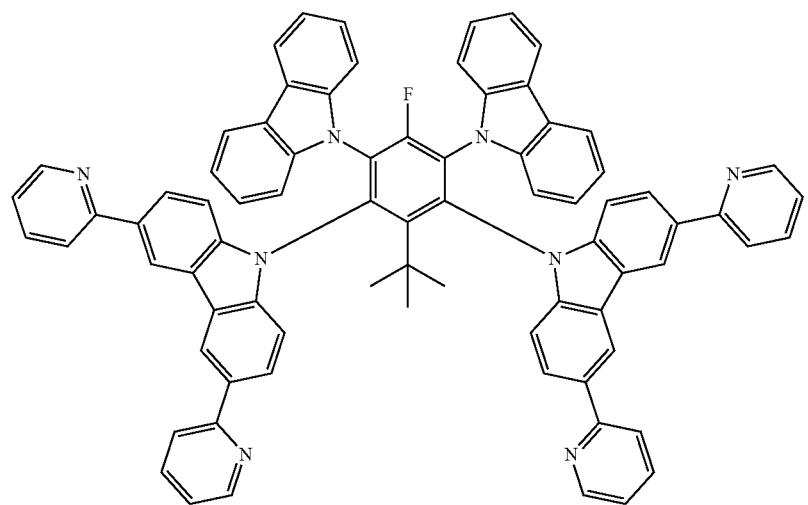

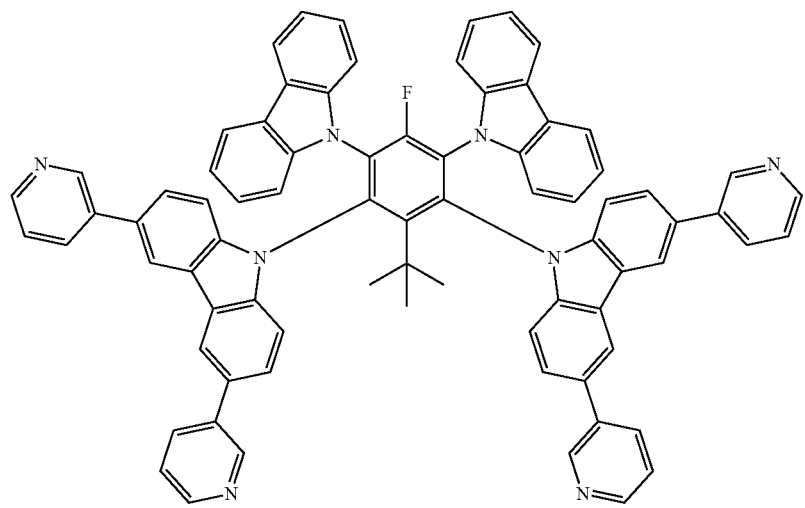
67
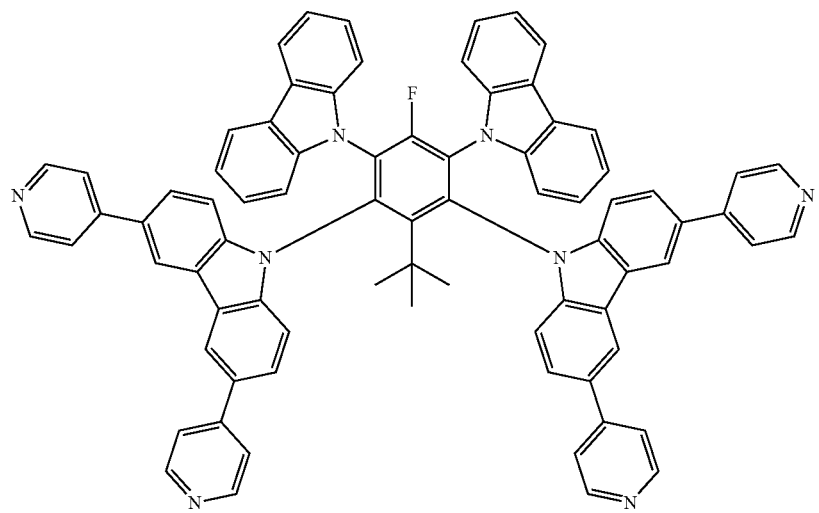
68
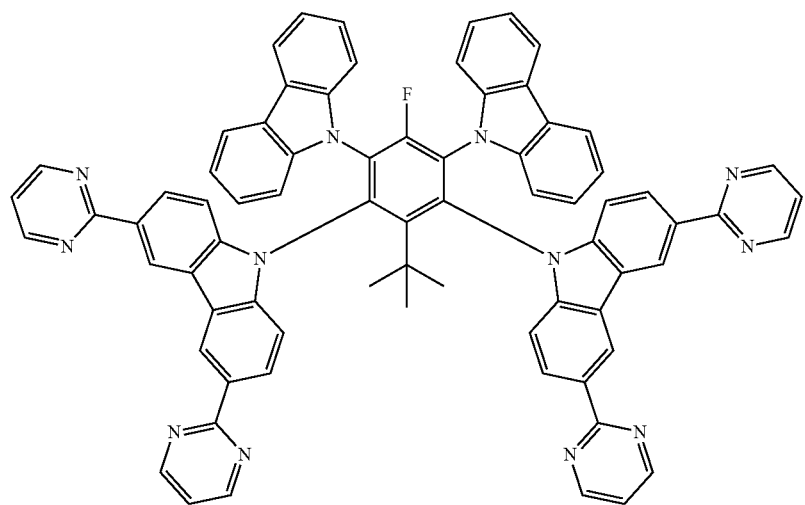
69

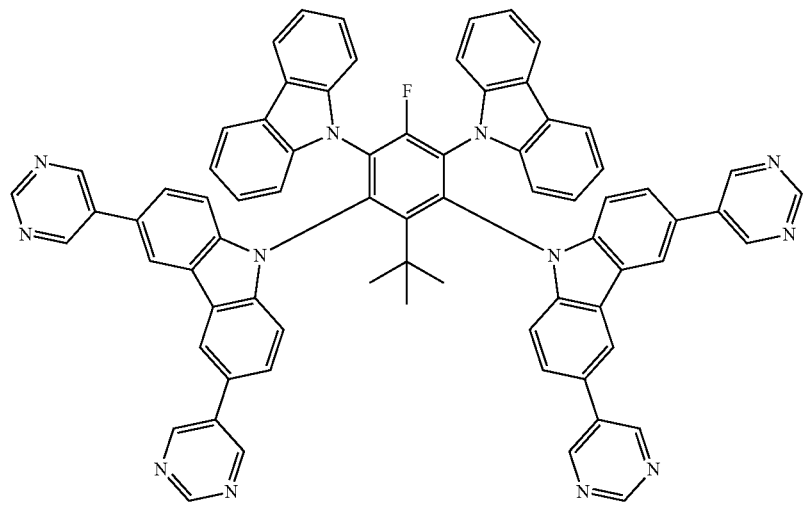
70
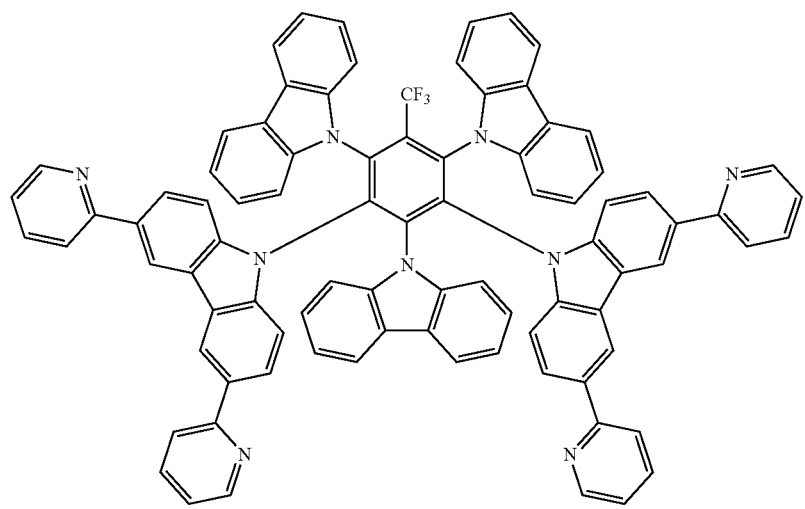
71
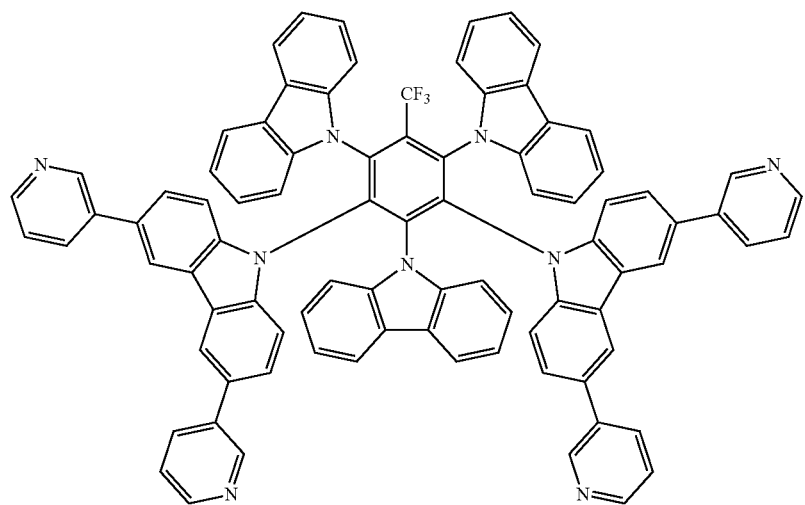
72

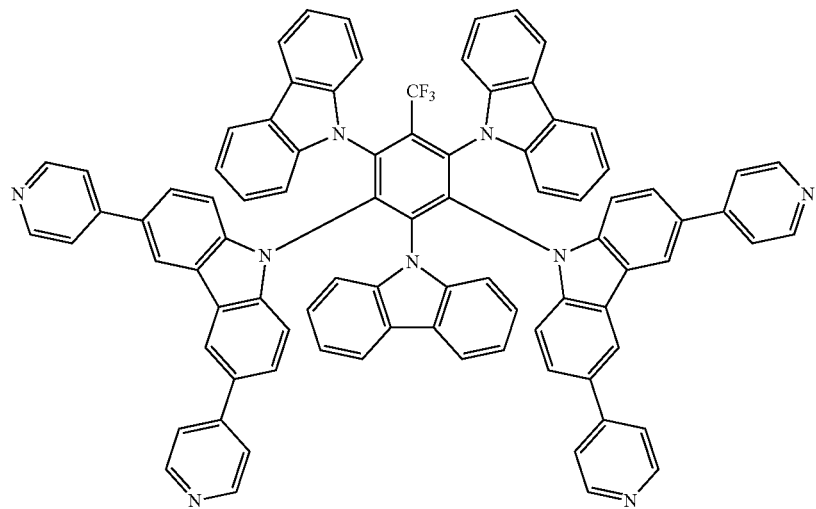
73
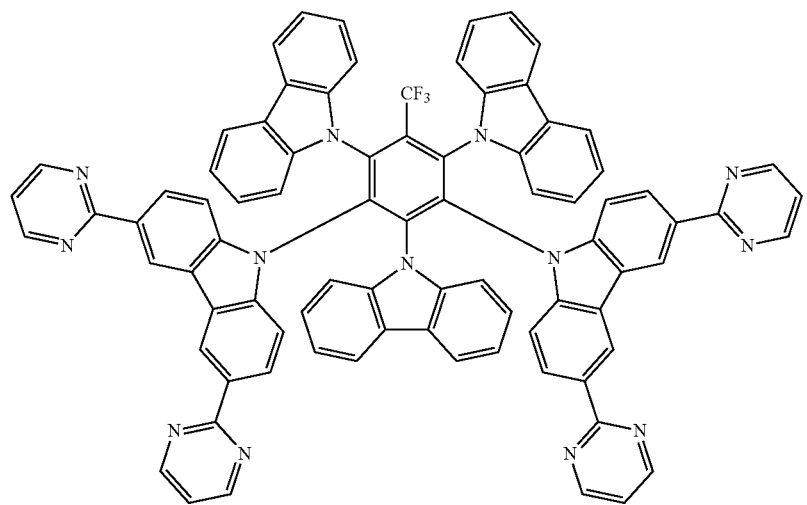
74
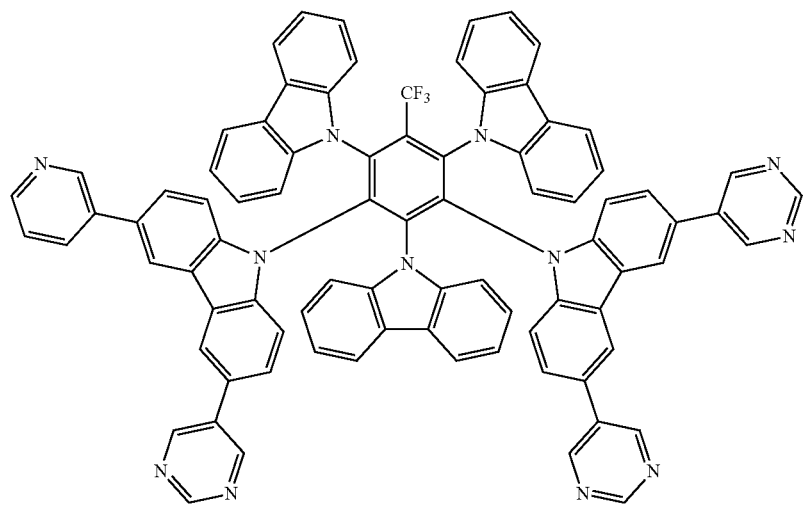
75

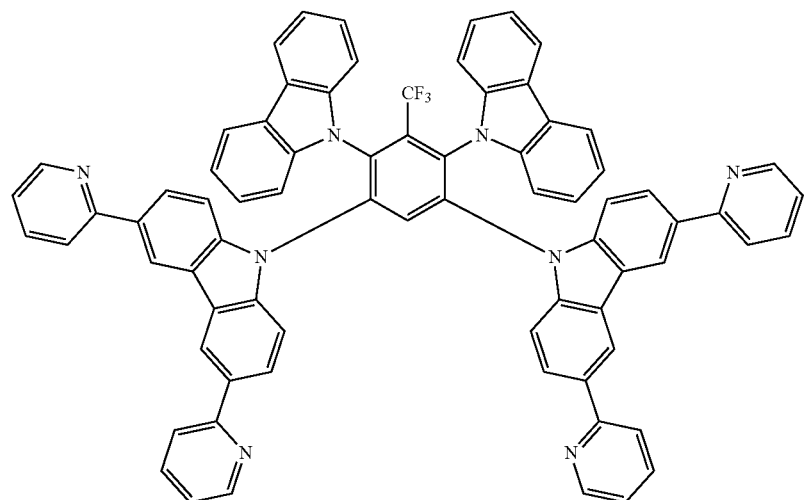
76
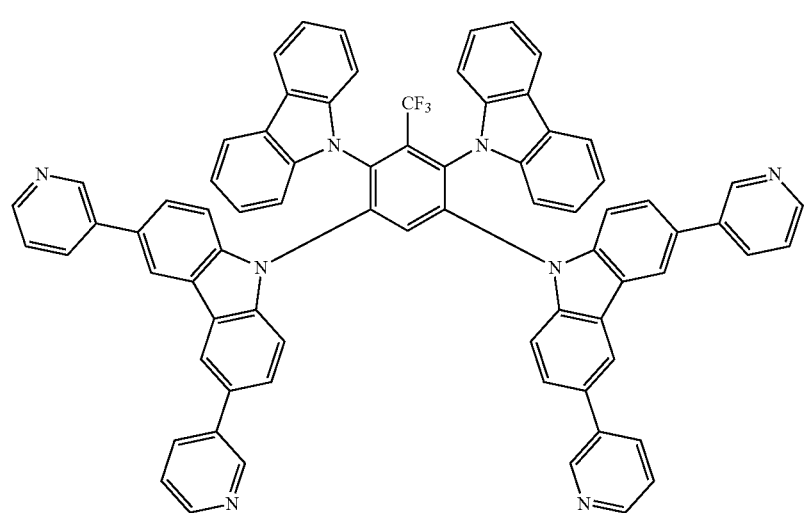
77
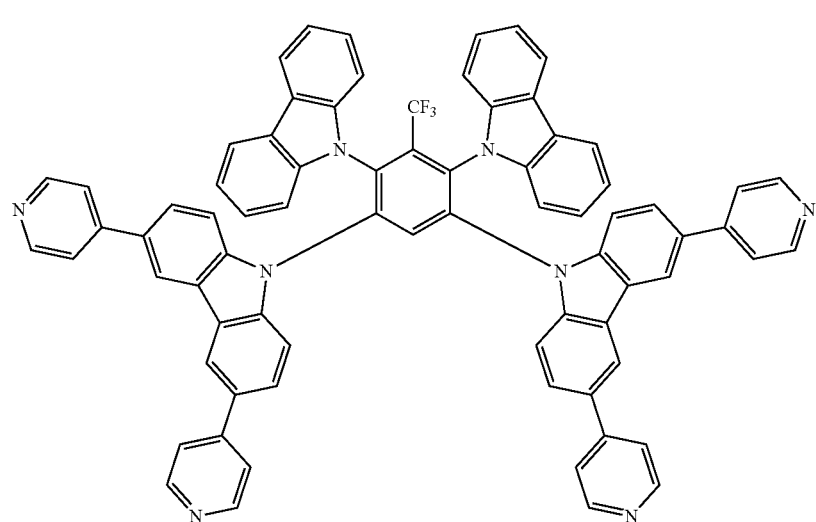
78

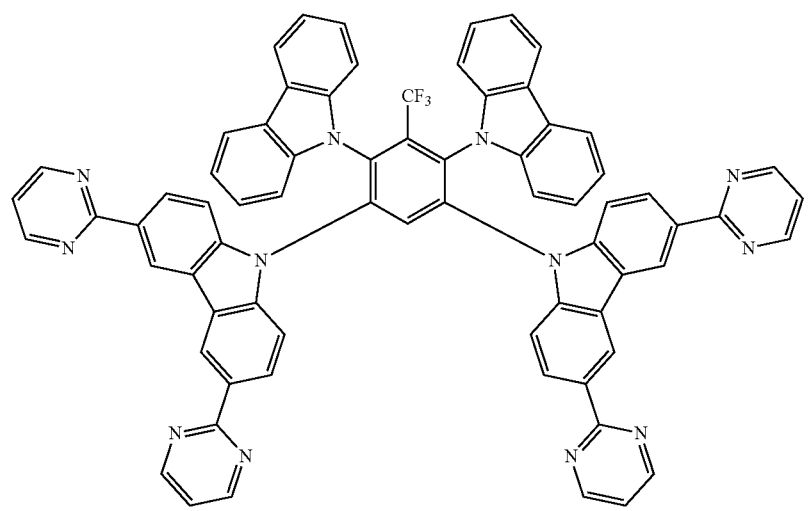
79
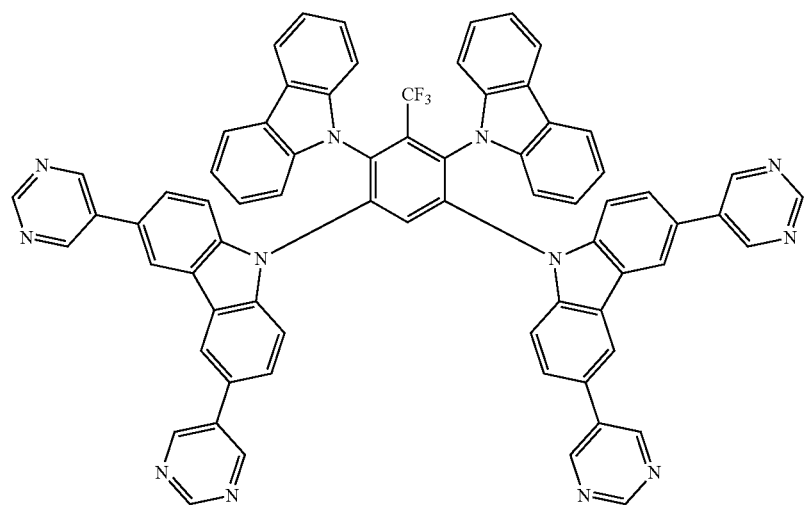
80
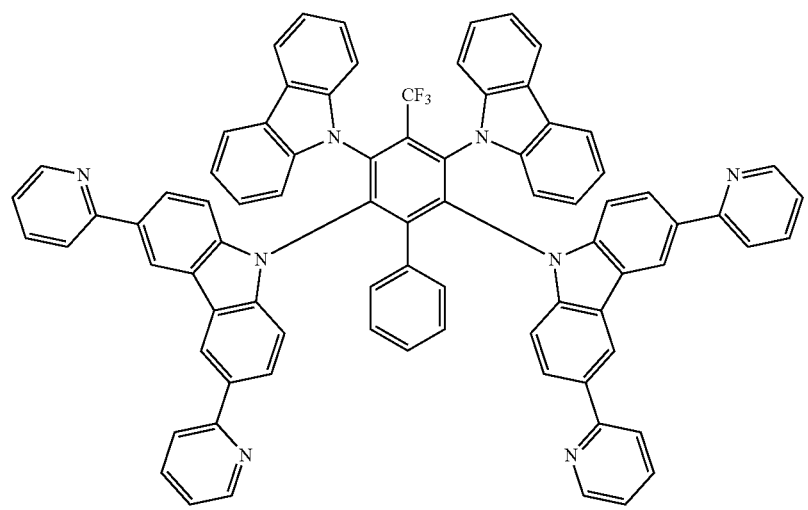
81

-continued
82
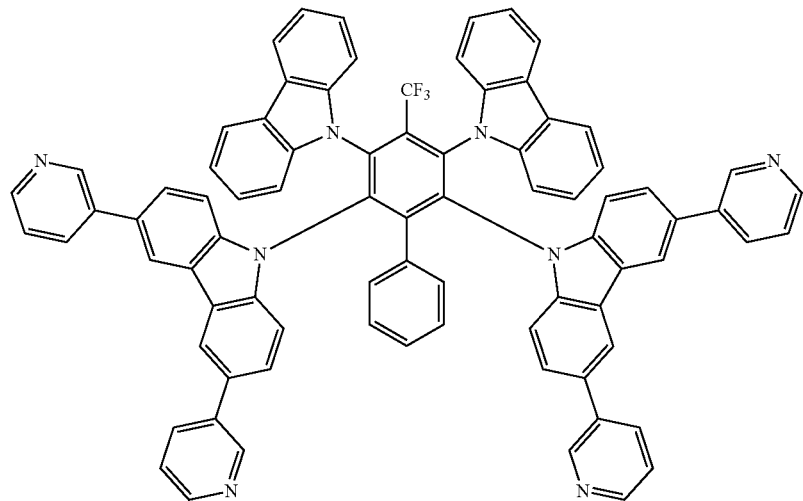
83
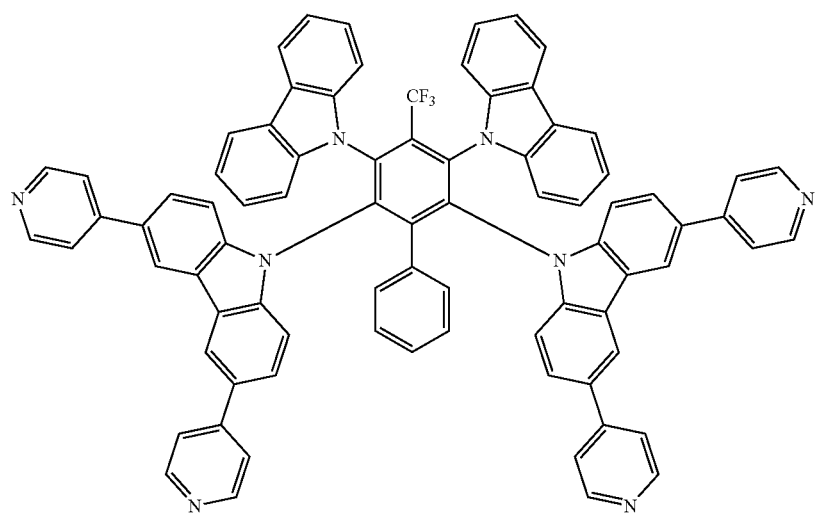
84
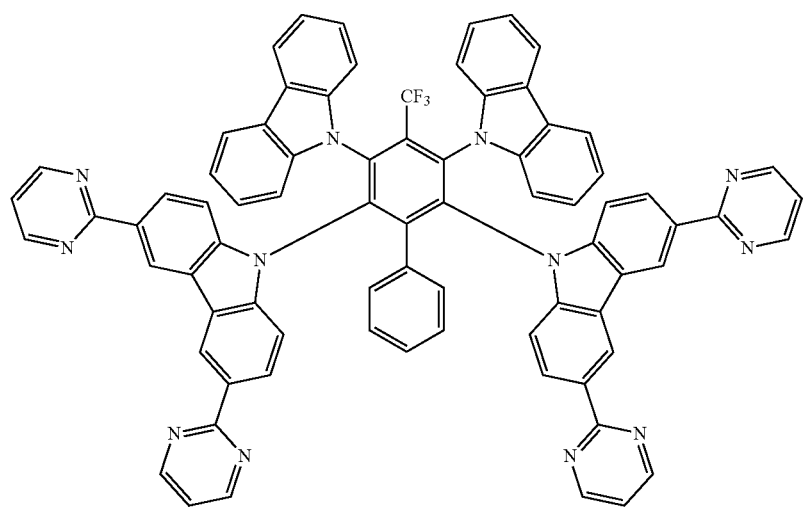

85
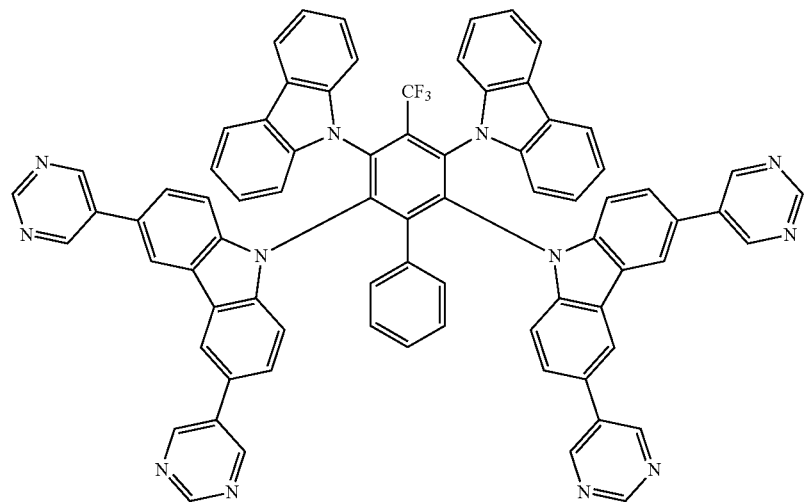
86
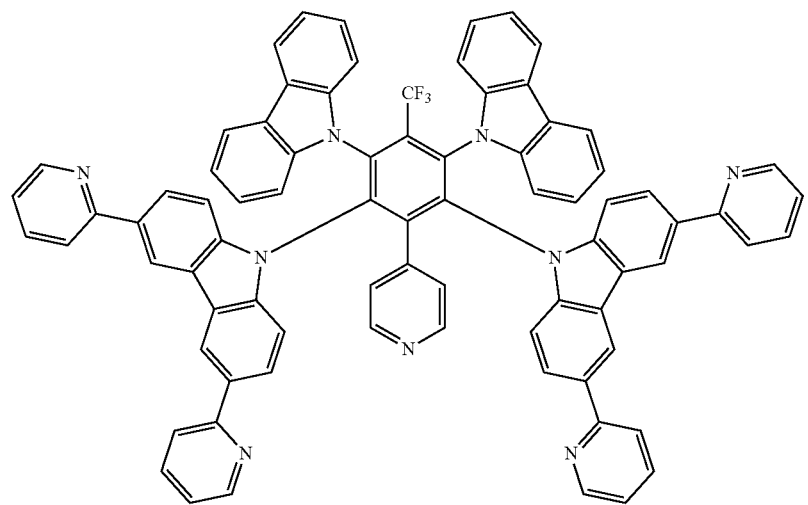
87
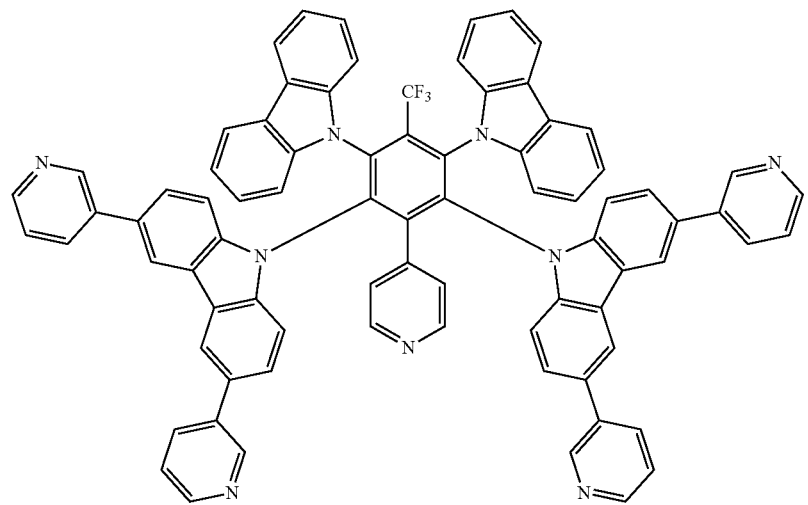

88
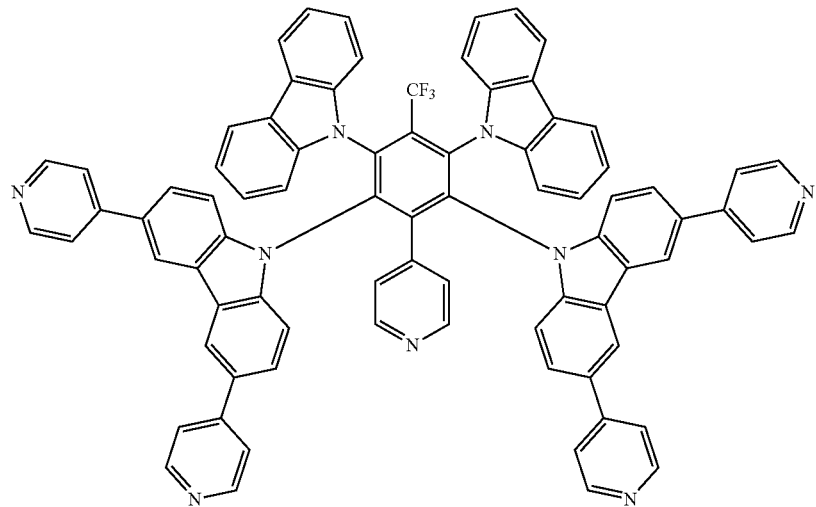
89
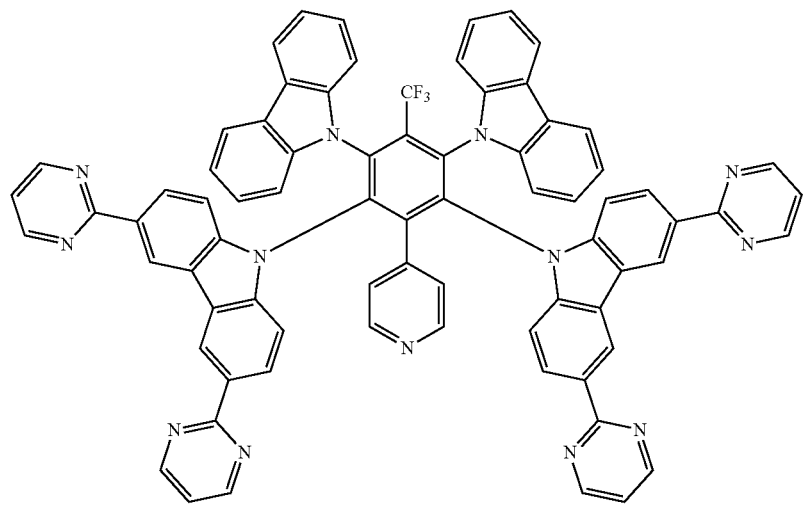
90
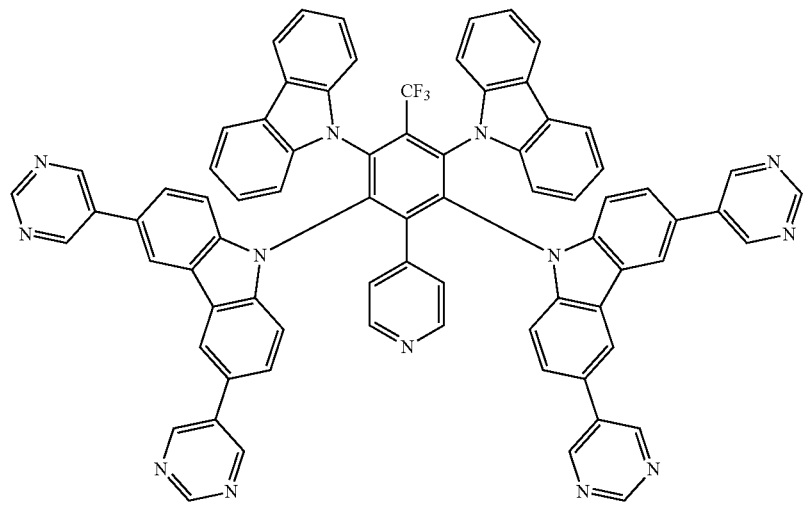

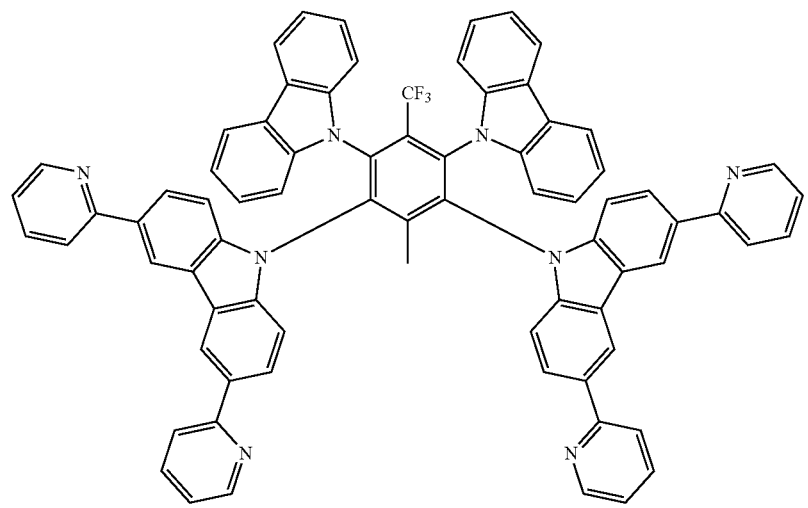
91
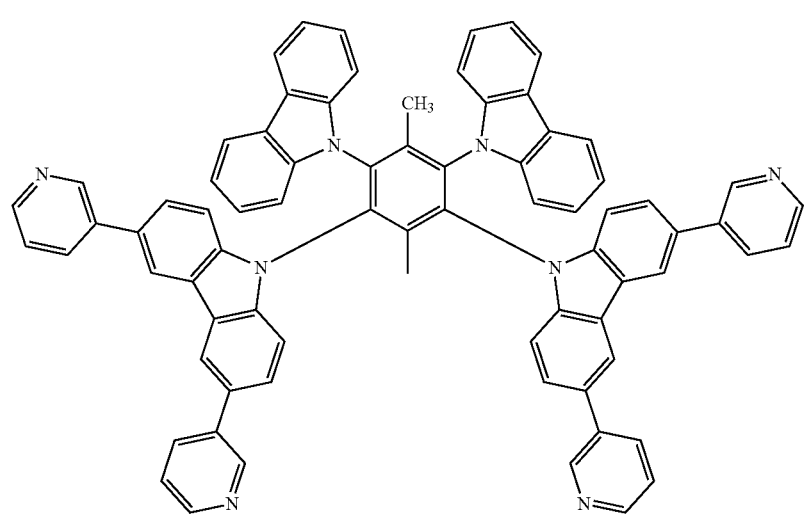
92
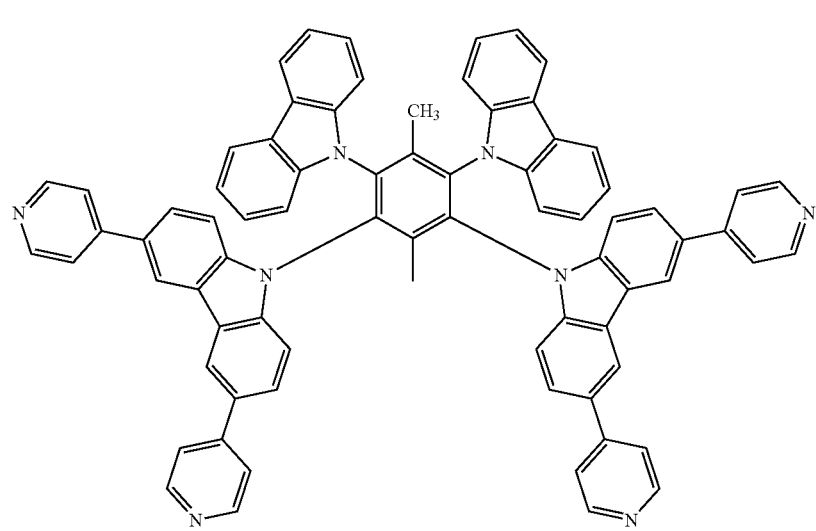
93

-continued
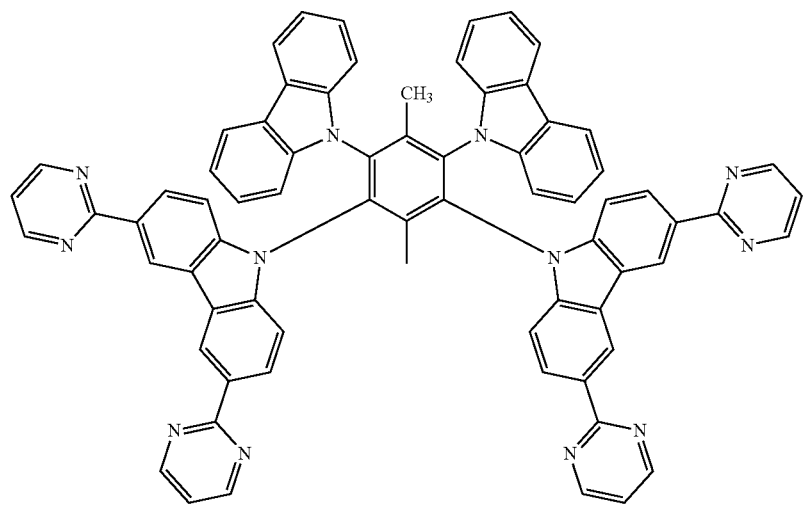
94
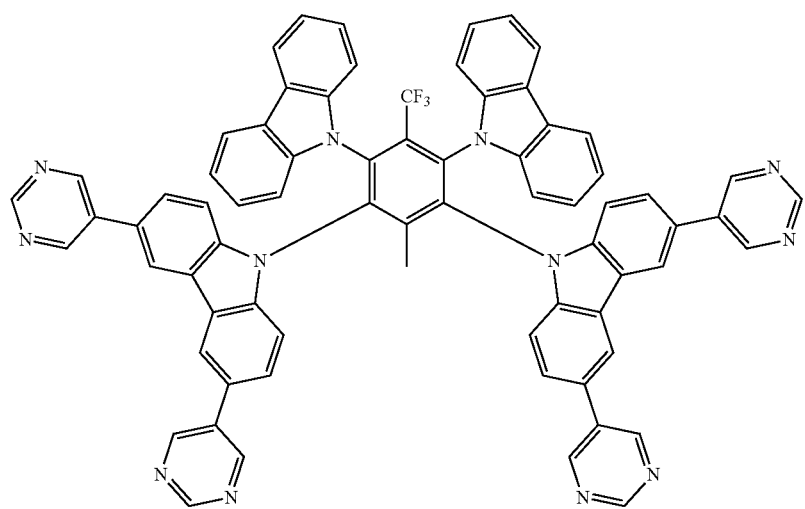
95
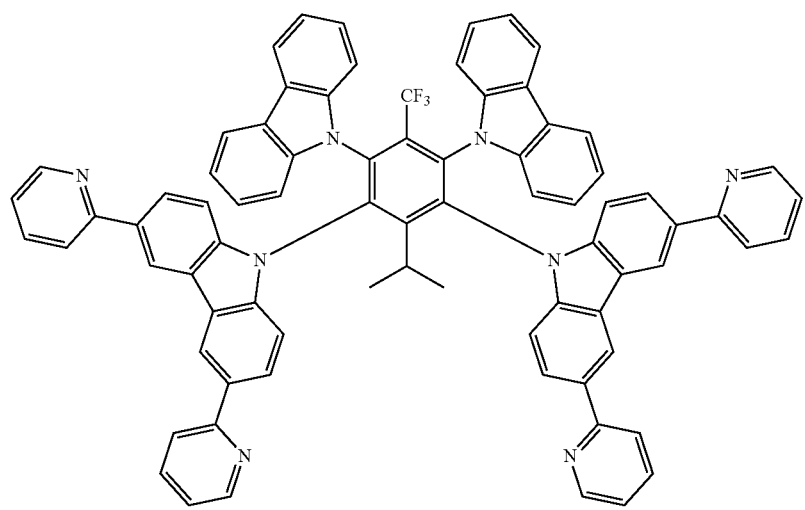
96

97
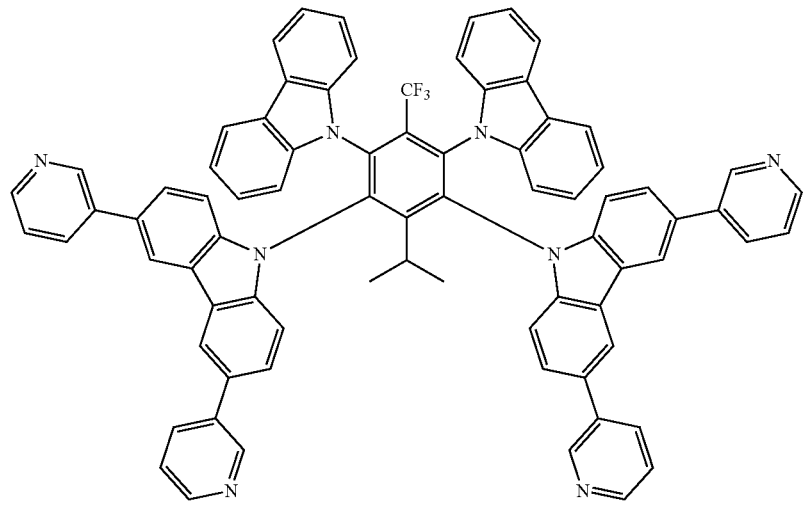
98
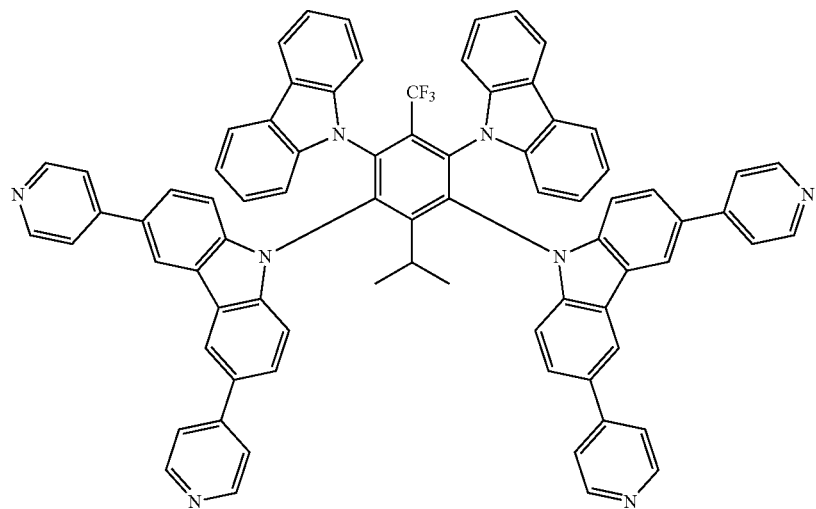
99
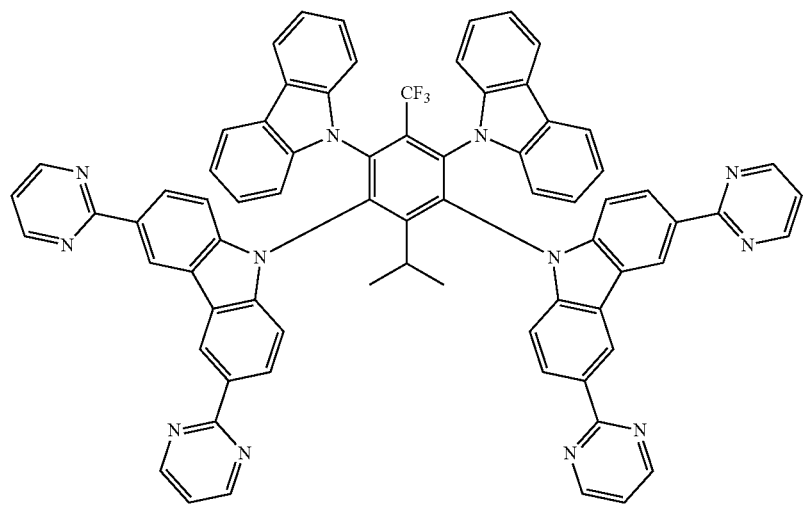

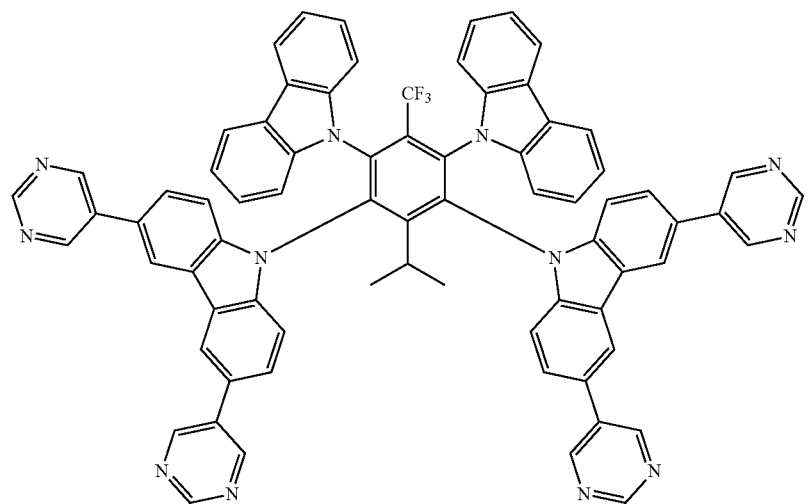
100
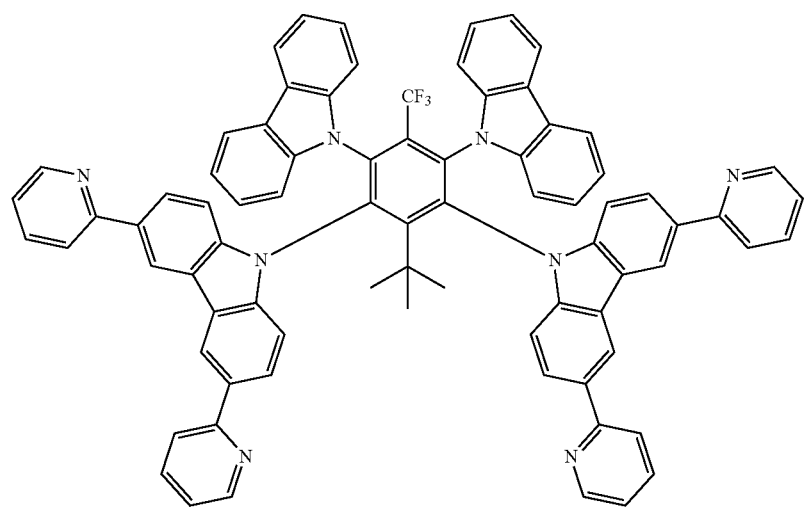
101
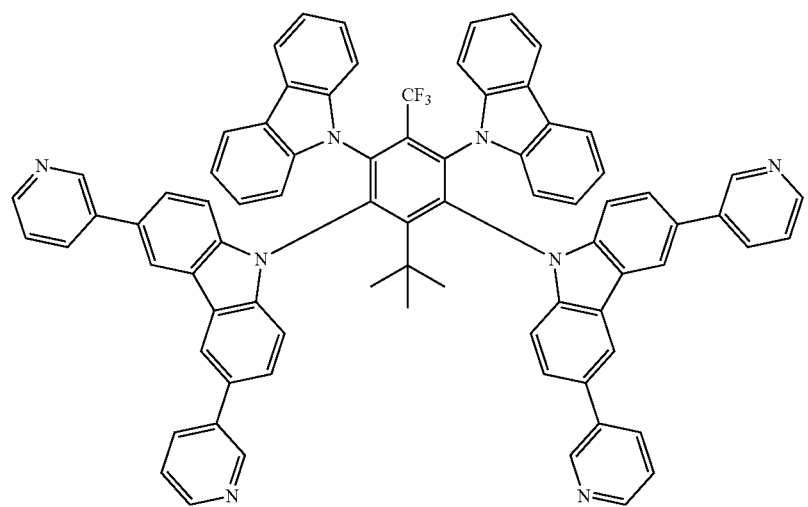
102

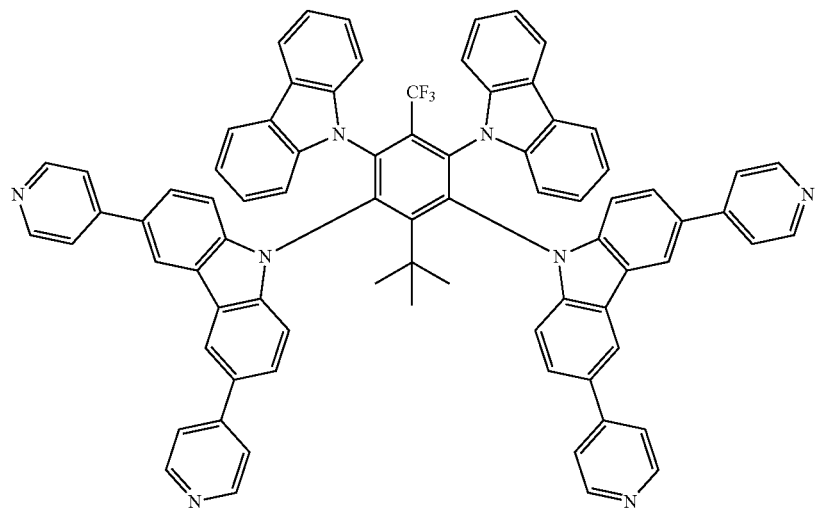
103
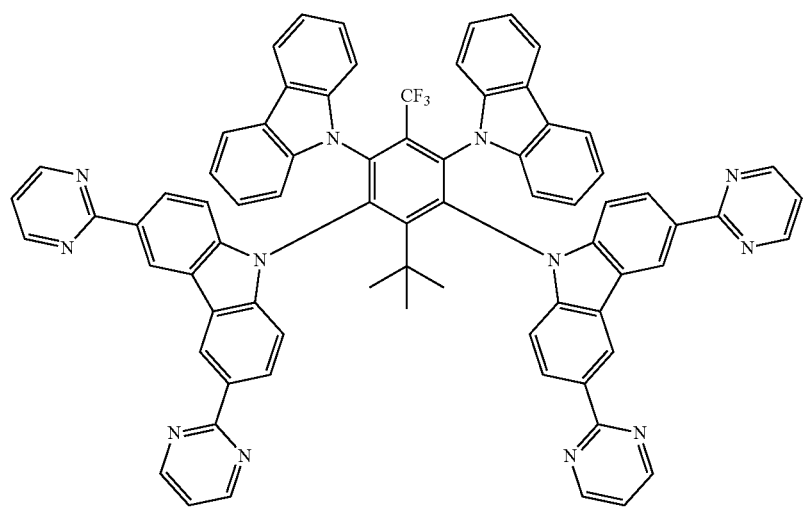
104
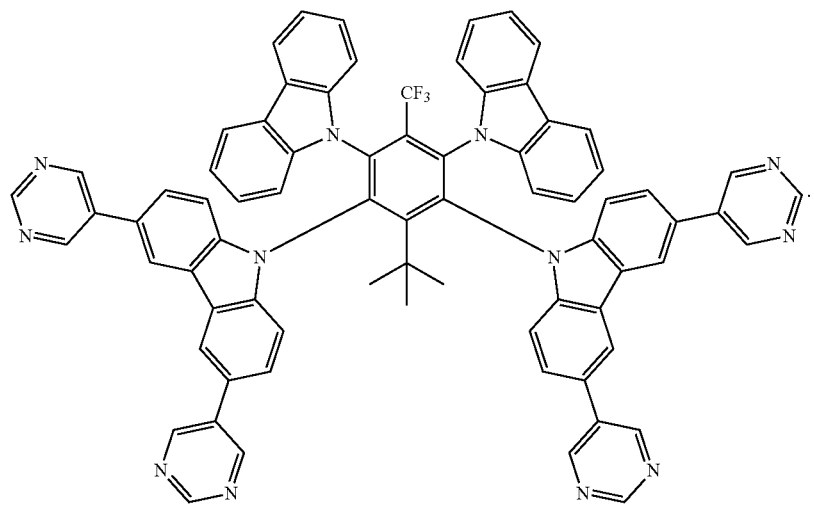
105

10. An aromatic compound represented by Formula 1:

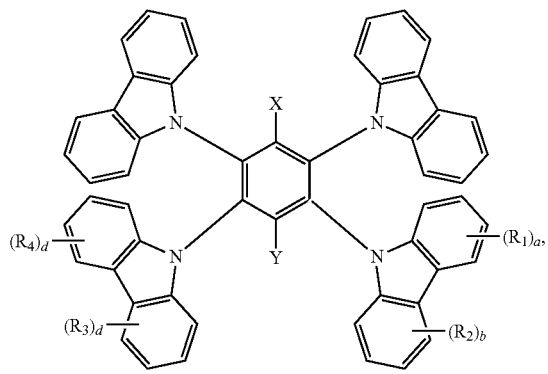

Formula 1 wherein in Formula 1,

X is a cyano group, a fluorine, or a C1-C10 alkyl group substituted with a fluorine, Y is a hydrogen atom, a deuterium atom, a halogen atom, a cyano group, an unsubstituted heteroaryl group having 3 to 20 ring-forming carbon atoms and at least one ring-forming nitrogen atom, a substituted or unsubstituted aryl group having 6 to 30 ring-forming carbon atoms, or a substituted or unsubstituted alkyl group having 1 to 20 carbon atoms, a to d are each independently an integer of 1 to 4, and at least one of $R_1$ to $R_4$ is represented by Formula 2 and the remaining ones of $R_1$ to $R_4$ are each independently a hydrogen atom, a deuterium atom, or a substituted or unsubstituted alkyl group having 1 to 4 carbon atoms,

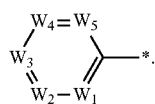

Formula 2 wherein in Formula 2, at least one of $W_1$ to $W_5$ is a nitrogen atom and the remaining ones of $W_1$ to $W_5$ are each independently $CR_5$, and $R_5$ is a hydrogen atom, a deuterium atom, or a substituted or unsubstituted alkyl group having 1 to 4 carbon atoms.

11. The aromatic compound of claim 10, wherein the aromatic compound represented by Formula 1 is a thermally activated delayed fluorescence emission material.

12. The aromatic compound of claim 10, wherein Formula 2 is represented by Formula 2-1 or Formula 2-2:

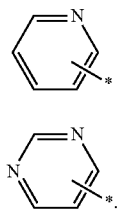

Formula 2-1

Formula 2-2

13. The aromatic compound of claim 10, wherein a to d are all 1, and $R_1$ to $R_4$ are all the same.

14. The aromatic compound of claim 10, wherein the aromatic compound represented by Formula 1 is laterally symmetric with respect to Y.

15. The aromatic compound of claim 10, wherein Y is an unsubstituted phenyl group, an unsubstituted pyridine group, an unsubstituted carbazole group, or an unsubstituted alkyl group having 1 to 4 carbon atoms.

16. The aromatic compound of claim 10, wherein Formula 1 is represented by Formula 3:

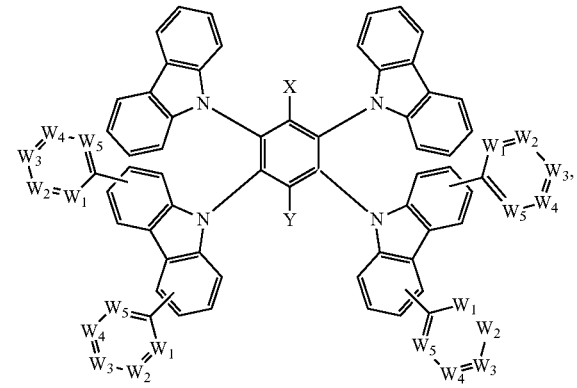

Formula 3 wherein in Formula 3,

X, Y, and $W_1$ to $W_5$ are the same as defined in Formulae 1 and 2.

17. The aromatic compound of claim 10, wherein Formula 1 is any one of the compounds represented by Compound Group 1:

Compound Group 1
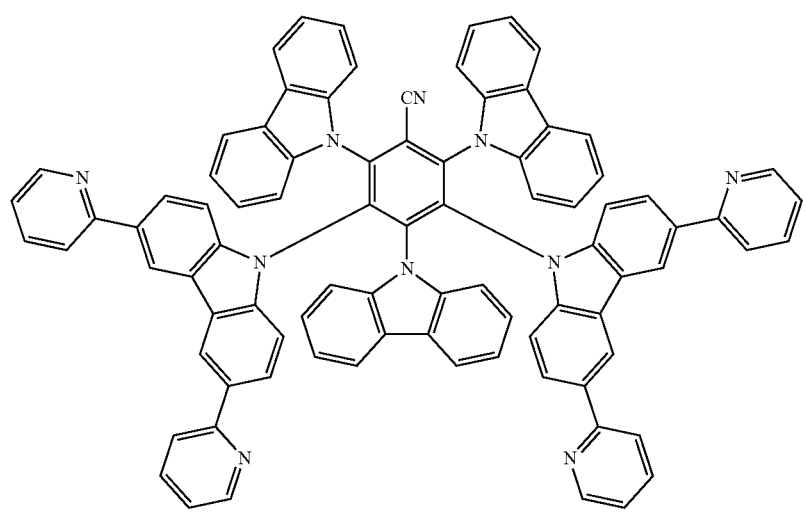
1
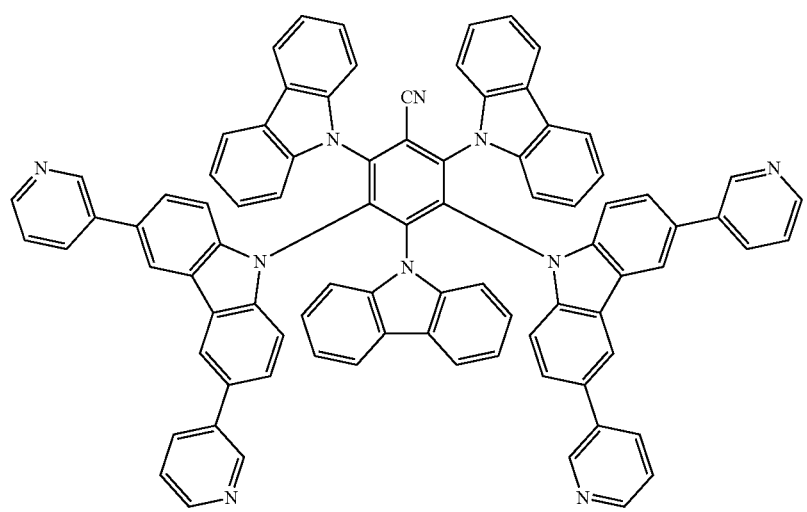
2
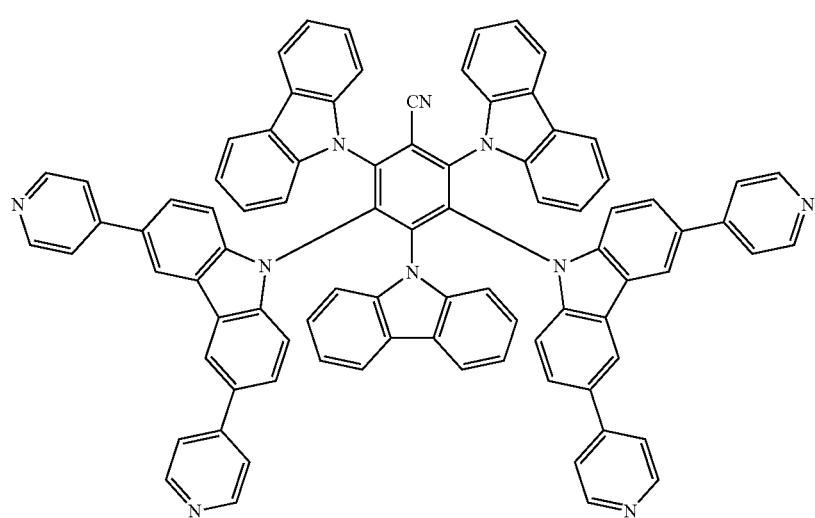
3

-continued
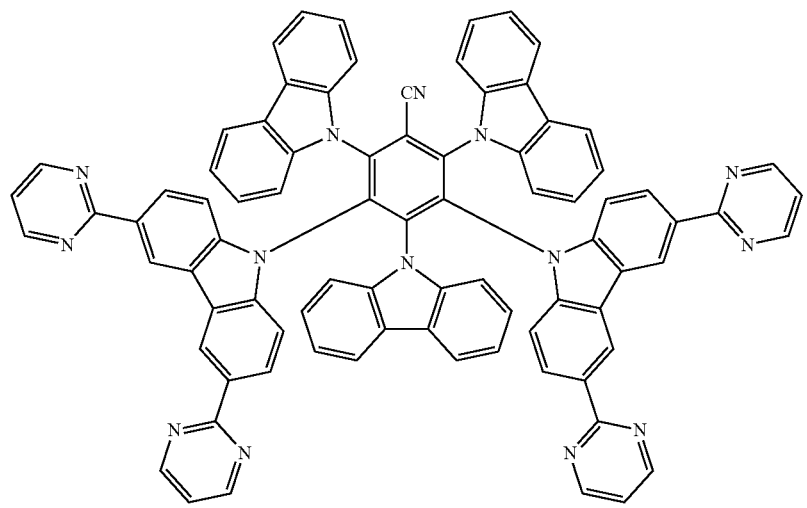
4
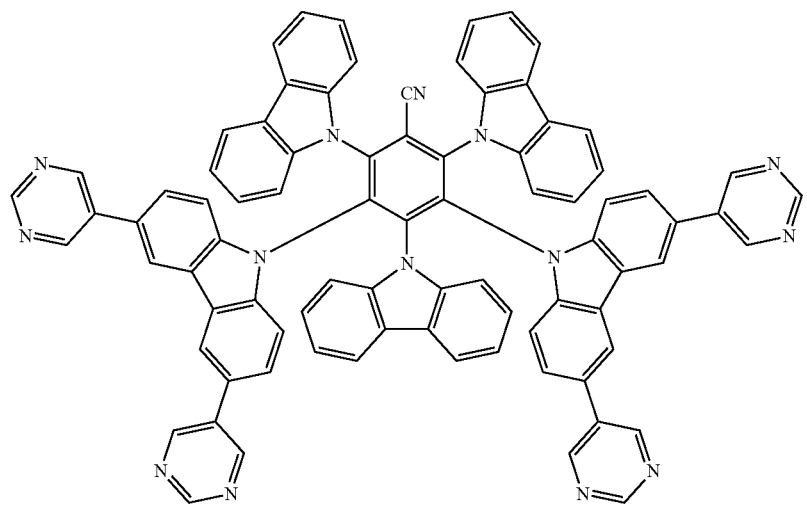
5
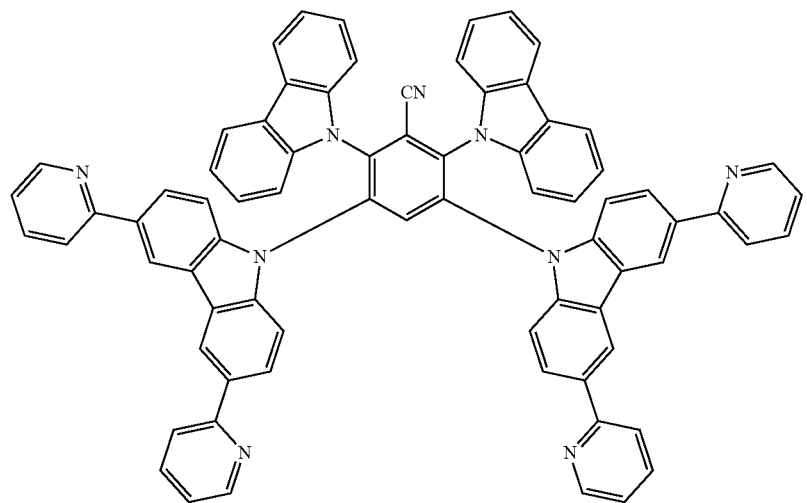
6

-continued
7
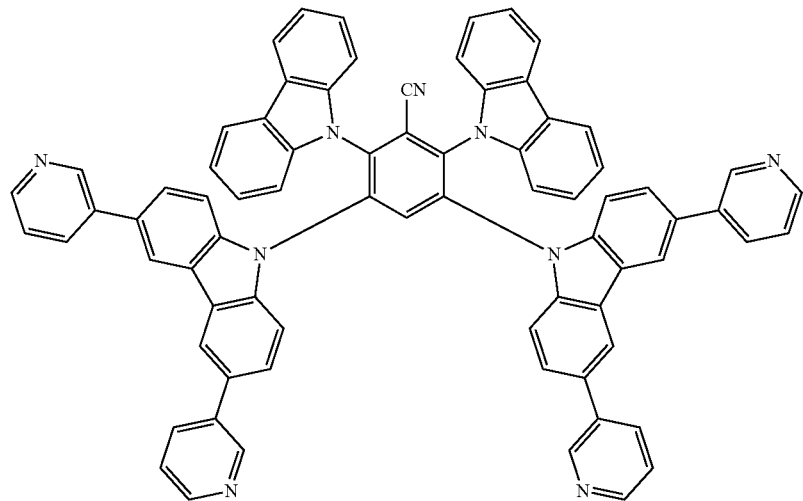
8
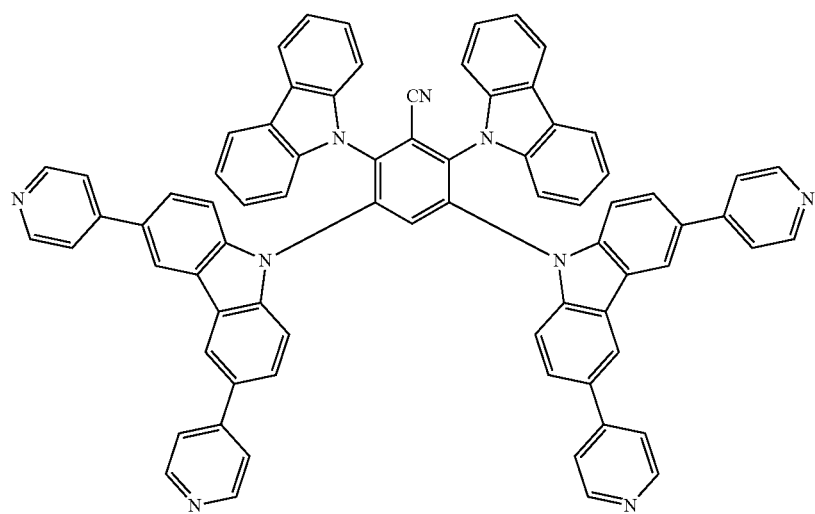
9
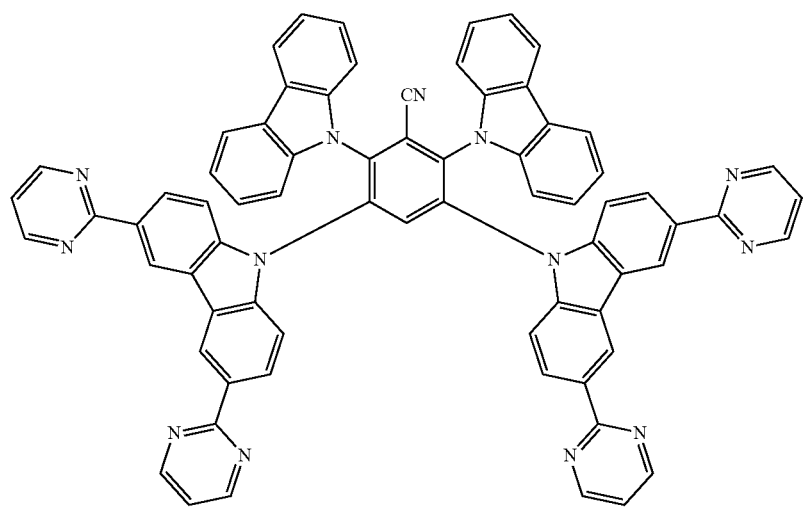

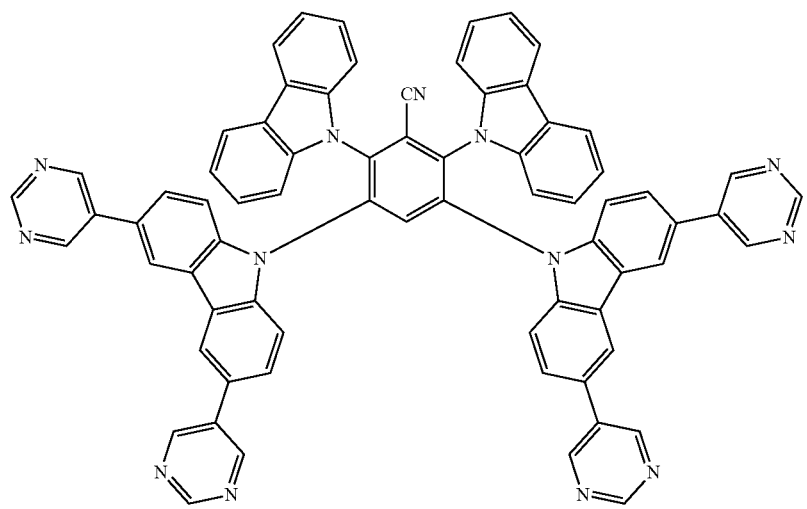
10
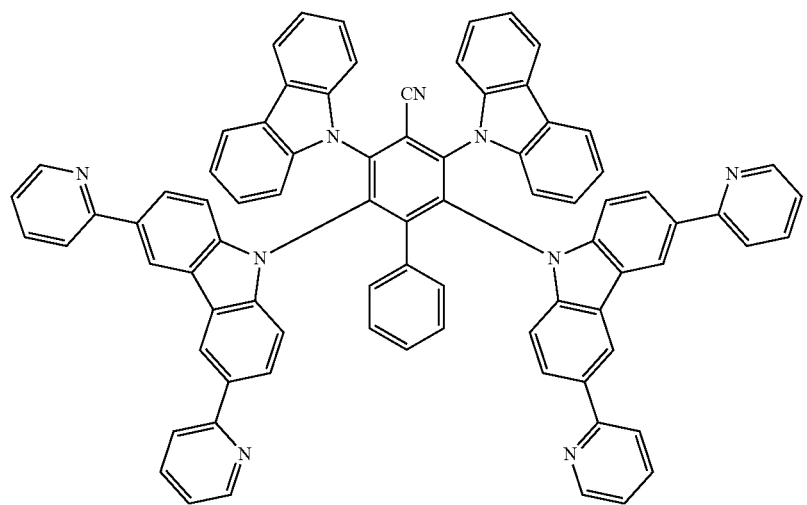
11
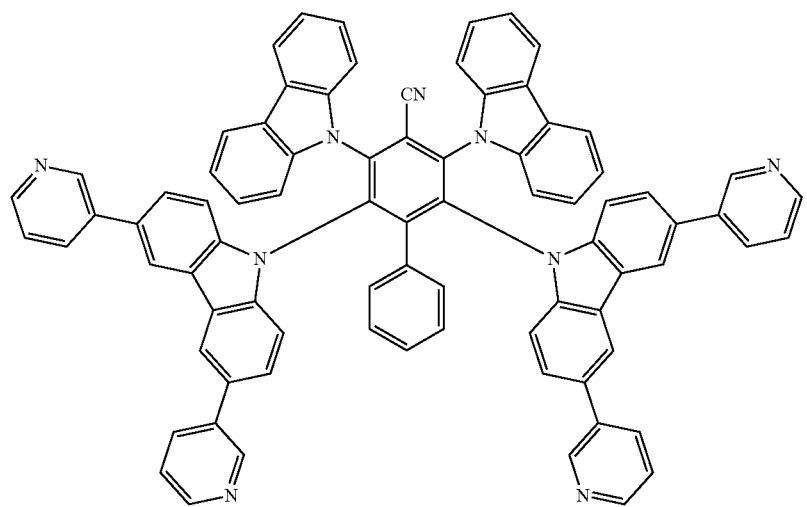
12

-continued
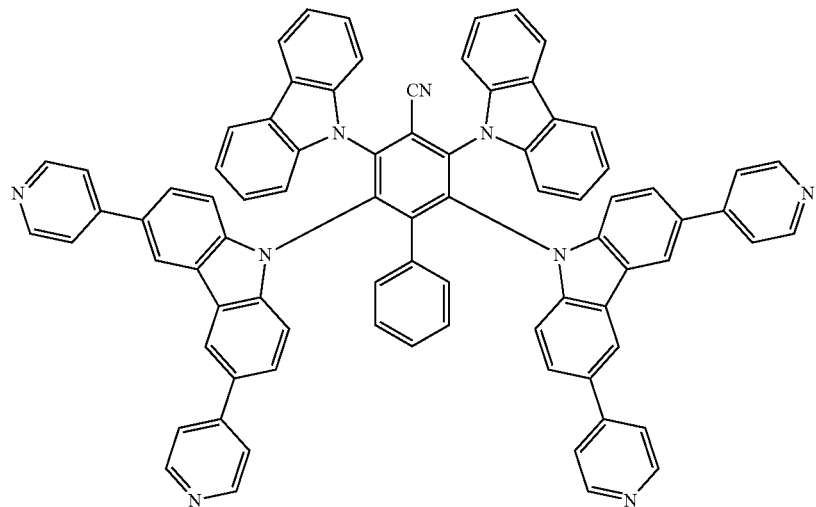
13
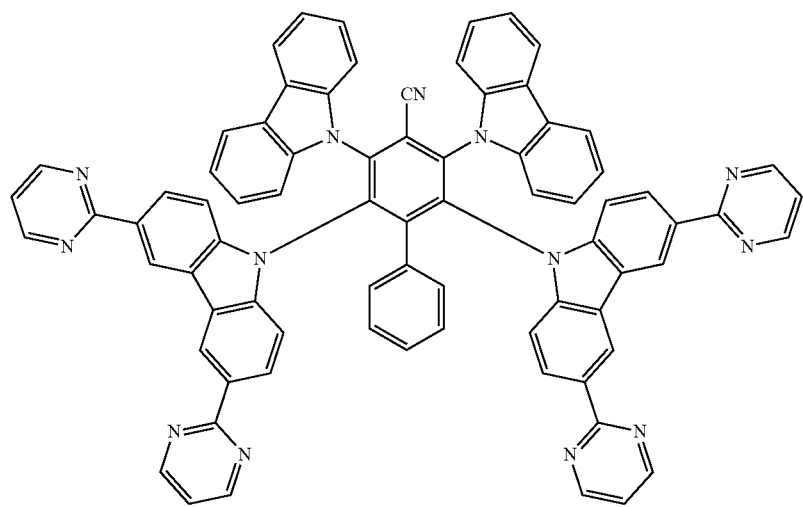
14
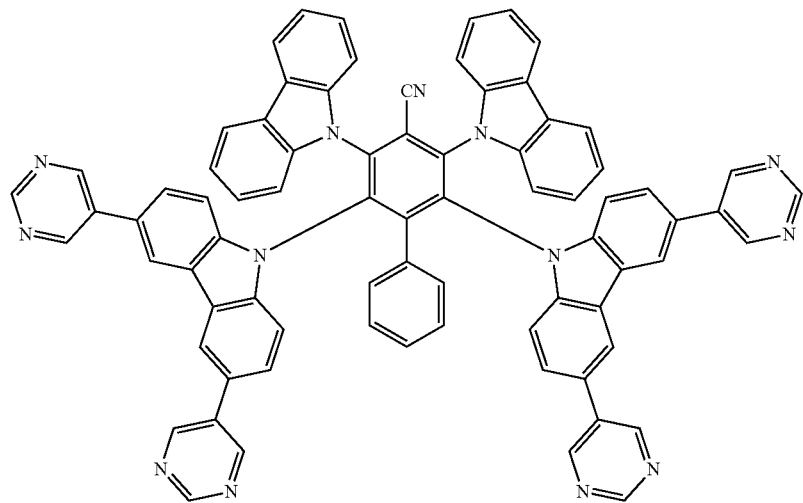
15

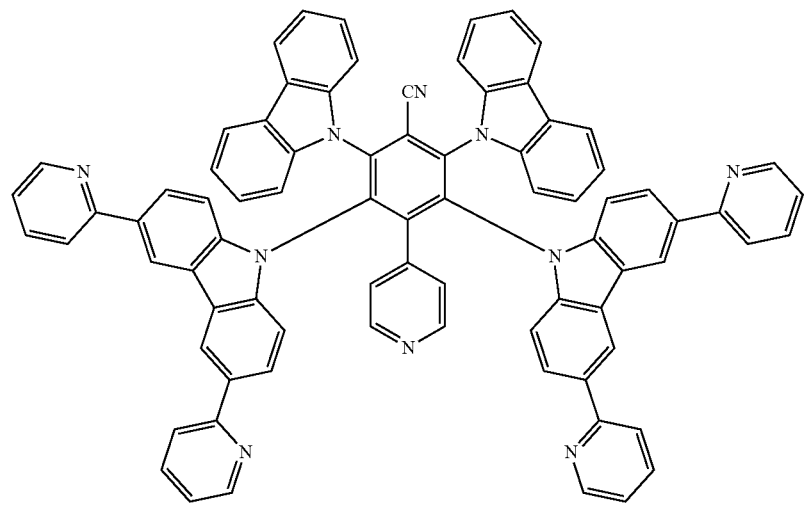
16
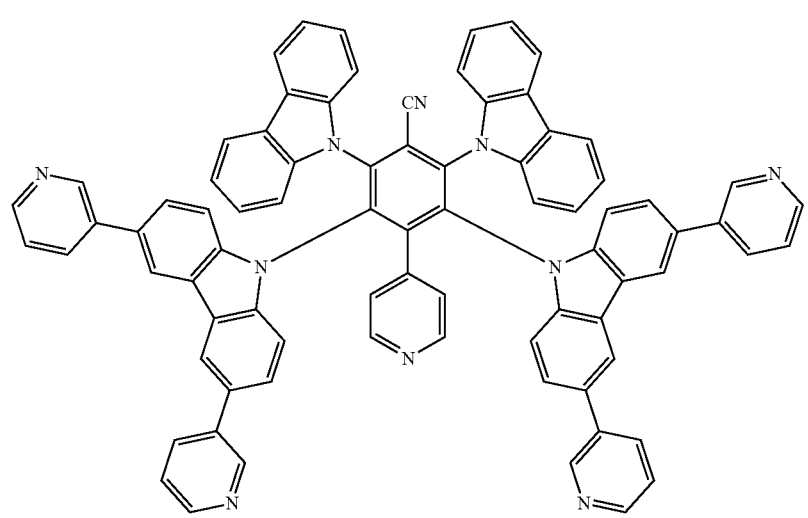
17
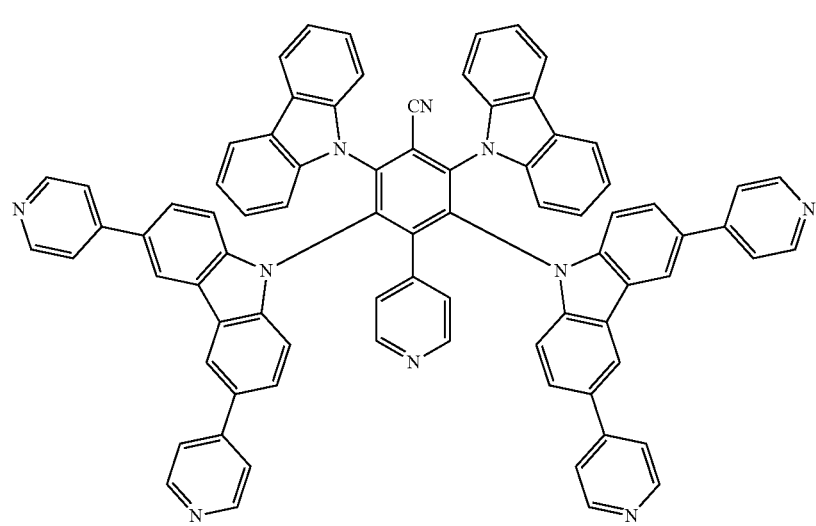
18

-continued
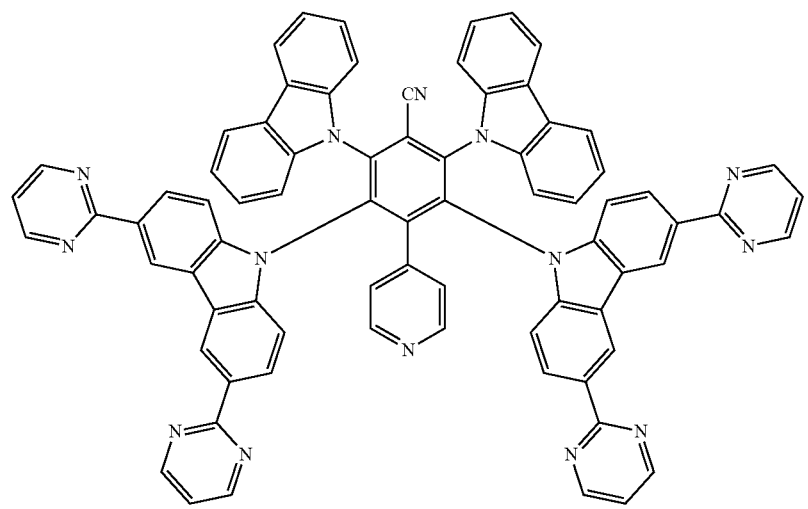
19
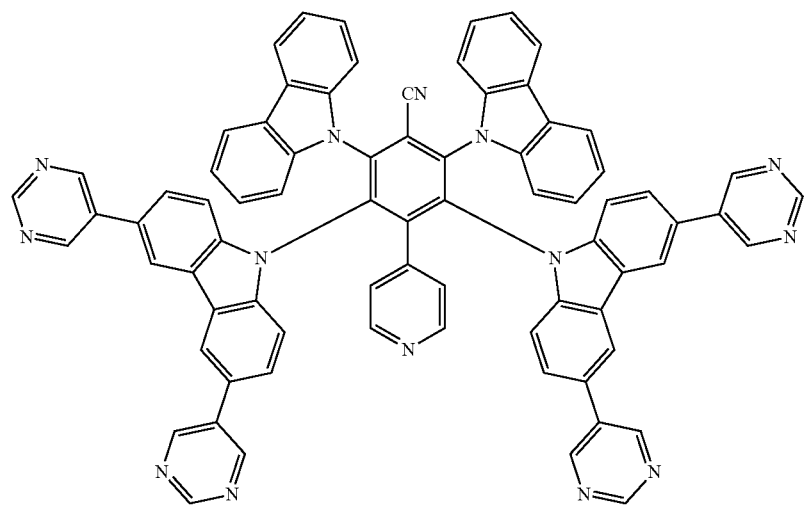
20
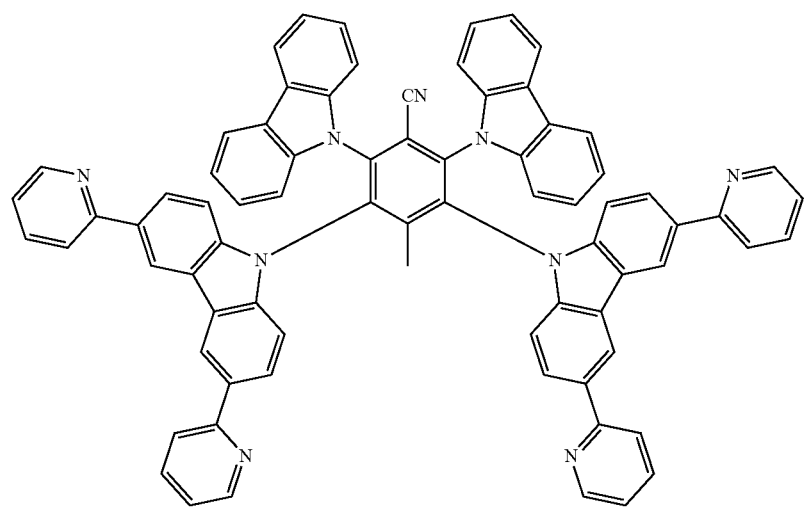
21

22
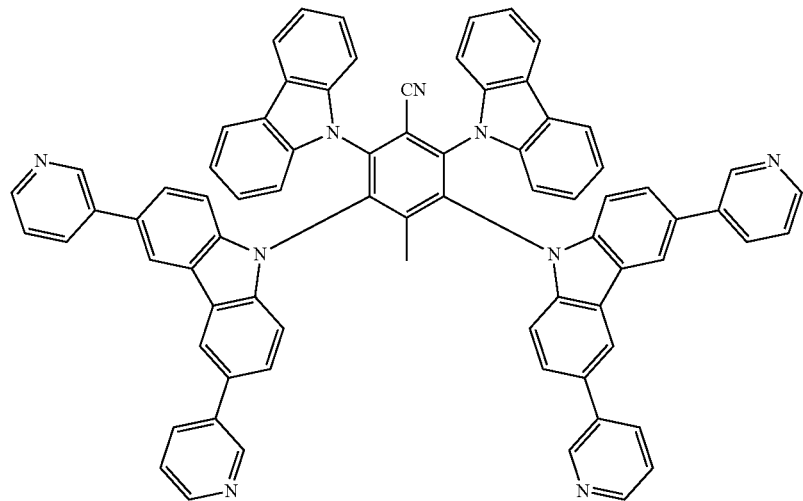
23
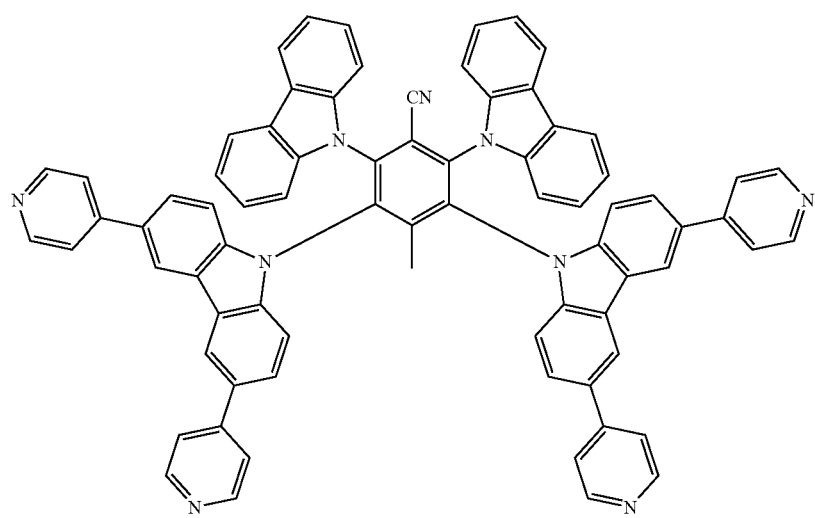
24
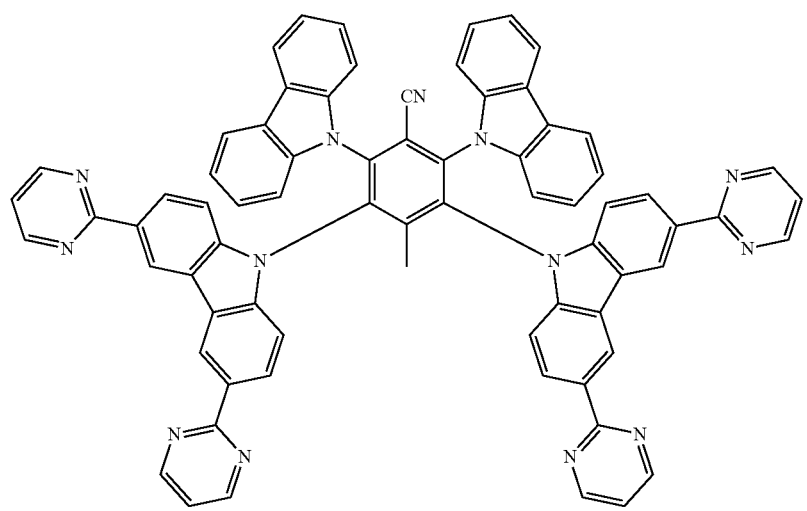

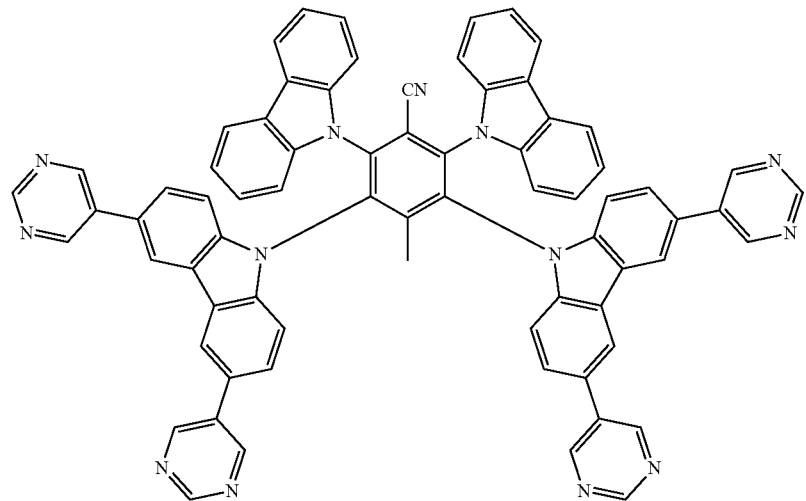
25
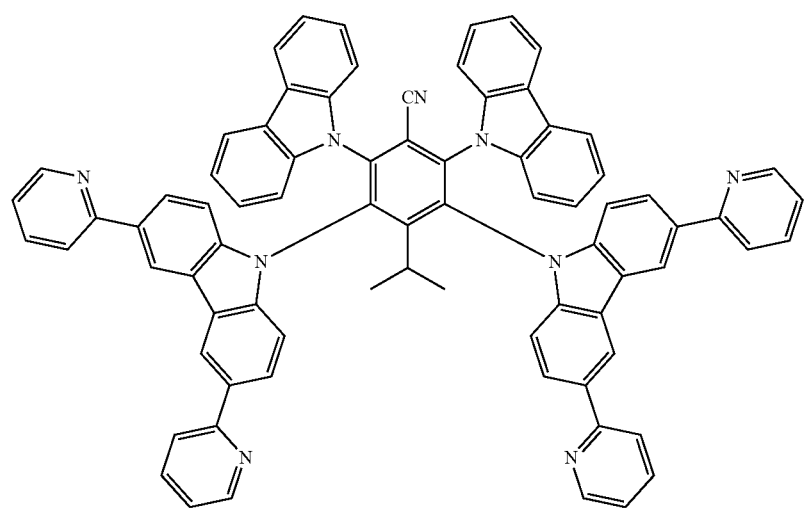
26
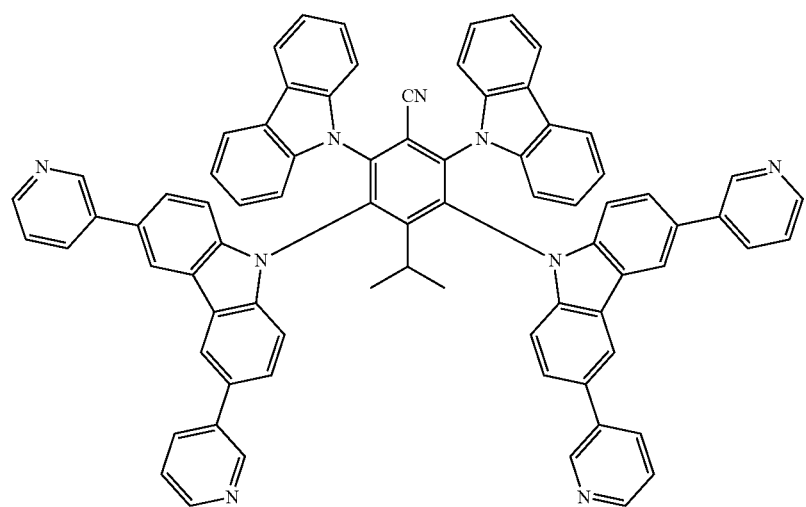
27

28
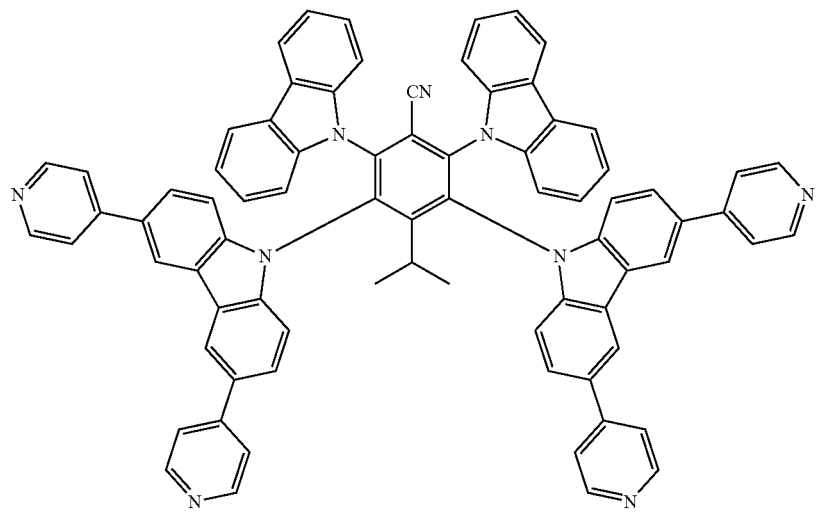
29
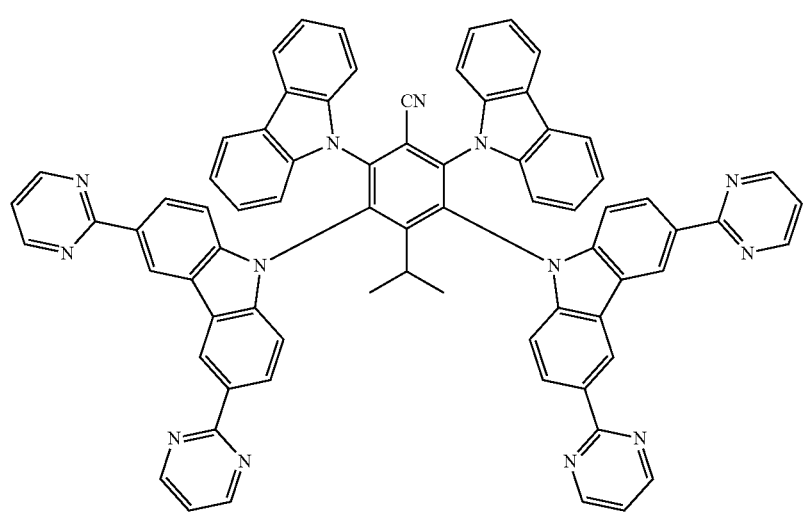
30
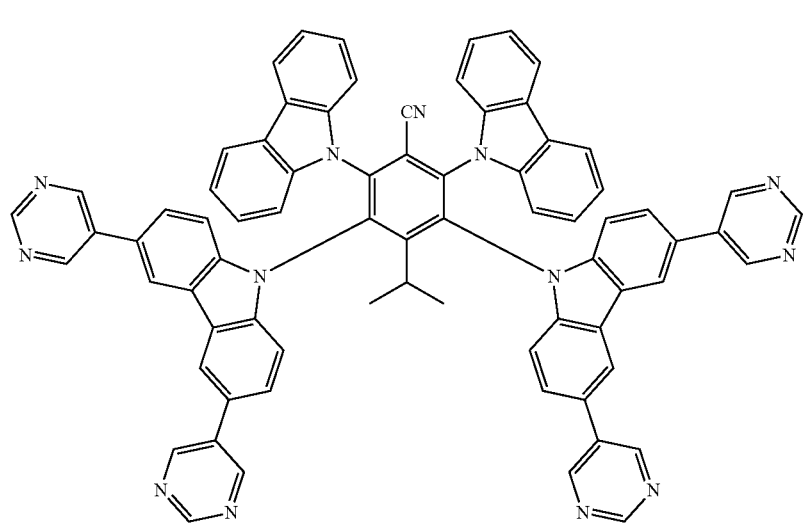

-continued
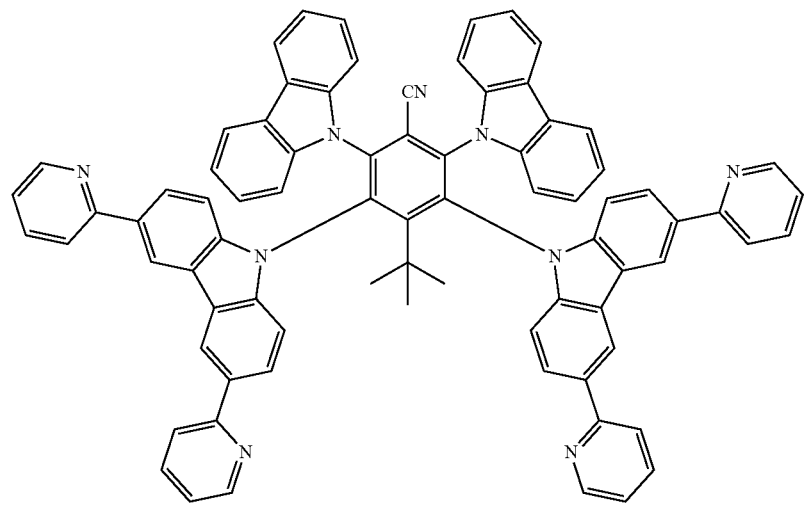
31
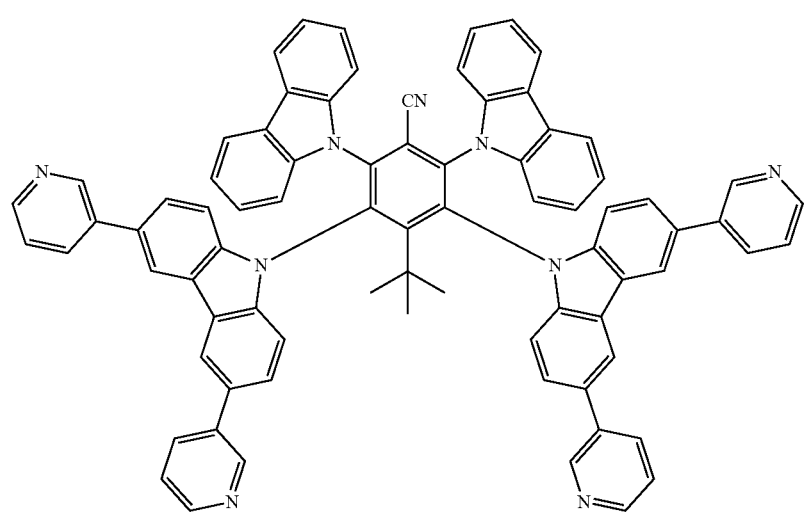
32
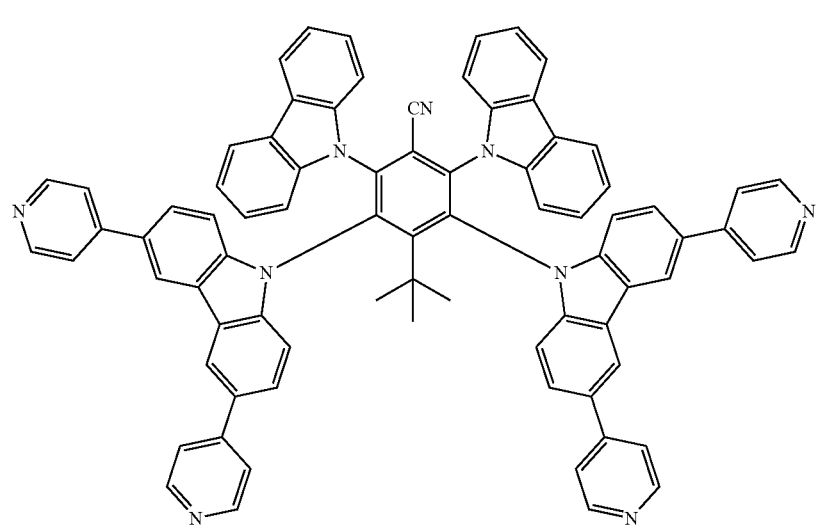
33

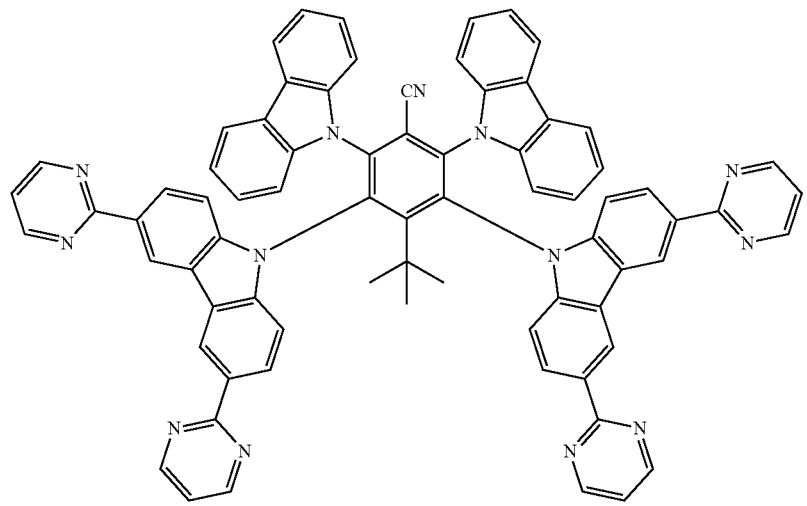
34
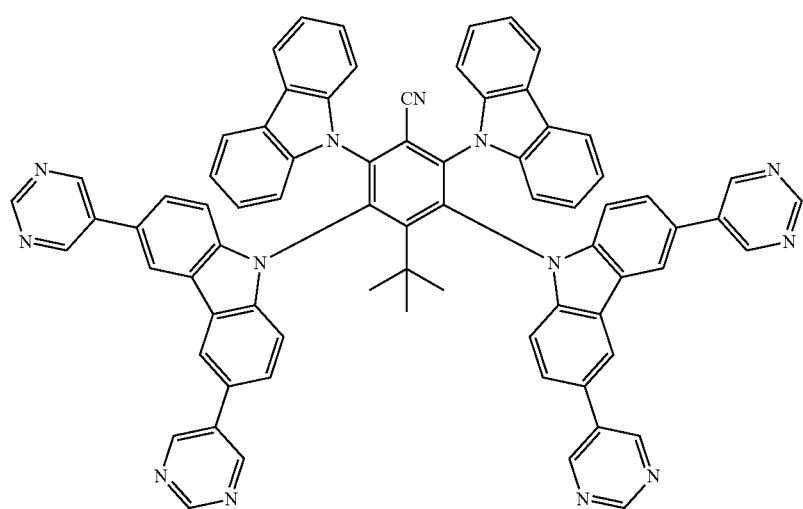
35
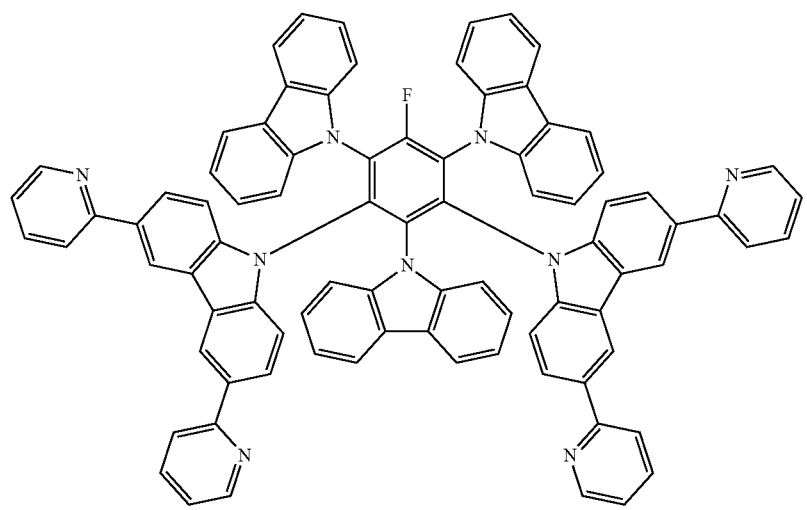
36

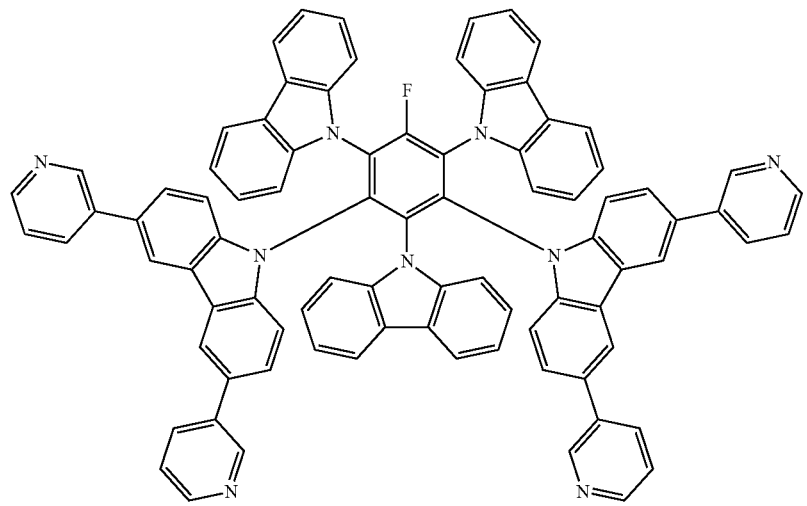
37
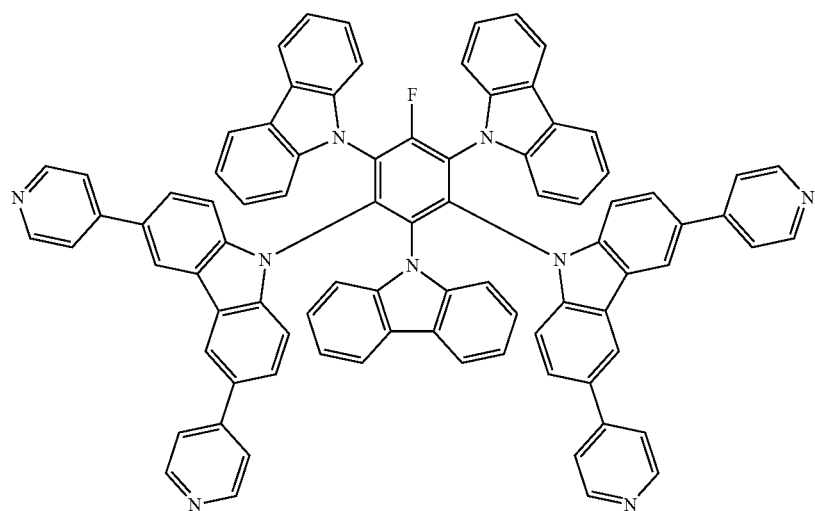
38
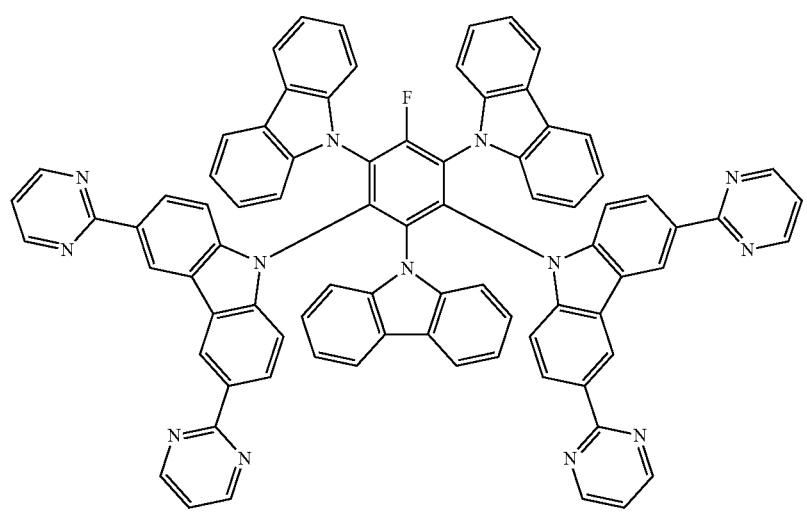
39

-continued
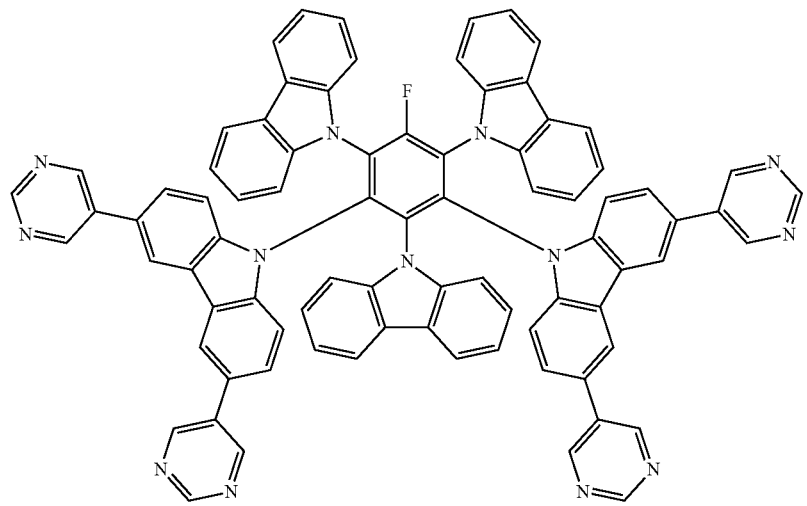
40
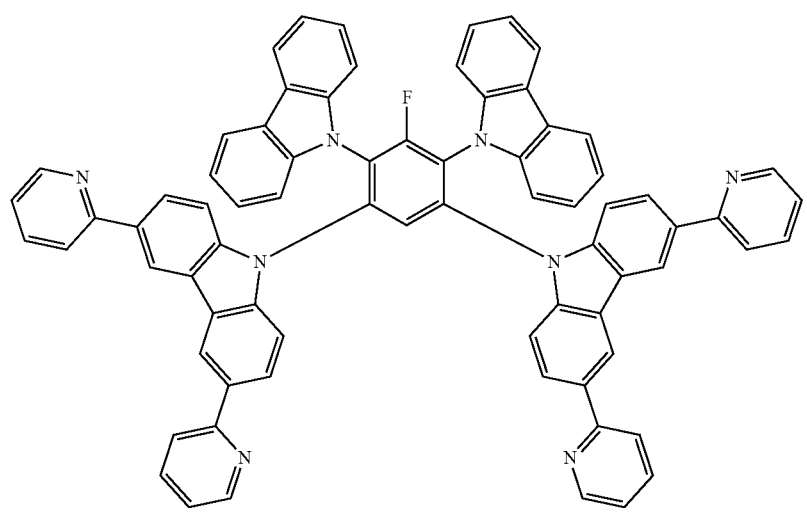
41
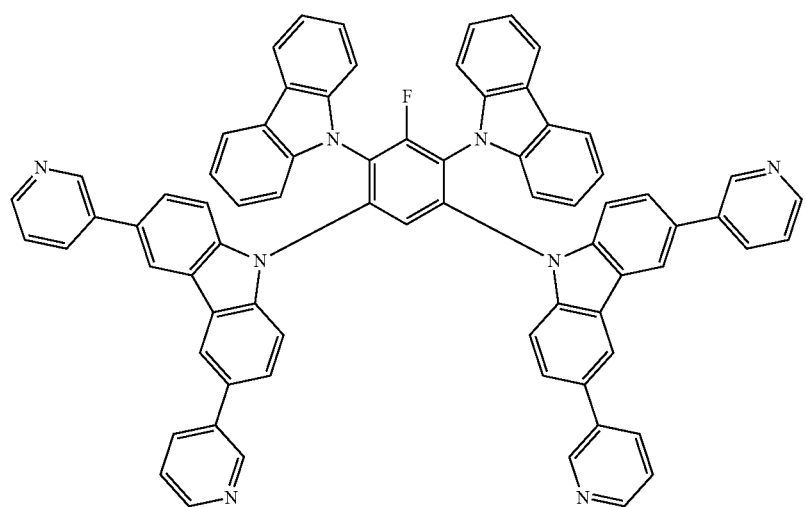
42

43
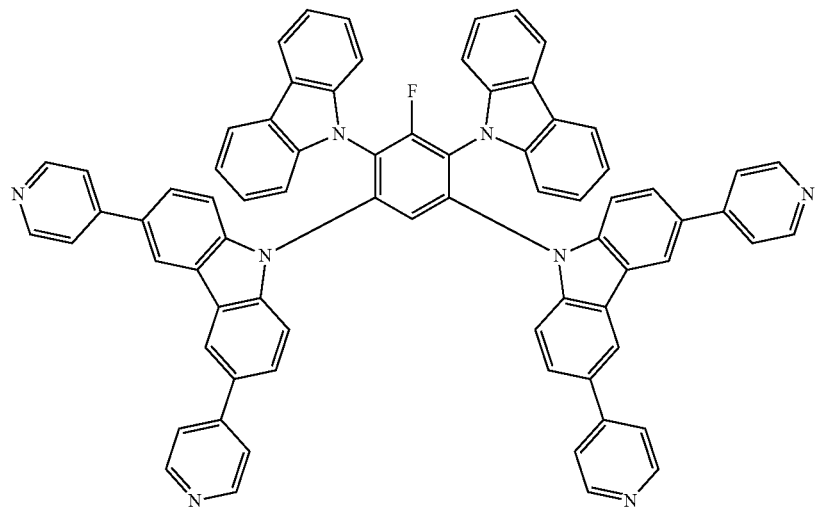
44
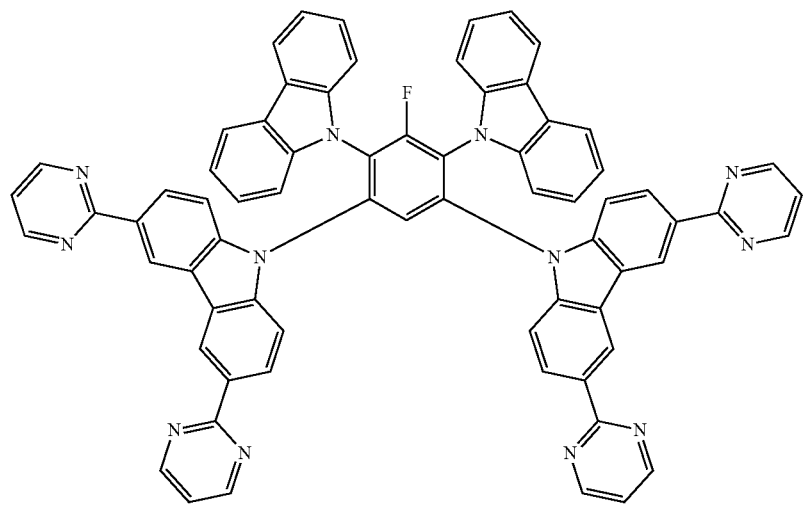
45
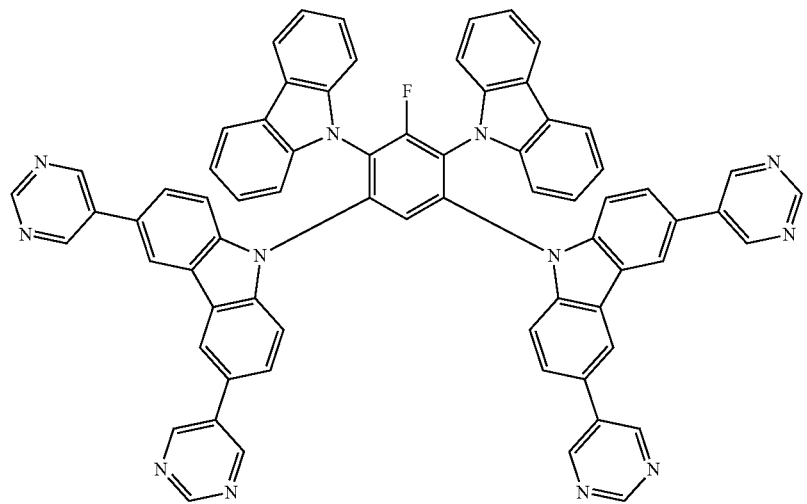

46
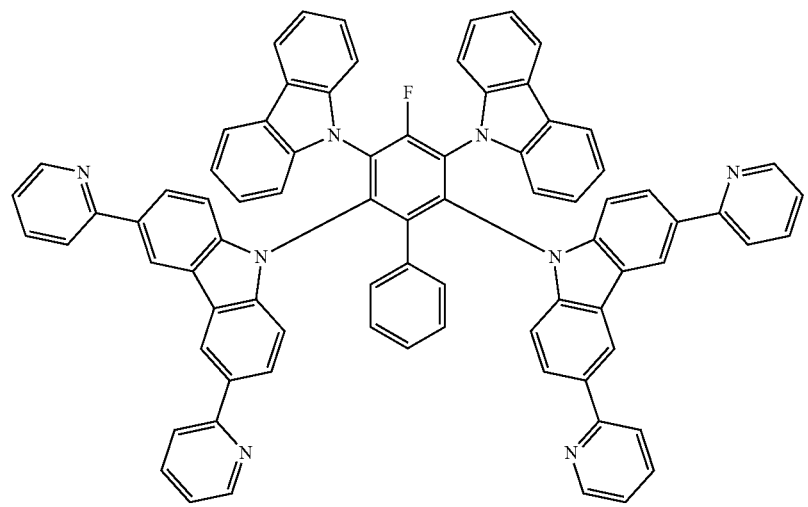
47
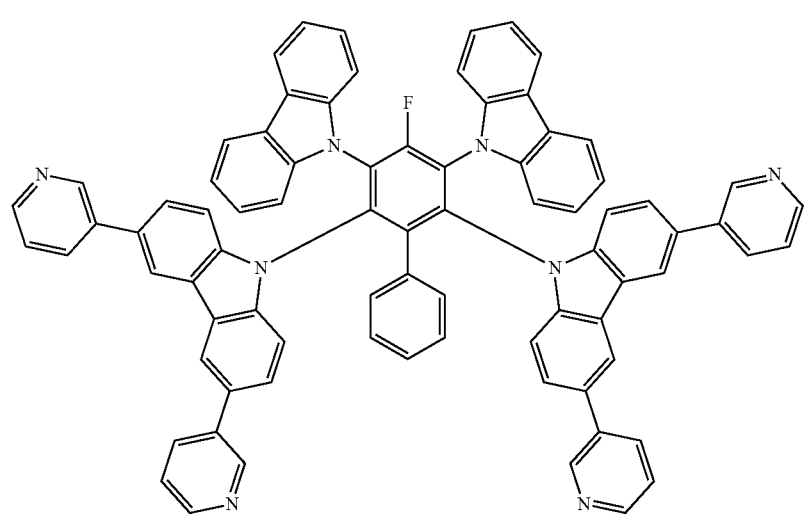
48
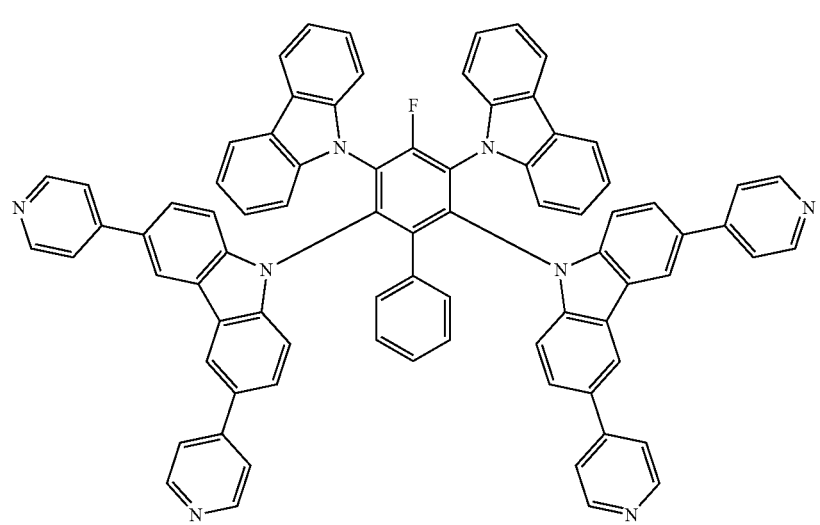

-continued
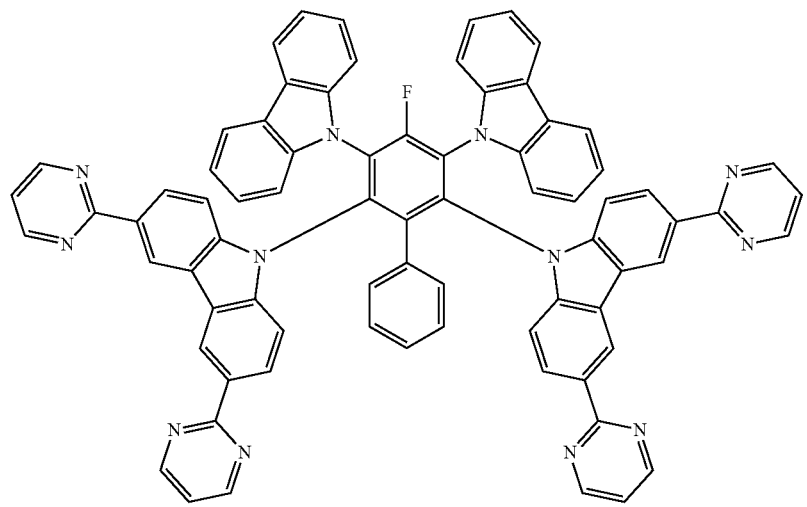
49
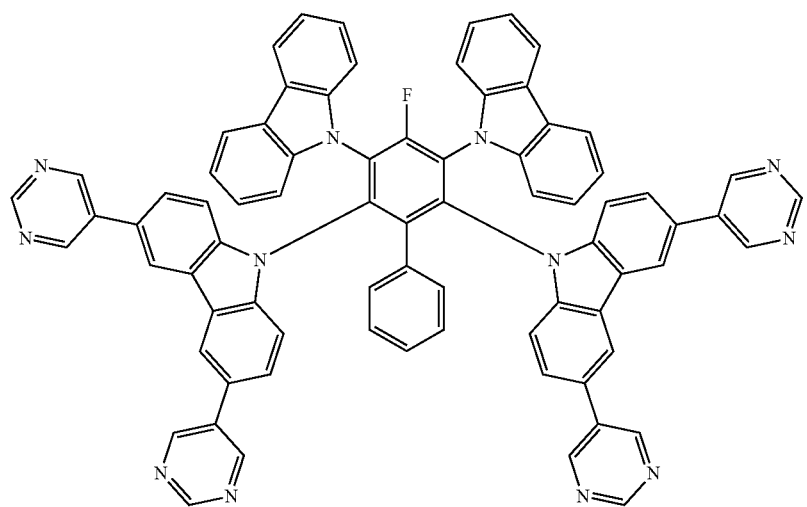
50
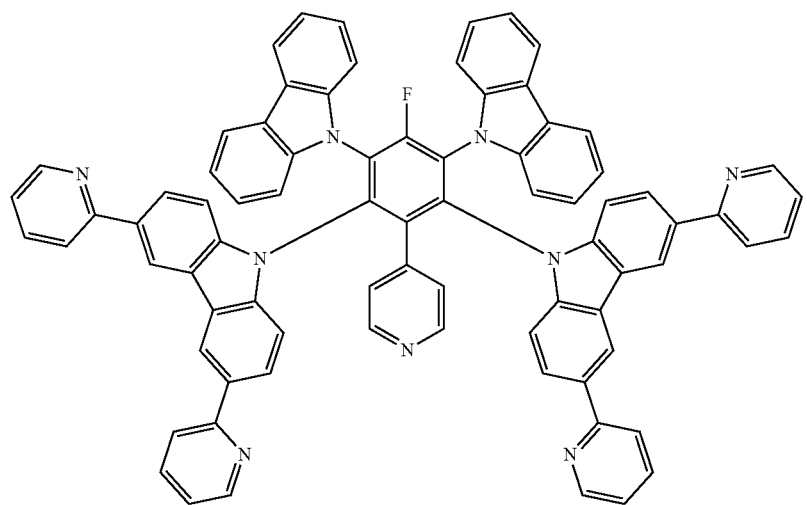
51

52
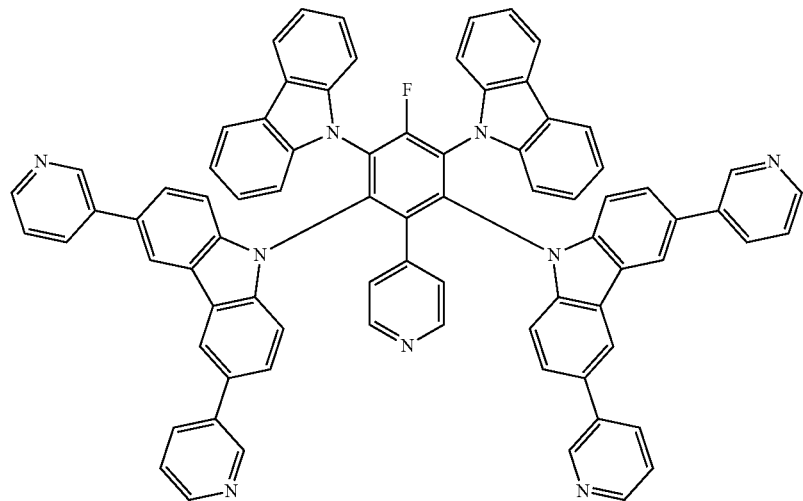
53
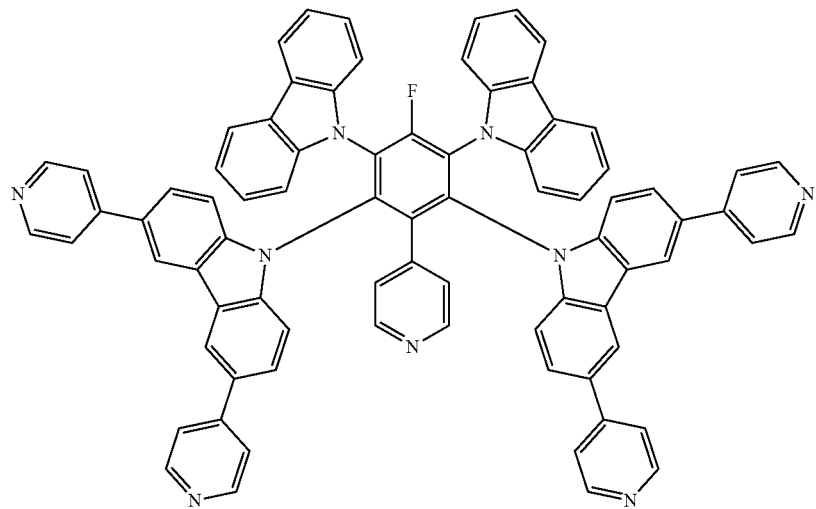
54
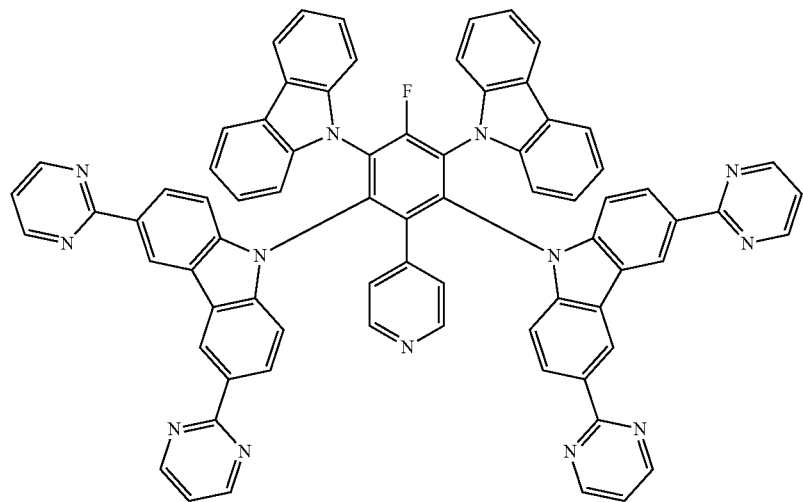

55
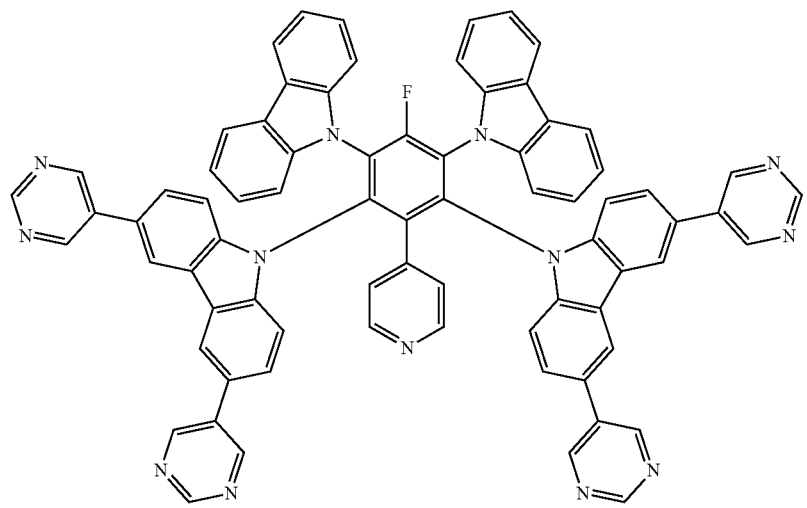
56
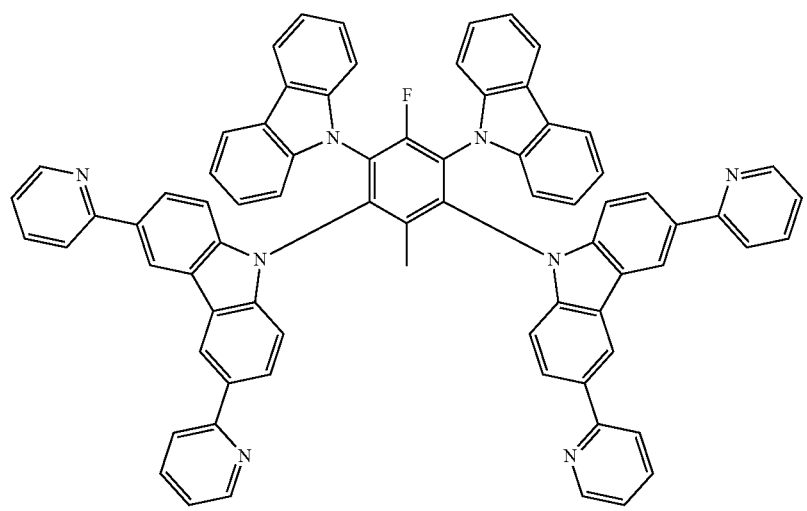
57
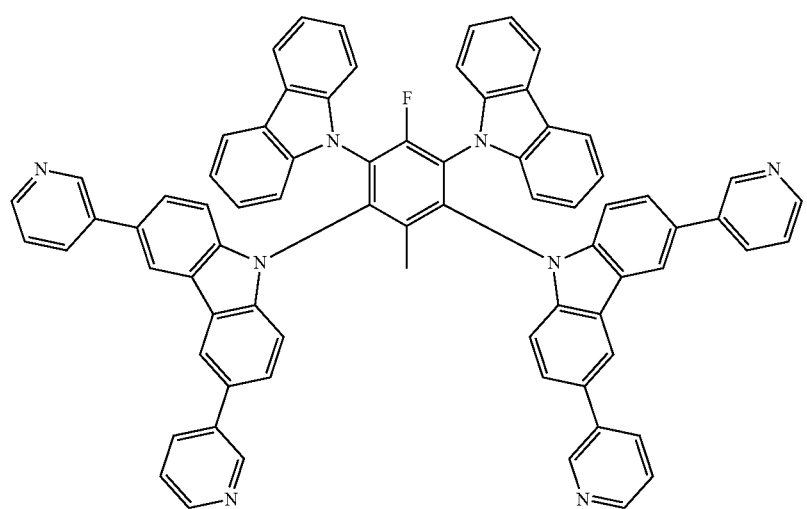

58
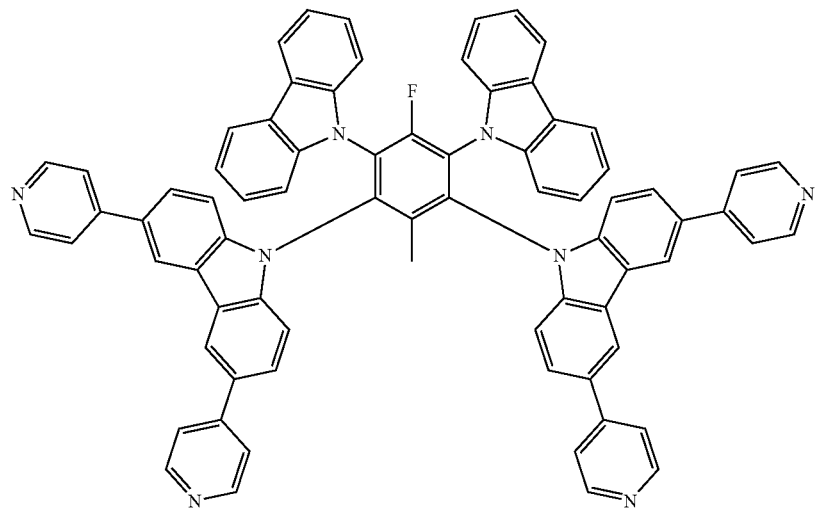
59
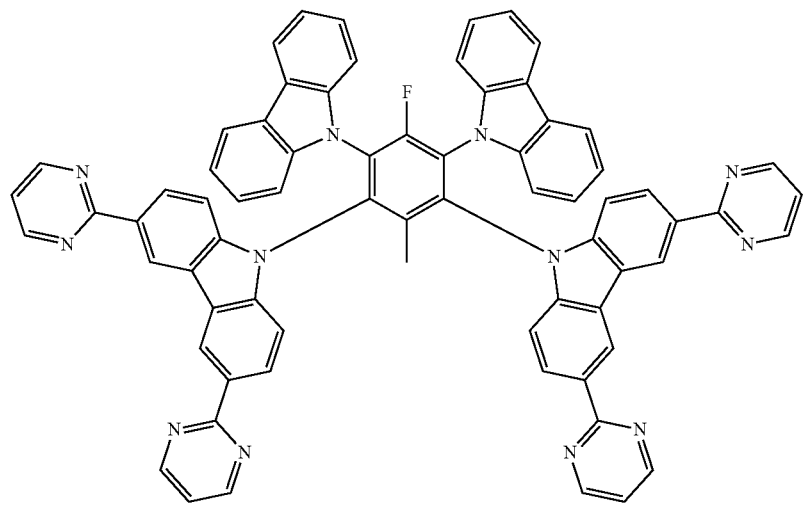
60
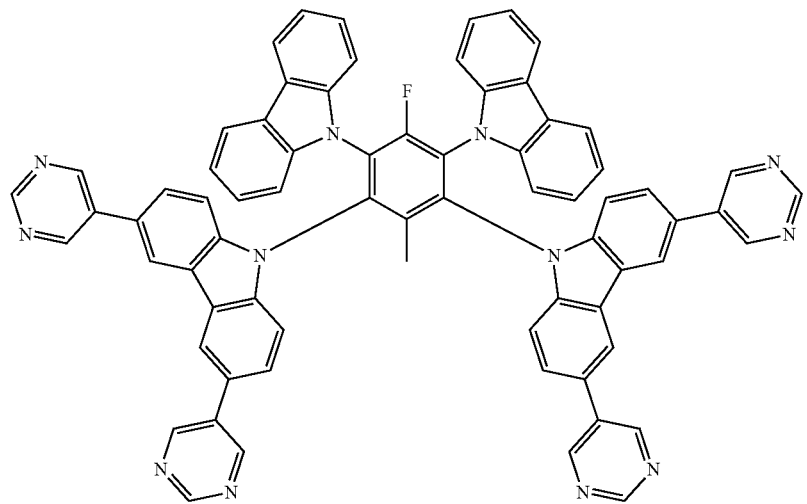

-continued
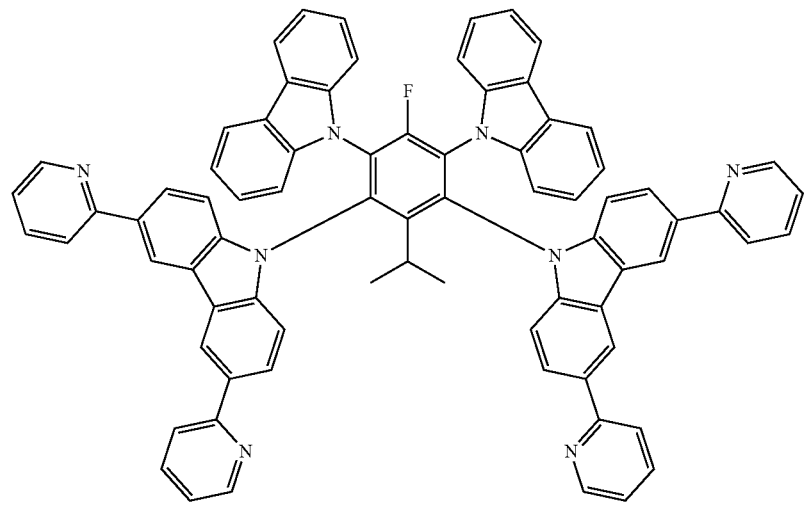
61
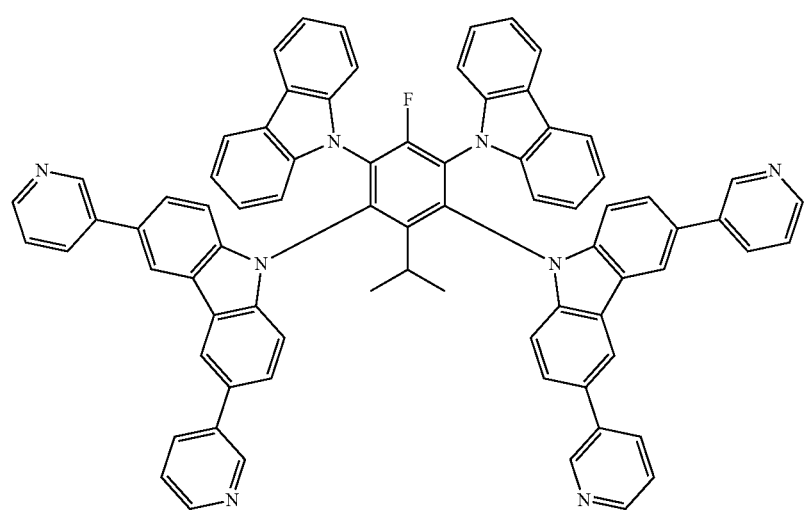
62
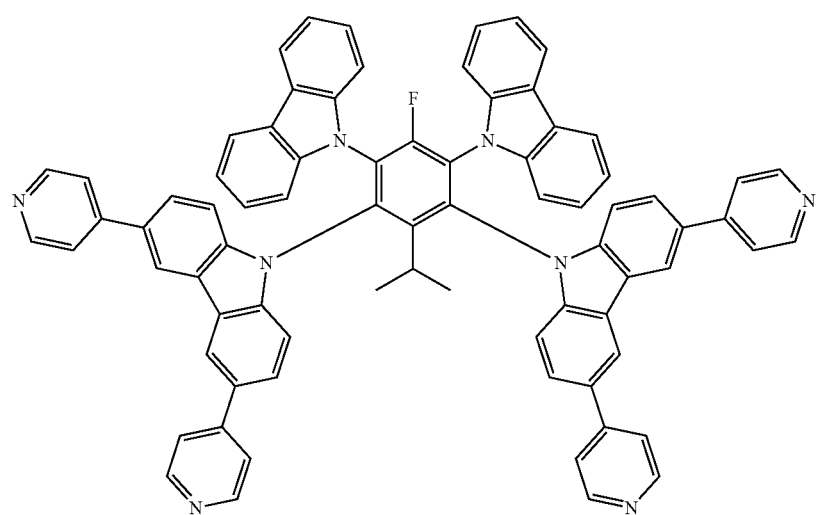
63

64
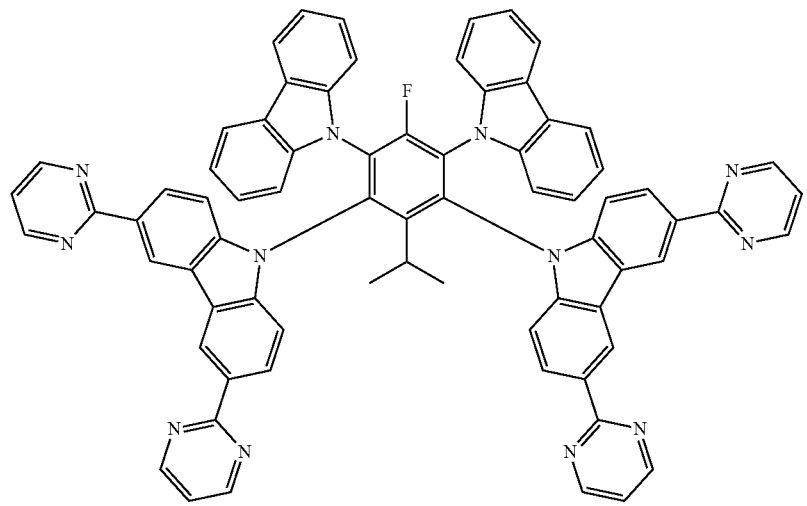
65
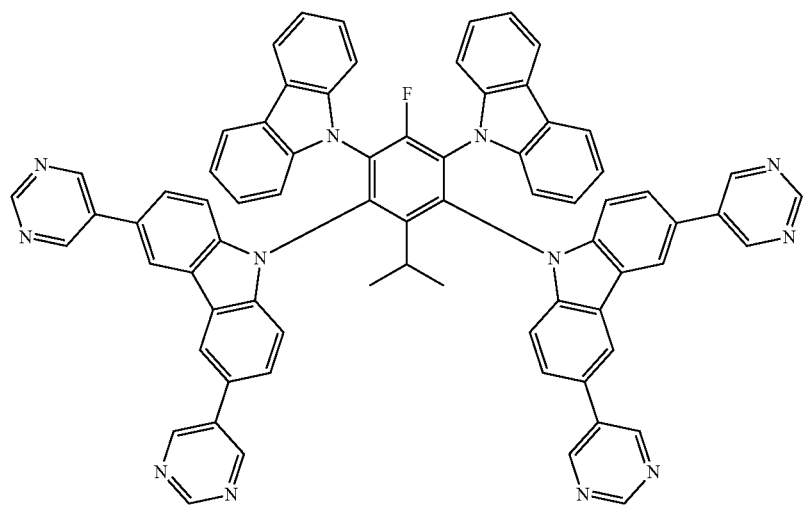
66
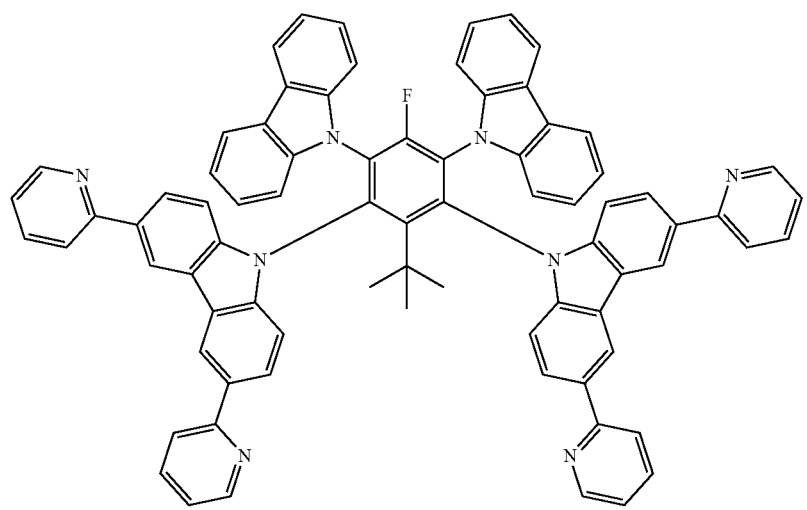

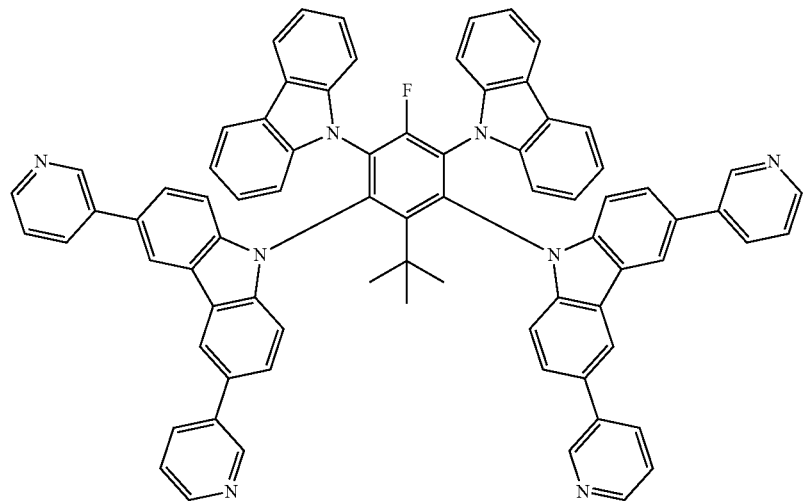
67
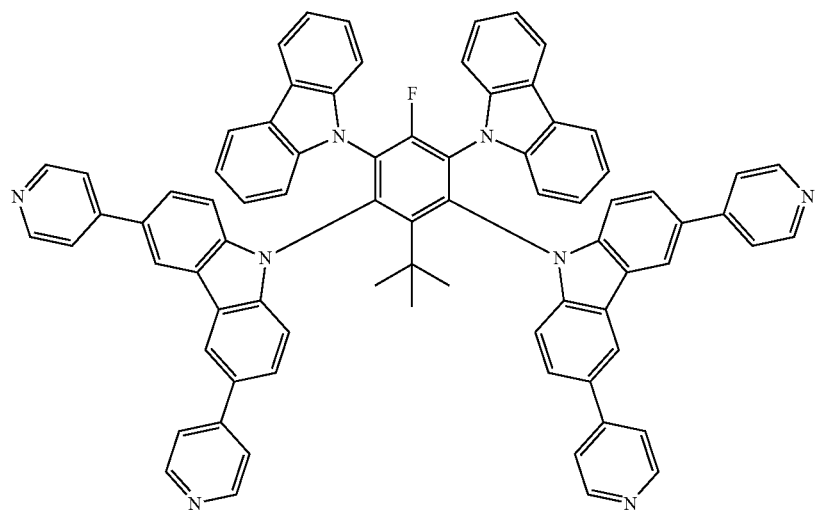
68
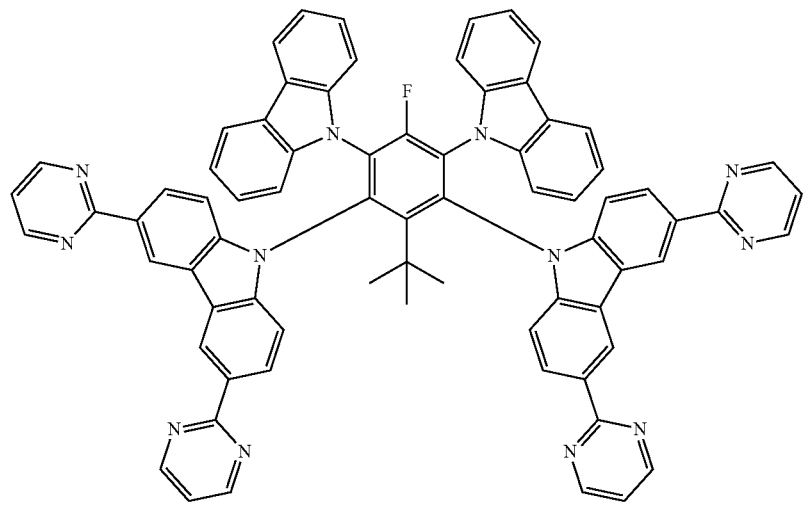
69

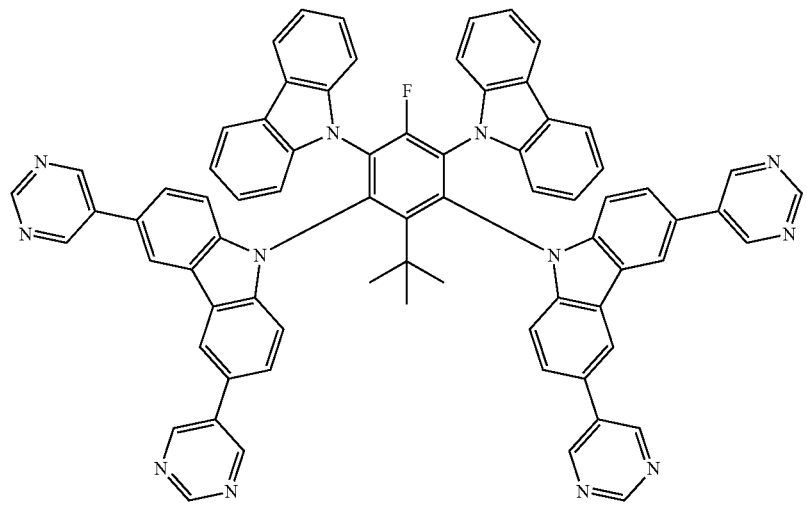
70
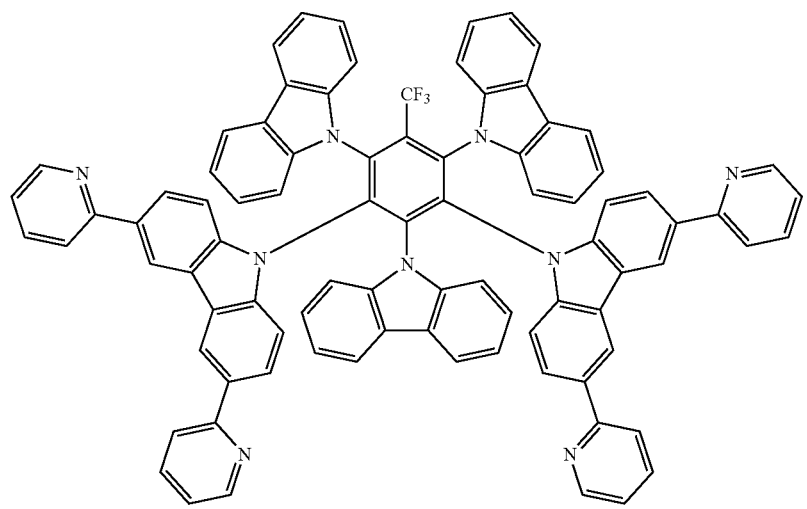
71
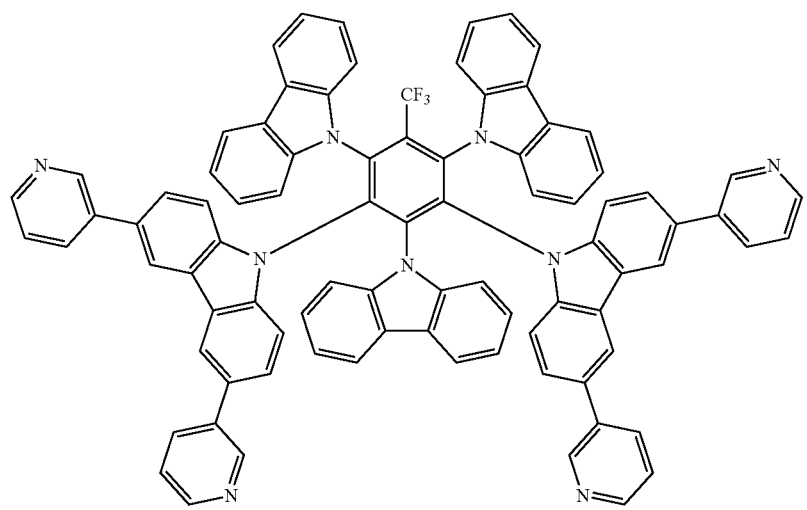
72

73
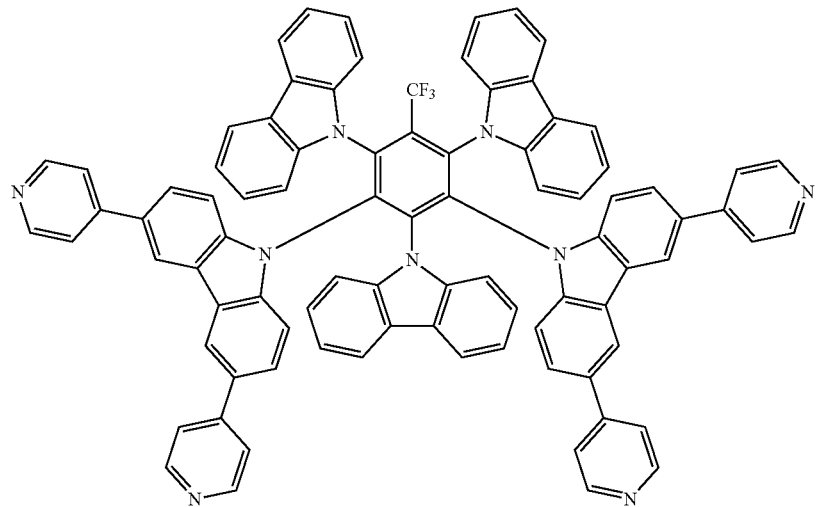
74
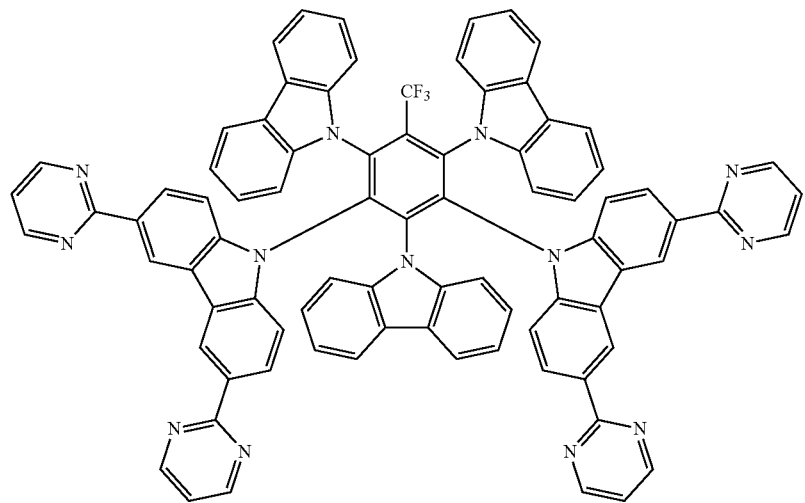
75
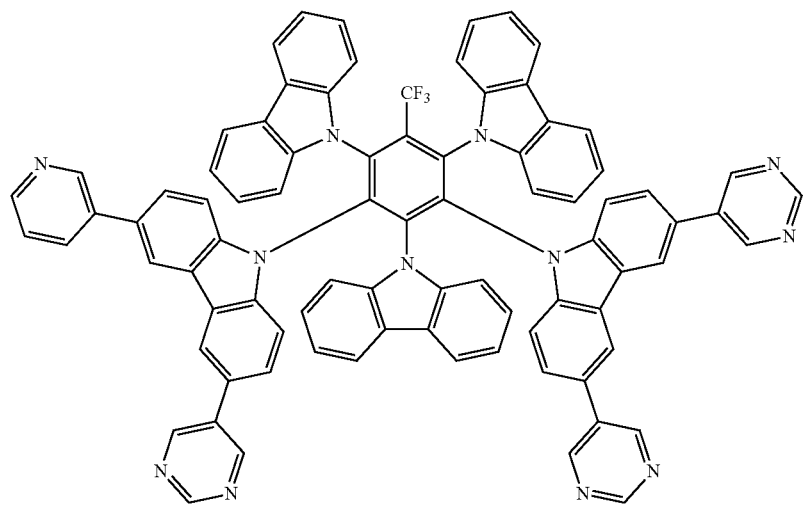

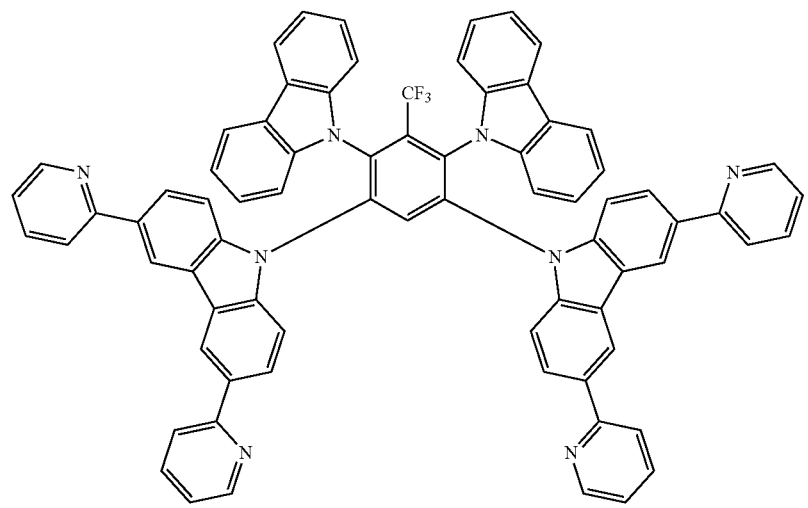
76
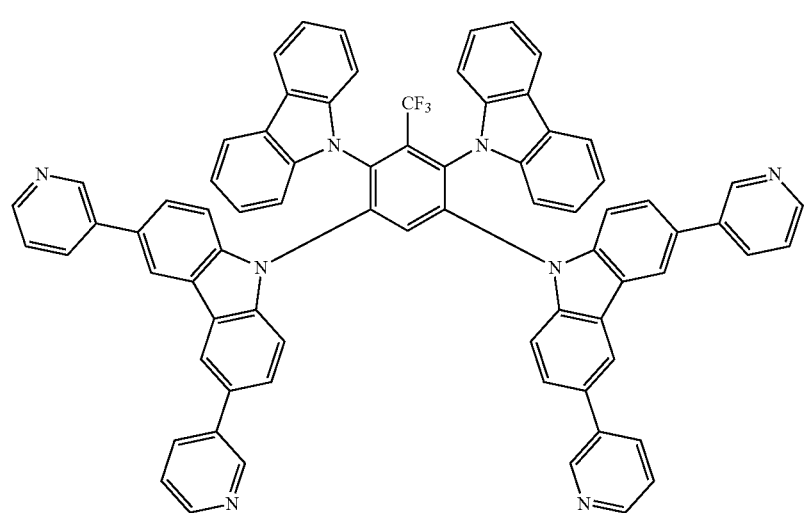
77
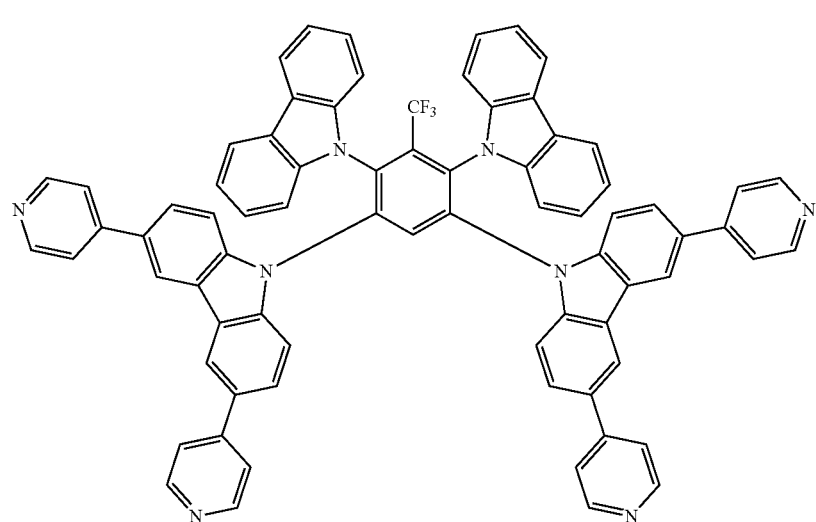
78

79
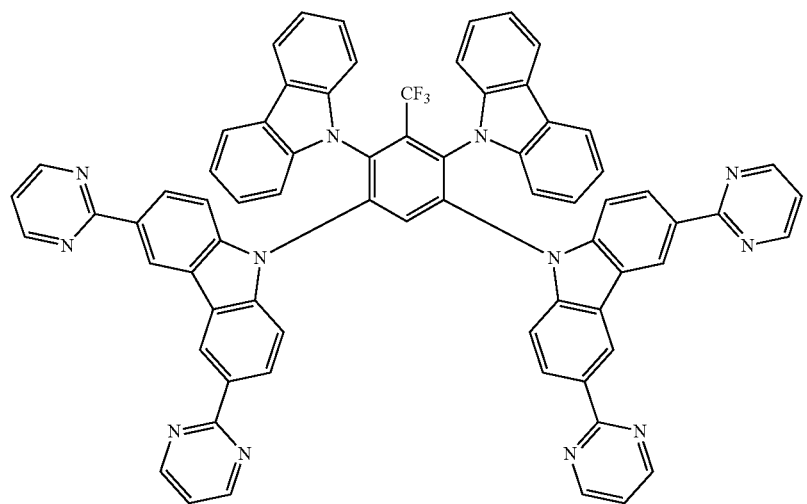
80
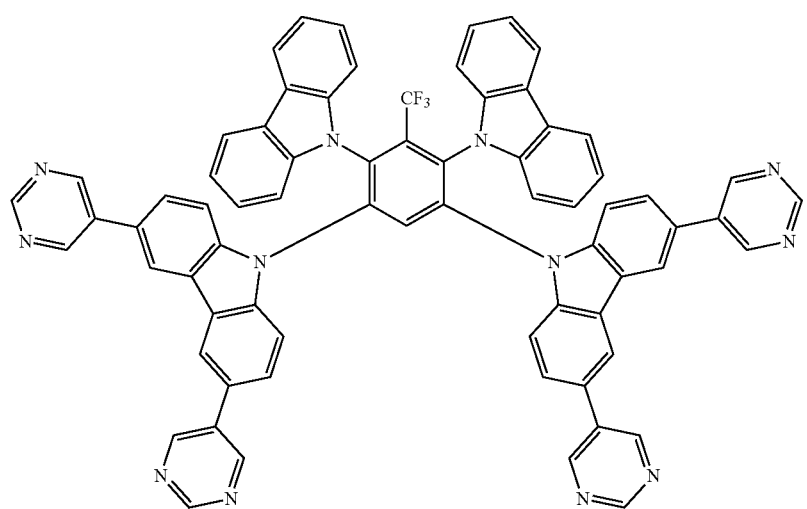
81
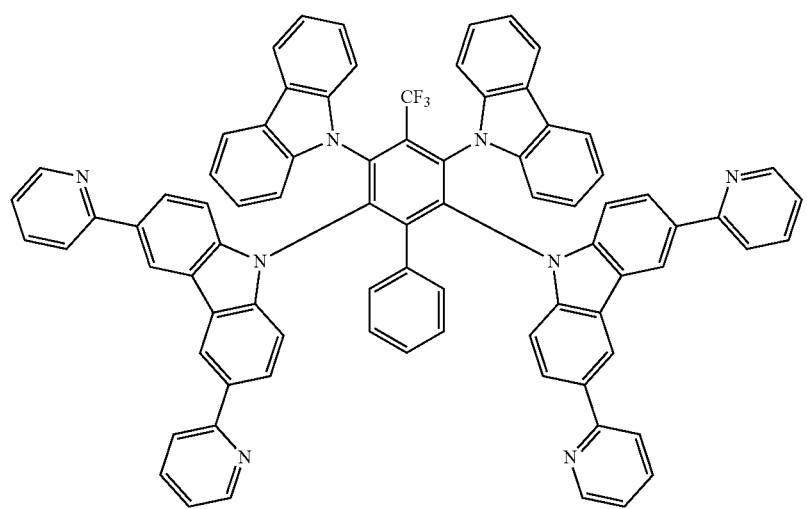

82
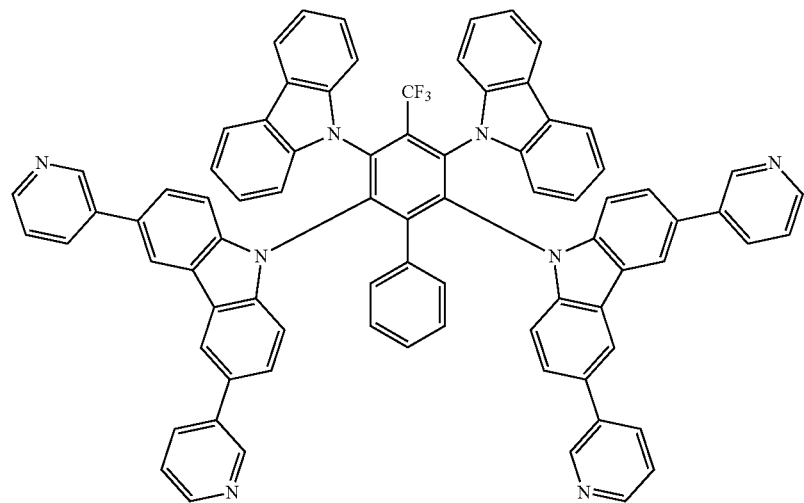
83
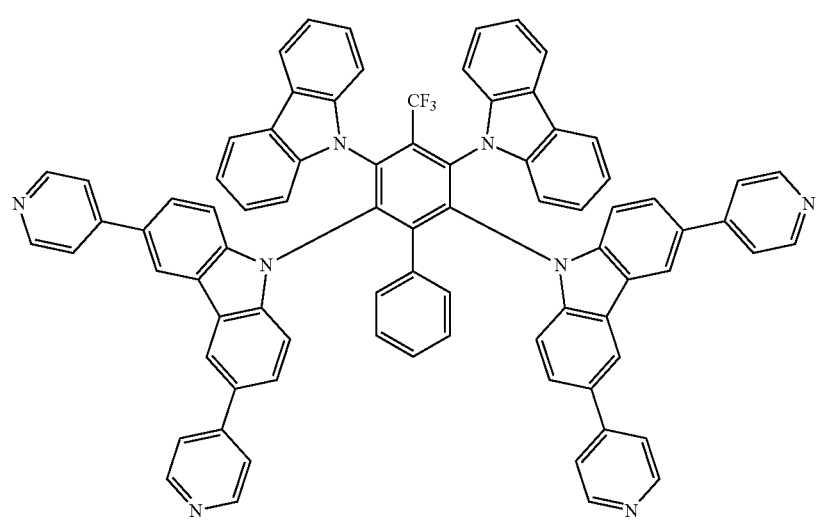
84
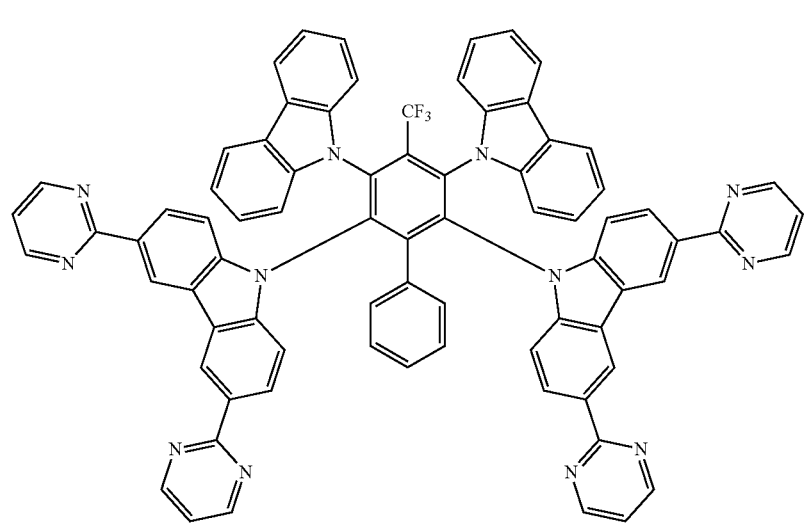

85
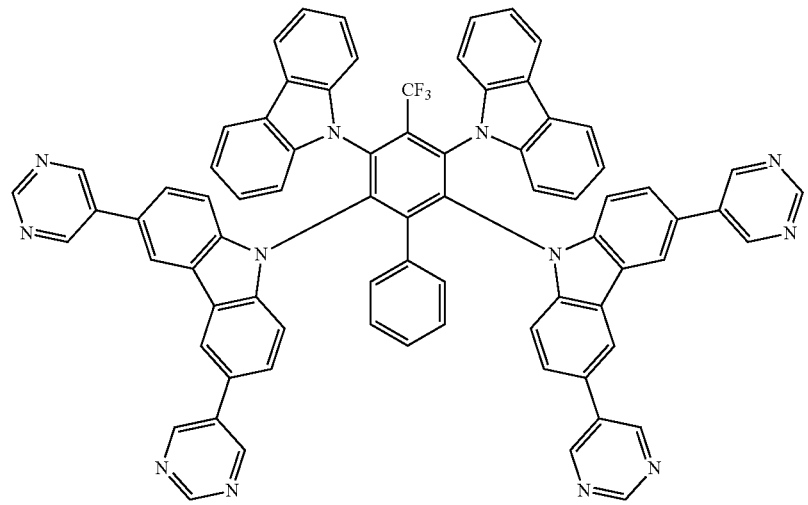
86
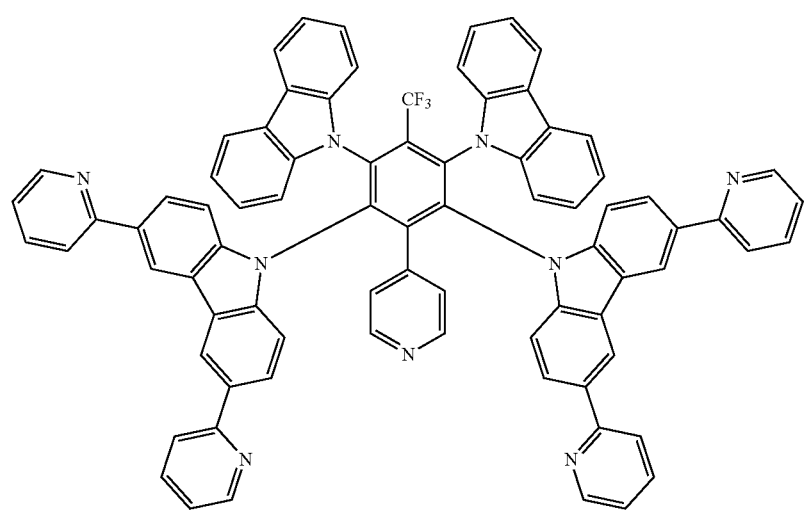
87
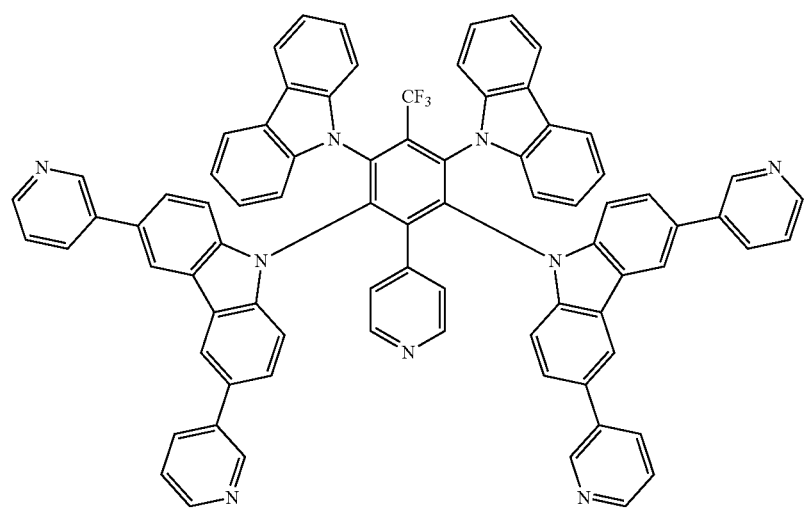

88
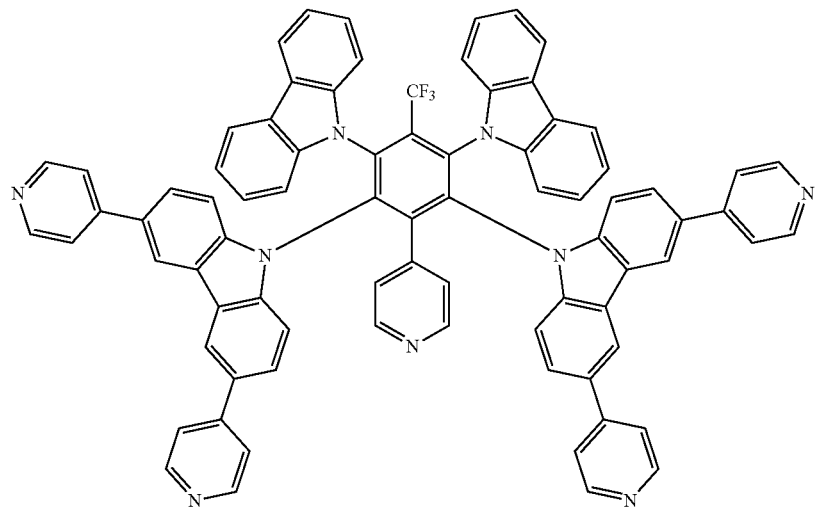
89
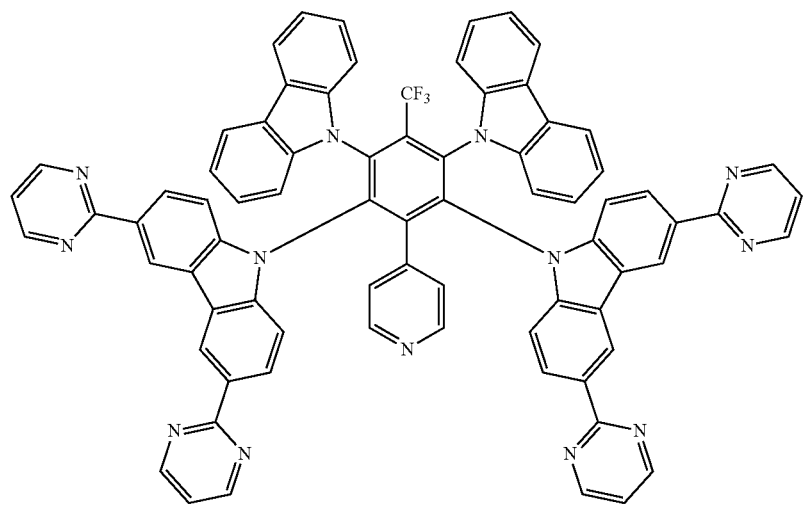
90
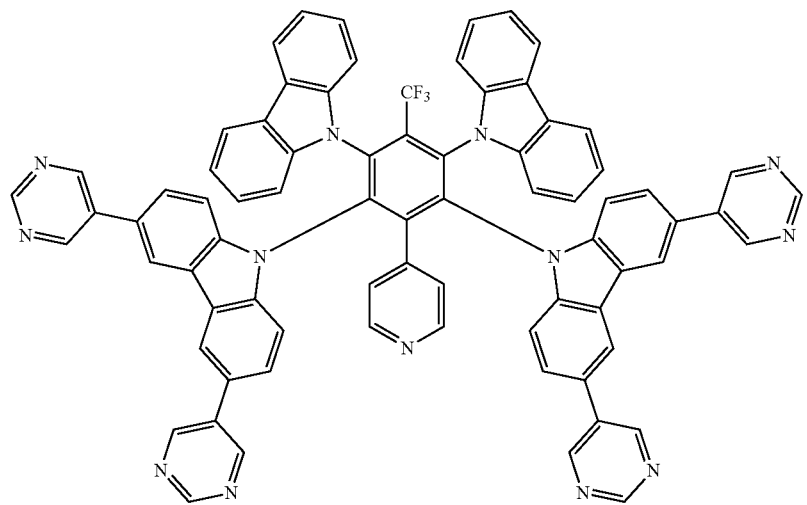

-continued
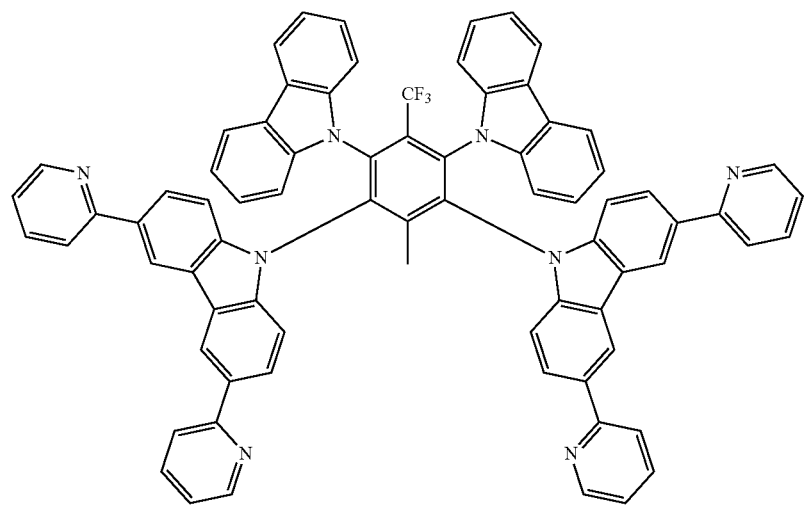
91
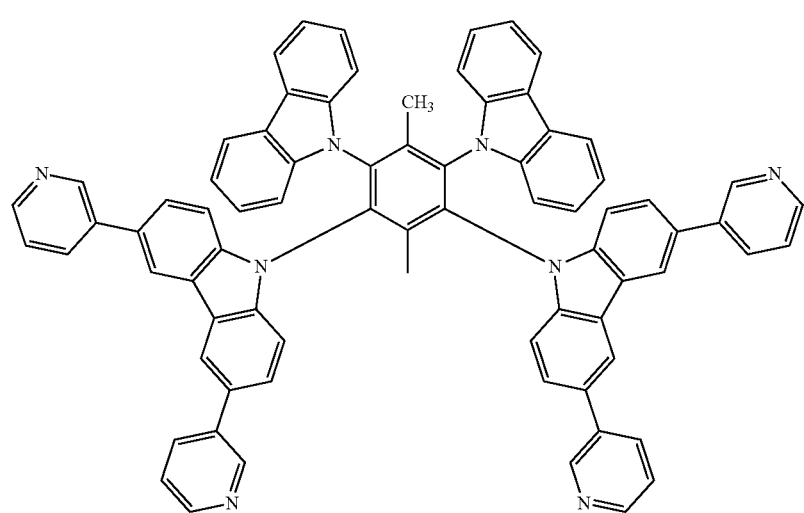
92
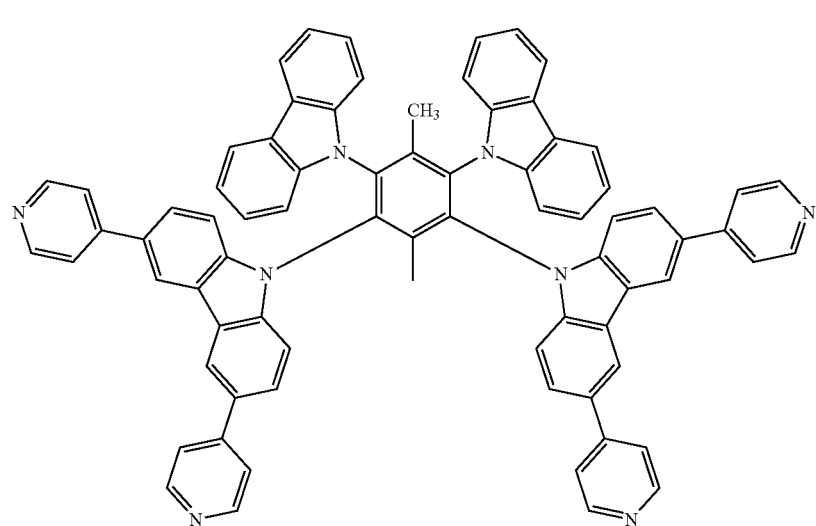
93

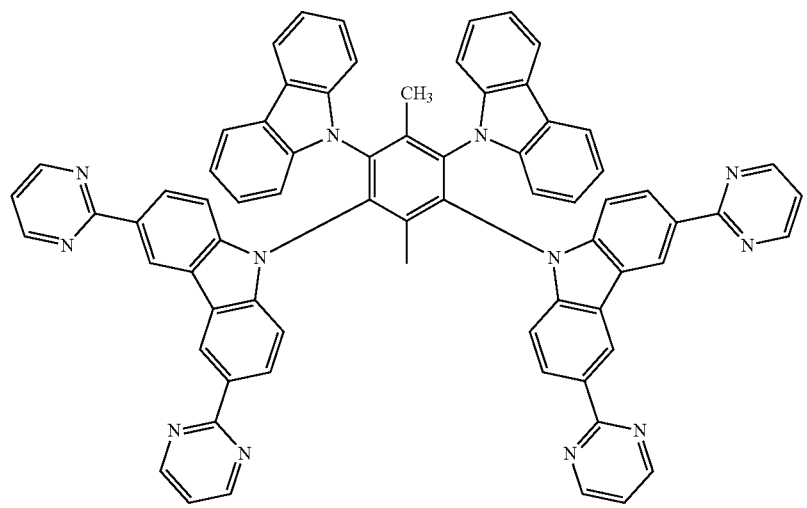
94
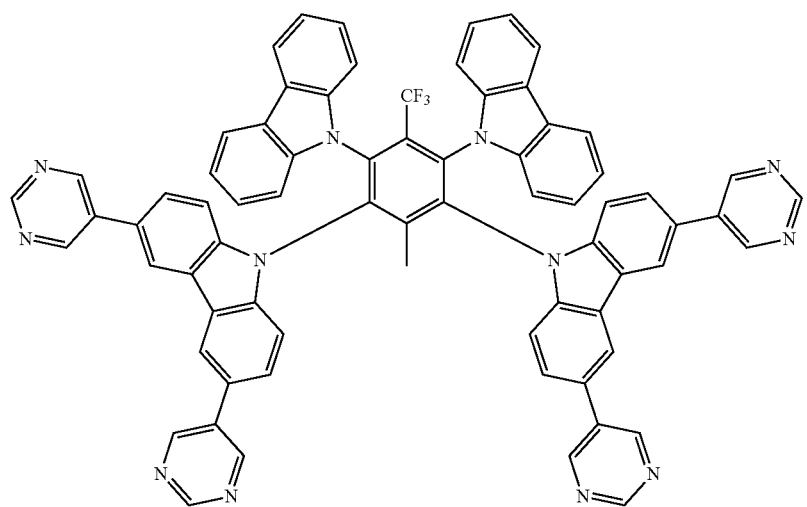
95
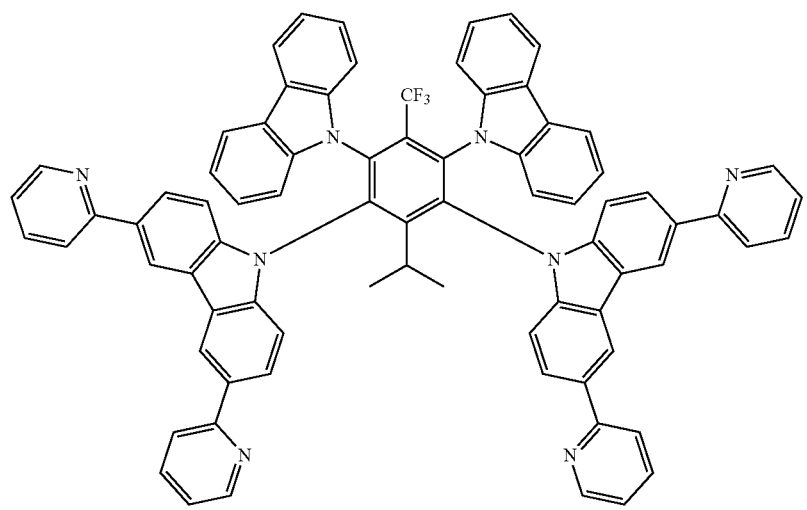
96

97
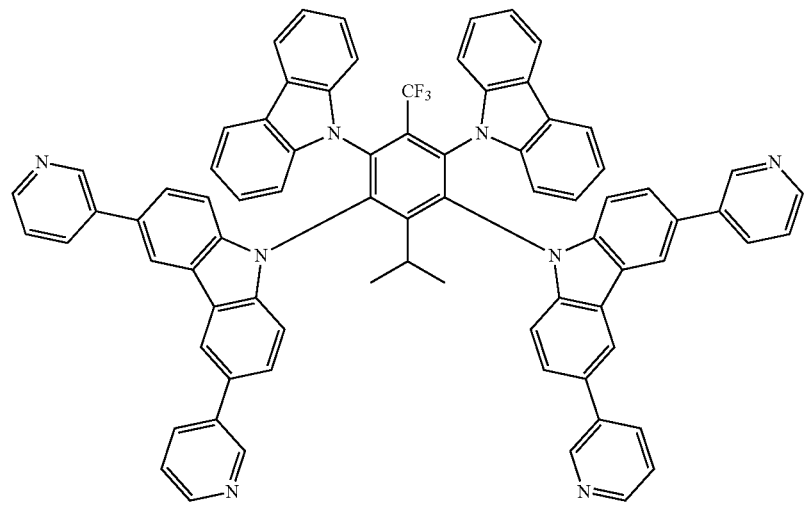
98
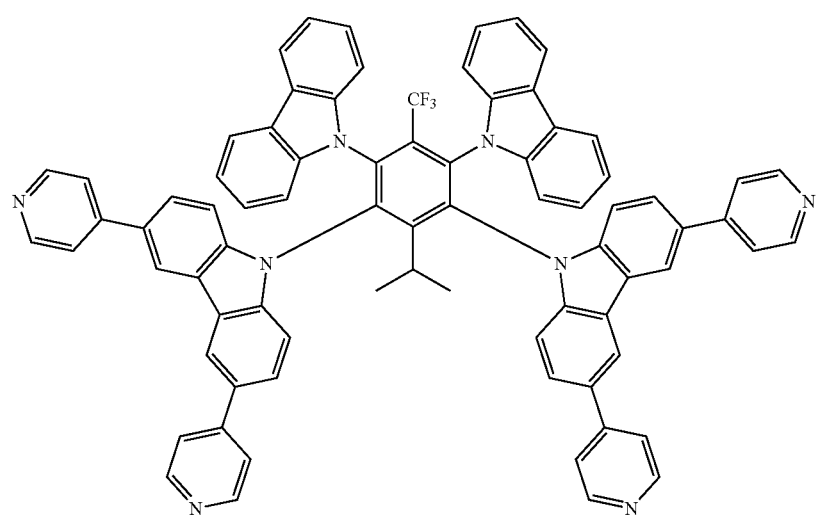
99
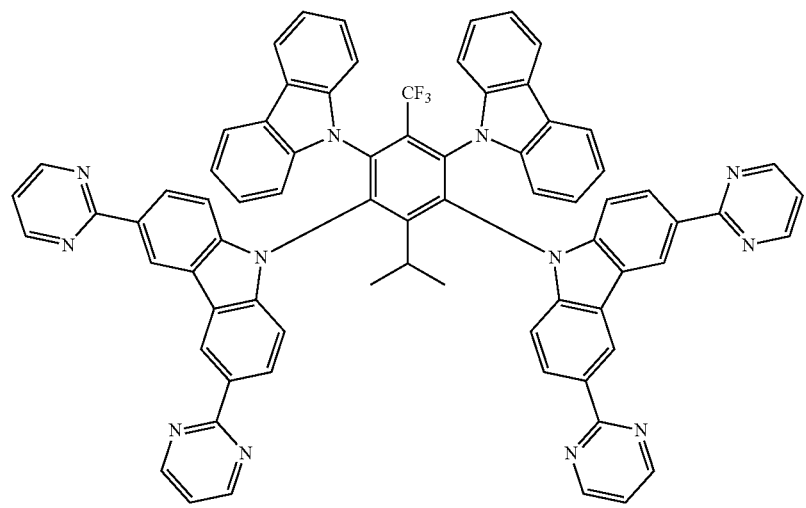

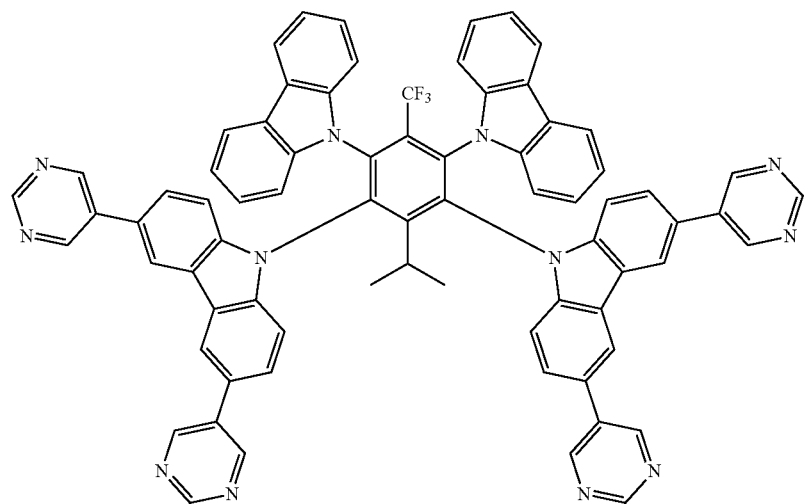
100
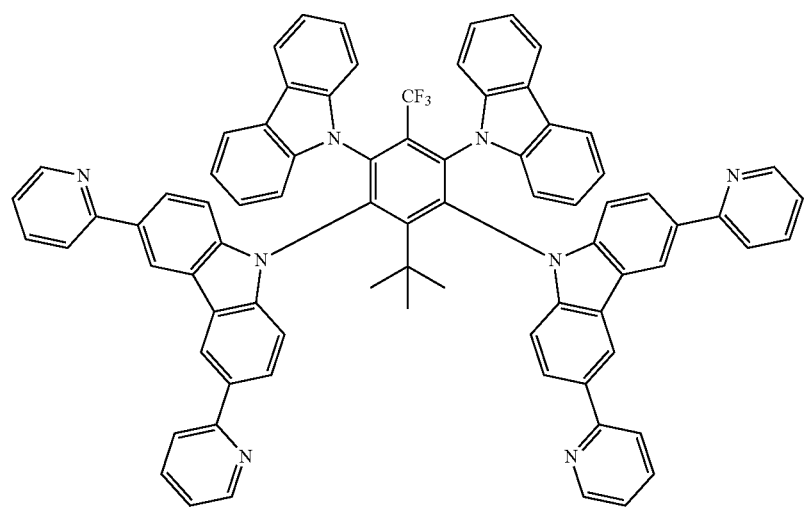
101
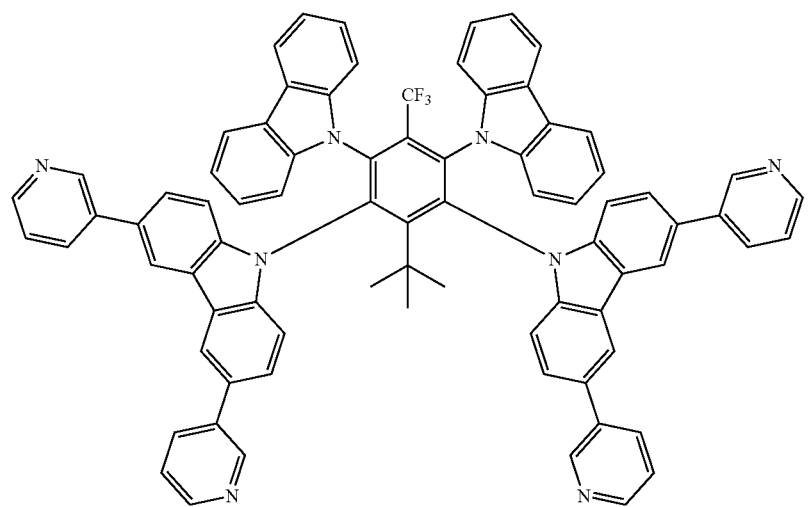
102

-continued
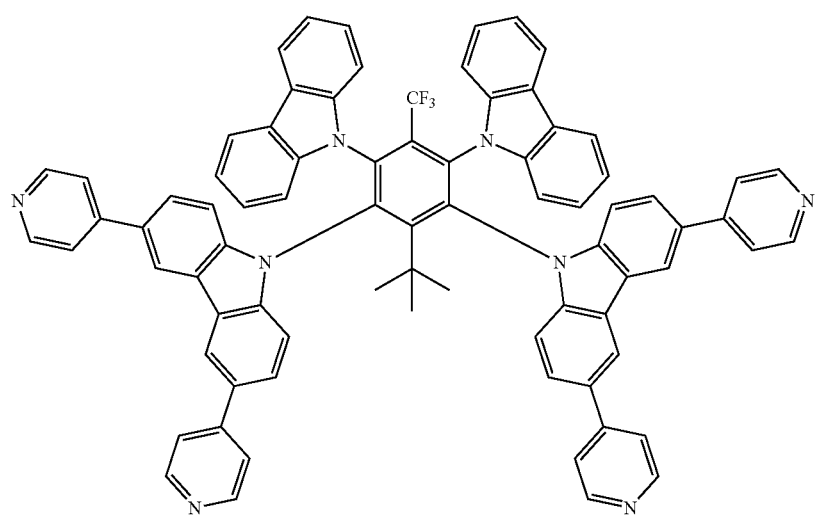
103
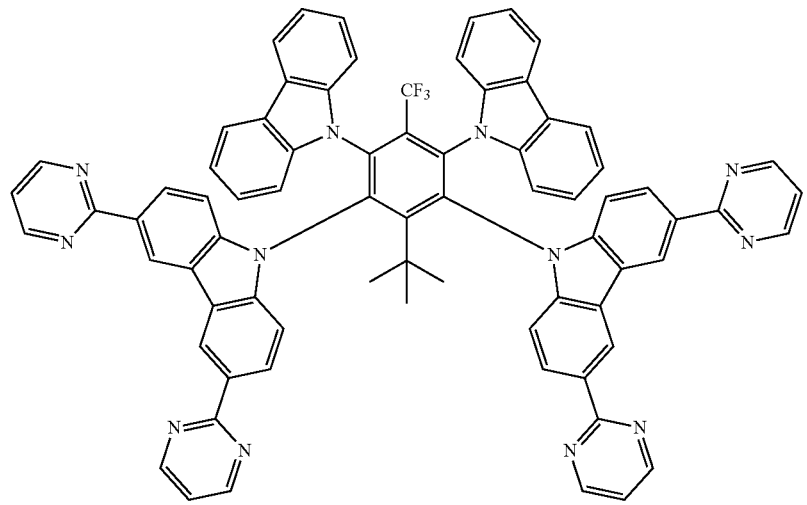
104
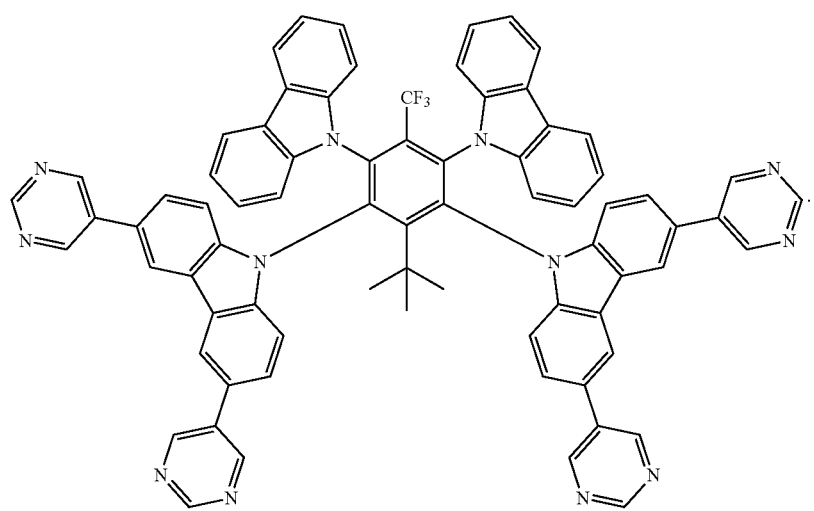
105
* * * * *